(12) United States Patent
Van Damme et al.

(10) Patent No.: US 10,787,673 B2
(45) Date of Patent: Sep. 29, 2020

(54) **DISEASE RESISTANT *BRASSICA* PLANTS**

(71) Applicant: Enza Zaden Beheer B.V., Enkhuizen (NL)

(72) Inventors: Mireille Maria Augusta Van Damme, Norwich (GB); Augustinus Franciscus Johannes Maria Van Den Ackerveken, Houten (NL); Mathieu André Pel, Enkhuizen (NL); Bartholomeus Laurentius Petrus Oud, Enkhuizen (NL); Tieme Zeilmaker, Amersfoort (NL)

(73) Assignee: Enza Zaden Beheer B.V., Enkhulzen (NL)

( * ) Notice: Subject to any disclaimer, the term of this patent is extended or adjusted under 35 U.S.C. 154(b) by 0 days.

(21) Appl. No.: 16/252,463

(22) Filed: Jan. 18, 2019

(65) Prior Publication Data
US 2019/0144878 A1 May 16, 2019

Related U.S. Application Data

(60) Continuation-in-part of application No. 15/975,670, filed on May 9, 2018, now abandoned, which is a continuation of application No. 15/190,675, filed on Jun. 23, 2016, now Pat. No. 9,994,861, which is a division of application No. 14/528,707, filed on Oct. 30, 2014, now Pat. No. 9,546,373, which is a division of application No. 14/250,875, filed on Apr. 11, 2014, now Pat. No. 9,121,029, which is a division of application No. 12/525,236, filed as application No. PCT/EP2008/000718 on Jan. 30, 2008, now Pat. No. 8,742,207.

(30) Foreign Application Priority Data

Feb. 1, 2007 (WO) .................. PCT/EP2007/050976

(51) Int. Cl.
| | |
|---|---|
| *C12N 15/82* | (2006.01) |
| *C12N 9/02* | (2006.01) |
| *A01H 1/06* | (2006.01) |
| *C12N 15/01* | (2006.01) |
| *A01H 5/08* | (2018.01) |
| *A01H 6/20* | (2018.01) |
| *A01H 5/02* | (2018.01) |

(52) U.S. Cl.
CPC .......... *C12N 15/8218* (2013.01); *A01H 1/06* (2013.01); *A01H 5/02* (2013.01); *A01H 5/08* (2013.01); *A01H 6/203* (2018.05); *C12N 9/0071* (2013.01); *C12N 15/01* (2013.01); *C12N 15/8239* (2013.01); *C12N 15/8279* (2013.01); *C12N 15/8281* (2013.01); *C12N 15/8282* (2013.01); *C12Y 114/11* (2013.01)

(58) Field of Classification Search
None
See application file for complete search history.

(56) References Cited

U.S. PATENT DOCUMENTS

| | | | |
|---|---|---|---|
| 5,866,776 | A | 2/1999 | de Wit |
| 6,100,451 | A | 8/2000 | Chappell et al. |
| 6,271,439 | B1 | 8/2001 | Gurmukh et al. |
| 7,323,338 | B2 | 1/2008 | Amir |
| 7,777,097 | B2 | 8/2010 | Glazebrook et al. |
| 8,237,019 | B2 | 8/2012 | Van Den Ackerveken et al. |
| 8,354,570 | B2 | 1/2013 | Van Den Ackerveken et al. |
| 8,569,064 | B2 | 10/2013 | Spangenberg et al. |
| 8,575,432 | B2 | 11/2013 | Van Den Ackerveken et al. |
| 8,742,207 | B2 | 6/2014 | Van Damme et al. |
| 8,796,511 | B2 | 8/2014 | Van Den Ackerveken et al. |
| 9,121,029 | B2 | 9/2015 | Van Damme et al. |
| 9,546,373 | B2 | 1/2017 | Van Damme et al. |
| 9,932,600 | B2 | 4/2018 | Van Damme et al. |
| 9,994,861 | B2 | 6/2018 | Van Damme et al. |
| 10,501,754 | B2 | 12/2019 | Van Damme et al. |
| 2003/0172396 | A1 | 9/2003 | Cohen |
| 2004/0031072 | A1 | 2/2004 | La Rosa et al. |
| 2006/0041949 | A1 | 2/2006 | Xu et al. |
| 2006/0048240 | A1 | 3/2006 | Alexandrov et al. |
| 2006/0143729 | A1 | 6/2006 | Alexandrov |
| 2009/0210965 | A1 | 8/2009 | McCarthy |
| 2010/0115658 | A1 | 5/2010 | Van Damme et al. |
| 2014/0289897 | A1 | 9/2014 | Van Damme et al. |
| 2015/0052634 | A1 | 2/2015 | Park et al. |
| 2016/0160233 | A1 | 6/2016 | Van Schie et al. |
| 2016/0272987 | A1 | 9/2016 | Gil et al. |
| 2016/0298130 | A1 | 10/2016 | Van Damme et al. |

(Continued)

FOREIGN PATENT DOCUMENTS

| | | |
|---|---|---|
| EP | 0474857 A1 | 3/1992 |
| EP | 1033405 A2 | 9/2000 |

(Continued)

OTHER PUBLICATIONS

Coelho et al. Euphytica (2003) 113:279-284.*

(Continued)

*Primary Examiner* — Medina A Ibrahim
(74) *Attorney, Agent, or Firm* — Morrison & Foerster LLP

(57) ABSTRACT

The present invention relates to a mutant *Brassica* plant, which is resistant to a pathogen of viral, bacterial, fungal or oomycete origin. The mutant *Brassica* plant has a reduced level, reduced activity or complete absence of DMR6-1 protein and DMR6-2 protein as compared to a wild type *Brassica* plant.

20 Claims, 49 Drawing Sheets
(6 of 49 Drawing Sheet(s) Filed in Color)
Specification includes a Sequence Listing.

(56) References Cited

U.S. PATENT DOCUMENTS

| | | |
|---|---|---|
| 2016/0298131 A1 | 10/2016 | Van Damme et al. |
| 2016/0312239 A1 | 10/2016 | Gan |
| 2016/0326543 A1 | 11/2016 | Van Damme et al. |
| 2016/0326544 A1 | 11/2016 | Van Damme et al. |
| 2016/0333370 A1 | 11/2016 | Van Schie et al. |
| 2017/0283826 A1 | 10/2017 | Van Schie et al. |
| 2017/0314039 A1 | 11/2017 | Van Schie et al. |
| 2018/0135071 A9 | 5/2018 | Van Damme et al. |
| 2018/0320191 A1 | 11/2018 | Van Damme et al. |
| 2018/0334681 A1 | 11/2018 | Van Schie et al. |
| 2019/0203223 A1 | 7/2019 | Van Schie et al. |
| 2019/0309319 A1 | 10/2019 | Van Schie et al. |
| 2019/0316143 A1 | 10/2019 | Van Damme et al. |
| 2020/0040354 A1 | 2/2020 | Van Damme et al. |

FOREIGN PATENT DOCUMENTS

| | | |
|---|---|---|
| EP | 2455473 A1 | 5/2012 |
| WO | WO1991015585 A1 | 10/1991 |
| WO | WO1996036697 A1 | 11/1996 |
| WO | WO1998004586 A2 | 2/1998 |
| WO | WO1998032325 A1 | 7/1998 |
| WO | WO1999045125 A2 | 9/1999 |
| WO | WO2000070016 A2 | 11/2000 |
| WO | WO2000078981 A1 | 12/2000 |
| WO | WO2001055347 A1 | 8/2001 |
| WO | WO2001061021 A2 | 8/2001 |
| WO | WO2002061101 A2 | 8/2002 |
| WO | WO2002088301 A2 | 11/2002 |
| WO | WO2003000906 A2 | 1/2003 |
| WO | WO2004024079 A2 | 3/2004 |
| WO | WO2006032707 A2 | 3/2006 |
| WO | WO2006047358 A1 | 5/2006 |
| WO | WO2006047495 A2 | 5/2006 |
| WO | WO2007051483 A1 | 5/2007 |
| WO | WO2007051626 A2 | 5/2007 |
| WO | WO2008092505 A1 | 8/2008 |
| WO | WO2008092659 A1 | 8/2008 |
| WO | WO2008153927 A2 | 12/2008 |
| WO | WO2009009142 A2 | 1/2009 |
| WO | WO2013086499 A2 | 6/2013 |
| WO | WO2015011101 A1 | 1/2015 |
| WO | WO2015029031 A1 | 3/2015 |
| WO | WO2015106796 A1 | 7/2015 |
| WO | WO2015193418 A1 | 12/2015 |
| WO | WO2019042935 A1 | 3/2019 |

OTHER PUBLICATIONS

"Federal Register", Feb. 9, 2011, vol. 76, No. 27, 7162-7175, 14 pages.
Ardi, et al., (Nov. 1998). "Involvement of Epicatechin Biosynthesis in the Activation of the Mechanism of Resistance of Avocado Fruits to Colletotrichum Gloeosporioides", Physiological and Molecular Plant Pathology, vol. 53, pp. 269-285.
Aubert, et al., (1998). "Transport, Compartmentation, and Metabolism of Homoserine in Higher Plant Cells", Plant Physiol., vol. 116, pp. 547-557.
Balass, et al., (1992). "Identification of a constitutive 45 kDa soluble protein associated with resistance to downy mildew in muskmelon (*Cucumis melo* L.), line PI 124111 F", Physiological and Molecular Plant Pathology, vol. 41, pp. 387-396.
Bhattacharyya, et al., (2005). "Identification of a Large Cluster of Coiled Coil-Nucleotide Binding Site—Leucine Rich Repeat-Type Genes from the Rps1 Region Containing Phytophthora Resistance Genes in Soybean", Theor. Appl. Genet., vol. 111, pp. 75-86.
Bouchez, et al., (1998). "Functional Genomics in Plants", Plant Physiology, vol. 118, pp. 725-732.
Brouwer, et al., (2004). "QTL analysis of quantitative resistance to *Phytophthora infestans* (late blight) in tomato and comparisons with potato", Genome, vol. 27, No. 3, pp. 475-492.
Brouwer, et al., (Feb. 2004). "Fine mapping of three quantitative trait loci for late blight resistance in tomato using near isogenic lines (NILs) and sub-NILs", Theoretical and Applied Genetics, vol. 108, pp. 628-638.
Budiman, et al., (2000). "A Deep-Coverage Tomato BAC Library and Prospects toward Development of an STC Framework for Genome Sequencing", Genome Research, vol. 10, pp. 129-136.
Burnham, et al., (2003). "Quantitative Trait Loci for Partial Resistance to Phytophthora sojae in Soybean", Crop Science, vol. 43, No. 5, pp. 1610-1617.
Cho, et al., (2005). "Constitutive expression of the Flavanone 3-hydroxylase gene related to pathotype-specific Ascochyta blight resistance in Cicer arietinum L.", vol. 67, Physiological and Molecular Plant Pathology, pp. 100-107.
Choi, et al., (2012). "Predicting the Functional Effect of Amino Acid Substitutions and Indels", PLoS ONE, vol. 7, No. 10, pp. 1-13.
Clough, et al., (1998). "Floral Dip: A Simplified Method for Agrobacterium-Mediated Transformation of *Arabidopsis thaliana*", Plant Journal, vol. 16, No. 6, pp. 735-743.
Conrath, et al., (2003). "Enhanced Resistance to Phytophthora Infestans and Alternaria Solani in Leaves and Tubers, Respectively, of Potato Plants with Decreased Activity of the Plastidic ATP/ADP Transporter", Planta, vol. 19, pp. 75-83.
Constantinescu, et al., (May 2002). "Peronospora-like Fungi (Chromista, Peronosporales) Parasitic on Brassicaceae and Related Hosts", Nova-Hedwigia, vol. 74, pp. 291-338.
Crowe, et al., (2003). "CATMA: a complete *Arabidopsis* GST database", Nucleic Acids Res., vol. 31, No. 1, pp. 156-158.
Database EMBL, (Apr. 15, 2002). "*Arabidopsis thaliana* Flavanone 3-Hydroxylase-like Protein (At5g24530) mRNA, complete Cds", Retrieved from EBI Accession No. EMBL: AY081455.
Database EMBL, (Jun. 16, 2001). "*Arabidopsis thaliana* Flavanone 3-Hydroxylase-like Protein {K 18P6.6) mRNA, Complete Cds", Retrieved from EBI Accession No. EMBL: AF386975.
Database EMBL, retrieved from EBI Accession No. EMBL: DQ208192, Database accession No. DQ208192.
Database EMBL, XP002386701, retrieved from EBI accession No. EM_PRO:AF082525, Database accession No. AF082525.
De Jong M, et al., (2006). "Membrane-associated transcripts in *Arabidopsis*; their isolation and characterization by DNA microarray analysis and bioinformatics", Plant J., vol. 46, No. 4, pp. 708-721.
De las Mercedes Dana, et al., (2006). "Transgenic Tobacco Plants Overexpressing Chitinases of Fungal Origin Show Enhanced Resistance to Biotic and Abiotic Stress Agents", Plant Physiol., vol. 142, No. 2, American Society of Plant Biologists, pp. 722-730.
De Wit, (1992). "Molecular characterization of gene-for-gene systems in plant-fungus interactions and the application of avirulence genes in control of plant pathogens", Annu. Rev. Phytopathol., vol. 30, pp. 391-418.
Elliott, (Jun. 15, 1992). "Relative Susceptibility to Pythium Root Rot of Twelve Dent Corn Inbreds", Journal of Agricultural Research, vol. 64, No. 12, p. 711-723.
Fischer, et al., (Feb. 2004). "Quantitative Trait Locus Analysis of Fungal Disease Resistance Factors on a Molecular Map of Grapevine", Theoretical and Applied Genetics, vol. 108, No. 3, pp. 501-515.
Flanagan, et al., (2010). "Using SIFT and PolyPhen to predict loss-of-function and gain-of-function mutations", Genetic Testing and Molecular Biomarkers, vol. 14, No. 4, pp. 533-537.
Franchel, et al., (Feb. 2013). "Positional cloning of a candidate gene for resistance to the sunflower downy mildew, Plasmopara halstedii race 300", Theoretical and Applied Genetics, vol. 126, No. 2, pp. 359-367.
Friedrich, et al., (2001). "NIM1 Overexpression in *Arabidopsis* Potentiates Plant Disease Resistance and Results in Enhanced Effectiveness of Fungicides", MPMI, vol. 14, No. 9, pp. 1114-1124.
Gaspero, et al., (Dec. 2002). "Resistance Gene Analogs are Candidate Markers for Disease-Resistance Genes in Grape (*Vitis* spp.)", Theoretical and Applied Genetics, vol. 106, No. 1, pp. 163-172.
Geneseq Database Accession No. AAG45151, Oct. 18, 2000, 4 pages.

(56) References Cited

OTHER PUBLICATIONS

Giovanini, et al., (2006). "Gene-for-gene defense of wheat against the Hessian fly lacks a classical oxidative burst", Molecular Plant-Microbe Interactions, vol. 19, No. 9, pp. 1023-1033.
Göker, et al., (2003). "Taxonomic aspects of Peronosporaceae inferred from Bayesian molecular phylogenetics", Canadian Journal of Botany, vol. 81, No. 7, pp. 672-683.
Göker, et al., (May 2004). "Phylogeny of Hyaloperonospora based on nuclear ribosomal internal transcribed spacer sequences", Mycological Progress, vol. 3, No. 2, pp. 83-94.
Grimplet, et al., (2007). "Tissue-Specific mRNA Expression Profiling in Grape Berry Tissues", BMC Genomics, vol. 8, No. 187, pp. 1-23.
Gurr, et al., (2005). "Engineering plants with increased disease resistance: how are we going to express it?", Trends Biotechnol., vol. 23, No. 6, pp. 283-290.
Gurr, et al., (2005). "Engineering plants with increased disease resistance: what are we going to express?", Trends Biotechnology, vol. 23, No. 6, pp. 275-282.
Guzzo Thesis, (Jun. 2004). "Isolation of cv. Mundo Novo coffee plant genes associated with systemic acquired resistance", 21 pages (including 10 pages of English Translation).
Hellens, et al., (2000). "pGreen: A Versatile and Flexible Binary Ti vector for Agrobacterium-Mediated Plant Transformation", Plant Molecular Biology, vol. 42, pp. 819-832.
Henikoff, et al., (2004). "TILLING. Traditional Mutagenesis Meets Functional Genomics", Plant Physiology, vol. 135, pp. 630-636.
Holub, et al., (1994). "Phenotypic and Genotypic Characterization of Interactions Between Isolates of Peronospora parasitica and Accessions of *Arabidopsis thaliana*", vol. 7, No. 2, pp. 223-239.
Hong, et al., (Aug. 2008). "First confirmed report of downy mildew caused by Hyaloperonospora parasitica on broccoli in Korea", Plant Pathology, vol. 57, No. 4, p. 777.
Karimi, M., et al., (May 2002). "Gateway Vectors for Agrobacterium-Mediated Plant Transformation", Trends in Plant Science, vol. 7, No. 5, pp. 193-195.
Kim, et al., (Sep. 2006). "Characterization of Late Blight Resistance Derived from Solanum pimpinellifolium L3708 against Multiple Isolates of the Pathogen Phytophthora infestans", Journal of the American Society for Horticultural Science, vol. 131 No. 5, pp. 637-645.
Kitz, Leilani, (2008). "Evaluation of Downy Mildew (*Peronospora farinosa* f. sp. *chenopodii*) Resistance among Quinoa Genotypes and Investigation of *P. farinosa* Growth using Scanning Electron Microscopy", All Theses and Dissertations, Brigham Young University, 134 pages.
Kofoet, et al., (1990). "Inheritance of Resistance to Downy Mildew (*Peronospora destructor* [Berk.] Casp.) from Allium Roylei Stearn in the Backcross Allium Cepa L.×(A. Roylei×A. Cepa)", Plant Breeding, vol. 105, No. 2, pp. 144-149.
Kortekamp, et al., (Jan. 2006). "Expression Analysis of Defence-Related Genes in Grapevine Leaves after Inoculation with a Host and a Non-Host Pathogen", Plant Physiology and Biochemistry, vol. 44, No. 1, pp. 58-67.
Ku, et al., (Aug. 1, 2000). "Comparing Sequenced Segments of the Tomato and *Arabidopsis* Genomes: Large-Scale Duplication Followed by Selective Gene Loss Creates a Network of Synteny", PNAS, vol. 97, No. 16, pp. 9121-9126.
Lacomme, et al., (1999). "Bax-induced cell death in tobacco is similar to the hypersensitive response", Proc. Natl. Acad. Sci. vol. 96, No. 14, pp. 7956-7961.
Lamour, et al., (2009). "Oomycete Genetics and Genomics: Diversity, Interactions and Research Tools", Wiley-Blackwell, 6 pages.
Lebeda, (1992). "Screening of wild *Cucumis* species against downy mildew (*Pseudoperonospora cubensis*) isolates from cucumbers", Phytoparasitica, vol. 20, No. 3, pp. 203-210.
Lee, et al., (2005). "Methionine and Threonine Synthesis are Limited by Homoserine availability and not the Activity of Homoserine Kinase in *Arabidopsis thaliana*", The Plant Journal, vol. 41, pp. 685-696.
Lee, et al., (Dec. 1999). "Identification of the Gene Encoding Homoserine Kinase from *Arabidopsis thaliana* and Characterization of the Recombinant Enzyme derived from the Gene", Arch. Biochem. Biophys., vol. 372, No. 1, pp. 135-142.
Mae, et al., (2001). "Transgenic Plants Producing the Bacterial Pheromone N-Acyl-Homoserine Lactone Exhibit Enhanced Resistance to the Bacterial Phytopathogen *Erwinia carotovora*", Molecular Plant-Microbe Interactions, vol. 14, No. 9, pp. 1035-1042.
McCallum, et al., (Apr. 2000). "Targeted Screening for Induced Mutations", Nature Biotechnology, vol. 18, pp. 455-457.
Meer, et al., (1990). "An Interspecific Cross between Allium Roylei Stearn and Allium Cepa L, and its Backcross to A. Cepa", Euphytica, vol. 47, pp. 29-31.
Mosher, et al., (Jul. 2006). "A Comprehensive Structure-Function Analysis of *Arabidopsis* SNI1 Defines Essential Regions and Transcriptional Repressor Activity", vol. 18, The Plant Cell, pp. 1750-1765.
Parker, et al., (1996). "Characterization of eds1, a mutation in *Arabidopsis* suppressing resistance to Peronospora parasitica specified by several different RPP genes", Plant Cell, vol. 8, No. 11, American Society of Plant Physiologists, pp. 2033-2046.
Perchepied, et al., (2005). "Relationship Between Loci Conferring Downy Mildew and Powdery Mildew Resistance in Melon Assessed by Quantitative Trait Loci Mapping", Phytopathology, vol. 95, No. 5, pp. 556-565.
Radwan, et al., (2011). "Molecular Characterization of Two Types of Resistance in Sunflower to *Plasmopara halstedii*, the Causal Agent of Downy Mildew", The American Phytopathological Society, vol. 101, No. 8, pp. 971-979.
Rostas, et al., (Jun. 2013). "Copper and Herbivory Lead to Priming and Synergism in Phytohormones and Plant Volatiles in the Absence of Salicylate-Jasmonate Antagonism", Plant Signaling & Behavior, vol. 8, No. 6, pp. e24264-1-e24264-3.
Russell, G. E.., (1966). "Some effects of inoculation with yellowing viruses on the susceptibility of sugar beet to fungal pathogens: I. Susceptibility to Peronospora farinosa", Transactions of the British Mycological Society, vol. 49, No. 4, pp. 611-619.
Sabetta, et al., (2011). "sunTILL: a TILLING resource for gene function analysis in sunflower", Plant Methods 2011, vol. 7, No. 20, pp. 1-13.
Sandhu, et al., (Jun. 15, 2005). "Soybean Phytophthora Resistance Gene Rps8 Maps Closely to the Rps3 Region", Journal of Heredity, vol. 96, No. 5, pp. 536-541.
Sim, et al., (2012). "SIFT web server: predicting effects of amino acid substitutions on proteins", Nucleic Acids Res., vol. 40, Web Server issue, 6 pages.
Sinapidou, et al., (Jun. 2004). "Two TIR:NB:LRR Genes are Required to Specify Resistance to Peronospora Parasitica Isolate Cala2 in *Arabidopsis*", The Plant Journal, vol. 38, No. 6, pp. 898-909.
Skadhauge, et al., (1997). "The role of the barley testa layer and its flavonoid content in resistance to Fusarium infections", vol. 126, Carlsberg Laboratory, Department of Physiology, pp. 147-160.
Sun, et al., (2016). "Silencing of Six Susceptibility Genes Results in Potato Late Blight Resistance", Transgenic Research, vol. 25, pp. 731-742.
Szwacka, et al., (Jun. 1, 2002). "Variable properties of transgenic cucumber plants containing the thaumatin II gene from Thaumatococcus daniellii", Acta Physiologiae Plantarum, vol. 24. No. 2, pp. 173-185.
Takatsuji, Hiroshi, (Nov. 2014). "Development of Disease-Resistant Rice Using Regulatory Components of Induced Disease Resistance", Frontiers in Plant Science, vol. 5, Article 630, 12 pages.
Thomas, et al., (Sep. 1, 2000). "Linkage of random amplified polymorphic DNA markers to downy mildew resistance in cucumber (*Cucumis sativus* L.)", Euphytica, vol. 115, No. 2, pp. 105-113.
Thomazella, et al., (Jul. 2016). "CRISPR-Cas9 Mediated Mutagenesis of a DMR6 Ortholog in Tomato Confers Broad-Spectrum Disease Resistance", bioRxiv doi: 10.1101/064824, pp. 1-23.
Till, et al., (2004). "Mismatch cleavage by single-strand specific nucleases", Nucleic Acids Research, vol. 32, No. 8, pp. 2632-2641.

(56) References Cited

OTHER PUBLICATIONS

Tor, et al., (Jun. 2004). "*Arabidopsis* Downy Mildew Resistance Gene RPP27 Encodes a Receptor-Like Protein Similar to CLAVATA2 and Tomato Cf-9 1", vol. 135, Plant Physiology, pp. 1100-1112.
UniProt, XP002730065, retrieved from EBI Accession No. UNIPROT:M0ZIQ1 Database Accession No. M0ZIQ1 Sequence.
UniProt, XP002730066, retrieved from EBI Accession No. UNIPROT:M1CK41 Database Accession No. M1CK41 Sequence.
UniProt, XP002730067, retrieved from EBI Accession No. UNIPROT:K4C928, Database Accession No. K4C928 sequence.
Vailleau, et al., (2002). "A R2R3-MYB gene, AtMYB30, acts as a positive regulator of the hypersensitive cell death program in plants in response to pathogen attack", PNAS, vol. 99, No. 15, pp. 10179-10184.
Van Damme, et al., (2005). "Identification of *Arabidopsis* Loci Required for Susceptibility to the Downy Mildew Pathogen *Hyaloperonospora parasitica*", Molecular Plant-Microbe Interactions, vol. 18, No. 6, pp. 583-592.
Van Damme, et al., (2008). "*Arabidopsis* DMR6 encodes a putative 2OG-Fe(II) oxygenase that is defense-associated but required for susceptibility to downy mildew", The Plant Journal, vol. 54, pp. 785-793.
Van Damme, et al., (Jul. 2009). "Downy Mildew Resistance in *Arabidopsis* by Mutation of Homoserine Kinase", The Plant Cell, vol. 21, pp. 2179-2189.
Van Damme, Mireille, (2007). "Genetic analysis of disease susceptibility in the *Arabidopsis*-Hyaloperonospora parasitica interaction.", Thesis, 134 pages.
Vandenbussche, et al., (2008). "Generation of a 3D Indexed Petunia Insertion Database for Reverse Genetics", The Plant Journal, 54(6):1105-14.
Vogel, et al., (2002). "PMR6, a Pectate Lyase-Like Gene Required for Powdery Mildew Susceptibility in *Arabidopsis*", The Plant Cell, vol. 14, pp. 2095-2106.
Voglmayr, Hermann, (2003). "Phylogenetic relationships of *Peronospora* and related genera based on nuclear ribosomal ITS sequences", Mycol. Res., vol. 107, No. 10, pp. 1132-1142.
Weaver, et al., (2006). "The *Arabidopsis thaliana* TIR-NB-LRR R-protein, RPP1A; protein localization and constitutive activation of defence by truncated alleles in tobacco and *Arabidopsis*", vol. 47, The Plant Journal, pp. 829-840.
Xu, et al., (Jul. 14, 2011). "Genome Sequence and Analysis of the Tuber Crop Potato", Nature, vol. 475, pp. 189-195.
Yang, et al., (Oct. 1, 2005). "Characterization and Mapping of Rpi1, A Gene that Confers Dominant Resistance to Stalk Rot in Maize", Molecular Genetics and Genomics, vol. 274, No. 3, pp. 229-234.
Zeilmaker, et al., (2015). "Downy Mildew Resistant 6 and DMR6-Like Oxygenase 1 are Partially Redundant but Distinct Suppressors of Immunity in *Arabidopsis*", The Plant Journal, vol. 81, No. 2, pp. 210-222.
Zeilmaker, Tieme, (2012). Functional and Applied Aspects of the Downy Mildew Resistant 1 and 6 Genes in *Arabidopsis*, Universiteit Utrecht, Available at <http://web.science.uu.nl/pmi/publications/PDF/2012/Proefschrift-Zeilmaker-2012.pdf>, 147 pages.
Zhang, et al., (Sep. 3, 2013). "Salicylic Acid 3-Hydroxylase Regulates *Arabidopsis* Leaf Longevity by Mediating Salicylic Acid Catabolism", Proceedings of The National Academy of Sciences of the United States of America, vol. 110, No. 36, pp. 14807-14812.
Zhang, James Z., (2003). "Overexpression analysis of plant transcription factors", Curr. Opin. Plant Biol., vol. 6, No. 5, pp. 430-440.
Zimmermann, et al., (2005). "Gene-expression analysis and network discovery using Genevestigator", Trends Plant Sci., vol. 10, No. 9, pp. 407-409.
Alignment of cucumber DMR6-specific primers with XP_008462902.2, filed on Apr. 29, 2019 in Opposition proceedings against EP2455475, 1 page.
Alignment of primers with the two copies of the cabbage DMR6 Gene, filed in Opposition against EP2455477, dated Sep. 7, 2016, 4 pages.
Amended claims filed after receipt of (European) search report, filed Feb. 10, 2017, during prosecution of EP3094722, 1 page.
Amended claims filed after receipt of (European) search report, filed Jan. 22, 2013, during prosecution of EP2455482, 2 pages.
Amended claims filed after receipt of (European) search report, filed Jan. 22, 2013, during prosecution of EP2455483, 2 pages.
Amended claims filed after receipt of (European) search report, filed Jul. 30, 2009, during prosecution of EP2115147, 5 pages.
Amended claims filed after receipt of (European) search report, filed Nov. 19, 2012, during prosecution of EP2455479, 2 pages.
Amended claims filed after receipt of (European) search report, filed Sep. 5, 2016, during prosecution of EP3024929, 2 pages.
Amended claims submitted by applicant on Sep. 25, 2017 for EP2681234 examination proceedings, filed Dec. 7, 2017 in Opposition against EP2455477, 1 page.
Amended claims with annotations, filed Apr. 26, 2018, during appeal of EP2455473, 2 pages.
Amended claims with annotations, filed Sep. 10, 2018, during appeal of EP2455473, 14 pages.
Amended claims, filed Apr. 17, 2018, during prosecution of EP3167051, 1 page.
Amended claims, filed Aug. 17, 2017, during prosecution of EP3167051, 2 pages.
Amended claims, filed Aug. 20, 2010, during prosecution of EP2115147, 4 pages.
Amended claims, filed Dec. 21, 2017, during prosecution of EP3024929, 2 pages.
Amended claims, filed Feb. 2, 2012, during prosecution of EP2115147, 2 pages.
Amended claims, filed Jan. 17, 2018, during prosecution of EP3094722, 1 page.
Amended claims, filed Mar. 17, 2017, during prosecution of EP2455474, 1 page.
Amended claims, filed May 26, 2011, during prosecution of EP2115147, 3 pages.
Amended claims, filed May 28, 2018, during prosecution of EP3094722, 1 page.
Amended claims, filed May 28, 2018, during prosecution of EP3167051, 1 page.
Amended claims, filed Oct. 15, 2018, during prosecution of EP3024929, 1 page.
Amended description with annotations, filed Apr. 17, 2018, during prosecution of EP3167051, 17 pages.
Amended description with annotations, filed Aug. 30, 2016, during prosecution of EP2455475, 30 pages.
Amended description with annotations, filed Aug. 30, 2016, during prosecution of EP2455481, 29 pages.
Amended description with annotations, filed Jan. 17, 2018, during prosecution of EP3094722, 19 pages.
Amended description with annotations, filed Jul. 21, 2016, during prosecution of EP2455476, 29 pages.
Amended description with annotations, filed Jul. 21, 2016, during prosecution of EP2455480, 29 pages.
Amended description with annotations, filed Jun. 5, 2012, during prosecution of EP2115147, 7 pages.
Amended description with annotations, filed Mar. 17, 2017, during prosecution of EP2455474, 29 pages.
Amended description with annotations, filed May 28, 2018, during prosecution of EP3094722, 19 pages.
Amended description with annotations, filed May 28, 2018, during prosecution of EP3167051, 34 pages.
Amended description with annotations, filed Oct. 10, 2016, during prosecution of EP2455474, 29 pages.
Amended description with annotations, filed Oct. 10, 2016, during prosecution of EP2455478, 29 pages.
Amended description with annotations, filed Oct. 21, 2013, during prosecution of EP2455473, 11 pages.
Amended description with annotations, filed Oct. 21, 2013, during prosecution of EP2455477, 11 pages.
Amended description with annotations, filed Oct. 5, 2016, during prosecution of EP2455479, 30 pages.
Amendments before examination, filed Aug. 17, 2017, during prosecution of EP3167051, 3 pages.

(56) References Cited

OTHER PUBLICATIONS

Amendments before examination, filed Feb. 10, 2017, during prosecution of EP3094722, 2 pages.
Amendments before examination, filed Jan. 22, 2013, during prosecution of EP2455482, 3 pages.
Amendments before examination, filed Jan. 22, 2013, during prosecution of EP2455483, 3 pages.
Amendments before examination, filed Nov. 19, 2012, during prosecution of EP2455479, 3 pages.
Amendments before examination, filed Sep. 5, 2016, during prosecution of EP3024929, 2 pages.
Analysis performed by Dr. Tieme Zeilmaker using the protein analysis program PROVEAN, filed Sep. 15, 2017, in Opposition against EP2455473, 3 pages.
Annex B, filed by the Applicant on Aug. 30, 2016, in the case EP2455475 during the examination, 6 pages.
Annexes (other than cited documents) regarding appeal procedure, Sep. 10, 2018, filed during appeal of EP2455473, 6 pages.
Applicant request for correction/amendment of the text proposed for grant and amended claims, filed Jan. 15, 2019 in case EP3167051, 3 pages.
Applicant request for correction/amendment of the text proposed for grant with amended claims and description, filed Feb. 5, 2019 in case EP3094722, 22 pages.
Applicant request for correction/amendment of the text proposed for grant, filed Aug. 17, 2017 in case EP2455475, 1 page.
Auxiliary request containing amended claims, filed Dec. 19, 2017, in Opposition against EP2455473, 1 page.
Auxiliary request containing amended claims, filed Sep. 15, 2017, in Opposition against EP2455473, 1 page.
Auxiliary Request I, filed Apr. 26, 2018, during appeal of EP2455473, 1 page.
Belhaj et al. (2013). "Plant genome editing made easy: targeted mutagenesis in model and crop plants using the CRISPR/Cas system," Plant Methods, 9(39):1-10.
BLAST comparison between the amino acid sequences of *Arabidopsis* DMR6 (query ID Query_190785) and XP 013593012.1, dated Sep. 21, 2017, 2 pages.
BLAST comparison between the amino acid sequences of *Arabidopsis* DMR6 (query ID Query_236939) and XP 013620820.1, dated Sep. 21, 2017, 2 pages.
BLAST comparison results of query ID 258413, filed during prosecution of EP2455475, dated Aug. 30, 2016, 6 pages.
BLAST comparison results of query ID 3871 and subject ID 3873, filed during prosecution of EP2455474, dated Jul. 3, 2013, 2 pages.
BLAST comparison results of query ID XP_003526765.1 and subject ID OAO94377.1, filed during prosecution of EP2455481, dated Aug. 30, 2016, 2 pages.
BLAST strategy and results on Solanum lycopersicum nucleotide sequence, filed Jul. 18, 2018, in Opposition against EP2455479, 2 pages.
BLAST strategy and results on Solanum lycopersicum protein sequence, filed Jul. 18, 2018, in Opposition against EP2455479, 5 pages.
BLAST-P query of AtF3H against *A. thaliana* genome, filed in Opposition against EP2455477, dated Dec. 7, 2017, 3 pages.
Brandenberger et al., (1992). "Evaluation of Spinach Germplasm for Resistance to a New Race (Race 4) of *Peronospora farinosa* f. sp. *spinaciae*," HortScience, 27(20):1118-1119.
Brandenberger et al., (1994). "Characterization of resistance of spinach to white rust (*Albugo occidentalis*) and downy mildew (*Peronospora farinosa* f. sp. *spinaciae*)," Phytopathology, 84(4):431-437.
Chen et al., (2008). "Host specificity and tomato-related race composition of Phytophthora infestans isolates in Taiwan during 2004 and 2005," Plant Disease, 92(5):751-755.
Coelho et al., (2003). "Expression of resistance to downy mildew at cotyledon and adult plant stages in *Brassica oleracea* L.," Euphytica, 133:279-284.

Communication from the Examining Division dated Mar. 20, 2014, filed in Opposition against EP2455474, 1 page.
Communication from the Examining Division dated Mar. 20, 2014, filed in Opposition against EP2455479, 1 page.
Communication from the Examining Division for EP2455473 dated Mar. 20, 2014, filed in Appeal proceedings for EP2455473, 1 page.
Communication from the Examining Division for EP2455477 dated Nov. 14, 2013, filed in Opposition against EP2455477, 2 pages.
Communication from the Examining Division for EP2681234 dated Nov. 20, 2017, filed in Opposition against EP245577, 4 pages.
Communication from the Examining Division in case EP2455475 dated Mar. 20, 2014, concerning the staying of examination proceedings, 1 page.
Communication pursuant to Art. 94(3) EPC dated Mar. 8, 2017, filed Dec. 14, 2018 in Opposition against EP2455474, 3 pages.
Cooke et al., (2000). "A molecular phylogeny of Phytophthora and related Oomycetes," Fungal Genetics and Biology, 30:17-32.
Curriculum vitae of Dr. Tieme Zeilmaker, filed Sep. 15, 2017, in Opposition against EP2455473, 2 pages.
CV of Dr. Adriaan Verhage, dated Oct. 20, 2017, submitted in opposition proceedings for EP2455473, 3 pages.
Data on sequence and resistance of spinach variants, filed Feb. 14, 2017, in Opposition against EP2455473, 3 pages.
Decision T 1063/18, filed on Apr. 29, 2019 in Opposition proceedings against EP2455475, 29 pages.
Declaration and CV of Dr. A. Rijpkema, dated Jul. 27, 2018, submitted in opposition proceedings for EP2455474, 4 pages.
Declaration and CV of Dr. B. D'hoop, dated Jul. 27, 2018, submitted in opposition proceedings for EP2455474, 3 pages.
Declaration and CV of Dr. P.M. Eggink, dated Jul. 14, 2018, submitted in opposition proceedings for EP2455479, 3 pages.
Declaration by Dr. A. Verhage, dated Jun. 26, 2017, submitted in opposition proceedings for EP2455474 and EP2455479, 1 page.
Declaration of Dr. Adriaan Verhage, dated Oct. 17, 2017, submitted in opposition proceedings for EP2455473, 2 pages.
Develey-Riviere et al., (2007). "Resistance to pathogens and host developmental stage: a multifaceted relationship within the plant kingdom," New Phytologist, 175:405-416.
Disease test results DMR6 Spinach mutants, filed Jul. 17, 2017, in Opposition against EP2455473, 1 page.
Enza lettuce catalogue, dated Jan. 17, 2014, filed in Opposition to EP2115147, p. 102-115.
Experimental data "Annex A—Overview supporting data DMR6 down regulation and disease resistance," filed Oct. 10, 2016 by the Applicant during the examination of EP2455474 (six page excerpt filed Jul. 18, 2018 in Opposition against EP2455479), 28 pages.
Experimental data on mutation in dmr6 conferring resistance to cabbage, filed during Opposition against EP2455477, dated Jan. 18, 2018, 3 pages.
Experimental data showing no Phytophthora resistance, filed during prosecution of EP3167051, dated Aug. 17, 2017, 1 page.
Experimental data showing that the claimed sunflower plants are resistant to downy mildew, filed during prosecution of EP3024929, dated Dec. 21, 2017, 2 pages.
Fall et al., (2015). "Infection Efficiency of Four Phytophthora infestans Clonal Lineages and DNA-based Quantification of Sporangia," PLoS ONE, 10(8): e0136312doi: 10.1371/journal.pone.0136312, 18 pages.
Further experimental data of pathogen resistance against Phytophthora infestans of mutated tomato plants, filed during Opposition against EP2455479, dated Jan. 4, 2019, 2 pages.
Instructions to the PhD candidate, filed Jul. 17, 2017, in Opposition against EP2455473, Utrecht University, 11 pages.
International Seed Federation Guidelines for Coding Pests of Vegetable and Cereal Crops, submitted in Opposition against EP2455477, dated Jan. 18, 2018, 4 pages.
Irish et al., (2007). "Three new races of the spinach downy mildew pathogen identified by a modified set of spinach differentials," Plant Disease, 91(11):1392-1396.
Kofoet et al., (1990). "Resistance to Downy Mildew (*Peronospora destructor* (Berk.) Casp.) in Allium Species//Resistenz Gegen Falschen Mehltau (*Peronospora destructor* (Berk.) Casp.) in Allium-Arten,"

(56) References Cited

OTHER PUBLICATIONS

Zeitschrift fuer Pflanzenkrankheiten und Pflanzenschutz//Journal of Plant Diseases and Protection, 97(1):13-23.
Letter accompanying subsequently filed items, filed during prosecution of EP2455473, dated Mar. 10, 2014, 1 page.
Letter accompanying subsequently filed items, filed during prosecution of EP2455474, dated Mar. 10, 2014, 1 page.
Letter accompanying subsequently filed items, filed during prosecution of EP2455475, dated Mar. 10, 2014, 1 page.
Letter accompanying subsequently filed items, filed during prosecution of EP2455476, dated Mar. 10, 2014, 1 page.
Letter accompanying subsequently filed items, filed during prosecution of EP2455477, dated Mar. 10, 2014, 1 page.
Letter accompanying subsequently filed items, filed during prosecution of EP2455481, dated Mar. 10, 2014, 1 page.
Letter accompanying subsequently filed items, filed during prosecution of EP2455482, dated Mar. 10, 2014, 1 page.
Letter regarding the opposition procedure (no time limit) and Auxiliary requests I and II, filed during Opposition against EP2455477, dated Dec. 8, 2017, 22 pages.
Letter regarding the opposition procedure (no time limit), filed during Opposition against EP2455473, dated Sep. 14, 2017, 3 pages.
Letter regarding the opposition procedure (no time limit), filed during Opposition against EP2455473, dated Sep. 15, 2017, 17 pages.
Letter regarding the opposition procedure (no time limit), filed during Opposition against EP2455477, dated Jan. 18, 2018, 15 pages.
Letter regarding the opposition procedure and Auxiliary requests I and II, filed during Opposition against EP2455474, dated Dec. 14, 2018, 39 pages.
Letter regarding the opposition procedure and Auxiliary requests I and II, filed during Opposition against EP2455479, dated Jan. 8, 2019, 48 pages.
Lukacin et al., (1997). "Identification of strictly conserved histidine and arginine residues as part of the active site in Petunia hybrida flavanone 3P-hydroxylase," Eur. J. Biochem., 249:748-757.
MRNA sequence ID XM_008464687.2 corresponding to melon DMR6 protein sequence ID XP_008462909.2, filed on Apr. 29, 2019 in Opposition proceedings against EP2455475, 2 pages.
Multiple alignment of cabbage DMR6 (B. oleracea) with known oxidoreductases, filed May 22, 2017, in Opposition against EP2455477, 2 pages.
Multiple alignment of spinach DMR6 (S. oleracea) with known oxidoreductases, filed Feb. 14, 2017, in Opposition against EP2455473, 1 page.
NCBI Reference Sequence NP_190692.1, dated Jul. 3, 2013, filed in Opposition against EP2455473 and during prosecution for EP2455474 and EP2455479, 1 page.
NCBI Reference Sequence NP_197841.1, dated Nov. 25, 2016, filed in Opposition against EP2455473 and during prosecution for EP2455474 and EP2455479, 2 pages.
Non-Final Office Action for U.S. Appl. No. 15/111,285, dated Feb. 7, 2018, 13 pages.
Notice of appeal by Bird&Bird, filed in relation to EP2455473, dated Feb. 22, 2018, 2 pages.
Notice of appeal by Bird&Bird, filed in relation to EP2455477, dated Jul. 19, 2018, 2 pages.
Nowicki et al., (2012). "Potato and Tomato late blight caused by Phytophthora infestans: An overview of pathology and resistance breeding," Plant Disease, 96(1):4-17.
Official variety description spinach variety Bandola by the Naktuinbouw (1995), filed in Opposition against EP2455473, 1 page.
Official variety description spinach variety Maracas by the Naktuinbouw (1950), filed in Opposition against EP2455473, 1 page.
Official variety description spinach variety Marimba by the Naktuinbouw (1950), filed in Opposition against EP2455473, 1 page.
Official variety description spinach variety Symphony by the Naktuinbouw (1950), filed in Opposition against EP2455473, 3 pages.
Pacific Pests and Pathogens Fact Sheet on cabbage downy mildew, dated Sep. 20, 2017, 3 pages.
Partial set of drawings filed in response to formal objections, filed during prosecution of EP2455474, dated Mar. 13, 2012, 4 pages.
Partial set of drawings filed in response to formal objections, filed during prosecution of EP2455475, dated Mar. 13, 2012, 4 pages.
Partial set of drawings filed in response to formal objections, filed during prosecution of EP2455476, dated Mar. 13, 2012, 4 pages.
Partial set of drawings filed in response to formal objections, filed during prosecution of EP2455477, dated Mar. 13, 2012, 4 pages.
Partial set of drawings filed in response to formal objections, filed during prosecution of EP2455478, dated Mar. 13, 2012, 4 pages.
Partial set of drawings filed in response to formal objections, filed during prosecution of EP2455479, dated Mar. 13, 2012, 4 pages.
Partial set of drawings filed in response to formal objections, filed during prosecution of EP2455480, dated Mar. 13, 2012, 4 pages.
Partial set of drawings filed in response to formal objections, filed during prosecution of EP2455481, dated Mar. 13, 2012, 4 pages.
Partial set of drawings filed in response to formal objections, filed during prosecution of EP2455482, dated Mar. 13, 2012, 4 pages.
Partial set of drawings filed in response to formal objections, filed during prosecution of EP2455483, dated Mar. 13, 2012, 4 pages.
Patentee's response to Notice of Opposition and Auxiliary requests I and II, filed on Apr. 29, 2019 in Opposition against EP2455475, 38 pages.
Pihlajamaa, Presentation slides taken from conference documentation, Presentation at the 8th conference on Intellectual Property Protection for Plant Innovation 2017, p. 197-205.
Preliminary Amendment, filed for U.S. Appl. No. 15/594,293, dated May 12, 2017, 7 pages.
Preliminary Amendment, filed for U.S. Appl. No. 15/975,670, dated Jul. 23, 2018, 5 pages.
Preliminary Amendment, filed for U.S. Appl. No. 15/990,182, dated Aug. 13, 2018, 5 pages.
Preliminary Amendment, filed for U.S. Appl. No. 16/055,697, dated Aug. 6, 2018, 9 pages.
Primrose et al., (2006). "Principles of Gene Manipulation and Genomics," Chapter 9 of Bioinformatics, Blackwell Publishing, 21 pages.
Protocol for Distinctness, Uniformity and Stability Tests for Spinach oleracea L. (2002). European Union Community Plant Variety Office, Final CPVO-TP-55-6 Final, 17 pages.
Qin et al., (2014). "Whole-Genome Sequencing of Cultivated and Wild Peppers Provides Insights into Capsicum Domestication and Specialization," PNAS, 111(14):5135-5140.
Reply of the patent proprietor to the notice(s) of opposition dated Feb. 13, 2017, filed during Opposition against EP2455473, 28 pages.
Reply of the patent proprietor to the notice(s) of opposition dated Jul. 11, 2014, filed during Opposition against EP2115147, 5 pages.
Reply of the patent proprietor to the notice(s) of opposition dated May 22, 2017, filed during Opposition against EP2455477, 30 pages.
Reply to appeal by Bird&Bird filed in relation to EP2455473, dated Sep. 10, 2018, 40 pages.
Reply to communication from the Examining Division, filed during prosecution of EP2115147, dated Aug. 20, 2010, 4 pages.
Reply to communication from the Examining Division, filed during prosecution of EP2115147, dated Feb. 2, 2012, 3 pages.
Reply to communication from the Examining Division, filed during prosecution of EP2115147, dated Jun. 5, 2012, 1 page.
Reply to communication from the Examining Division, filed during prosecution of EP2115147, dated May 26, 2011, 3 pages.
Reply to communication from the Examining Division, filed during prosecution of EP2455473, dated Jul. 4, 2013, 4 pages.
Reply to communication from the Examining Division, filed during prosecution of EP2455473, dated Oct. 21, 2013, 1 page.
Reply to communication from the Examining Division, filed during prosecution of EP2455474, dated Dec. 8, 2015, 7 pages.

(56) References Cited

OTHER PUBLICATIONS

Reply to communication from the Examining Division, filed during prosecution of EP2455474, dated Jul. 4, 2013, 4 pages.
Reply to communication from the Examining Division, filed during prosecution of EP2455474, dated Mar. 17, 2017, 2 pages.
Reply to communication from the Examining Division, filed during prosecution of EP2455475, dated Dec. 8, 2015, 7 pages.
Reply to communication from the Examining Division, filed during prosecution of EP2455475, dated Jul. 5, 2013, 4 pages.
Reply to communication from the Examining Division, filed during prosecution of EP2455476, dated Dec. 3, 2015, 7 pages.
Reply to communication from the Examining Division, filed during prosecution of EP2455476, dated Jul. 5, 2013, 4 pages.
Reply to communication from the Examining Division, filed during prosecution of EP2455477, dated Jul. 5, 2013, 4 pages.
Reply to communication from the Examining Division, filed during prosecution of EP2455477, dated Oct. 21, 2013, 1 page.
Reply to communication from the Examining Division, filed during prosecution of EP2455478, dated Dec. 11, 2015, 7 pages.
Reply to communication from the Examining Division, filed during prosecution of EP2455478, dated Jul. 5, 2013, 4 pages.
Reply to communication from the Examining Division, filed during prosecution of EP2455479, dated Dec. 8, 2015, 7 pages.
Reply to communication from the Examining Division, filed during prosecution of EP2455479, dated Jul. 5, 2013, 4 pages.
Reply to communication from the Examining Division, filed during prosecution of EP2455480, dated Dec. 3, 2015, 7 pages.
Reply to communication from the Examining Division, filed during prosecution of EP2455480, dated Jul. 8, 2013, 5 pages.
Reply to communication from the Examining Division, filed during prosecution of EP2455481, dated Dec. 3, 2015, 7 pages.
Reply to communication from the Examining Division, filed during prosecution of EP2455482, dated Jul. 8, 2013, 5 pages.
Reply to communication from the Examining Division, filed during prosecution of EP2455483, dated Jul. 8, 2013, 5 pages.
Reply to communication from the Examining Division, filed during prosecution of EP3024929, dated Oct. 15, 2018, 2 pages.
Reply to communication from the Examining Division, filed during prosecution of EP3094722, dated Jan. 17, 2018, 2 pages.
Reply to communication from the Examining Division, filed during prosecution of EP3094722, dated May 28, 2018, 1 page.
Reply to communication from the Examining Division, filed during prosecution of EP3167051, dated Apr. 17, 2018, 2 pages.
Reply to communication from the Examining Division, filed during prosecution of EP3167051, dated May 28, 2018, 1 page.
Reply to the invitation to remedy deficiencies, filed during prosecution of EP2115147, dated Jan. 27, 2010, 2 pages.
Reply to Written Opinion prepared by the EPO, filed during prosecution of EP2455473, dated Nov. 14, 2012, 3 pages.
Reply to Written Opinion prepared by the EPO, filed during prosecution of EP2455474, dated Nov. 14, 2012, 3 pages.
Reply to Written Opinion prepared by the EPO, filed during prosecution of EP2455475, dated Nov. 14, 2012, 3 pages.
Reply to Written Opinion prepared by the EPO, filed during prosecution of EP2455476, dated Nov. 14, 2012, 3 pages.
Reply to Written Opinion prepared by the EPO, filed during prosecution of EP2455477, dated Nov. 19, 2012, 3 pages.
Reply to Written Opinion prepared by the EPO, filed during prosecution of EP2455478, dated Nov. 19, 2012, 3 pages.
Reply to Written Opinion prepared by the EPO, filed during prosecution of EP2455480, dated Nov. 19, 2012, 3 pages.
Reply to Written Opinion prepared by the EPO, filed during prosecution of EP2455481, dated Nov. 19, 2012, 3 pages.
Request for further processing, filed during prosecution of EP3024929, dated Dec. 21, 2017, 2 pages.
Request for interpreters during oral proceedings, dated Sep. 14, 2017, filed during Opposition against EP2455473, 1 page.
Response to Final Office Action, filed for U.S. Appl. No. 15/191,919, dated Apr. 25, 2019, 9 pages.
Response to Non-Final Office Action, filed for U.S. Appl. No. 15/314,778, dated Nov. 21, 2018, 8 pages.
Response to Non-Final Office Action, filed for U.S. Appl. No. 15/594,293, dated Feb. 28, 2019, 11 pages.
Rijk Zwaan General Information Website, dated Jul. 11, 2014, filed in Opposition proceedings against EP2115147, Available Online at <http://www.rijkzwaan.com/wps/wcm/connect/RZ+Corporate/Rijk+ Zwaan/Company/About+us/General+Information>, 1 page.
Rothrock et al., (2006). "Identification of Pythium-Resistant Cold-Tolerant Rice Germplasm through Controlled Environmental and Field Evaluations," Proceedings of the Thirty-First Rice Technical Working Group, Retrieved from the Internet http://www.uaex.edu/rtwg/Proceedings/2006/RTWG%20Proc%202006.pdf, [retrieved on Apr. 24, 2012], pp. 108-109.
Schlegel (2003). Encyclopedic dictionary of plant breeding and related subjects, Haworth Press Inc., Binghamton, New York, p. 234-237.
Sequence alignment of Spinacia oleracea DMR6 gene (SEQ ID 80) and DMR6 protein (SEQ ID 81) from EP2455473 with an alternative Spinacia oleracea DMR6 gene and DMR6 protein as identified in Spinacia oleracea L. accession SPI 173 (IPK, Gatersleben, Germany) and a number of spinach varieties, filed Aug. 24, 2016, in Opposition against EP2455473, 2 pages.
Smart et al., "Best Control of Downy Mildew in Cole Crops", Dept. of Plant Pathology and Plant-Microbe Biology, Cornell University, Geneva NY, filed Dec. 8, 2017, in Opposition against EP2455477, 2 pages.
Somssich et al., (2003). "Closing another gap in the plant SAR puzzle," Cell, 113(7):815-816.
Statement of grounds of appeal by Bird&Bird, filed in relation to EP2455473, dated Apr. 26, 2018, 10 pages.
Summary of the legal entity "Rijk Zwaan Zaadteelt en Zaadhandel B.V." obtained from the Dutch Chamber of Commerce, filed Jul. 11, 2014, in Opposition against EP2115147, 4 pages.
Summons to attend Oral Proceedings for case EP2455475, dated Mar. 22, 2016, in order to discuss outstanding objections under Articles 56 and 83 EPC, 7 pages.
Summons to attend Oral Proceedings pursuant to Rule 115(1) EPC, filed in Opposition against EP2455474, dated Jul. 13, 2016, 1 page.
Summons to attend Oral Proceedings pursuant to Rule 115(1) EPC, filed in Opposition against EP2455479, dated May 31, 2016, 5 pages.
Table 1: Spinach DMR6 mutants presented in O18, filed in Opposition against EP2455473, dated Oct. 20, 2017, 1 page.
Table on insufficiency of disclosure issues, filed Jul. 18, 2018, in Opposition against EP2455479, 3 pages.
Table on insufficiency of disclosure issues, filed Jul. 30, 2018, in Opposition against EP2455474, 3 pages.
Table on insufficiency of disclosure issues, filed Oct. 1, 2018, in Opposition against EP2455475, 3 pages.
Table with all insufficiency of disclosure issues, filed Apr. 26, 2018, in Appeal against EP2455473, 3 pages.
Third Party Observations, filed in Opposition against EP 2455474, filed Feb. 9, 2017 for EP Application No. 12155887, 2 pages.
Thomas et al., (1992). "Resistance to Race 2 of Peronospora parasitica in U.S. Plant Introductions of Brassica oleracea var. capitata," HortScience, 27(10):1120-1122.
TWV/40/11, "Report of the Technical Working Party for Vegetables," Jun. 16, 2006, UPOV, 40th session, Mexico, 57 pages.
Vicente et al. (2013). "Xanthomonas campestris pv. campestris (cause of black rot of crucifers) in the genomic era is still a worldwide threat to Brassica crops," Molecular Plant Pathology, 14(1): 2-18.
Vogel et al., (2013). "Insights into the regulation of protein abundance from proteomic and transcriptomic analyses," Nat. Rev. Genet., 13(4):227-232.
Wikipedia, "Expressed sequence tag", website as of Dec. 11, 2018, available online at <https://en.wikipedia.org/wiki/Expressed_sequence_tag>, filed during opposition of EP2455479, 4 pages.
Wikipedia, "Gene silencing", website as of Jul. 10, 2018, available online at <https://en.wikipedia.org/wiki/Gene_silencing>, filed during opposition of EP2455479, 12 pages.

(56) References Cited

OTHER PUBLICATIONS

Wikipedia, "Hyaloperonospora Brassicae", website as of Sep. 20, 2017, available online at <https://en.wikipedia.org/wiki/Hyaloperonospora_brassicae>, filed during opposition of EP2455477, 2 pages.
Wikipedia, "Hyaloperonospora Parasitica", website as of Sep. 20, 2017, available online at <https://en.wikipedia.org/wiki/Hyaloperonospora_parasitica>, filed during opposition of EP2455477, 3 pages.
Wilmouth et al., (2002). "Structure and Mechanism of Anthocyanidin Synthase from *Arabidopsis thaliana*," Structure, 10:93-103.
Withdrawal of a request for oral proceedings, filed during prosecution of EP2455482, dated Jan. 8, 2016, 1 page.
Withdrawal of a request for oral proceedings, filed during prosecution of EP2455483, dated Jan. 8, 2016, 1 page.
Withdrawal of an appeal, filed during appeal of EP2455477, dated Sep. 20, 2018, 1 page.
Written submission in preparation to/during oral proceedings, filed during prosecution of EP2455474, dated Oct. 10, 2016, 2 pages.
Written submission in preparation to/during oral proceedings, filed during prosecution of EP2455475, dated Aug. 30, 2016, 3 pages.
Written submission in preparation to/during oral proceedings, filed during prosecution of EP2455476, dated Jul. 21, 2016, 4 pages.
Written submission in preparation to/during oral proceedings, filed during prosecution of EP2455478, dated Oct. 10, 2016, 2 pages.
Written submission in preparation to/during oral proceedings, filed during prosecution of EP2455479, dated Oct. 5, 2016, 4 pages.
Written submission in preparation to/during oral proceedings, filed during prosecution of EP2455480, dated Jul. 21, 2016, 4 pages.
Written submission in preparation to/during oral proceedings, filed during prosecution of EP2455481, dated Aug. 30, 2016, 3 pages.
Written submission in preparation to/during oral proceedings, filed during prosecution of EP2455482, dated Oct. 13, 2015, 8 pages.
Written submission in preparation to/during oral proceedings, filed during prosecution of EP2455483, dated Oct. 13, 2015, 8 pages.
Zhang et al. (2017). "S5H/DMR6 Encodes a Salicylic Acid 5-Hydroxylase that Fine-Tunes Salicylic Acid Homeostasis," Plant Physiology Preview, DOI:10.1104/pp.17.00695, 41 pages.
Ferreyra et al. (2015). "The Identification of Maize and *Arabidopsis* Type 1 FLAVONE SYNTHASEs Links Flavones with Hormones and Biotic Interactions," Plant Physiology, 169:1090-1107.
Unpublished U.S. Appl. No. 16/055,697, filed Aug. 6, 2018, titled "Phytophthora Resistant Plants Belonging to the Solanaceae Family."
Unpublished U.S. Appl. No. 16/361,089, filed Mar. 21, 2019, titled "Phytophthora Resistant Plants Belonging to the Solanaceae Family."
Blast query of the sequence of Fig. 4 against Spinacia oleracea, filed in Opposition against EP2455473, dated Sep. 4, 2018, 6 pages.
Communication from the Examining Division in case EP3024929 dated Jul. 9, 2019, concerning the staying of examination proceedings, 3 pages.
Communication from the Examining Division in case EP3094722 dated Jun. 27, 2019, concerning the staying of examination proceedings, 3 pages.
Communication from the Examining Division in case EP3167051 dated Jun. 27, 2019, concerning the staying of examination proceedings, 3 pages.
Communication from the Opposition Division in case EP2455474 dated Jan. 3, 2020, concerning the staying of opposition proceedings, 5 pages.
Communication from the Opposition Division in case EP2455474 dated Jun. 27, 2019, concerning the staying of opposition proceedings, 2 pages.
Communication from the Opposition Division in case EP2455475 dated Jan. 10, 2020, concerning the staying of opposition proceedings, 5 pages.
Communication from the Opposition Division in case EP2455475 dated Jun. 27, 2019, concerning the staying of opposition proceedings, 2 pages.
Communication from the Opposition Division in case EP2455479 dated Jan. 13, 2020, concerning the staying of opposition proceedings, 5 pages.
Communication from the Opposition Division in case EP2455479 dated Jun. 28, 2019, concerning the staying of opposition proceedings, 4 pages.
Communication from the Proprietor in case EP2455474 dated Nov. 11, 2019, concerning the staying of opposition proceedings, 4 pages.
Communication from the Proprietor in case EP2455475 dated Nov. 11, 2019, concerning the staying of opposition proceedings, 4 pages.
Communication from the Proprietor in case EP2455479 dated Nov. 8, 2019, concerning the staying of opposition proceedings, 3 pages.
Database EMBL, (Dec. 18, 2014). "Glycine soja Flavanone 3-dioxygenase", XP002785532, Retrieved from EBI Accession No. EMBL: KHN19568, Database accession No. KHN19568, 2 pages.
Database UniProt, (Jun. 13, 2012). "*Glycine max* (Soybean); belongs to the iron/ascorbate-dependent oxidoreductase family", XP002785533, Retrieved from EBI Accession No. UNIPROT: I1KB21, Database accession No. I1KB21, 2 pages.
Database UniProt, (Nov. 22, 2017). "Putative Homoserine Kinase," XP002780503, Retrieved from Database Accession No. A0A251RZI8, 4 pages.
Jacobs et al., (2015). "Targeted genome modifications in soybean with CRISPR/Cas9," BMC Biotechnology, 15(1):16.
Li et al., (2016). "Loci and candidate gene identification for resistance to Phytophthora sojae via association analysis in soybean [*Glycine max* (L.) Merr.]," Molecular Genetics and Genomics, 291(3):1095-1103.
Preliminary Amendment, filed for U.S. Appl. No. 16/450,881, dated Jun. 25, 2019, 6 pages.
Preliminary Amendment, filed for U.S. Appl. No. 16/659,470, dated Dec. 12, 2019, 6 pages.
Response to Final Office Action, filed for U.S. Appl. No. 15/314,778, dated Aug. 26, 2019, 10 pages.
Response to Non-Final Office Action, filed for U.S. Appl. No. 15/990,182, dated Nov. 21, 2019, 11 pages.
Response to Notice to File Missing Parts and Notice of Omitted Items in a Nonprovisional Application, and Preliminary Amendment, filed for U.S. Appl. No. 16/361,089, dated Jul. 2, 2019, 37 pages.
Solanum tuberosum naringenin, 2-oxoglutarate 3-dioxygenase-like (LOC102590513), mRNA, Dec. 12, 2013, cited in Chinese Application No. 2014800731630 Office Action dated Feb. 19, 2019, 2 pages.
Solanum tuberosum naringenin, 2-oxoglutarate 3-dioxygenase-like (LOC102604390), mRNA, Dec. 12, 2013, cited in Chinese Application No. 2014800731630 Office Action dated Feb. 19, 2019, 2 pages.
Unpublished U.S. Appl. No. 16/773,781, filed Jan. 27, 2020, titled "Downy Mildew Resistance Providing Genes in Sunflower."
Unpublished U.S. Appl. No. 16/642,257, filed Feb. 26, 2020, titled "Soybean Plants Resistant to Phytophthora Sojae."

\* cited by examiner

| Species | | |
|---|---|---|
| Arabidopsis | ---------- | |
| Aquilegia_sp | ---------- | |
| Citrus_sinensis | ---------- | |
| Coffea_canephora | ---------- | |
| Cucumis_sativus | PP-------- | 342 |
| Gossypium_hirsutum | ---------- | |
| Lactuca_sativa | ---------- | |
| Medicago_truncatula | ---------- | |
| Oryza_sativa_1 | ---------- | |
| Oryza_sativa_2 | PTDTS----- | 342 |
| Oryza_sativa_3 | ---------- | |
| Populus_trichocarpa_1 | ---------- | |
| Populus_trichocarpa_2 | ---------- | |
| Solanum_lycopersicum_1 | GT-------- | 342 |
| Solanum_lycopersicum_2 | T--------- | 339 |
| Sorghum_bicolor | ---------- | |
| Spinacia_oleracea | ---------- | |
| Vitis | ---------- | |
| Zea_mays | ---------- | |
| Zingiber_officinale | REMCPDAPT | 346 |

>Arabidopsis thaliana DMR6 CDS (gi 42568064, Genbank NM_122361)
ATGGCGGCAAAGCTGATATCCACCGGTTTCCGTCATACTACTTTGCCGGAAAACTATGTCCGGCCAATCT
CCGACCGTCAGCGTCTCAGTCTCCAACTCGAAGATTCCCTCTCATCGATCTCTCCACTGA
TCGATCTTTCTCATCCAACACAAATCCACCAAGCTTGTGCCGATTCGGATTTTCAGTCATATAATCAC
GGAGTTAACAACAAATAATAGAGATGAGAGCGATGACTATCAGACGAAGATTATCGAGAGTTCTTTAGCGAGCTTGAAG
AAAAATGAAGAAGTCAACAATCAGACGATGACTATCAGACGAAGAGATTATCGACGAGCTTCTTTAGCGAGCTTGAAG
AGAAGAAGTCAACAATCAGACGATGACTACTAAGACTCCATTGTTATCCTATCAACAAGTATGTCAATGAG
TGGCCGTCAAACCCTCCTTCTTTCAAGGAAATAGTTAGGTTTAGAAATACAGTAAGAAGTGCTGGTGA
TTAAAATAGAGGAATTAATATCAGAGAGTCAACTATATCCTCAACGTCCGAAGCTTCACTTACGGTTTACCT
ACAAGGTCAACACATGGCAGTCAACTATTATCCTCAACGTGCTGAGTTCACTTACGGTTTACCT
GCTCATACCGACCGTCAGTGGTTCGCCGTTAATCAGACGCCTAATCAACAAGATCGTGTCCCAGATCTTGA
TCGACGGTCAGTGGTTCGCCGTTAATCAAAAGAGTGTTTGGCATCGCGTGTGTAACACAAGATCGTGTCCCAGATCTTGA
GCCATTAAGTAATGACCAAACCAGTCTACAAAAGATTTCACTTATGCAGAGTATTACAAAATGAAGTGAGACTA
TCGGTCGCATCGTTTCTGTGCCAGCTGACTGTGTCATGAGCCCAAGCCCTGTGGGAAGCTG
AGGACGATGAAACGAAAACCAGTCTACAAAAGATTTCACTTATGCAGAGTATTACAAGAAGTTTTGGAGTAG
GAATCTGGACCAAGAACATTGCCTCGAGAATTTTCTAAACAACTAA > Arabidopsis thaliana DMR6 protein (gi 15238567, Genbank NP_197841)
MAAKLISTGFRHTTLPENYVRPISDRPRLSEVSQLEDFPLIDLSSTDRSFLIQQIHQACAREGFFQVINH
GVNKQIIDEMVSVAREFFSMSMEEKMKLYSDDPIKTTRLSTSFNVKKEEVNNWRDYLRLHCYPIHKYVNE
WPSNPPSFKEIVSKYSREVREVGFKIEELISESLGLEKDYMKKVLGEQQHMAVNYYPPCPEPELTIGLP
AHTDPNALTILIQDTTVCGLQILIDCQWFAVNPHPDAFVINIGDQLQAISNGVYKSVWHRAVTNTENPRL
SVASFLCPADCAVMSPAKPLWEADDETKPVYKDFTYAEYYKKFWSRNLDQEHCLENFLNN*

FIG. 3

>Lactuca sativa DMR6 ortholog CDS
ATGGCCGCAAAAGTCATCTCCAGTGGATTCCGGTATACTACTCTACCGGAGAGCTACGTCCGGTTAA
CGACAGACCTACCTATCTCAAGTTCCGATTGCAACGACGTTCCTGTTATTGACATCGGTTGTGTGATA
GACACTCATAAGCCAACAAATTGGCGATGCTTGTAGAAGATACGGTTTTTTTCCAGGTGATTAATCATGGT
GTGCCTGATGAAGAATAGTGGAGAAAATGCAACAAGTAGGGAGTTGTCCTGTTGCCTGTGGAAGAGAA
GATGAAGCTTTACTGAGAGGATCCATCGAAGACGATGAGGGCTATCCCAGCTTTAACGTCCAAAAGAAC
AAATTCATAACTGGCGAGATTATCTCCCCTTCACTGTTATCCTCGATCAATACAGTCCTGAATGCCCT
TCAAATCCTTCTTATTCAAGGAATAGTTCAAGCAAAGTTGTACAGCAGAAATTAGGAATGAGAAT
ATTAGAATCAATATCAGAATATCAGGGTTACAAAAGAAGAAATAAAACTATATTAGGCCGATCAAGGTC
AACACATGGCCATCAACCATTACCCAGTGCCCTGAGCCGCTACCTAACGAGCTACCGGCCACACA
GACCCCAATGCTCAACAACCTCTCACGAGGACAGCCCAATGGTTGTTCTCTTGGTCTCTCAGGTTGTGAGCAA
ATGGTTAGCCGTTAAACCTAATGGCGTTGTAATTAACATTGGTAATTGGTGTAGAGGCGGTGAGTA
ATGGTGAATATAAAGTGTCCTGGTTAACTCAGACAAATAATAAAGGAGGATCGAAACCTGT
TTTTGTCCTTGTAATGACACCGTTATTAGGCTCCTAAAGAAGTTTTGGACAAGAAACCTTGATCAAGAACATTGCT
TTTCAAGAAATTTACTTATGCAGAATACGCCAAGAACCTTGATCAAGAACATTGCT
TAGAATTCTTCAAGAACTAG >Lactuca sativa DMR6 ortholog protein
MAAKVISSGFRYTTLPESYVRPVNDRPNLSQVSDCNDVPVIDIGCGDRQLISQQIGDACRRYGFFQVINHG
VPDEIVEKMQQVGREFFLLPVEERMKLYSEDPSKTMRLSTSFNVQKEQIHNWRDYLRLHCYPLDQYSPEWP
SNPSYFKEYVGNYCTAVRNLGMRILESISESLGLQKEEIKTILGDQGQHMAINHYPVCPEPELTYGLPGHT
DPNALTILLQDTLVSGLQVLKDGKNLAVKPHPNAFVINIGDQLEAVSNGEYKSVWHRAVVNSDNPRMSIAS
FLCPCNDTVIRAPKEIIKEGSKPVFKEFTYAEYYAKFWTRNLDQEHCLEFFKN*

FIG. 4

>Spinacia oleracea DMR6 ortholog CDS
ATGGCAAACAAGATATTATCCACCGGAATTCCTTACAAAACCCTCCCGAAAGCTACATCCGACCGAAAA
TGAGAGGCCCAACTTATCTCAAGTCTCTCCGATTGCGAGAATGTCCCGTGTTATTGACTTGGGTGCCAAAGACC
GTACTCAAACAATCCACCAAGTCTTCAATGCTTGTAAAATTACGGGTTTTTCCAGTGATTAATCATGGG
GTGTCAAAGGAATTAGCGGAAGAAGATGCAAAAGTAGCTCGAGAGTTCTTCGATATGTCCGTTGAGGAAAA
AATGAAATTATATAGTGACGATCCAACTAAAACACTAAGATTGTCTACAAGTTTTAACGTTAACAAAGAGG
AAGTTCATAATTGGAGAGATTATCTTAGGCTCCATTGTTGTGGCCCTTCTTGAGCAATATGTCCCCGAATGGCCT
TCTAACCCCCCTCCTTCAAGAAATAGTGAAGCAAGTACATAAAGAAGTTAGGAACTTGGTTTCAGAGT
CCAAGAACTAATATCAGAGAGTTTAGGTTGGAGAAAGATTACATAAAGAATGTCCTAGCAGATCAACGAC
AACACATGGCTCTTAATTATTACCCTGAGTGCCCCGAGCTCAAGACTTGCAAGTATATCTGGCCCTTCAAATTTTTAAGGATGGTAA
GACCCTAATGCCCTTACCATCCTTCTCCAAGACTGCTTTTGTCATTAACATTGGTGATCAATTGCAGGCATTAAGTA
ATGGCTTCCTGTCAAACTTCAAACCTGATGCTTTTGTCATTAACATTGGTGATCAATTGCAGGCATTAAGTA
ACGGTATATACAAGAGTGTATGGCACAGATAAGCGCGCCAACACCTCTGACCGCCAACGGATCACCGGCTGT
TTCCTCTGCCCCGCCAATGATGCGTTGATAAGCGCGCCAACACCTCTGACCGCCAACGGATCACCGGCTGT
ATATAGAGACTATACGTATCCTGAGTACTACAAGACTTTCTGGAGTAGGAACTTGGACCAAGAGCACTGCT
TGGAGCTTTTTAAAACCAAACCTAG >Spinacia oleracea DMR6 ortholog protein
MANKILSTGIPYKTLPESYIRPENERPNLSQVSDCENVPVIDLGAKDRTQTIHQVENACKNYGFFQVINHG
VSKELAEKMQKVAREFFDMSVEEKMKLYSDDPTKTLRLSTSFNVNKEEVHNWRDYLRLHCWPLEQYVPEMP
SNPPSFKEIVSKYIKEVRELGFRVQELISESLGLEKDYIKNVLGDQGHMALNYYPECPEPEMTYGLPGHT
DPNALTILQDLQVSGLQIFKDGKWLAVKFQPDAFVINIGDQLQALSNGIYKSWHRAVVNTDKPRLSVAS
FLCPANDALISAPTPLTANGSPAVIRDYTYPEYYKTFWSRNLDQEHCLELFKNQT*

FIG. 5

>Cucumis sativus DMR6 ortholog CDS
ATGAGCAGTGTGATGGAGATCCAACTTTTGTGTTCAGGGGACGTCACGAGAAGTTGCCAGAGAAGTAATGA
ACGGCCTGAATCGGATAGGCCGCCTGTCCGAACTTTGTGTTCAGGGGACGTCACGAGAAGTTGCCAGAGAAGTAATGACTTGG
GATGCGAGGAGAGAGATGATTGTGAAGCAAGTGGAGGAGCCCTGCAAGTCTTACGGCTTTTTCCAGGTT
ATAAATCATGGTGTGAGGAAGAATTGGTGGAGAAGTGATAGAGTTGGCAAGCAGTTCTTTTGAGCTGCC
GATGCCAGGAGAAGTTCAAATTTTATTCAGACGACCCTTCCAACGACCCTCAGACTCTCCACAAGTTTCAATG
TCCGGAAAGAGCAATTCGCAACTGGAGGATTATTCAGAGGATTATTCAGACTTCCTATCCTCTCCAACTACACC
CCCCATTGGCCCTCTAACCCCACCATCCTTCAGGGAAATAGTGAGTAGTTATTGCAATGAAGTACGAAAAGT
TGGGTACAGAATAGGAGGCTAATATCGGAGAGCTTGGGCTGGAGAAGGAATACATAAGGAGGAAGAAGTTGG
GTGACAAGGTCAGCACATGGCTATAAATTATTATCCGCCAACCCAGAACTCACCTACGGCTC
CCTGGCCATACGGATCCCAACCGGTCCTCCTTTCAGGATCCTCCCAATGCCCTTTGTAATCATATGAAGTCCT
CAAAGATGGAAAGTGGCTAGCCGTTGGGTGTACAAGAGCCCCTTGTGATGACGCCCTCATTACTCCTGCACCGCTCCCAGCCTG
ACGCATTGAGCAGCAATGGGGTGTACAAGAGCGGTTTGGCACCCCTCATTACTCCTGCACCGCTCCCAGCCTG
TCGGTCGCTTCTTTTCTCTGCCCCTTGTGATGACGCCCCAGTACTACAATACTTTTTGGAGCAGAACTTGGATCAACAAC
CCCCATTTACAGACCTTTCACCTACGGCCCAGTACTACAATACTTTTTGGAGCAGAACTTGGATCAACAAC
ATTGCTTGGAACTATTTAAAAACCACCCTCCTTAA >Cucumis sativus DMR6 ortholog protein
MSSVMEIQLLCSGGRHEKLPEKYERPESDRPRLSEVCCNDKVPIIDLGCEEREMIVKQVEEACKSYGFFQV
INHGVRKELVEKVIEVGKQFELPMEEKLKFYSDDPSKPVRLSTSFNVRKEQFRNWRDYLRLHCYPLSNYT
PHWPSNPPSEREIVSSYCNEVRKVGYRIEELISESLGLEKEYIRKLGEQQHMAINYPPCPQPELTYGL
PGHTDPNALTLLQDLHVAGLQVLKDGKWLAVNPHPNAFVINIGDQLQALSNGVYKSVWHRAVVNVDKPRL
SVASFLCPCDDALITPAPLLSQPSPIYRPFTYAQYYNTFWSRNLDQQHCLELEKNHPP*

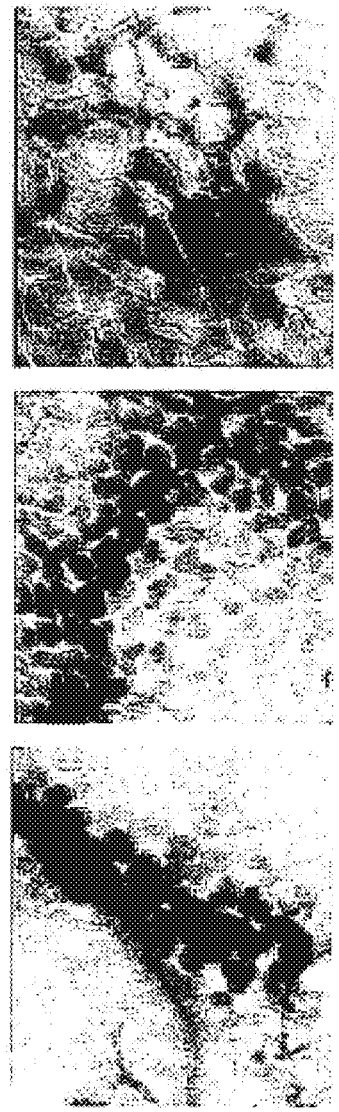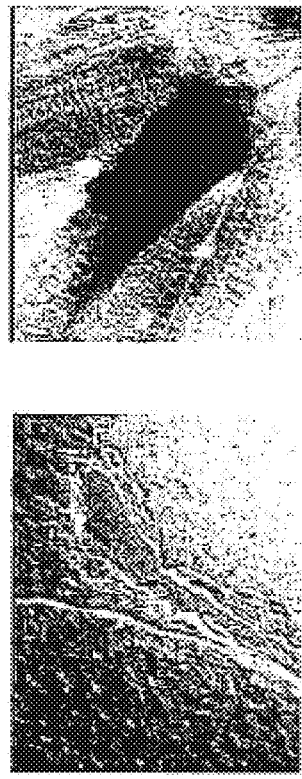

FIG. 11

```
cattttctctaaatctataaatccaaactaacatctacttt
cttaaaatctataaatctaacctaaaccactttttaaattaacactctaaattaattaaaaatctaaaccgatatataatttgttaaatctaaaatctagtgacttatttgtaaaatctaaaccaaa
cctaaaaataattcgttttattcgttaattaacactctaaattaacactcaaactaaactctaaattaacactgactaatatgactatattaaactgacttaattgttaaatgacttaatcaaatttta
aatataattaaactcgttgttaattaaagtatacagattgtttatttcgtttcgttttaattaaatatatgatataaatctaaaattctaaatattgatataatagtttattaaattaagtaagagttt
attcttagaggtaaaatgcaagtattgtccgaaaaacaaatctaattcaagtagtgtccgaaaaaatctaaactagtttgatagttaaattaaaaatctaagattagtgttaaaattttgatt
taaaaaaggaaaaaaatcaaacaaccatgatggcaccactccacaaaatatctaatctccactagaagtgtgagacacagtgagacacgaagtcacaagagtcacaagagtcacaagagtagaagcacaagagtacagattggactgtctga
gtctgaagtcccaaaaccatgatggcaccactccacaaaatatctaatctccactagaagtgtcccgtattgtgatagaatacggacagtgtgtttcgttttggacagtgtcct
gcttcatcctcgtcgccaaaatatacaaactcacatgtcttatcgaatttaaatttcgatttttagttcaagaaaatcatcctgatggtactttgtctta
ttcatggaagttgtatactcgttataaattatcaatgttctgccaaatgaatcaattaaatgaaaataacatttcaagaatgatgttcattgttaattcaaaaatagttacatatcttgtttaacat
aaattctgtgtctagttcattaaatcatgaatataaattatttcaaaactctaaaaaatcgattcagttttcaaaatgtttagaagttacgctctaaataactctaaatgacattcaaaatctatactctaaatgttacataa
aatgctgtttaagacgcaatctatgtaaatcataataatcaacaaatctataattaacaacatctcaaactctaaaaaacgagaatacattcaaaactaaatctaatctatatctaattagcattactattaggaaatcttggactacg
tctaccaaattaactctatgtcaatgttttagtaacactgatttagtaaccacaattataagtagtatatattactaattaagcagtagcagcagtataagctagaaatttatagtcgttatctgtttaaagctctaagcagaatagaattaaaata
tttgaatactctgtttttaaataactaaatcaaacaaaaatcacaaatcacaaataaataaagaagatattgttataattaaaatgaataatcaataaatgattgtcttatattcaaccaattaatagttgactacg
aaaaaacccaaaattactctcaaaccacggatttccaaaccaaaccgcaaaattcctgactctccgttttgttgttcgttcgcacttatgcacttatcgctaccagatttaattactaaccaattatgtttgttgttaatgtcatcgaa
attaacctagatcgtctggttgttcgttcgcacttatgcacttatcgataatgttcaatgtttgtaaaccactcagatcacaactcactgactccacctgcaattgaaaaatgtcaaagaaaagtcaaacactaagcaaaagtcaacatcgaaa
tattgtacgttagtatcgaatctgtaatcgtaatgttcatgcaatgcaatggttatcatgttttatcaatgcaattaattctcatttctccttttcatctcctccgaaggtcagaaggcagcaatgacaatccaaagatcaaaaaaccagtagtagcagtcaaagtcaagaaaaggaagtttc
aggaaatttattcgaatgtcatcgtcatgatcgtgtgctgagctgcagtcgtgatatgtaagaatcgtgaccttgaaaatggaatgtgtatatcttggaaagctttaaataaaatattacttttgtgttaatgtttcttgttgttgtagaatgcattacttttcgtttctgttgaa
gatgaaattacgaagtactattacttcgtttttcgtcttgaatcttctgtgtaattcgtaatttcgtaattacttatgaaatgaattacttcgtgtaatttcgtaaactatgtttgtaagctctaaatactctaaataaattactgtaaatgacgctagaat
gatgactattaaactcgatcttgagcagctaatagctggttagagtcttcgtaattcttaaagttagcttataaactatttcgtagatcttcaagaaactatttgttcttagaaaactggtagcttcgtcgcacactaaactaaacta
gtaatctctttaataaaatactctgagatttctcttatgaagttagagtttagtttagattagaattgaattgtttgttcttagaaaactatttcaagatgtttttcagatgttttaagatctgtaagcagatgttcctagtttgtccattctta
catcccttaataaggaaaaaaattgagataaatgaagaaaattaggaaataaagttttttggatttcacggaagctaataaacaatttaaactaagatctaagttctaaatatgcccaaaaaaaataaacaaccataatccgcaatcattctgtatttatgaatt
aagaaggaaaaaaatgaagataaaaacattaacgcaagtaaaatgtttaaactaagatttgataaaaacactaaaacactaaaaaatatcgataaaactcgataatatatgcgaatgaattagttaatctttaatcat
ttgtaagaggattacaaacattaaccaagctcctaataaccattcggtggattaagaacactcctatattcggtggattaagaaataaaaacattcaaaaaatatcgaataatatatcgcatactactaatatatactca
aataccacactgaaaacataaccacaccgtgcttcgaaatccactatatatcggtggattaagaaataaaaacattcaaaaaatatcgaataatatatcgcatactactaatatatactca
aacaattccactgaaaacataaccacacccgtgttcgaaatcgacagtggaaccgactatatgtcttcgattctttgattctctcaattcttcaaatttgatcatraa
```

FIG. 12

>Solanum lycopersicum DMR6 ortholog CDS
ATGGAAACCAAAGTTATTTCTAGCGGAATCAACCACTCTACTCTTCCTCAAGTTCCATAATTG
ACCCGATAGACCACGTCTATCGGAAGTGGTCGATTGTGAAAATGTTCCAATAATTG
ACTTAAGTTGCGGAGATCAAGCTCAAATAATTCGTCAAGAAGCTTGTCAACTTAT
GGTTTCTTTCAGTAATTAATCATGGTGTACCAAGGAAGTTGAGAAATGCTAGGGGT
AGCTGGGAATTTTTCAATTACCAGTAGAAGAAACTAAAATTATATTCAGATGATCCTT
CAAGACCACCATGAGATTATCAACAAGTTTAAATGTTAAAAGGAGACAGTTCATAATTGGAGA
GATTATCTCAGACTTCATTGTTATCCTAGAGAAGATGCTCCTGAATGGCCTTCTAATCC
ATCATCTTTCAGGGAAATCGTGAGCAGATATTGCAGGGAAATTCGTCAACTCGGATTTAGAT
TAGAAGAAGCCATAGCCAGAAGAAGCCCTGGGTTAGATAAAGCAGTGTATAAAGATGTATTGGGT
GAACAAGGACAACATATGGCTATCAATTATTATCCTCCTGTCCACCAGAACTTACTTA
TGGGCTTCCGCCCATACTGATCCAATTCACTTACAATTCTCTCAAGATTGCAAGTTG
CGGGTCTTCAAGTTCTTAAAGATCAATTGCAGGCAAATGGTTAGCTGTAAAACCTAACCTGACGCCTTT
GTCATTAATCTTGGGATCAATTCAGGCAGTAAGTAACGTAAGTACAGAAGTGTATGGCA
TCGAGCTATTGTGAATTCAGATCAAGTGACCAAGATGTCAGTGGCTTCGTTCTATGCTGTG
ATAGCGCGAAATCAGTGCACCAAGCTGCTGACAGAAGATGGATCTCCAGTGATTATCAA
GACTTTACGTATGCTGAGTATTACAACAAG
TTCTGGACCAGGAATTTGGACCAACATTGTTTGGAACTTTCAAGAATAA >Solanum lycopersicum DMR6 ortholog protein
METKVISSGINHSTLPQSYIRPESDREFRLSEVDCENVPIIDLSCGDQAQIIRQIGEACQTY
GFFQVINHGVPKEVVEKMLGVAGEFFNLPVEERIKLYSDDPSKTMRLSTSFNVKKETVHNMR
DYLRLHCYPLEKYAPEWPSNPSSFREIVSRYCREIRQLGFRLEEAIAESLGLDKECIKDVLG
EQGQHMAINYYPPCPQPELTYGLPAHTDPNSLITILLQDLQVAGLQVLKDGKWLAVKPQDAF
VINLGDQLQAVSNGKYRSVWHRAIVNSDQARMSVASFLCPCDSAKISAPKLITEDGSPVIYQ
DFTYAEYYNKFWSRNLDQHCLELFKN.

FIG. 13

>Nicotiana benthamiana DMR6 ortholog CDS
ATGGAAGCAAAAGTTCTTTCCAGCGGAATCCGCCACTCTACTATCCCTCAAGTTACATCCG
CCCTCAATCCGATAGGCCGCCCTTTCTGAAGTTGTGCTGATTGTGAAAACGTTCCAGTAGTTG
ATATAGTTGGCGGTGATAGAAACCTTATTGTTCATCAAATTGGTGAGCCTGTCGTCTTTAT
GGTTTTTCAGTAGTAATTAATCATGGTGTACCCAAAGAATTTAATAGACGAAATGCTAGAGAT
AGCTGGGGAATTTTTTAGGCTTGACTAGTTTTAATGTGAAAAGGAGTTACTCAGATGACCAT
CGAAGACCATGAGATTGTCGACTAGTGTTAATGTGAAAAGGAGGTTACAATTGGAGA
GATTATCTCAGACTTCATTGTTATCCTCTGAAGATATTGCATGGAAGTTCGACAACGGGGTCAGAT
TTCCTCTTTCAGGAAGCCATAGCCAGAGAGCCTAGAGCTTAGAGAAGAGTGTATAAAGGATGTATTGGGC
GAACAAGTTCAACACATGGCTATCGATCCAAATGCCCTTACATTCTATCCTCCTTGTCCACAACCAGAACTCACTTA
TGGGCTGCCAGCACACATAGTTCTTAAAGATGGCGAATGGTTGGCGTCAAGCTCAACCAGATGCCTTT
CTGGTCTTCAAGTTCTGTGATCAACTGACACAAAGCCAGGTGAGTAATGGAGATACAAAGCCTATGCCA
GTCATTAATCTTGTGTAAATTCAGTGCCTCCAAAGCCTCCAAGCTCCACTGAAGATGGATCCCGTCATTATCAG
TCGAGTATTGCGAAAATCAGTGCCTCCAAAGCCTCCAAGCTCCACTGAAGATGGATCCCGTCATTATCAG
ATAGGCGCAAAATCAGTGCTCGAGTATTACAAAAAAGTTCTGAGAGGAATTGGACCAGGAACATTG
GACTTTACCTATGCTGCTGAGTATTACAAAAAAGTTCTGGAGGAATTGGACCAGGAACATTG
TTTGGAACTTTTCAAGAACTAA >Nicotiana benthamiana DMR6 ortholog protein
MEAKVLSSGIRHSTIPQSYIRPQSDRPRLSEVADCENVPVVDIGCGDRNLIVHQIGEACRLY
GFFQVINHGVPRNLIDEMLEIAGEFFRLPVEEKLKLYSDDPSKTMRLSTSFNVKKERVHNWR
DYIRLHCYPLENYAPEWPSNPSSFREIVSRYCMEVRQLGFRLQEATAESLGLEKECIKDVLG
EQQRMAINFYPPCPQPELTYGLPAHTDPNALTILLQDLEVAGLQVLKDGEWLAVKPQPDAF
VINLGDQLQAVSNGRYKSVWHRAIVNSDKARLSVASFLCPCDSAKISAPKLLITEDGSPVIYQ
DFTYAEYYKKFWSRNLDQEHCLELFKN.

FIG. 16
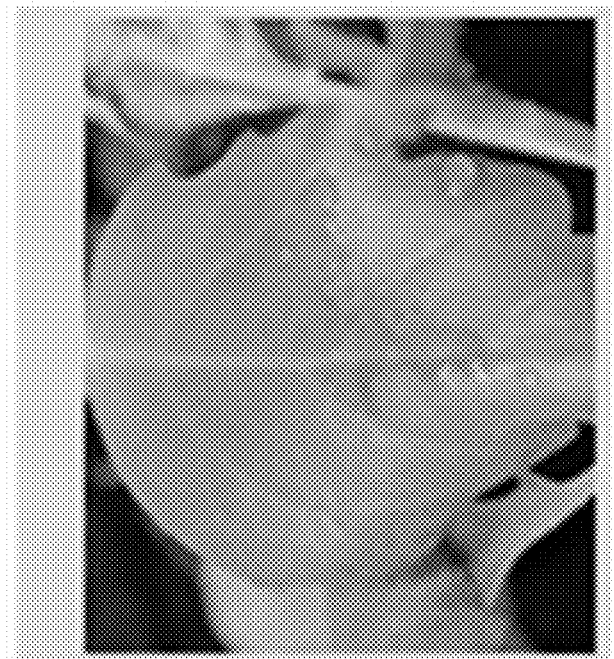

| | | | |
|---|---|---|---|
| BoDMR6_WT_scf108 | CGATTCGGTTTTTCAGGTCATAAATCACAGAGTTAGCAAGATCAATAGATGGAATG | GTGAGTCTTGCCAACGAGTTCTTTAGCATGTCTATGAGGCAAAAATCGAGCTGTACTCG | GACGATCCAACGAAGACGACGAGATTATCAACGAGCTTCAATGTCAAAAGAAGAGGTC |
| BoDMR6_C191T_scf | TGATTCGGTTTTTCAGGTCATAAATCACAGAGTTAGCAAGATCAATAGATGGAATG | GTGAGTCTTGCCAACGAGTTCTTTAGCATGTCTATGAGGCAAAAATCGAGCTGTACTCG | GACGATCCAACGAAGACGACGAGATTATCAACGAGCTTCAATGTCAAAAGAAGAGGTC |
| BoDMR6_C691T_scf | CGATTCGGTTTTTCAGGTCATAAATCACAGAGTTAGCAAGATCAATAGATGGAATG | GTGAGTCTTGCCAACGAGTTCTTTAGCATGTCTATGAGGCAAAAATCGAGCTGTACTCG | GACGATCCAACGAAGACGACGAGATTATCAACGAGCTTCAATGTCAAAAGAAGAGGTC |
| BoDMR6_G714A_scf | CGATTCGGTTTTTCAGGTCATAAATCACAGAGTTAGCAAGATCAATAGATGGAATG | GTGAGTCTTGCCAACGAGTTCTTTAGCATGTCTATGAGGCAAAAATCGAGCTGTACTCG | GACGATCCAACGAAGACGACGAGATTATCAACGAGCTTCAATGTCAAAAGAAGAGGTC |
| BoDMR6_-5bp_scf1 | CGATTCGGTTTTTCAGGTCATAAATCACAGAGTTAGCAAGATCAATAGATGGAATG | GTGAGTCTTGCCAACGAGTTCTTTAGCATGTCTATGAGGCAAAAATCGAGCTGTACTCG | GACGATCCAACGAAGACGACGAGATTATCAACGAGCTTCAATGTCAAAAGAAGAGGTC |
| | ********* ************************************ ******* | ************************************************* ******* | ********************************************************* |

FIG. 22C

```
BoDMR6_WT_scf108      AACAATTGGAGAGACTATCTTAGACTACATTGTTATCCTATCAGCAAGTATGTCCATGAG
BoDMR6_C181T_scf      AACAATTGGAGAGACTATCTTAGACTACATTGTTATCCTATCAGCAAGTATGTCCATGAG
BoDMR6_C691T_scf      AACAATTGGAGAGACTATCTTAGACTACATTGTTATCCTATCAGCAAGTATGTCCATGAG
BoDMR6_G714A_scf      AACAATTGGAGAGACTATCTTAGACTACATTGTTATCCTATCAGCAAGTATGTCCATGAG
BoDMR6_-5bp_scf1      AACAATTGGAGAGACTATCTTAGACTACATTGTTATCCTATCAGCAAGTATGTCCATGAG
                      ************************************************************

BoDMR6_WT_scf108      TGGCCTTCAAACCCTCCTTCTTTCAAGGAAGTTGTGAGTAGATACAGTACAGATGTAAGA
BoDMR6_C181T_scf      TGGCCTTCAAACCCTCCTTCTTTCAAGGAAGTTGTGAGTAGATACAGTACAGATGTAAGA
BoDMR6_C691T_scf      TGGCCTTCAAACCCTCCTTCTTTCAAGGAAGTTGTGAGTAGATACAGTACAGATGTAAGA
BoDMR6_G714A_scf      TGGCCTTCAAACCCTCCTTCTTTCAAGGAAGTTGTGAGTAGATACAGTACAGATGTAAGA
BoDMR6_-5bp_scf1      TGGCCTTCAAACCCTCCTTCTTTCAAGGAAGTTGTGAGTAGATACAGTACAGATGTAAGA
                      ************************************************************

BoDMR6_WT_scf108      GAACTGGGATTTACTATAGAGGAACTGATATCAGAGAGCCTGGGTTTAGAAAAAGATCAC
BoDMR6_C181T_scf      GAACTGGGATTTACTATAGAGGAACTGATATCAGAGAGCCTGGGTTTAGAAAAAGATCAC
BoDMR6_C691T_scf      GAACTGGGATTTACTATAGAGGAACTGATATCAGAGAGCCTGGGTTTAGAAAAAGATCAC
BoDMR6_G714A_scf      GAACTGGGATTTACTATAGAGGAACTGATATCAGAGAGCCTGGGTTTAGAAAAAGATCAC
BoDMR6_-5bp_scf1      GAACTGGGATTTACTATAGAGGAACTGATATCAGAGAGCCTGGGTTTAGAAAAAGATCAC
                      ************************************************************
```

FIG. 22D

```
BoDMR6_WT_scf108    ATGAGGAAAGTGCTTGGTGAACAAGTCAACACAATGGCAGTCAACTATTACCCTCCATGT
BoDMR6_C181T_scf    ATGAGGAAAGTGCTTGGTGAACAAGTCAACACAATGGCAGTCAACTATTACCCTCCATGT
BoDMR6_C691T_scf    ATGAGGAAAGTGCTTGGTGAACAAGTCAACACAATGGCAGTCAACTATTACCCTCCATGT
BoDMR6_G714A_scf    ATGAGGAAAGTGCTTGGTGAACAAGTCAACACAATGGCAGTCAACTATTACCCTCCATGT
BoDMR6_-5bp_scf1    ATGAGGAAAGTGCTTGGTGAACAAGTCAACACAATGGCAGTCAACTATTACCCTCCATGT
                    ************************************************************

BoDMR6_WT_scf108    CCTGAGCCTGAGCTCACTTATGTTACCTGCTCACCAAACGCACTCACCATT
BoDMR6_C181T_scf    CCTGAGCCTGAGCTCACTTATGTTACCTGCTCACCAAACGCACTCACCATT
BoDMR6_C691T_scf    CCTGAGCCTGAGCTCACTTATGTTACCTGCTCACCGAACCGCACTCACCATT
BoDMR6_G714A_scf    CCTGAGCCTGAGCTCACTTATGTTACCTGCTCACCGACCGCACTCACCATT
BoDMR6_-5bp_scf1    CCTGAGCCTGA-----GCCTGA
                    ***********      ******

BoDMR6_WT_scf108    CTTCTCCAAGATGCTACCGTTTGTGGTCTACAGATCTTGATCGACGACCAGTGGTTCGCC
BoDMR6_C181T_scf    CTTCTCCAAGATGCTACCGTTTGTGGTCTACAGATCTTGATCGACGACCAGTGGTTCGCC
BoDMR6_C691T_scf    CTTCTCCAAGATGCTACCGTTTGTGGTCTACAGATCTTGATCGAGGGCCAGTGGTTCGCC
BoDMR6_G714A_scf    CTTCTCCAAGATGCTACCGTTTGTGGTCTATAGATCTTGATCGAGGGCCAGTGGATTCGCC
BoDMR6_-5bp_scf1    
```

FIG. 22E

| | | | |
|---|---|---|---|
| BoDMR6_WT_scf108 | GTTAATCCACAATCCTGATGCTTTTGTCATCAACATTGGTGACCAGTTCGAGGCATTGAGT | AACCGGAATATACAAAGTGTTTGGCATCGAGCAGTAACAAACCGAAAACCGAGATTA | TCGGTCGCATCATTTCTGTCGCTGACTGCCCAGCTGCGCCTGTCATAAGCCCAAGCCCTTG |
| BoDMR6_C181T_scf | GTTAATCCACAATCCTGATGCTTTTGTCATCAACATTGGTGACCAGTTCGAGGCATTGAGT | AACCGGAATATACAAAGTGTTTGGCATCGAGCAGTAACAAACCGAAAACCGAGATTA | TCGGTCGCATCATTTCTGTCGCTGACTGCCCAGCTGCGCCTGTCATAAGCCCAAGCCCTTG |
| BoDMR6_C691T_scf | GTTAATCCACAATCCTGATGCTTTTGTCATCAACATTGGTGACCAGTTCGAGGCATTGAGT | AACCGGAATATACAAAGTGTTTGGCATCGAGCAGTAACAAACCGAAAACCGAGATTA | TCGGTCGCATCATTTCTGTCGCTGACTGCCCAGCTGCGCCTGTCATAAGCCCAAGCCCTTG |
| BoDMR6_G714A_scf | GTTAATCCACAATCCTGATGCTTTTGTCATCAACATTGGTGACCAGTTCGAGGCATTGAGT | AACCGGAATATACAAAGTGTTTGGCATCGAGCAGTAACAAACCGAAAACCGAGATTA | TCGGTCGCATCATTTCTGTCGCTGACTGCCCAGCTGCGCCTGTCATAAGCCCAAGCCCTTG |
| BoDMR6_-5bp_scf1 | ------------------------------------------------------------ | ------------------------------------------------------------ | ------------------------------------------------------------ |

FIG. 22F

```
BoDMR6_WT_scf108    TGGGAAGCCGAGGAGGACGAGGGCTAAGCCAATATACAGAGACTACACTTACGCAGAGTAC
BoDMR6_C181T_scf    TGGGAAGCCGAGGAGGACGAGGGCTAAGCCAATATACAGAGACTACACTTACGCAGAGTAC
BoDMR6_C691T_scf    TGGGAAGCCGAGGAGGACGAGGGCTAAGCCAATATACAGAGACTACACTTACGCAGAGTAC
BoDMR6_G714A_scf    TGGGAAGCCGAGGAGGACGAGGGCTAAGCCAATATACAGAGACTACACTTACGCAGAGTAC
BoDMR6_-5bp_scf1    ------------------------------------------------------------

BoDMR6_WT_scf108    TACAAAAGTTTTGACTAGGAATCTGGACCAAGAGCATTGCCTTGAGAACTTTCTAAAC
BoDMR6_C181T_scf    TACAAAAGTTTTGACTAGGAATCTGGACCAAGAGCATTGCCTTGAGAACTTTCTAAAC
BoDMR6_C691T_scf    TACAAAAGTTTTGACTAGGAATCTGGACCAAGAGCATTGCCTTGAGAACTTTCTAAAC
BoDMR6_G714A_scf    TACAAAAGTTTTGACTAGGAATCTGGACCAAGAGCATTGCCTTGAGAACTTTCTAAAC
BoDMR6_-5bp_scf1    ---------------------------------------------------------

BoDMR6_WT_scf108    GACTAG
BoDMR6_C181T_scf    GACTAG
BoDMR6_C691T_scf    GACTAG
BoDMR6_G714A_scf    GACTAG
BoDMR6_-5bp_scf1    ------
```

```
BoDMR6_WT_scf155    GTGAGTGTTGCGCATGAGTTTTTTGGACCTATGGACGAAAAATGAAGCTATACTCG
BoDMR6_G368A_scf    GTGAGTGTTGCGCATGAGTTTTTTGGACCTATGGACGAAAAATGAAGCTATACTCG
BoDMR6_-1bp_scf1    GTGAGTGTTGCGCATGAGTTTTTGGACCTATGGACGAAAAATGAAGCTATACTCG
                    ********************** ********************************

BoDMR6_WT_scf155    GACGATCCAACAAGACACCGAGATTATCGACGAGCTTAATGTGAAGGAAGAGAGGTT
BoDMR6_G368A_scf    GACGATCCAACAAGACACCGAGATTATCGACGAGCTTAATGTGAAGGAAGAGAGGTT
BoDMR6_-1bp_scf1    GACGATCCAACAAGACACCGAGATTATCGACGAGCTTAATGTGAAGGAAGAGAGGTT
                    ********************************************************

BoDMR6_WT_scf155    AATAATTGGAGAGACTATCTAAGACTTCATTGTTATCCTATCGACAAGTATGTCCATGAG
BoDMR6_G368A_scf    AATAATTGGAGAGACTATCTAAGACTTCATTGTTATCCTATCGACAAGTATGTCCATGAG
BoDMR6_-1bp_scf1    AATAATTGGAGAGACTATCTAAGACTTCATTGTTATCCTATCGACAAGTATGTCCATGAG
                    ********************************************************

BoDMR6_WT_scf155    TGGCCCTTCCAACCCACCTTCTTCAAGGAAGTTGTGAGTAAATACAGTAGAAATAAGA
BoDMR6_G368A_scf    TGGCCCTTCCAACCCACCTTCTTCAAGGAAGTTGTGAGTAAATACAGTAGAAATAAGA
BoDMR6_-1bp_scf1    TGGCCCTTCCAACCCACCTTCTTCAAGGAAGTTGTGAGTAAATACAGTAGAAATAAGA
                    ********************************************************
```

FIG. 23C

```
BoDMR6_WT_scf155    GAATTGGGACTTAAAATAGAGGAATTGATATCAGAGAGCTTAGGTTTAGAAAAGATTAC
BoDMR6_G368A_scf    GAATTGGGACTTAAAATAGAGGAATTGATATCAGAGAGCTTAGGTTTAGAAAAGATTAC
BoDMR6_-1bp_scf1    GAATTGGGACTTAAAATAGAGGAATTGATATCAGAGAGCTTAGGTTTAGAAAAGATTAC
                    ************************************************************

BoDMR6_WT_scf155    ATGAAGAAAGTGCTTGGTGAACAGGTCAACACATGGCAGTCAACTATTATCCTCCATGT
BoDMR6_G368A_scf    ATGAAGAAAGTGCTTGGTGAACAGGTCAACACATGGCAGTCAACTATTATCCTCCATGT
BoDMR6_-1bp_scf1    ATGAAGAAAGTGCTTGGTGAACAGGTCAACACATGGCAGTCAACTATTATCCTCCATG-
                    *********************************************************

BoDMR6_WT_scf155    CCTGAGCCTGAGCTCACCTATGCTTACCTGTTTACCGACCAATGCCCTCATCCAATT
BoDMR6_G368A_scf    CCTGAGCCTGAGCTCACCTATGCTTACCTGTTTACCGACCAATGCCCTCATCCAATT
BoDMR6_-1bp_scf1    CCTGAGCCTGAGCTCACCTATGCTTACCTGTTTACCGACCAATGCCCTCATCCAATT
                    ***********************************************************

BoDMR6_WT_scf155    CTTCTCCAAGATGCTACCGTTTGCGGTCTCCAGATCTTGATCGACGGTCACTGGTTTGCT
BoDMR6_G368A_scf    CTTCTCCAAGATGCTACCGTTTGCGGTCTCCAGATCTTGATCGACGGTCACTGGTTTGCT
BoDMR6_-1bp_scf1    CTTCTCCAAGATGCTACCGTTTGCGGTCTCCAGATCTTGA--------------------
                    ****************************************
```

FIG. 23D

| | | |
|---|---|---|
| BoDMR6_WT_scf155 | GTTAATCCTCGTCCTGATCCTTTGTCATCAACATTGGTGACCAGTTGCAGGCATTGAGT |
| BoDMR6_G368A_scf | GTTAATCCTCGTCCTGATCCTTTGTCATCAACATTGGTGACCAGTTGCAGGCATTGAGT |
| BoDMR6_-1bp_scf1 | ----------------------------------------------------------- |

| | | |
|---|---|---|
| BoDMR6_WT_scf155 | AACGGACTATACAAAGTGTTTGGCATCGAGCAGTGACAAACTGAAACCGAGACTA |
| BoDMR6_G368A_scf | AACGGACTATACAAAGTGTTTGGCATCGAGCAGTGACAAACTGAAACCGAGACTA |
| BoDMR6_-1bp_scf1 | ----------------------------------------------------------- |

| | | |
|---|---|---|
| BoDMR6_WT_scf155 | TCGATCGCATCATTTATGTCTCCTGATAACCGGTGCTGTTCATAAGCCCGGCAAGCCCCTG |
| BoDMR6_G368A_scf | TCGATCGCATCATTTATGTCTCCTGATAACCGGTGCTGTTCATAAGCCCGGCAAGCCCCTG |
| BoDMR6_-1bp_scf1 | ----------------------------------------------------------- |

| | | |
|---|---|---|
| BoDMR6_WT_scf155 | TGGGAAGCCAGGAGGAAGAGGCCAATCTACAGAGACTACACTTATGCAGAGTAC |
| BoDMR6_G368A_scf | TGGGAAGCCAGGAGGAAGAGGCCAATCTACAGAGACTACACTTATGCAGAGTAC |
| BoDMR6_-1bp_scf1 | ----------------------------------------------------------- |

FIG. 23E

```
BoDMR6_WT_scf155    TACAAGAAGTTTTGGAGTAGGAATCTGGACCAAGAACATTGCCTCGAAAACTTTCTAAAC
BoDMR6_G368A_scf    TACAAGAAGTTTTGGAGTAGGAATCTGGACCAAGAACATTGCCTCGAAAACTTTCTAAAC
BoDMR6_-1bp_scf1    ------------------------------------------------------------

BoDMR6_WT_scf155    GACTAG
BoDMR6_G368A_scf    GACTAG
BoDMR6_-1bp_scf1    ------
```

FIG. 24A

```
BoDMR6_WT_scf108    MAAKLISTGIRHTTLPENYVRPLSNRPCLSDVSPLKDFPIIDLSSTDRSRLVQQIHQACS
BoDMR6_C181T_scf    MAAKLISTGIRHTTLPENYVRPLSNRPCLSDVSPLKDFPIIDLSSTDRSRLVQQIHQACS
BoDMR6_C691T_scf    MAAKLISTGIRHTTLPENYVRPLSNRPCLSDVSPLKDFPIIDLSSTDRSRLVQQIHQACS
BoDMR6_G714A_scf    MAAKLISTGIRHTTLPENYVRPLSNRPCLSDVSPLKDFPIIDLSSTDRSRLVQQIHQACS
BoDMR6_-5bp_scf     MAAKLISTGIRHTTLPENYVRPLSNRPCLSDVSPLKDFPIIDLSSTDRSRLVQQIHQACS
                    ************************************************************

BoDMR6_WT_scf108    RFGFFQVINHRVSKDTIDGMVSVANEFFSMSMEEKMKLYSDDPTKTTRLSTSFNVRKEEY
BoDMR6_C181T_scf    RFGFFQVINHRVSKDTIDGMVSVANEFFSMSMEEKMKLYSDDPTKTTRLSTSFNVRKEEY
BoDMR6_C691T_scf    RFGFFQVINHRVSKDTIDGMVSVANEFFSMSMEEKMKLYSDDPTKTTRLSTSFNVRKEEY
BoDMR6_G714A_scf    RFGFFQVINHRVSKDTIDGMVSVANEFFSMSMEEKMKLYSDDPTKTTRLSTSFNVRKEEY
BoDMR6_-5bp_scf     ------------------------------------------------------------

BoDMR6_WT_scf108    NNWRDYLRLHCYPISKYVHEWPSNPDSFKEVVSRYSTDVRELGFTIEELISESLGLEKDH
BoDMR6_C181T_scf    NNWRDYLRLHCYPISKYVHEWPSNPDSFKEVVSRYSTDVRELGFTIEELISESLGLEKDH
BoDMR6_C691T_scf    NNWRDYLRLHCYPISKYVHEWPSNPDSFKEVVSRYSTDVRELGFTIEELISESLGLEKDH
BoDMR6_G714A_scf    NNWRDYLRLHCYPISKYVHEWPSNPDSFKEVVSRYSTDVRELGFTIEELISESLGLEKDH
BoDMR6_-5bp_scf     NNWRDYLRLHCYPISKYVHEWPSNPDSFKEVVSRYSTDVRELGFTIEELISESLGLEKDH
```

FIG. 24B

BoDMR6_WT_scf108    MRKVLGEQGQRMAVYNYYPPCPEPELTYGLPAHTDPNALTILLQDATVCGLQILLIDGQWFA
BoDMR6_C181T_scf    MRKVLGEQGQRMAVYNYYPPCPEPELTYGLPAHTDPNALTILLQDATVCGL----------
BoDMR6_C691T_scf    MRKVLGEQGQRMAVYNYYPPCPEPELTYGLPAHTDPNALTILLQDATVCGLQILLIDGQ---
BoDMR6_G714A_scf    MRKVLGEQGQRMAVYNYYPPCPEPELTYGLPAHTDPNALTILLQDATVCGLQILLIDGQ---
BoDMR6_-5bp_scf1    MRKVLGEQGQRMAVYNYYPPCA--------------------------------------

BoDMR6_WT_scf108    VNPHPDAFVINTGDQFEALSWGIYKSVWHRAVINTEKPRLSVASPLCPADCAVISPAKPL
BoDMR6_C181T_scf    -----------------------------------------------------------
BoDMR6_C691T_scf    -----------------------------------------------------------
BoDMR6_G714A_scf    -----------------------------------------------------------
BoDMR6_-5bp_scf1    -----------------------------------------------------------

BoDMR6_WT_scf108    WEAEDEAKPIYRDYTYAEYYKRFWSRNLDQEHCLEMFLND
BoDMR6_C181T_scf    ----------------------------------------
BoDMR6_C691T_scf    ----------------------------------------
BoDMR6_G714A_scf    ----------------------------------------
BoDMR6_-5bp_scf1    ----------------------------------------

FIG. 25A

```
BoDMR6_WT_scf155    MAAKLLSTGFRHSTLPEMYVRPLSDRPLSQVSQLEDFPLIDISSTDRSRLVQKIHQACA
BoDMR6_G368A_scf    MAAKLLSTGFRHSTLPEMYVRPLSDRPLSQVSQLEDFPLIDISSTDRSRLVQKIHQACA
BoDMR6_-1bp_scf1    MAAKLLSTGFRHSTLPEMYVRPLSDRPLSQVSQLEDFPLIDISSTDRSRLVQKIHQACA
                    ************************************************************

BoDMR6_WT_scf155    RFGFFQVINHGVSKATIDEMVSVAHEFFGMPMDEKMKLYSDDPTKTPRLSTSFNVKEEEV
BoDMR6_G368A_scf    RFGFFQVINHGVSKATIDEMVSVAHEFFGMPMDEKMKLYSDDPTKTPRLSTSFNVKEEEV
BoDMR6_-1bp_scf1    RFGFFQVINHGVSKATIDEMVSVAHEFFGMPMDEKMKLYSDDPTKTPRLSTSFNVKEEEV
                    ************************************************************

BoDMR6_WT_scf155    NNWRDYLRLHCYPIDKYVHEWPSNFPSFKEVVSKYSREIRELGLKIEELISESIGLEKDY
BoDMR6_G368A_scf    NN----------------------------------------------------------
BoDMR6_-1bp_scf1    NNWRDYLRLHCYPIDKYVHEWPSNFPSFKEVVSKYSREIRELGLKIEELISESIGLEKDY
                    **

BoDMR6_WT_scf155    MKKVLGEQCQHMAVNYYPPCPEPELTYGLPAHTDPNALTILLQDATVCGLQILIDGHWPA
BoDMR6_G368A_scf    ------------------------------------------------------------
BoDMR6_-1bp_scf1    MKKVLGEQCQHMAVNYYPPC----------------------------------------
```

FIG. 25B

```
BoDMR6_WT_scf155   VNPRPDAFVINIGDQLQAISNGVYRSVWHRAVTNTENPRLSIASFMCPDNGAVISPAKPL
BoDMR6_G369A_scf   ------------------------------------------------------------
BoDMR6_-1bp_scf1   ------ISLSSPMVZ--------LLIPTQMP-------------------SP--------

BoDMR6_WT_scf155   WEAKEEEAKPIYRDYTYAEYYKKFWSRNIDQEHCIEMFIND
BoDMR6_G369A_scf   -----------------------------------------
BoDMR6_-1bp_scf1   ------------------FFSRMLFFAVSRS----------
```

DISEASE RESISTANT *BRASSICA* PLANTS

CROSS-REFERENCE TO RELATED APPLICATIONS

This application is a continuation-in-part application of U.S. patent application Ser. No. 15/975,670, filed May 9, 2018, which is a continuation application of U.S. patent application Ser. No. 15/190,675 filed Jun. 23, 2016 and issued as U.S. Pat. No. 9,994,861, which is a divisional application of U.S. patent application Ser. No. 14/528,707, filed Oct. 30, 2014 and issued as U.S. Pat. No. 9,546,373, which is a divisional application of U.S. patent application Ser. No. 14/250,875, filed Apr. 11, 2014 and issued as U.S. Pat. No. 9,121,029, which is a divisional application of U.S. patent application Ser. No. 12/525,236, internationally filed Jan. 30, 2008 and issued as U.S. Pat. No. 8,742,207, which is a U.S. National Phase application under 35 U.S.C. § 371 of International Application No. PCT/EP2008/000718, filed Jan. 30, 2008, which claims priority to International Application No. PCT/EP2007/050976, filed Feb. 1, 2007, each of which is incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 701802011721SEQLIST.TXT, date recorded: Jan. 17, 2019, size: 136 KB).

BACKGROUND OF THE INVENTION

Field of the Invention

The present invention relates to disease resistant plants, in particular plants resistant to organisms of the kingdom Fungi and the phylum Oomycota, the oomycetes. The invention further relates to plant genes conferring disease resistance and methods of obtaining such disease resistant plants for providing protection to Oomycota pathogens.

Description of Related Art

Resistance of plants to fungal and oomycete pathogens has been extensively studied, for both pathogen specific and broad resistance. In many cases resistance is specified by dominant genes for resistance. Many of these race-specific or gene-for-gene resistance genes have been identified that mediate pathogen recognition by directly or indirectly interacting with avirulence gene products or other molecules from the pathogen. This recognition leads to the activation of a wide range of plant defense responses that arrest pathogen growth.

In plant breeding there is a constant struggle to identify new sources of mostly monogenic dominant resistance genes. In cultivars with newly introduced single resistance genes, protection from disease is often rapidly broken, because pathogens evolve and adapt at a high frequency and regain the ability to successfully infect the host plant.

Therefore, the availability of new sources of disease resistance is highly needed.

Alternative resistance mechanisms act for example through the modulation of the defense response in plants, such as the resistance mediated by the recessive mlo gene in barley to the powdery mildew pathogen *Blumeria graminis* f. sp. *hordei*. Plants carrying mutated alleles of the wildtype MLO gene exhibit almost complete resistance coinciding with the abortion of attempted fungal penetration of the cell wall of single attacked epidermal cells. The wild type MLO gene thus acts as a negative regulator of the pathogen response. This is described in WO9804586.

Other examples are the recessive powdery mildew resistance genes, found in a screen for loss of susceptibility to *Erysiphe cichoracearum*. Three genes have been cloned so far, named PMR6, which encodes a pectate-lyase-like protein, PMR4 which encodes a callose synthase, and PMR5 which encodes a protein of unknown function. Both mlo and pmr genes appear to specifically confer resistance to powdery mildew and not to oomycetes such as downy mildews.

Broad pathogen resistance, or systemic forms of resistance such as SAR, has been obtained by two main ways. The first is by mutation of negative regulators of plant defense and cell death, such as in the cpr, lsd, and acd mutants of *Arabidopsis*. The second is by transgenic overexpression of inducers or regulators of plant defence, such as in NPR1 overexpressing plants.

The disadvantage of these known resistance mechanisms is that, besides pathogen resistance, these plants often show detectable additional and undesirable phenotypes, such as stunted growth or the spontaneous formation of cell death.

SUMMARY OF THE INVENTION

It is an object of the present invention to provide a form of resistance that is broad, durable and not associated with undesirable phenotypes.

In the research that led to the present invention, an *Arabidopsis thaliana* mutant screen was performed for reduced susceptibility to the downy mildew pathogen *Hyaloperonospora parasitica*. EMS-mutants were generated in the highly susceptible *Arabidopsis* line Ler eds 1-2. Eight downy mildew resistant (dmr) mutants were analyzed in detail, corresponding to 6 different loci. Microscopic analysis showed that in all mutants *H. parasitica* growth was severely reduced. Resistance of dmr3, dmr4 and dmr5 was associated with constitutive activation of plant defense. Furthermore, the dmr3 and dmr4, but not dmr5 mutants, were also resistant to *Pseudomonas syringae* and *Golovinomyces orontii*.

In contrast, enhanced activation of plant defense was not observed in the dmr1, dmr2, and dmr6 mutants. The results of this research have been described in Van Damme et al. (2005) Molecular Plant-Microbe Interactions 18(6) 583-592. This article does not disclose the identification and characterization of the DMR genes.

The dmr6 mutant was identified in a loss-of-susceptibility screen in the *Arabidopsis* Ler eds 1-2 background. The DMR6 gene now has been cloned and characterized. Thus, it was found that DMR6 is the gene At5g24530, encoding for an oxidoreductase (DNA and amino acid sequence are depicted in FIG. 2). Oxidoreductases are enzymes that catalyze the transfer of electrons from one molecule, the oxidant, to another, the reductant. According to the present invention, it has been found that lack of a functional DMR6 protein results in downy mildew resistance.

The present disclosure thus provides a plant, such as a *Brassica* plant which is resistant to a pathogen of viral, bacterial, fungal or oomycete origin, characterized in that the plant has a reduced level, reduced activity or complete absence of the DMR6 protein as compared to a plant that is not resistant to the said pathogen. In some embodiments, the *Brassica* plant is a plant of the family Brassicaceae (i.e., Cruciferae). In some embodiments, the plant is *Brassica oleracea*. In some embodiments, the oomycete pathogen is *Hyaloperonospora parasitica/Hyaloperonospora brassicae*. In some embodiments, the bacterial pathogen is *Xanthomonas campestris campestris*.

This form of resistance is in particular effective against pathogens of the phylum Oomycota, such as *Albugo, Aphanomyces, Basidiophora, Bremia, Hyaloperonospora, Pachymetra, Paraperonospora, Perofascia, Peronophythora, Peronospora, Peronosclerospora, Phytium, Phytophthora, Plasmopara, Protobremia, Pseudoperonospora, Sclerospora, Viennotia* species, as well as to pathogens belonging to the Fungi. In some embodiments, the pathogen of the phylum *Hyaloperonospora* is *Hyaloperonospora parasitica/Hyaloperonospora brassicae*.

The resistance according to the invention is based on an altered, in particular a reduced level, reduced activity or complete absence of the DMR6 protein in planta. The term "DMR6 protein" in this respect relates to the DMR6 gene product, such as the protein encoded by the At5g24530 gene in *Arabidopsis*. Such alterations can be achieved in various ways.

In one embodiment of the invention, the reduced level of DMR6 protein is the result of a reduced endogenous DMR6 gene expression. Reducing the expression of the DMR6 gene can be achieved, either directly, e.g., by targeting DMR6, or indirectly by modifying the regulatory sequences thereof, or by stimulating repression of the gene. In some embodiments, endogenous DMR6 gene expression may be reduced by any suitable methodology including, without limitation, gene silencing, RNA interference (RNAi), virus-induced gene silencing (VIGS), small RNA-mediated post-transcriptional gene silencing, transcription activator-like effector nuclease (TALEN) gene editing techniques, clustered Regularly Interspaced Short Palindromic Repeat (CRISPR/Cas9) gene editing techniques, and zinc-finger nuclease (ZFN) gene editing techniques.

Modulating the DMR6 gene to lower its activity or expression can be achieved at various levels. First, the endogenous gene can be directly mutated. This can be achieved by means of a mutagenic treatment. Alternatively, a modified DMR6 gene can be brought into the plant by means of transgenic techniques or by introgression, or the expression of DMR6 can be reduced at the regulatory level, for example by modifying the regulatory sequences or by modulating gene expression by, for example, gene silencing, RNA interference (RNAi), virus-induced gene silencing (VIGS), small RNA-mediated post-transcriptional gene silencing, transcription activator-like effector nuclease (TALEN) gene editing techniques, clustered Regularly Interspaced Short Palindromic Repeat (CRISPR/Cas9) gene editing techniques, or zinc-finger nuclease (ZFN) gene editing techniques.

In another embodiment of the present disclosure, the reduced level of DMR6 protein is the result of a mutation in the DMR6 gene resulting in a reduced DMR6 expression as compared to the wild-type DMR6 gene wherein no such mutation is present, or resulting in a reduced mRNA or protein stability. In a particular embodiment this is achieved by mutations in the DMR6 coding sequence that result in a non-functional DMR6 protein, i.e. without or with reduced enzymatic activity.

In another embodiment of the invention, reduced expression can be achieved by down-regulation of DMR6 gene expression either at the transcriptional or the translational level, e.g. by gene silencing or by mutations that affect the expression of the DMR6 gene.

This invention is based on research performed on resistance to *Hyaloperonospora parasitica* in *Arabidopsis* but is a general concept that can be more generally applied in plants, in particular in crop plants that are susceptible to infections with pathogens, such as Oomycota and Fungi.

The invention is suitable for a large number of plant diseases caused by oomycetes such as, but not limited to, *Bremia lactucae* on lettuce, *Peronospora farinosa* on spinach, *Pseudoperonospora cubensis* on members of the Cucurbitaceae family, e.g. cucumber and melon, *Peronospora destructor* on onion, *Hyaloperonospora parasitica* on members of the Brassicaceae family, e.g. cabbage, *Plasmopara viticola* on grape, *Phytophthora infestans* on tomato and potato, and *Phytophthora sojae* on soybean.

When the modification of DMR6 gene expression in a plant is to be achieved via genetic modification of the DMR6 gene or via the identification of mutations in the DMR6 gene, and the gene is not yet known it must first be identified. To generate pathogen-resistant plants, in particular crop plants, via genetic modification of the DMR6 gene or via the identification of mutations in the DMR6 gene, the orthologous DMR6 genes must be isolated from these plant species.

Various methods are available for the identification of orthologous sequences in other plants.

A method for the identification of DMR6 orthologous sequences in a plant species, may for example comprise identification of DMR6 ESTs of the plant species in a database; designing primers for amplification of the complete DMR6 transcript or cDNA; performing amplification experiments with the primers to obtain the corresponding complete transcript or cDNA; and determining the nucleotide sequence of the transcript or cDNA. Suitable methods for amplifying the complete transcript or cDNA in situations where only part of the coding sequence is known are the advanced PCR techniques 5'RACE, 3'RACE, TAIL-PCR, RLM-RACE and vectorette PCR.

Alternatively, if no nucleotide sequences are available for the plant species of interest, primers are designed on the DMR6 gene of a plant species closely related to the plant of interest, based on conserved domains as determined by multiple nucleotide sequence alignment, and used to PCR amplify the orthologous sequence. Such primers are suitably degenerate primers.

Another reliable method to assess a given sequence as being a DMR6 ortholog is by identification of the reciprocal best hit. A candidate orthologous DMR6 sequence of a given plant species is identified as the best hit from DNA databases when searching with the *Arabidopsis* DMR6 protein or DNA sequence, or that of another plant species, using a Blast program. The obtained candidate orthologous nucleotide sequence of the given plant species is used to search for homology to all *Arabidopsis* proteins present in the DNA databases (e.g. at NCBI or TAIR) using the BlastX search method. If the best hit and score is to the *Arabidopsis* DMR6 protein, the given DNA sequence can be described as being an ortholog, or orthologous sequence.

DMR6 is encoded by a single gene in *Arabidopsis* as deduced from the complete genome sequence that is publicly available. In the genome of rice 3 orthologs, and in poplar 2 orthologs have been identified. In most other plant species tested so far, DMR6 appears to be encoded by a single gene, as determined by the analysis of mRNA sequences and EST data from public DNA databases. The orthologous genes and proteins are identified in these plants by nucleotide and amino acid comparisons with the information that is present in public databases.

Alternatively, if no DNA sequences are available for the desired plant species, orthologous sequences are isolated by heterologous hybridization using DNA probes of the DMR6 gene of *Arabidopsis* or another plant or by PCR methods, making use of conserved domains in the DMR6 coding sequence to define the primers. For many crop species, partial DMR6 mRNA sequences are available that can be used to design primers to subsequently PCR amplify the complete mRNA or genomic sequences for DNA sequence analysis.

In a specific embodiment the ortholog is a gene of which the encoded protein shows at least 50% identity with the *Arabidopsis* DMR6 protein (At5g24530) or that of other plant DMR6 proteins. In a more specific embodiment the identity is at least 55%, more specifically 60%, even more specifically 65%, 70%, 75%, 80%, 85%, 90%, 95% or 99%.

Accordingly, certain aspects of the present disclosure relate to a mutant *Brassica* plant, wherein the plant has a reduced activity or a reduced level of a DMR6-1 polypeptide as compared to a corresponding wild type *Brassica* plant, and wherein the mutant *Brassica* plant has at least one non-natural mutation introduced into the DMR6-1 gene; and wherein the mutant *Brassica* plant has a reduced activity or a reduced level of a DMR6-2 polypeptide as compared to a corresponding wild type *Brassica* plant, and wherein the mutant *Brassica* plant has at least one non-natural mutation introduced into the DMR6-2 gene. In some embodiments, the plant exhibits resistance selected from the group of resistance to *Hyaloperonospora parasitica/Hyaloperonospora brassicae*, intermediate resistance to *Xanthomonas campestris campestris*, or any combination thereof. In some embodiments, the DMR6-1 polypeptide is selected from the group consisting of a polypeptide with at least 85% sequence identity, at least 88% sequence identity, at least 90% sequence identity, at least 95% sequence identity, and at least 99% sequence identity to SEQ ID NO: 112; and wherein the DMR6-2 polypeptide is a polypeptide selected from the group consisting of a protein with at least 85% sequence identity, at least 88% sequence identity, at least 90% sequence identity, at least 95% sequence identity, and at least 99% sequence identity to SEQ ID NO: 113. In some embodiments, the DMR6-1 gene is selected from the group of a nucleotide with at least 85% sequence identity, at least 88% sequence identity, at least 90% sequence identity, at least 95% sequence identity, or at least 99% sequence identity to SEQ ID NO: 114; and wherein the DMR6-2 gene is selected from the group of a nucleotide with at least 85% sequence identity, at least 88% sequence identity, at least 90% sequence identity, or least 95% sequence identity, and at least 99% sequence identity to SEQ ID NO: 115. In some embodiments, the non-natural mutation in DMR6-1 is a premature stop codon, and wherein the non-natural mutation in DMR6-2 is a premature stop codon. In some embodiments, the at least one non-natural mutation introduced into the DMR6-1 gene reduces an activity or a level of a DMR6-1 polypeptide as compared to a corresponding wild type *Brassica* plant; and wherein the at least one non-natural mutation introduced into the DMR6-2 gene reduces an activity or a level of a DMR6-2 polypeptide as compared to a corresponding wild type *Brassica* plant. In some embodiments, the DMR6-1 polypeptide is selected from the group of a polypeptide with at least 85% sequence identity, at least 88% sequence identity, at least 90% sequence identity, at least 95% sequence identity, or at least 99% sequence identity to SEQ ID NO: 112; and wherein the DMR6-2 polypeptide is a polypeptide selected from the group of a protein with at least 85% sequence identity, at least 88% sequence identity, at least 90% sequence identity, at least 95% sequence identity, or at least 99% sequence identity to SEQ ID NO: 113. In some embodiments, the DMR6-1 gene is selected from the group of a nucleotide with at least 85% sequence identity, at least 88% sequence identity, at least 90% sequence identity, at least 95% sequence identity, or at least 99% sequence identity to SEQ ID NO: 114; and wherein the DMR6-2 gene is selected from the group consisting of a nucleotide with at least 85% sequence identity, at least 88% sequence identity, at least 90% sequence identity, at least 95% sequence identity, or at least 99% sequence identity to SEQ ID NO: 115. In some embodiments, the at least one non-natural mutation that reduces the activity or level of the DMR6-1 protein is selected from the group of a premature stop codon introduced into the DMR6-1 coding sequence, a frameshift mutation introduced into the DMR6-1 coding sequence, an insertion introduced into the DMR6-1 coding sequence, a deletion of a part or a whole of the DMR6-1 coding sequence, an altered amino acid in a conserved domain of the DMR6-1 protein, a modified upstream sequence, a mutated promoter element, or an activated repressor element; and wherein the at least one non-natural mutation that reduces the activity or level of the DMR6-2 protein is selected from the group of a premature stop codon introduced into the DMR6-2 coding sequence, a frameshift mutation introduced into the DMR6-2 coding sequence, an insertion introduced into the DMR6-2 coding sequence, a deletion of a part or a whole of the DMR6-2 coding sequence, an altered amino acid in a conserved domain of the DMR6-2 protein, a modified upstream sequence, a mutated promoter element, or an activated repressor element. In some embodiments, the plant is a *Brassica oleracea* cultivar selected from the group of cabbage, kohlrabi, kale, Brussels sprouts, collard greens, broccoli, Romanesco broccoli, or cauliflower. In some embodiments, the non-natural mutation introduced into the DMR6-1 gene is selected from the group of a C to T mutation at a position corresponding to nucleotide 181 of reference sequence SEQ ID NO: 114, a C to T mutation at a position corresponding to nucleotide 691 of reference sequence SEQ ID NO: 114, a G to A mutation at a position corresponding to nucleotide 714 of reference sequence SEQ ID NO: 114, or a deletion of five nucleotides starting at a position corresponding to nucleotide 601 of reference sequence SEQ ID NO: 114; and wherein the non-natural mutation introduced into the DMR6-2 gene is selected from the group of a G to A mutation at a position corresponding to nucleotide 368 of reference sequence SEQ ID NO: 115, or a deletion of the nucleotide at a position corresponding to nucleotide 600 of reference sequence SEQ ID NO: 115.

In some embodiments, the present disclosure relates to a seed, tissue, or plant part of the *Brassica* plant of the above embodiments that includes a reduced activity or a reduced level of a DMR6-1 polypeptide as compared to a corresponding wild type *Brassica* plant and a reduced activity or a reduced level of a DMR6-2 polypeptide as compared to a corresponding wild type *Brassica* plant, and wherein the seed, tissue, or plant part comprises at least one non-natural mutation in the DMR6-1 gene and at least one non-natural mutation in the DMR6-2 gene.

Further aspects of the present disclosure relate to a method for obtaining a mutant *Brassica* plant including: introducing at least one non-natural mutation into the DMR6-1 nucleotide coding sequence and introducing at least one non-natural mutation into the DMR6-2 nucleotide coding sequence to produce a mutant *Brassica* plant with a reduced activity or a reduced level of a DMR6-1 polypeptide as compared to a corresponding wild type *Brassica* plant and a reduced activity or a reduced level of a DMR6-2 polypeptide as compared to a corresponding wild type *Brassica* plant. In some embodiments, the mutant *Brassica* plant exhibits resistance selected from the group of resistance to *Hyaloperonospora parasitica/Hyaloperonospora brassicae*, intermediate resistance to *Xanthomonas campestris campestris*, or any combination thereof. In some embodiments, the non-natural mutation is achieved by a mutagenic treatment, a radiation treatment, or a gene editing technique. In some embodiments, the mutant *Brassica* plant produced from the above methods includes at least at least one non-natural mutation in the DMR6-1 gene and at least one non-natural mutation in the DMR6-2 gene, wherein the plant further comprises a reduced activity or a reduced level of a DMR6-1 polypeptide as compared to a corresponding wild type *Brassica* plant and a reduced activity or a reduced level of a DMR6-2 polypeptide as compared to a corresponding wild type *Brassica* plant, and wherein the plant exhibits resistance selected from the group of resistance to *Hyaloperonospora parasitica/Hyaloperonospora brassicae*, intermediate resistance to *Xanthomonas campestris campestris*, or any combination thereof. In some embodiments, the mutant *Brassica* plant produced from the above methods includes at least one non-natural mutation in the DMR6-1 nucleotide coding sequence that reduces an activity or a level of a DMR6-1 polypeptide as compared to a corresponding wild type *Brassica* plant; wherein the plant comprises at least one non-natural mutation in the DMR6-2 nucleotide coding sequence that reduces an activity or a level of a DMR6-2 polypeptide as compared to a corresponding wild type *Brassica* plant; and wherein the plant exhibits resistance selected from the group of resistance to *Hyaloperonospora parasitica/Hyaloperonospora brassicae*, intermediate resistance to *Xanthomonas campestris campestris*, or any combination thereof.

In some embodiments, the DMR6-1 polypeptide is selected from the group of a polypeptide with at least 85% sequence identity, at least 88% sequence identity, at least 90% sequence identity, at least 95% sequence identity, or least 99% sequence identity to SEQ ID NO: 112; and wherein the DMR6-2 polypeptide is a polypeptide selected from the group of a protein with at least 85% sequence identity, at least 88% sequence identity, at least 90% sequence identity, at least 95% sequence identity, or at least 99% sequence identity to SEQ ID NO: 113. In some embodiments, the DMR6-1 gene is selected from the group of a nucleotide with at least 85% sequence identity, at least 88% sequence identity, at least 90% sequence identity, at least 95% sequence identity, or at least 99% sequence identity to SEQ ID NO: 114; and wherein the DMR6-2 gene is selected from the group of a nucleotide with at least 85% sequence identity, at least 88% sequence identity, at least 90% sequence identity, at least 95% sequence identity, or at least 99% sequence identity to SEQ ID NO: 115. In some embodiments, the present disclosure relates to a seed, tissue, or plant part of the mutant *Brassica* plant produced from the above methods.

In some embodiments of any of the above embodiments, the present disclosure relates to a plant part, wherein the plant part is a leaf, a stem, a root, a flower, a seed, a fruit, a cell, or a portion thereof. In some embodiments, the plant part is a leaf.

In some aspects, the present disclosure relates to a pollen grain or an ovule of the plant of any of the above embodiments.

In some aspects, the present disclosure relates to a protoplast produced from the plant of any of the above embodiments.

In some aspects, the present disclosure relates to a tissue culture produced from protoplasts or cells from the plant of any of the above embodiments, wherein the cells or protoplasts are produced from a plant part selected from the group=of leaf, anther, pistil, stem, petiole, root, root primordia, root tip, fruit, seed, flower, cotyledon, hypocotyl, embryo, or meristematic cell.

In some aspects, the present disclosure relates to a plant seed produced from the plant of any of the above embodiments.

BRIEF DESCRIPTION OF THE DRAWINGS

The patent or application file contains at least one drawing executed in color. Copies of this patent or patent application publication with color drawings will be provided by the office upon request and payment of the necessary fee.

FIGS. 1A-1D shows the alignment of the amino acid sequences of the DMR6 protein of *Arabidopsis thaliana* (SEQ ID NO: 62) and orthologs from *Aquilegia* species (SEQ ID NO: 63), *Citrus sinensis* (SEQ ID NO: 64), *Coffea canephora* (SEQ ID NO: 65), *Cucumis sativus* (SEQ ID NO: 67), *Gossypium hirsutum* (SEQ ID NO: 68), *Lactuca sativa* (SEQ ID NO: 70), *Medicago truncatula* (SEQ ID NO: 71), *Oryza sativa* (SEQ ID NOs. 72-74), *Populus trichocarpa* (SEQ ID NOs. 75 and 76), *Solanum lycopersicum* (SEQ ID NOs. 77 and 78), *Sorghum bicolor* (SEQ ID NO: 79), *Spinacia oleracea* (SEQ ID NO: 81), *Vitis vinifera* (SEQ ID NO: 82), *Zea mays* (SEQ ID NO: 83), and *Zingiber officinale* (SEQ ID NO: 84), using the CLUSTAL W (1.83) multiple sequence alignment program (EBI). Below the sequences the conserved amino acids are indicated by the dots, and the identical amino acids are indicated by the asterisk.

FIG. 2 shows the nucleotide (SEQ ID NO: 61) and amino acid sequence (SEQ ID NO: 62) of the DMR6 gene (At5g24530, gi 42568064, Genbank NM_122361) and protein (gi 15238567, Genbank NP_197841) of *Arabidopsis thaliana*, respectively.

FIG. 3 shows the nucleotide (SEQ ID NO: 69) and derived amino acid sequence (SEQ ID NO: 70) of the DMR6 ortholog of *Lactuca sativa*, respectively.

FIG. 4 shows the nucleotide (SEQ ID NO: 80) and derived amino acid sequence (SEQ ID NO: 81) of the DMR6 ortholog of *Spinacia oleracea*, respectively.

FIG. 5 shows the nucleotide (SEQ ID NO: 66) and derived amino acid sequence (SEQ ID NO: 67) of the DMR6 ortholog of *Cucumis sativus* and *Cucumis melo*.

FIG. 6A shows quantification of sporangiophores of *H. parasitica* isolate Waco9, 7 days post inoculation, on the dmr6-1 mutant (BC2, line E37) compared to its parental line Ler eds 1-2 and on the dmr6-2 mutant (FLAG 445D09 T-DNA line) compared to its parental line Ws-4. FIG. 6B shows restoration of susceptibility by complementation with the At5g24530 gene in the dmr6-1 mutant. *H. parasitica* spores per mg seedling weight were quantified on Ler eds 1-2, dmr6-1 and 5 complementation lines (#121, 122, 211,231, and 241).

FIGS. 9A-9E shows the expression of the DMR6 promoter-reporter (pDMR6::GUS) construct in transgenic *Arabidopsis* lines, visualized with only X-gluc as substrate (FIGS. 9D and 9E) or Magenta-X-gluc (FIGS. 9A-9C) and trypan blue staining of *H. parasitica* growth. FIG. 9A shows Ler eds 1-2 (pDMR6::GUS) 3 dpi with *H. parasitica*, Cala2 isolate. FIG. 9B shows Col-0 (pDMR6::GUS) 3 dpi with *H. parasitica*, Waco9 isolate. FIG. 9C shows Ler eds 1-2 (pDMR6::GUS) 3 dpi with *H. parasitica*, Emoy2 isolate. FIG. 9D shows Col-0 (pDMR6::GUS) 3 dp wounding. FIG. 9E shows Col-0 (pDMR6::GUS) 3 dp BTH application.

FIG. 10A shows transcription levels of the six genes in dmr6-1 compared to Ler eds 1-2 and additionally the DMR6 transcript. FIG. 10B shows elevated gene transcripts of six defence-associated genes in dmr6-2 versus Ws-4. ΔCT reflects the number of additional PCR amplification cycles required to reach the level of ACTIN2 transcripts. A lower ΔCT value indicates a higher transcript level.

FIG. 11 shows the nucleotide sequence (SEQ ID NO: 107) of the 3 kb region upstream of the start codon of the DMR6 gene (at5g24530) of *Arabidopsis thaliana*, including the promoter and 5'-UTR (underlined).

FIG. 12 shows the nucleotide (SEQ ID NO: 95) and derived amino acid sequence (SEQ ID NO: 96) of the DMR6 ortholog of *Solanum lycopersicum*, respectively.

FIG. 13 shows the nucleotide (SEQ ID NO: 97) and derived amino acid sequence (SEQ ID NO: 98) of the DMR6 ortholog of *Nicotiana benthamiana*, respectively.

FIG. 16 shows the phenotypic difference between homozygous double mutant for mutant alleles bodmr6-1-1 and bodmr6-2 ("aa bb") and wild type ("AA BB") rapid cycling *Brassica oleracea* (FastPlant®, https://fastplants.org/origin/) plants inoculated with downy mildew (*Hyaloperonospora parasitica/Hyaloperonospora brassicae*) at 8 dpi.

FIG. 17A shows the results from F2 pop. 1 containing the mutant alleles bodmr6-1-1 and bodmr6-2. The y-axis lists the genotypes, and provides the number of plants tested: wild type ("AA BB"), 5 plants; and homozygous double mutant for mutant alleles bodmr6-1-1 and bodmr6-2 ("aa bb"), 15 plants. FIG. 17B shows the results from F2 pop. 2 containing the mutant alleles bodmr6-1-2 and bodmr6-2. The y-axis lists the genotypes, and provides the number of plants tested: wild type ("AA BB"), 8 plants; and homozygous double mutant for mutant alleles bodmr6-1-2 and bodmr6-2 ("aa bb"), 15 plants. FIG. 17C shows the results from F2 pop. 3 containing the mutant alleles bodmr6-1-3 and bodmr6-2. The y-axis lists the genotypes, and provides the number of plants tested: wild type ("AA BB"), 5 plants; and homozygous double mutant for mutant alleles bodmr6-1-2 and bodmr6-2 ("aa bb"), 10 plants. For FIGS. 17A-17C, "+" is the sample mean, "0" is a single data point, the box reflects the variation within each genotype, and the disease score shown on the x-axis ranges from 0 (susceptible) to 9 (resistant) (see Table 6).

FIG. 18A shows a plant with disease severity score 1 (i.e., local symptom=all leaves are more than 50% infected; systemic symptom=plant is dead; see Table 9). FIG. 18B shows a plant with disease severity score 3 (i.e., local symptom=all leaves are less than 50% infected; systemic symptom=all new leaves are infected; see Table 9). FIG. 18C shows a plant with disease severity score 5 (i.e., local symptom=1 or 2 leaves infected with V-shaped lesions; systemic symptom=1 or 2 new leaves infected with a V-shaped lesion; see Table 9). FIG. 18D shows a plant with disease severity score 7 (i.e., local symptom=no clear infection, but some leaves show spots; systemic symptom=no clear infection, but older leaves show some symptoms; see Table 9). For FIGS. 18A-18D, the red ring marks the youngest leaf developed at the time of infection, and symptoms observed above the red ring are considered systemic, while symptoms observed below the red ring are considered local.

FIG. 19A shows scores of local infection from an Xcc test that used Xcc race 1 (Xcc 1) to test resistant control plants (R1, 26 plants; R2, 30 plants), susceptible control plants (KT38, 30 plants), DMR6-1 and DMR6-2 double knockout plants (GE, 38 plants), and wild type plants processed with the same protocol as the GE plants (i.e., plants regenerated from protoplasts that did not contain the double mutation; GE.WT, 37 plants). FIG. 19B shows scores of systemic infection from an Xcc test that used Xcc 1 to test resistant control plants (R1, 26 plants; R2, 30 plants), susceptible control plants (KT38, 30 plants), DMR6-1 and DMR6-2 double knockout plants (GE, 38 plants), and wild type plants processed with the same protocol as the GE plants (i.e., plants regenerated from protoplasts that did not contain the double mutation; GE.WT, 37 plants). FIG. 19C shows scores of local infection from an Xcc test that used Xcc race 4 (Xcc 4) to test resistant control plants (R1, 5 plants; R2, 4 plants), susceptible control plants (KT38, 6 plants), DMR6-1 and DMR6-2 double knockout plants (GE, 33 plants), and wild type plants processed with the same protocol as the GE plants (i.e., plants regenerated from protoplasts that did not contain the double mutation; GE.WT, 27 plants). FIG. 19D shows scores of systemic infection from an Xcc test that used Xcc 4 to test resistant control plants (R1, 5 plants; R2, 4 plants), susceptible control plants (KT38, 6 plants), DMR6-1 and DMR6-2 double knockout plants (GE, 33 plants), and wild type plants processed with the same protocol as the GE plants (i.e., plants regenerated from protoplasts that did not contain the double mutation; GE.WT, 27 plants). For FIGS. 19A-19D, "+" is the sample mean, "∘" is a single data point, the box reflects the variation within each genotype, the results are the combined results from two independent tests, and the disease score shown on the x-axis ranges from 0 (susceptible) to 9 (resistant).

Figure 22A:
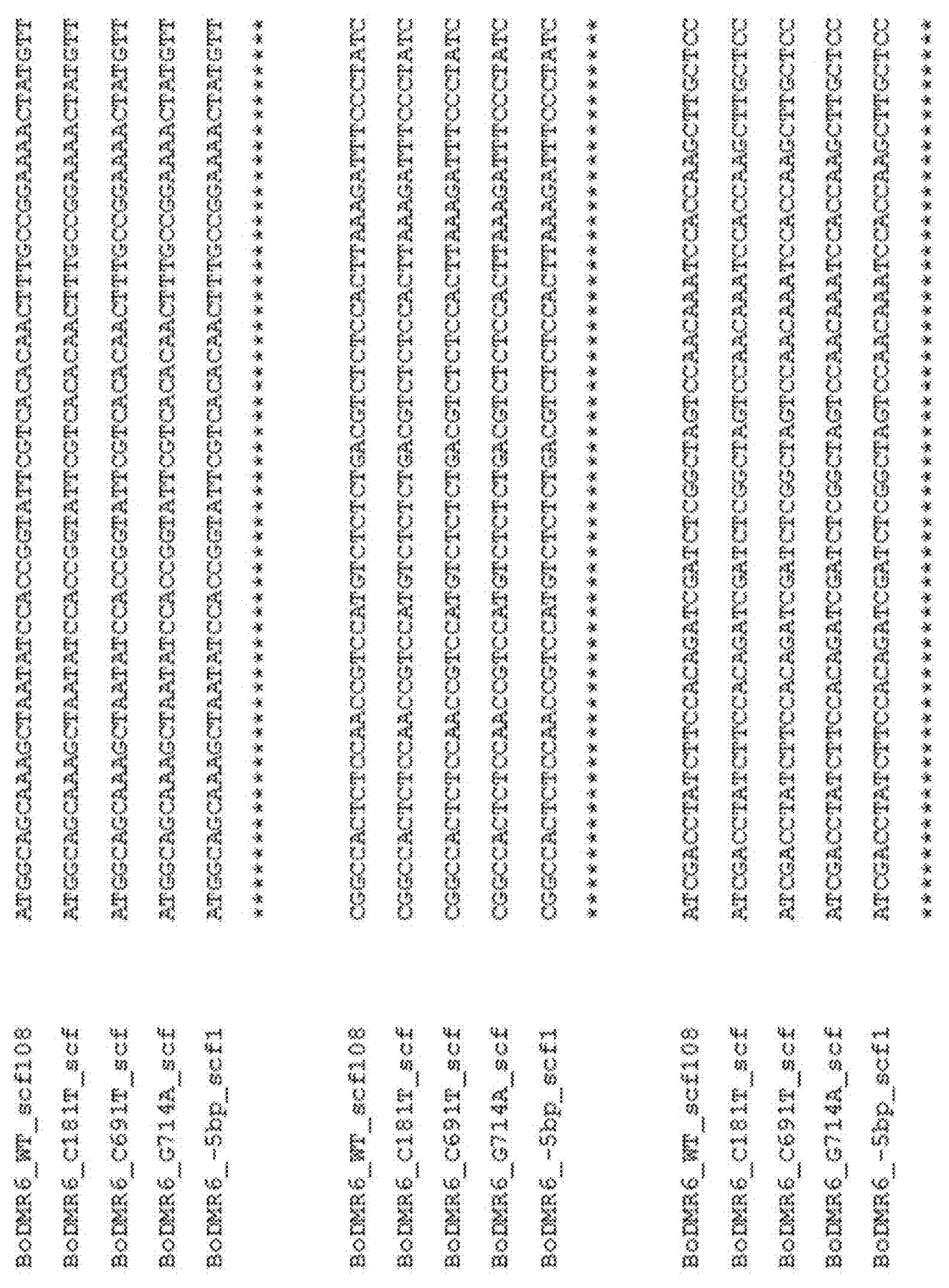

FIGS. 22A-22F show the alignment of the wild type DMR6-1 nucleotide sequence (BoDMR6_WT_scf108=SEQ ID NO: 114; top row) with mutated DMR6-1 nucleotide sequences (BoDMR6_C181T_scf=SEQ ID NO: 128; BoDMR6_C691T_scf=SEQ ID NO: 129; BoDMR6_G714A_scf=SEQ ID NO: 130; BoDMR6_-5 bp_scf1=SEQ ID NO: 137; bottom four rows).

Figure 23A:
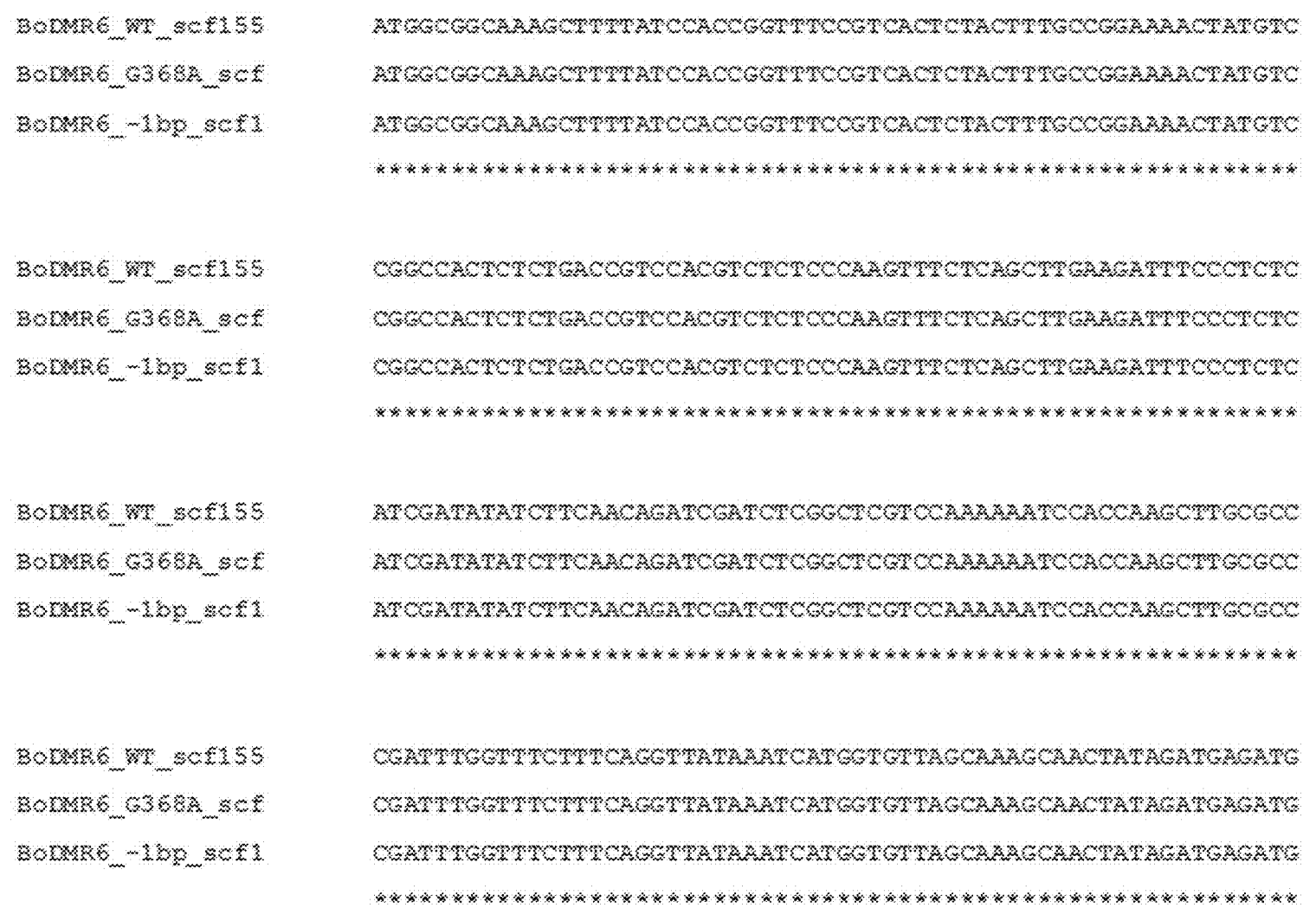

FIGS. 23A-23E show the alignment of the wild type DMR6-2 nucleotide sequence (BoDMR6_WT_scf155=SEQ ID NO: 115; top row) with mutated DMR6-2 nucleotide sequences (BoDMR6_G368A_scf=SEQ ID NO: 131; BoDMR6_-1bp_scf1=SEQ ID NO: 138; bottom two rows).

FIGS. 24A-24B show the alignment of the wild type DMR6-1 polypeptide sequence (BoDMR6_WT_scf108=SEQ ID NO: 112; top row) with mutated DMR6-1 polypeptide sequences (BoDMR6_C181T_scf=SEQ ID NO: 141; BoDMR6_C691T_scf=SEQ ID NO: 142; BoDMR6_G714A_scf=SEQ ID NO: 143; BoDMR6_-5 bp_scf1=SEQ ID NO: 139; bottom four rows).

FIGS. 25A-25B show the alignment of the wild type DMR6-2 polypeptide sequence (BoDMR6_WT_scf155=SEQ ID NO: 113; top row) with mutated DMR6-2 nucleotide sequences (BoDMR6_G368A_scf=SEQ ID NO: 144; BoDMR6_-1bp_scf1=SEQ ID NO: 140; bottom two rows).

DETAILED DESCRIPTION OF THE INVENTION

Figure 1A:
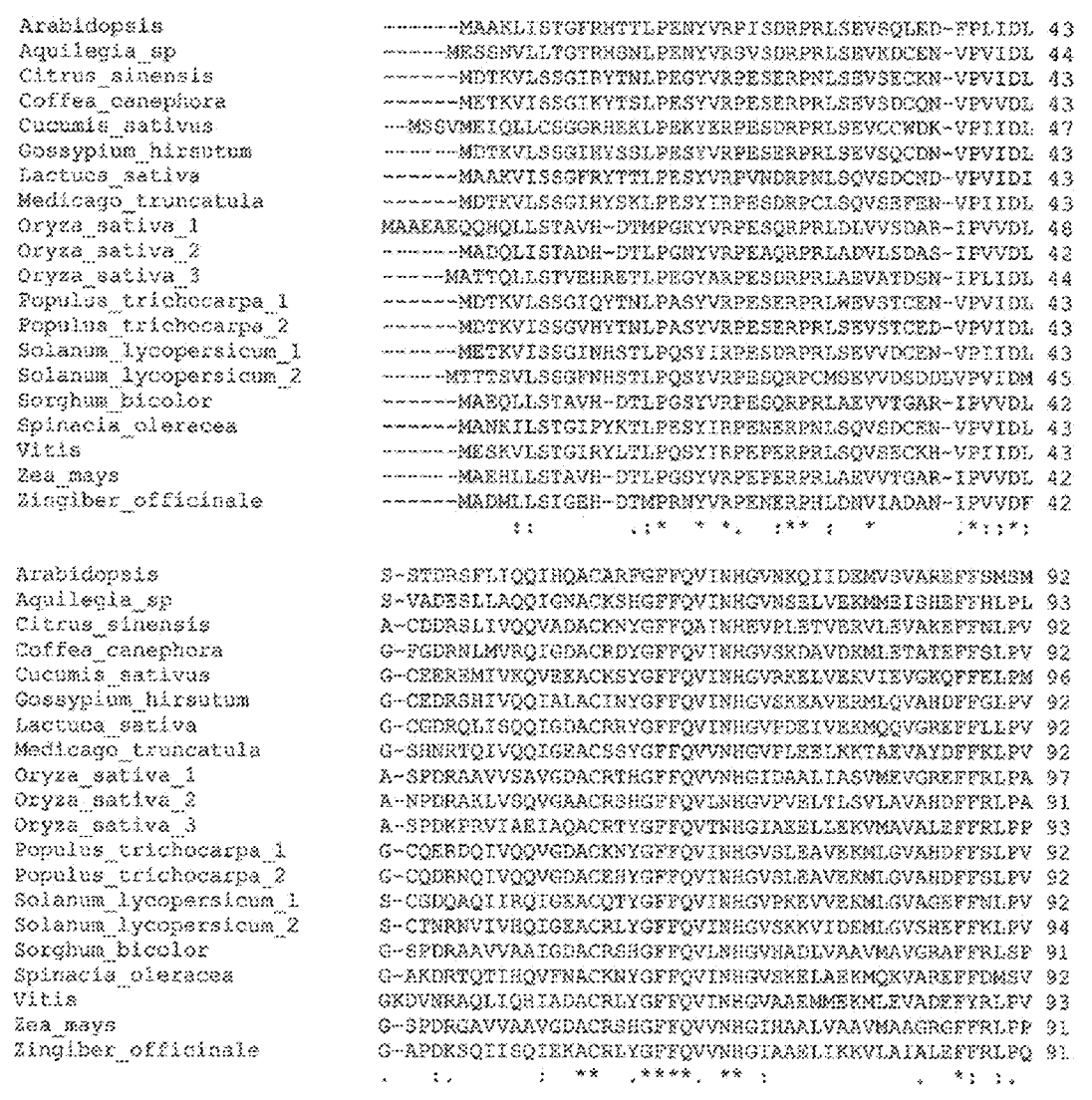
Figure 1B:
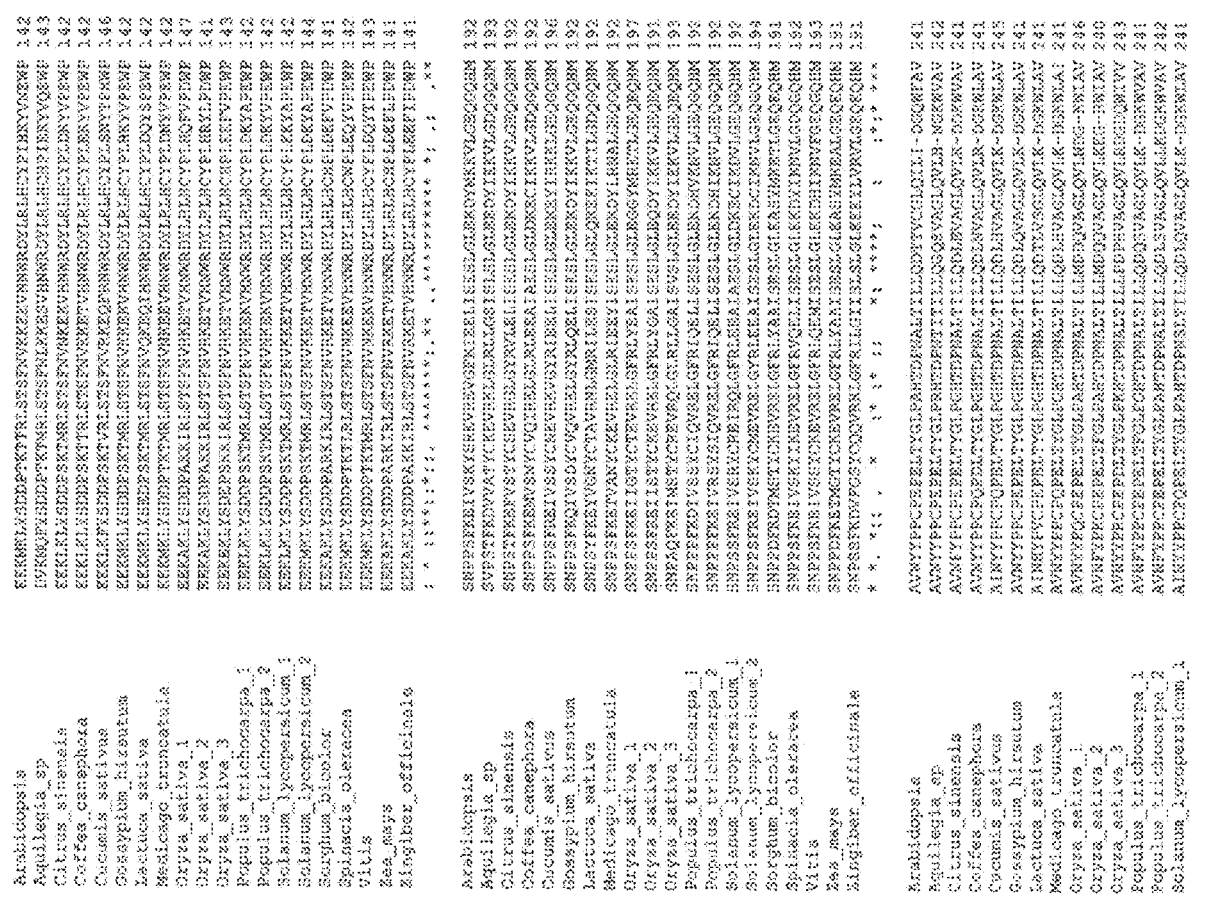
Figure 1C:
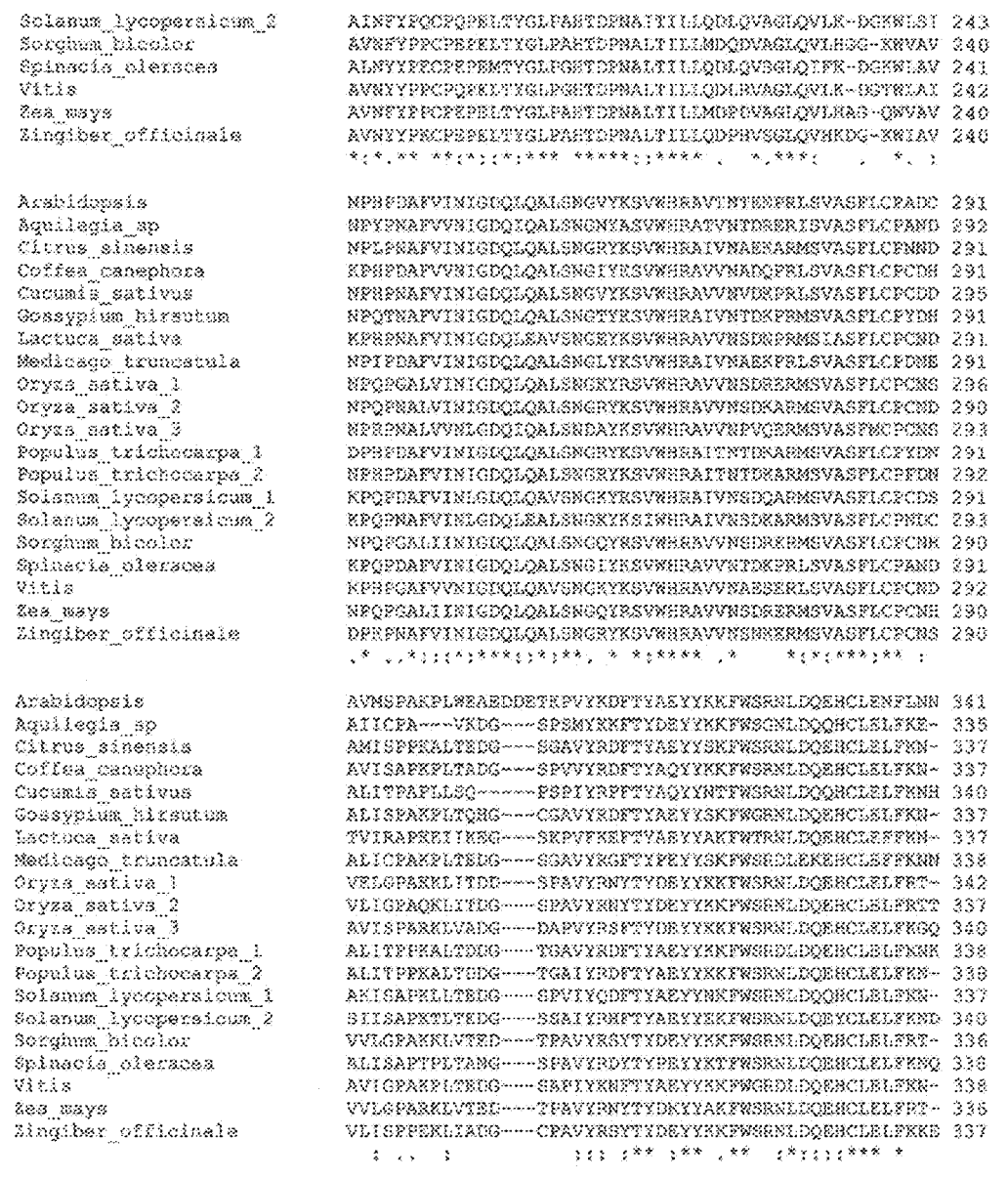
Figure 6A:
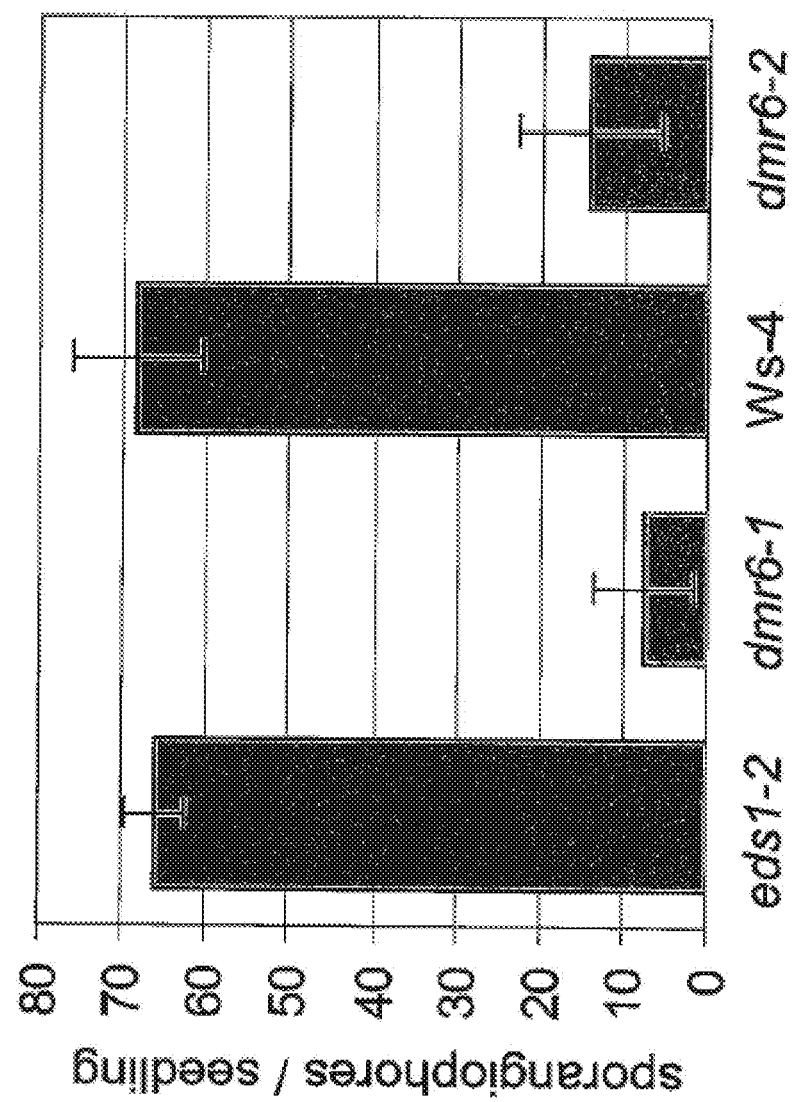
FIGS. 6A and 6B show the downy mildew resistance of the *Arabidopsis* dmr6 mutants.

FIG. 1 shows orthologous DMR6 sequences (described in Table 1) that have been identified in publicly available databases and obtained by PCR amplification on cDNA and subsequent sequencing. After orthologous DMR6 sequences are identified, the complete nucleotide sequence of the regulatory and coding sequence of the gene is identified by standard molecular biological techniques. For this, genomic libraries of the plant species are screened by DNA hybridization or PCR with probes or primers derived from a known DMR6 gene to identify the genomic clones containing the DMR6 gene. Alternatively, advanced PCR methods, such as RNA ligase-mediated RACE (RLM-RACE), can be used to directly amplify gene and cDNA sequences from genomic DNA or reverse-transcribed mRNA. DNA sequencing subsequently results in the characterization of the complete gene or coding sequence.

Once the DNA sequence of the gene is known this information is used to prepare the means to modulate the expression of the DMR6 gene.

To achieve a reduced DMR6 protein level, the expression of the DMR6 gene can be down-regulated or the enzymatic activity of the DMR6 protein can be reduced by amino acid substitutions resulting from nucleotide changes in the DMR6 coding sequence.

In a particular embodiment of the invention, downregulation of DMR6 gene expression is achieved by gene-silencing using RNAi. For this, transgenic plants are generated expressing a DMR6 anti-sense construct, an optimized micro-RNA construct, an inverted repeat construct, or a combined sense-anti-sense construct, so as to generate dsRNA corresponding to DMR6 that leads to gene silencing.

In an alternative embodiment, one or more regulators of the DMR6 gene are downregulated (in case of transcriptional activators) by RNAi.

In another embodiment regulators are upregulated (in case of repressor proteins) by transgenic overexpression. Overexpression is achieved in a particular embodiment by expressing repressor proteins of the DMR6 gene from a strong promoter, e.g. the 35S promoter that is commonly used in plant biotechnology.

The downregulation of the DMR6 gene can also be achieved by mutagenesis of the regulatory elements in the promoter, terminator region, or potential introns. Mutations in the DMR6 coding sequence in many cases leads to amino acid substitutions or premature stop codons that negatively affect the expression or activity of the encoded DMR6 protein. In a particular embodiment of the invention, the mutations in the DMR6 coding sequence are the introduction of a premature stop codon. In a further embodiment, mutations in the two cabbage DMR6 genes (i.e., DMR6-1 and DMR6-2) introduce a premature stop codon into each of the cabbage DMR6 genes.

These mutations are induced in plants by using mutagenic chemicals such as ethyl methane sulfonate (EMS), by irradiation of plant material with gamma rays or fast neutrons, or by other means. The resulting nucleotide changes are random, but in a large collection of mutagenized plants the mutations in the DMR6 gene can be readily identified by using the TILLING (Targeting Induced Local Lesions IN Genomes) method (McCallum et al. (2000) Targeted screening for induced mutations. Nat. Biotechnol. 18, 455-457, and Henikoff et al. (2004) TILLING. Traditional mutagenesis meets functional genomics. Plant Physiol. 135, 630-636). The principle of this method is based on the PCR amplification of the gene of interest from genomic DNA of a large collection of mutagenized plants in the M2 generation. By DNA sequencing or by looking for point mutations using a single-strand specific nuclease, such as the CEL-I nuclease (Till et al. (2004) Mismatch cleavage by single-strand specific nucleases. Nucleic Acids Res. 32, 2632-2641) the individual plants that have a mutation in the gene of interest are identified.

By screening many plants, a large collection of mutant alleles is obtained, each giving a different effect on gene expression or enzyme activity. The gene expression or protein levels can for example be tested by analysis of DMR6 transcript levels (e.g. by RT-PCR) or by quantification of DMR6 protein levels with antibodies.

Plants with the desired reduced DMR6 level or DMR6 expression are then back-crossed or crossed to other breeding lines to transfer only the desired new allele into the background of the crop wanted.

The invention further relates to mutated DMR6 genes. In a particular embodiment, the invention relates to dmr6 alleles with premature stop codons, such as the dmr6-1 allele and the dmr6-2 allele.

In another embodiment, the invention relates to mutated versions of the DMR6 genes of *Lactuca sativa*, *Cucumis sativus*, and *Spinacia oleracea* as shown in FIGS. 3-5.

The present invention demonstrates that plants having no or a reduced level of functional DMR6 gene product show resistance to pathogens, in particular of oomycete and fungal origin. With such knowledge the skilled person can identify so far unknown natural variants of a given plant species that have variants of the DMR6 gene that lead to a reduced level or absence of a functional DMR6 protein, or mutated versions of the DMR6 protein, and to use these natural variants according to the invention.

The present invention further relates to the use of a DMR6 promoter for providing disease resistance into plants, i.e. for providing plants with a resistance to a pathogen of viral, bacterial, fungal or oomycete origin. According to the present invention, the transcriptional up-regulation of DMR6 in response to pathogen infection has been demonstrated. Both transcript analysis as well as promoter DMR6-reporter lines support this finding (see Example 1, below). The pathogen-inducible DMR6 promoter according to the invention thus is particularly useful to control the expression of inducible systems that lead to disease resistance in plants.

One example of such inducible system that leads to disease resistance in plants, and in which the DMR6 promoter according to the present invention may be effective, has e.g. been described in WO 99/45125, wherein an antisense nucleotide sequence for a gene involved in the regulation of the C-5 porphyrin metabolic pathway is operably linked to a pathogen-inducible promoter and used to transform plant cells. Expression of the antisense nucleotide sequence in response to the pathogen effectively disrupts porphyrin metabolism of the transformed plant cell, and development of a localized lesion wherein the spread of the pathogen is contained. WO 96/36697 also discloses inducible systems leading to disease resistance in plants, wherein an inducible promoter controls the expression of a protein capable of evoking the hypersensitivity response in a plant. EP 0474857 furthermore discloses a method for the induction of pathogen resistance in plants, comprising transforming plants with polynucleotide sequences encoding a pair of pathogen-derived-avirulence-gene/plant-derived-resistance gene, wherein the expression of one of or both the elicitor peptide and the resistance gene is regulated by a pathogen inducible promoter. Further examples of inducible systems leading to resistance to pathogens in plants have been described in e.g. WO 98/32325.

In a particular preferred embodiment, the present invention relates to a method of providing disease resistance in a plant, comprising transforming a plant cell with a DNA construct comprising at least one expressible nucleic acid which is operably linked to a pathogen-inducible promoter that is operable within a plant cell, and regenerating transformed plants from said plant cells, wherein the pathogen-inducible promoter is a DMR6 promoter, and wherein the expression of the expressible nucleic acid confers disease resistance to the transgenic plant.

The invention also relates to disease resistance plants, obtainable by said method, as well as to plant tissue, and seeds obtained from said plants.

The invention in particular relates to plants, which are resistant to a pathogen of viral, bacterial, fungal or oomycete origin, wherein the plant comprises in its genome a DNA construct, comprising at least one expressible nucleic acid which is operably linked to a pathogen-inducible promoter, wherein the pathogen-inducible promoter is a DMR6 promoter.

The present invention also relates to the DNA construct per se, comprising at least one expressible nucleic acid which is operably linked to a pathogen-inducible promoter, wherein the pathogen-inducible promoter is a DMR6 promoter. The construct of the invention can be used to transform plant cells which may be regenerated into transformed plants. Furthermore, transformed plant tissue and seed may be obtained. Suitable methods for introducing the construct of the invention into plant cells are known to the skilled person.

According to the invention, by "operably linked" is meant that a promoter and an expressible nucleic acid, e.g. a gene, are connected in such way as to permit initiation of transcription of the expressible nucleic acid (e.g. gene) by the promoter.

By "expressible nucleic acid" is meant a nucleic acid (e.g. a gene, or part of a gene) that can be expressed in the cell, i.e., that can be transcribed into mRNA, and eventually may be translated into a protein. The expressible nucleic acid may be genomic DNA, cDNA, or chemically synthesized DNA or any combination thereof.

According to the present invention, a DNA construct comprises all necessary nucleic acid elements which permit expression (i.e. transcription) of a particular nucleic acid in a cell. Typically, the construct includes an expressible nucleic acid, i.e. a nucleic acid to be transcribed, and a promoter. The construct can suitably be incorporated into e.g. a plasmid or vector.

The expressible nucleic acid preferably is a gene involved in a plant defence response, e.g. a gene associated with the hypersensitivity response of a plant. In the hypersensitivity response (HR) of a plant, the site in the plant where the pathogen invades undergoes localized cell death by the induced expression of a suicide mechanism that triggers said localized cell death in response to pathogens. In this way, only a few plant cells are sacrificed and the spread of the pathogen is effectively arrested. Examples of said genes involved in a plant defence response are the regulatory protein NPR1/NIM1 (Friedrich et al., Mol. Plant Microbe Interact. 14(9): 1114-1124, 2001) and the transcription factor MYB30 (Vailleau et al., Proc. Natl. Acad. Sci. USA 99(15): 10179-10184, 2002).

In a particular embodiment, the expressible nucleic acid encodes an autologous or heterologous polypeptide capable of conferring disease-resistance to a plant. By "autologous polypeptide" is meant any polypeptide that is expressed in a transformed plant cell from a gene that naturally occurs in the transformed plant cell. By "heterologous polypeptide" is meant any polypeptide that is expressed in a transformed plant cell from a gene that is partly or entirely foreign (i.e. does not naturally occur in) to the transformed plant cell. Examples of such polypeptides are the mammalian Bax protein, which encodes a pro-apoptotic protein and results in cell death in plants (Lacomme and Santa Cruz, Proc. Natl.

Acad. Sci. USA 96(14): 7956-61, 1999) and fungal chitinases (de las Mercedes Dana et al., Plant Physiol. 142(2): 722-730, 2006).

Preferably, the DMR6 promoter is the *Arabidopsis* DMR6 promoter. The DMR6 promoter comprises a region of 3000 bp that is upstream of the *Arabidopsis* DMR6 coding sequence (ATG start codon) and includes the 5'UTR. Preferably the DMR6 promoter comprises a nucleotide sequence as defined in FIG. 11, and/or any functional fragment thereof, i.e. any fragment (or part) of said sequence which still is capable of initiating transcription of the expressible nucleic acid(s) to which it is operably linked, and/or natural variants thereof, i.e. natural variants of this promoter which may contain small polymorphisms, but which are generally at least 90% identical.

In a further preferred embodiment, the DMR6 promoter is an orthologous DMR6 promoter, i.e. a promoter of an orthologous DMR6 gene. Methods for identifying DMR6 orthologs have been described in Example 2 below. Once the DMR6 orthologs have been identified, the skilled person will be able to isolate the respective promoter of said orthologs, using standard molecular biological techniques.

According to the present invention, the DMR6 promoter has been shown to be strongly pathogen-induced, and the DMR6 promoter is not highly expressed in other non-infected tissues. Thus, it is a very suitable promoter for use in inducible systems for providing resistance to pathogens of viral, bacterial, fungal or oomycete origin in plants. Examples of specific pathogens and plants for which the inducible system, using the DMR6 promoter of the present invention, suitably can be used, have been given above.

In a particular embodiment, downregulation of DMR6 gene expression is achieved by gene silencing, RNA interference (RNAi), virus-induced gene silencing (VIGS), small RNA-mediated post-transcriptional gene silencing, transcription activator-like effector nuclease (TALEN) gene editing techniques, clustered Regularly Interspaced Short Palindromic Repeat (CRISPR/Cas9) gene editing techniques, and/or zinc-finger nuclease (ZFN) gene editing techniques. For this, transgenic plants are generated expressing one or more constructs targeting DMR6. These constructs may include, without limitation, an anti-sense construct, an optimized small-RNA construct, an inverted repeat construct, a targeting construct, a guide RNA construct, a construct encoding a targeting protein, and/or a combined sense-anti-sense construct, and may work in conjunction with a nuclease, an endonuclease, and/or an enzyme, so as to downregulate DMR6 gene expression.

In an alternative embodiment, one or more regulators of the DMR6 gene are downregulated (in case of transcriptional activators) by RNA interference (RNAi), virus-induced gene silencing (VIGS), small RNA-mediated post-transcriptional gene silencing, transcription activator-like effector nuclease (TALEN) gene editing techniques, clustered Regularly Interspaced Short Palindromic Repeat (CRISPR/Cas9) gene editing techniques, and/or zinc-finger nuclease (ZFN) gene editing techniques.

*Brassica* Plants of the Present Disclosure

Accordingly, certain aspects of the present disclosure relate to a mutant *Brassica* plant, wherein the plant has a reduced activity or a reduced level of a DMR6-1 polypeptide as compared to a corresponding wild type *Brassica* plant, and wherein the mutant *Brassica* plant has at least one non-natural mutation introduced into the DMR6-1 gene; and wherein the mutant *Brassica* plant has a reduced activity or a reduced level of a DMR6-2 polypeptide as compared to a corresponding wild type *Brassica* plant, and wherein the mutant *Brassica* plant has at least one non-natural mutation introduced into the DMR6-2 gene. In some embodiments, the plant exhibits resistance selected from the group of resistance to *Hyaloperonospora parasitica*/*Hyaloperonospora brassicae*, intermediate resistance to *Xanthomonas campestris campestris*, or any combination thereof. In some embodiments, the DMR6-1 polypeptide is selected from the group of a polypeptide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 112; and wherein the DMR6-2 polypeptide is a polypeptide selected from the group of a protein with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 113. In some embodiments that may be combined with any of the above embodiments, the DMR6-1 gene is selected from the group of a nucleotide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 114; and wherein the DMR6-2 gene is selected from the group of a nucleotide with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 115. In some embodiments that may be combined with any of the above embodiments, the non-natural mutation in DMR6-1 is a premature stop codon, and the non-natural mutation in DMR6-2 is a premature stop codon.

In some embodiments, the at least one non-natural mutation introduced into the DMR6-1 gene reduces an activity or a level of a DMR6-1 polypeptide as compared to a corresponding wild type *Brassica* plant; and the at least one non-natural mutation introduced into the DMR6-2 gene reduces an activity or a level of a DMR6-2 polypeptide as compared to a corresponding wild type *Brassica* plant. In some embodiments, the DMR6-1 polypeptide is selected from the group of a polypeptide with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 112; and wherein the DMR6-2 polypeptide is a polypeptide selected from the group of a protein with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 113. In some embodiments that may be combined with any of the above embodiments, the DMR6-1 gene is selected from the group of a nucleotide with at least 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 114; and wherein the DMR6-2 gene is selected from the group of a nucleotide with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 115.

In some embodiments, the at least one non-natural mutation that reduces the activity or level of the DMR6-1 protein is selected from the group of a premature stop codon introduced into the DMR6-1 coding sequence, a frameshift mutation introduced into the DMR6-1 coding sequence, an insertion introduced into the DMR6-1 coding sequence, a deletion of a part or a whole of the DMR6-1 coding sequence, an altered amino acid in a conserved domain of the DMR6-1 protein, a modified upstream sequence, a mutated promoter element, or an activated repressor element; and the at least one non-natural mutation that reduces the activity or level of the DMR6-2 protein is selected from the group of a premature stop codon introduced into the DMR6-2 coding sequence, a frameshift mutation introduced into the DMR6-2 coding sequence, an insertion introduced into the DMR6-2 coding sequence, a deletion of a part or a whole of the DMR6-2 coding sequence, an altered amino acid in a conserved domain of the DMR6-2 protein, a modified upstream sequence, a mutated promoter element, or an activated repressor element.

In one embodiment, the plant of the present disclosure may be obtained through introduction of a premature stop codon into *Brassica* DMR6-1 and DMR6-2 genes. In some embodiments, the introduction of a premature stop codon may be through a single nucleotide change, a single nucleotide deletion, the deletion of five nucleotides, the deletion of nucleotides such that a frameshift mutation is produced, or the insertion of nucleotides such that a frameshift mutation is produced. In a particular embodiment, the Cytosine (C) is replaced with a Thymine (T) at a position of DMR6-1 corresponding to nucleotide 181 of the reference sequence SEQ ID NO: 114 (e.g., producing SEQ ID NO: 128), resulting in a change from Arginine (R) to a stop codon (e.g., producing SEQ ID NO: 141). In another particular embodiment, the C is replaced with a T at a position of DMR6-1 corresponding to nucleotide 691 of the reference sequence SEQ ID NO: 114 (e.g., producing SEQ ID NO: 129), resulting in a change from Glutamine (Q) to a stop codon (e.g., producing SEQ ID NO: 142). In a further particular embodiment, the Guanine (G) is replaced with an Adenine (A) at a position of DMR6-1 corresponding to nucleotide 714 of the reference sequence of the reference sequence SEQ ID NO: 114 (e.g., producing SEQ ID NO: 130) resulting in a change from Tryptophan (W) to a stop codon (e.g., producing SEQ ID NO: 143). In yet another particular embodiment, five nucleotides (e.g., CCTGA) are deleted beginning at a position of DMR6-1 corresponding to nucleotide 601 of the reference sequence SEQ ID NO: 114 (e.g., producing SEQ ID NO: 137), producing a frameshift mutation and a premature stop codon (e.g., producing SEQ ID NO: 139). In an additional particular embodiment, the G is replaced with an A at a position of DMR6-2 corresponding to nucleotide 368 of the reference sequence SEQ ID NO: 115 (e.g., producing SEQ ID NO: 131) resulting in a change from W to a stop codon (e.g., producing SEQ ID NO: 144). In a further particular embodiment, the nucleotide is deleted at a position of DMR6-2 corresponding to nucleotide 600 of the reference sequence SEQ ID NO: 115 (e.g., producing SEQ ID NO: 138), producing a frameshift mutation and a premature stop codon (e.g., producing SEQ ID NO: 140). In some embodiments, the non-natural mutation introduced into the DMR6-1 gene is selected from the group of a C to T mutation at a position corresponding to nucleotide 181 of reference sequence SEQ ID NO: 114, a C to T mutation at a position corresponding to nucleotide 691 of reference sequence SEQ ID NO: 114, a G to A mutation at a position corresponding to nucleotide 714 of reference sequence SEQ ID NO: 114, or a deletion of five nucleotides starting at a position corresponding to nucleotide 601 of reference sequence SEQ ID NO: 114; and the non-natural mutation introduced into the DMR6-2 gene is selected from the group of a G to A mutation at a position corresponding to nucleotide 368 of reference sequence SEQ ID NO: 115, or a deletion of the nucleotide at a position corresponding to nucleotide 600 of reference sequence SEQ ID NO: 115.

Without wishing to be limited by theory, in some embodiments, the premature stop codon is located before or within the essential iron binding residue conserved in all 2OG oxygenases such as DMR6 (Wilmouth et al. (2002), Structure, 10:93-103). Without wishing to be limited by theory, in another embodiment, the plant of the present disclosure may be obtained through introduction of at least one amino acid change in the essential iron binding residue of DMR6-1 and the introduction of at least one amino acid change in the essential iron binding residue of DMR6-2. Without wishing to be limited by theory, in a further embodiment, the plant of the present disclosure may be obtained through introduction of at least one mutation in DMR6-1 and at least one mutation in DMR6-2 resulting in altered DMR6-1 function and altered DMR6-2 function that can be detected as an increase of salicylic acid (SA) accumulation.

In some embodiments, the non-natural mutation introduced into the DMR6-1 gene is selected from the group of a C to T mutation at position 181 corresponding to the reference sequence SEQ ID NO: 128, a C to T mutation at position 691 corresponding to the reference sequence SEQ ID NO: 129, a G to A mutation at position 714 corresponding to the reference sequence SEQ ID NO: 130, or deletion of CCTGA at position 601 corresponding to reference sequence SEQ ID NO: 137; and wherein the non-natural mutation introduced into the DMR6-2 gene is selected from the group of a G to A mutation at position 368 corresponding to reference sequence SEQ ID NO: 131, or deletion of T at position 600 corresponding to reference sequence SEQ ID NO: 138.

In some embodiments that may be combined with any of the above embodiments, the *Brassica* plant is a plant of the family Brassicaceae (i.e., Cruciferae). In some embodiments, the plant is *Brassica oleracea*. In some embodiments, the plant is a *Brassica oleracea* cultivar selected from the group of cabbage, kohlrabi, kale, Brussels sprouts, collard greens, broccoli, Romanesco broccoli, or cauliflower.

In some embodiments, the present disclosure relates to a seed, tissue, or plant part of the *Brassica* plant of any of the above embodiments that includes a reduced activity or a reduced level of a DMR6-1 polypeptide as compared to a corresponding wild type *Brassica* plant and a reduced activity or a reduced level of a DMR6-2 polypeptide as compared to a corresponding wild type *Brassica* plant, and wherein the seed, tissue, or plant part includes at least one non-natural mutation in the DMR6-1 gene and at least one non-natural mutation in the DMR6-2 gene.

In some embodiments of any of the above embodiments, the present disclosure relates to a plant part, wherein the plant part is a leaf, a stem, a root, a flower, a seed, a fruit, a cell, or a portion thereof. In some embodiments, the plant part is a leaf.

In some aspects, the present disclosure relates to a pollen grain or an ovule of the plant of any of the above embodiments. In some aspects, the present disclosure relates to a protoplast produced from the plant of any of the above embodiments. In some aspects, the present disclosure relates to a tissue culture produced from protoplasts or cells from the plant of any of the above embodiments, wherein the cells or protoplasts are produced from a plant part selected from the group of leaf, anther, pistil, stem, petiole, root, root primordia, root tip, fruit, seed, flower, cotyledon, hypocotyl, embryo, or meristematic cell. In some aspects, the present disclosure relates to a plant seed produced from the plant of any of the above embodiments.

In order to determine whether a plant is a plant of the present disclosure, and therefore whether said plant has the same alleles as plants of the present disclosure, the phenotype of the plant can be compared with the phenotype of a known plant of the present disclosure. In one embodiment, the phenotype can be assessed by, for example, the susceptibility to downy mildew in a whole plant test assay.

In the whole plant assay, plant with the 1$^{st}$ leaf pair are inoculated with $2 \times 10^4$ spores (20,000 spores/mL) of a downy mildew isolate (e.g., *Hyaloperonospora parasitica/Hyaloperonospora brassicae* Y113). Inoculated plants are kept in a climate cell kept at 15° C. with a day-night cycle of 16 hours light-8 hours dark (16:8 cycle). Then, the whole plant downy mildew test results are scored 8 to 9 days after inoculation using the scoring scale in Table 6.

In another embodiment, the phenotype can be assessed by measuring salicylic acid (SA) accumulation in the plant leaves. A plant of the present disclosure will have increased SA accumulation as compared to a WT plant. Methods of measuring SA accumulation are described in Zeilmaker et al. (2015), The Plant Journal, 81: 210-222 and Zhang et al. (2017), Plant Physiology, DOI:10.1104/pp. 17.00695.

In addition to phenotypic observations, the genotype of a plant can also be examined. There are many laboratory-based techniques known in the art that are available for the analysis, comparison and characterization of plant genotype. Such techniques include, without limitation, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs, which are also referred to as Microsatellites), and Single Nucleotide Polymorphisms (SNPs). By using these techniques, it is possible to assess the presence of the alleles, genes, and/or loci involved in the downy mildew resistance phenotype of the plants of the present disclosure.

Methods for Obtaining *Brassica* Plants of the Present Disclosure

Further aspects of the present disclosure relate to methods for obtaining a mutant *Brassica* plant including: introducing at least one non-natural mutation into the DMR6-1 gene and introducing at least one non-natural mutation into the DMR6-2 gene to produce a mutant *Brassica* plant with a reduced activity or a reduced level of a DMR6-1 polypeptide as compared to a corresponding wild type *Brassica* plant and a reduced activity or a reduced level of a DMR6-2 polypeptide as compared to a corresponding wild type *Brassica* plant. In some embodiments, the mutant *Brassica* plant exhibits resistance selected from the group of resistance to *Hyaloperonospora parasitica/Hyaloperonospora brassicae*, intermediate resistance to *Xanthomonas campestris campestris*, or any combination thereof. In some embodiments, the non-natural mutation is achieved by a mutagenic treatment (e.g., EMS), a radiation treatment, or a gene editing technique. In some embodiments, the gene editing technique is selected from the group of transcription activator-like effector nuclease (TALEN) gene editing techniques, clustered Regularly Interspaced Short Palindromic Repeat (CRISPR/Cas9) gene editing techniques, or zinc-finger nuclease (ZFN) gene editing techniques.

In some embodiments, the mutant *Brassica* plant produced from the above methods includes at least one non-natural mutation in the DMR6-1 gene and at least one non-natural mutation in the DMR6-2 gene, wherein the plant further comprises a reduced activity or a reduced level of a DMR6-1 polypeptide as compared to a corresponding wild type *Brassica* plant and a reduced activity or a reduced level of a DMR6-2 polypeptide as compared to a corresponding wild type *Brassica* plant, and wherein the plant exhibits resistance selected from the group of resistance to *Hyaloperonospora parasitica/Hyaloperonospora brassicae*, intermediate resistance to *Xanthomonas campestris campestris*, or any combination thereof. In some embodiments, the mutant *Brassica* plant produced from the above methods includes least one non-natural mutation in the DMR6-1 gene that reduces an activity or a level of a DMR6-1 polypeptide as compared to a corresponding wild type *Brassica* plant; wherein the plant includes at least one non-natural mutation in the DMR6-2 gene that reduces an activity or a level of a DMR6-2 polypeptide as compared to a corresponding wild type *Brassica* plant; and wherein the plant exhibits resistance selected from the group of resistance to *Hyaloperonospora parasitica/Hyaloperonospora brassicae*, intermediate resistance to *Xanthomonas campestris campestris*, or any combination thereof. In some embodiments, the DMR6-1 polypeptide is selected from the group of a polypeptide with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 112; and wherein the DMR6-2 polypeptide is a polypeptide selected from the group of a protein with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 113. In some embodiments, the DMR6-1 gene is selected from the group of a nucleotide with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 114; and wherein the DMR6-2 gene is selected from the group of a nucleotide with 85% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to SEQ ID NO: 115. In some embodiments that may be combined with any of the above embodiments, the *Brassica* plant produced from any of the above methods is a plant of the family Brassicaceae (i.e., Cruciferae). In some embodiments, the *Brassica* plant produced from any of the above methods is *Brassica oleracea*. In some embodiments, the *Brassica* plant produced from any of the above methods is a *Brassica oleracea* cultivar selected from the group of cabbage, kohlrabi, kale, Brussels sprouts, collard greens, broccoli, Romanesco broccoli, or cauliflower. In some embodiments, the present disclosure relates to a seed, tissue, or plant part of the *Brassica* plant produced from any of the above methods.

The present invention is illustrated in the following examples that are not intended to limit the invention in any way. In the examples reference is made to the figures described above.

EXAMPLE 1

The *Arabidopsis* DMR6 (At5g24530) Gene is Required for Downy Mildew Susceptibility
Experimental Procedures
*Hyaloperonospora parasitica* Growth and Infection

*H. parasitica* isolate Waco9 was provided by Dr. M. Aarts (WUR, Wageningen, NL) and isolate Cala2 provided by Dr. E. Holub (Warwick HRI, Wellsboume, UK) and maintained on *Arabidopsis* Ws-0 and Ler, respectively. Inocula (400,000 spores per ml) were weekly transferred to 10 day old healthy seedlings (Holub, E. B. et al., Mol. Plant Microbe Interact. 7: 223-239, 1994) by use of a spray gun. Seedlings were air-dried for approximately 45 minutes and incubated under a sealed lid at 100% relative humidity in a growth chamber at 16° C. with 9 hours of light per day (100mE/m2/s). The sporulation levels were quantified 7 days post inoculation (dpi) by counting the number of sporangiophores per seedling, for at least 40 seedlings per tested line (FIG. 6A) or by isolating spores in water 5 dpi and determining the spore concentration to give the number per mg leaf tissue (FIG. 6B).

Generation of Backcrossed Dmr6 Lines

The dmr6 mutants were back crossed twice (BC2) to the parental line Ler eds 1-2 as well as Ler. The BC2 lines generated with Ler were selected for the presence of the wild type EDS1 gene by PCR analysis.

Cloning DMR6

Fine mapping of the dmr6 gene was done with PCR markers designed using the Cereon database to identify insertion and deletion (IND) differences between Col-0 and Ler. The markers: IND_MOP9 in gene At5G24210; IND_K16H17 in gene At5G24420; IND_T4C12 in gene At5G24820; IND_T11H3 in between genes At5G24950_60 and IND_F21J6 in gene At5G25270 were used for mapping (Table 2). An additional screen for new recombinants was initiated on 300 F2 plants resulting in eight F2 recombinant plants between the two IND based markers IND_MOP9 and IND_T4C12, which flanked a region of 61 genes. Seven additional markers (M450-M590; Table 2) reduced the region to eighteen candidate genes for the dmr6 locus, between At5g24420 and At5g24590. Sequence analysis of At5g24530 indicated a point mutation leading to a stop codon in exon 2 in the dmr6-1 mutant.

TABLE 2

PCR primers for the markers used for the map-based cloning of DMR6.

| Name primer | Gene | INDEL/enzyme | Forward primer | Reverse primer |
|---|---|---|---|---|
| IND_MOP9 | At5G24210 | | tttgggaacagaaaaagt tggaggt (SEQ ID NO: 37) | catattcaaaagggaaaatc ccaga (SEQ ID NO: 38) |
| IND_K16H17 | At5g24420 | | tggggttgtggtttattctg ttgac (SEQ ID NO: 39) | tggccaatagtagttgatac gcaaga (SEQ ID NO: 40) |
| IND_T4C12 | At5g24820 | | tctcgggtaagacacaa gtcgagat (SEQ ID NO: 41) | tattccaacttgcgacgtag agcat (SEQ ID NO: 42) |
| IND_T11H3 | At5g24950-60 | | cggcttttaacaacatattttc gat (SEQ ID NO: 43) | ccaattgggttatttacttc ca (SEQ ID NO: 44) |

TABLE 2-continued

PCR primers for the markers used for the map-based cloning of DMR6.

| Name primer | Gene | INDEL/ enzyme | Forward primer | Reverse primer |
| --- | --- | --- | --- | --- |
| IND_F21J6 | At5g25270 | | aacacatcaccaagatg aatccaga (SEQ ID NO: 45) | cctctgccccaagaaatatt gagat (SEQ ID NO: 46) |
| M450 | At5G24450 | 18 | agctttgtatggtagtgcc aatga (SEQ ID NO: 47) | gcggtatacgggggttaaa atcta (SEQ ID NO: 48) |
| M490 | At5g24490 | TaqI | atggccaaccactctttgt tac (SEQ ID NO: 49) | acaagcaagaagaacagc gaag (SEQ ID NO: 50) |
| M525 | At5g24520-30 | TaqI | gaaatttggttgttggcat ttatc (SEQ ID NO: 51) | tcaagatcttcatattctcatt cca (SEQ ID NO: 52 |
| M545 | At5G24540/50 | 41 | cagctgaagtatgtttcat cccttt (SEQ ID NO: 53) | cttgcaattgttgggactag gtaa (SEQ ID NO: 54) |
| M555 | At5G24550/60 | 14 | tcactaaccagtgaaaaa ggttgc (SEQ ID NO: 55) | tatacagcgaatagcaaag ccaag (SEQ ID NO: 56) |
| M470 | At5g24470 | HphI | ccgcgagtgtaatatatct ctcct (SEQ ID NO: 57) | cagtttaacgcatgaagtgc tagt (SEQ ID NO: 58) |
| M590 | At5g24590 | PdmI | gcatcatttgtaccgtact gagtc (SEQ ID NO: 59 | tagtggatactctgtccctg aggt (SEQ ID NO: 60) |

Identification of a Dmr6 T-DNA Insertion Line

A second dmr6 allele was identified, 445D09 a FLAG T-DNA insertion line generated by INRA Versailles in the Ws-4 accession background. The T-DNA insertion was confirmed by PCR using a primer designed in the At5g24530 gene, LP primer (5'-caggtttatggcatatctcacgtc-3') (SEQ ID NO: 108), in combination with the T-DNA right border primer, Tag3' (5'-tgataccagacgttgcccgcataa-3') (SEQ ID NO: 109) or RB4 (5'-tcacgggttggggtttctacaggac-3') (SEQ ID NO: 110). The exact T-DNA insertion in the second intron of At5g24530 was confirmed by sequencing of amplicons generated with the T-DNA primers from both the left and right border in combination with the gene specific primers LP or RP (5'-atgtccaagtccaatagccacaag-3') (SEQ ID NO: 111).

cDNA Synthesis

RNA was isolated (from approximately 100 mg leaf tissue from 10 day old seedlings) with the RNaesy kit (Qiagen, Venlo, The Netherlands) and treated with the RNase-free DNase set (Qiagen). Total RNA was quantified using an UVmini-1240 spectrophotometer (Shimadzu, Kyoto, Japan). cDNA was synthesized with Superscript III reverse transcriptase (Invitrogen, Carlsbad, Calif., USA) and oligo (dT)15 (Promega, Madison, Wis., USA), according to the manufacturer's instructions.

Complementation of the Dmr6-1 Mutant

Complementation lines were generated by transforming dmr6 plants by the floral dip method with *Agrobacterium tumefaciens* (Clough and Bent, 1998) containing the At5g24530 gene from Col-0 behind the 35S promoter. The construct was generated by PCR amplification of the full length At5g24530 from Col-0 cDNA with primers which included restriction sites that were used for directional cloning. A forward primer (5'-ttctgggatccaATGGCG-GCAAAGCTGATATC-3') (SEQ ID NO: 1) containing a BamHI restriction site near the start codon (ATG), amplified the 5'-end of DMR6 and at the 3'-end after the stop codon an EcoRI site was generated with a reverse primer (5'-gatatat-gaattcttagttgtttagaaaattctcgaggc-3') (SEQ ID NO: 2). The 35S-DMR6-Tn was cloned into the pGreenII0229 (Hellens, R. P., Edwards, E. A., Leyland, N. R., Bean, S., and Mullineaux, P. M. (2000)). pGreen: a versatile and flexible binary Ti vector for *Agrobacterium*-mediated plant transformation. Plant Mol. Biol. 42, 819-832). 300 µM DL-Phosphinothricin (BASTA) resistant seedlings were isolated and analyzed for *H. parasitica* susceptibility and for DMR6 expression levels by RT-PCR.

Knock Down Lines of DMR6 by RNAi

RNAi lines were generated in the Ler eds 1-2 and Col-0 background. A 782 bp long cDNA amplicon of Col-0 At5g24530 gene was generated. The PCR was done with the Phusion DNA polymerase (2 U/µL) and two different primer combinations. The amplicon from the first DMR6 gene specific primer combination (RNAiDMR6F:
(SEQ ID NO: 3)
5'-aaaaagcaggctGACCGTCCACGTCTCTCTGAA-3'
and RNAiDMR6R:
(SEQ ID NO: 4)
5'-AGAAAGCTGGGTGAAACGATGCGACCGATAGTC-3')

was used as a template for the second PCR amplification with general primers allowing recombination into the pDONR7 vector of the GateWay cloning system. For the second PCR 10 µl of the first PCR (denaturation for 30 sec. at 98° C. followed by 10 cycles of: 10 sec. at 98° C.; 30 sec. at 58° C.; 30 sec. at 72° C.) in a total volume of 20 µl was used as template. The second PCR (denaturation for 30 sec. at 98° C. followed by 5 cycles of: 10 sec. at 98° C.; 30 sec. at 45° C.; 30 sec. at 72° C. and 20 cycles of 10 sec. at 98° C.; 30 sec. at 55° C.; 30 sec. at 72° C. finished by a final extension of 10 min. at 72° C.) with the attB1 (5'-GGGA-CAAGTTTGTACAAAAAAGCAGGCT-3') (SEQ ID NO: 5) and the

```
attB2
                                        (SEQ ID NO: 6)
(5'-ggggaccactttgtacaagaaagctgggt-3')
``` were performed in a 50 µl reaction volume. PCR product was gel purified and 50 ηg insert was recombined into 150 ηg pDONR7 vector with the clonase BP enzyme. The vector was transformed into electrocompotent DH5a *E. coli* cells and plasmids containing the correct insert were isolated and 100 ηg of the pDONR7 with the DMR6 amplicon were used in the LR reaction to recombine the insert in two opposite direction into 150 g3g pHellsgate8 vector. After transformation into *E. coli*, Spectomycin resistant clones were selected and the isolated plasmids were verified by a NotI digest for the right insert size and by colony PCR with a single internal primer for At5G24530 (DfragmentF: 5'-gagaagtgggatttaaaatagaggaa-3') (SEQ ID NO: 7), if the inserts was inserted twice in opposite direction an amplicon of 1420 bp could be detected. Correct pHellsgate8 plasmids with the double insert in opposite directions were transformed into electrocompotent *Agrobacterium* strain, C58C1. Plasmids were isolated from the *Agrobacterium* and retransformed into the *E. coli* to confirm the right size of the plasmid and the insert by NotI digestion. The reconfirmed *Agrobacterium* strains were used for the floral dip transformation of the Col-0 and Ler eds 1-2 plants. The developed seeds were screened for Kanamycin resistance on ½×GM plates, the T1 seedlings were transferred and the next generation of seeds the T2 was analysed for DMR6 expression and *H. parasitica* susceptibility.

Gene Expression Profiling of the Dmr6 Mutant

Total RNA was isolated as described above. mRNA was amplified with the MessageAmp aRNA kit (Ambion). CATMA array (Crowe et al., 2003) slides containing approximately 25,000 gene specific tags were hybridized according to standardized conditions described by de Jong et al. (de Jong M., van Breukelen B., Wittink, F. R., Menke, F. L., Weisbeek, P. J., and Van den Ackerveken G. (2006). Membrane-associated transcripts in *Arabidopsis*; their isolation and characterization by DNA microarray analysis and bioinformatics. Plant J. 46, 708-721). For quantitative PCR, cDNA templates were generated as described previously. Cycle thresholds were determined per transcript in triplicate using the ABI PRISM 7700 sequence detection system (Applied Biosystems, Foster City, Calif., USA) using SYBR Green I (Applied Biosystems, Foster City, Calif., USA) as reporter dye. Primer sets for the transcripts are DMR6 (QDMR6F:5'-TGTCATCAACATAGGTGACCAG-3' (SEQ ID NO: 8) and QDMR6R: 5'-CGATAGTCACG-GATTTCTGTG-3') (SEQ ID NO: 9), At1g14880 (QAt1g14880F:5'-CTCAAGGAGAATGGTCCACA-3' (SEQ ID NO: 10) and QAt1g14880R: 5'-CGACTTGGC-CAAATGTGATA-3') (SEQ ID NO: 11), At4g14365 (QAt4g14365F: 5'-TGGTTTTCTGAGGCATGTAAA-3' (SEQ ID NO: 12) and QAt4g14365R:5'-AGTGCAG-GAACATTGGTTGT-3') (SEQ ID NO: 13), ACD6 (QACD6F:5'-TGGACAGTTCTGGAGCAGAT-3' (SEQ ID NO: 14) and QACD6R: 5'-CAACTCCTCCGCTGTGAG-3') (SEQ ID NO: 15), PR-5 (QPR-5F:5'-GGCAAATATCTC-CAGTATTCACA-3' (SEQ ID NO: 16) and QPR-5R: 5'-GG-TAGGGCAATTGTTCCTTAGA-3') (SEQ ID NO: 17), PR-2 (QPR-2 F:5'-AAGGAGCTTAGCCTCACCAC-3' (SEQ ID NO: 18) and QPR-2R: 5'-GAGGGAAGCAAGAATGGAAC-3') (SEQ ID NO: 19), PR-1 (QPR-1F:5'-GAACACGTGCAATGGAGTTT-3' (SEQ ID NO: 20) and QPR-1R: 5'-GGTTCCACCATTGT-TACACCT-3') (SEQ ID NO: 21) and ACT-2 (QACT2 F:5'-AATCACAGCACTTGCACCA-3' (SEQ ID NO: 22) and QACT2R: 5'-GAGGGAAGCAAGAATGGAAC-3') (SEQ ID NO: 23) generating 100 base pair fragments.

Results

Characterization of the Gene Responsible for Pathogen Resistance in the Dmr6 Mutant Van Damme et al., 2005, supra disclose a dmr6 mutant that is resistant to *H. parasitica*. The level of resistance can be examined by counting the number of sporangiophores per seedling seven day post inoculation with the *H. parasitica* (isolate Waco9 or Cala2, obtainable from Dr. G. Van den Ackerveken, Plant-Microbe Interactions Group, University of Utrecht, Utrecht, NL). The parental line, Ler eds 1-2 (Parker et al., 1996, Plant Cell 8:2033-2046), which is highly susceptible, is used as a positive control (and is set at 100%).

Figure 6B:
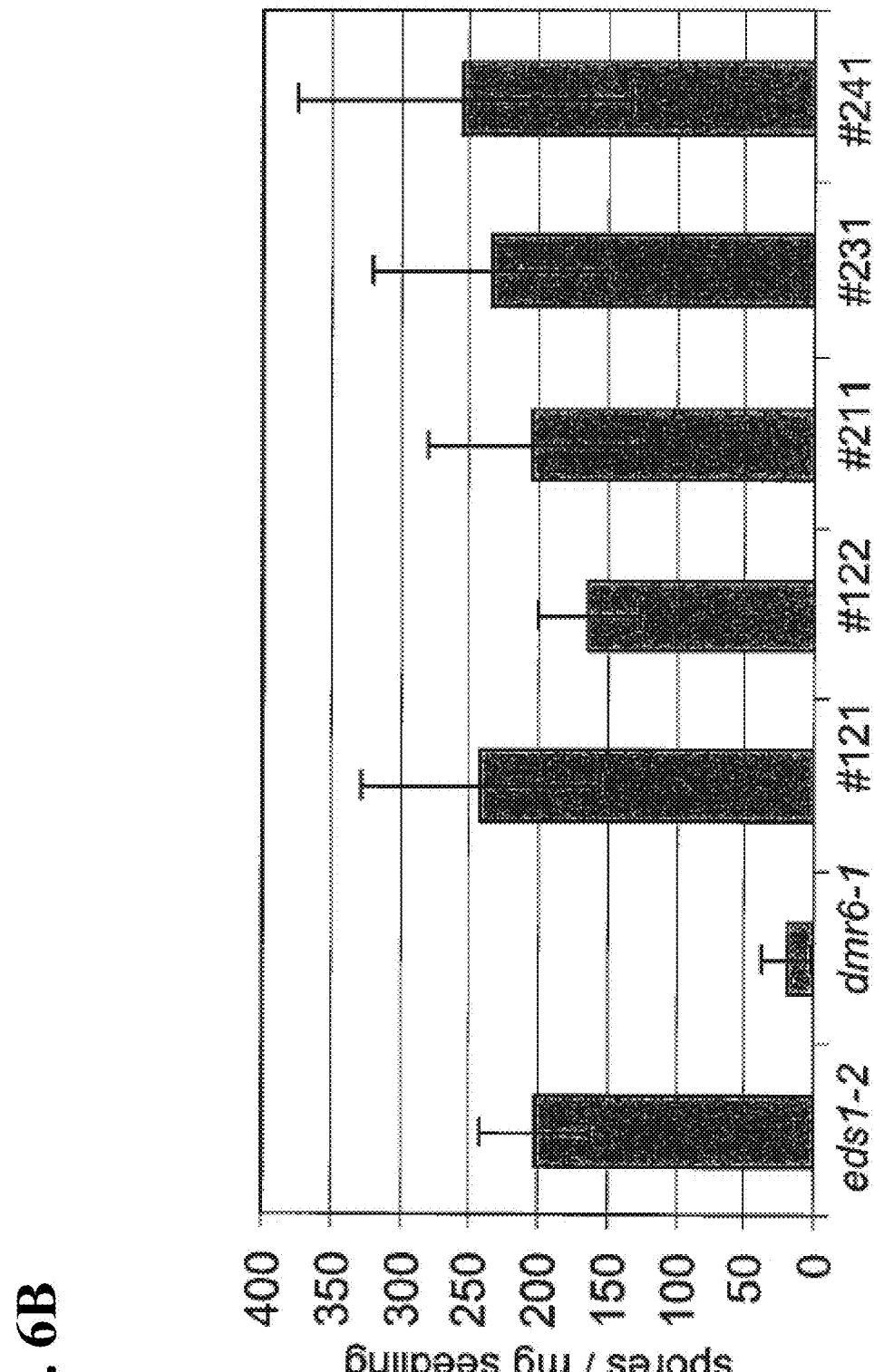

The reduction in sporangiophore formation on the infected dmr6 mutants compared to seedlings of the parental lines is shown in FIG. 6A, wherein the results of the quantification of *Hyaloperonospora parasitica*, Waco9 sporulation (sporangiophores/seedling) on the downy mildew resistant dmr6-1 mutant, back-crossed twice to the parental line Ler eds 1-2, and on mutant dmr6-2 (FLAG_445D09 T-DNA line) compared to the control lines is shown.

Figure 7:
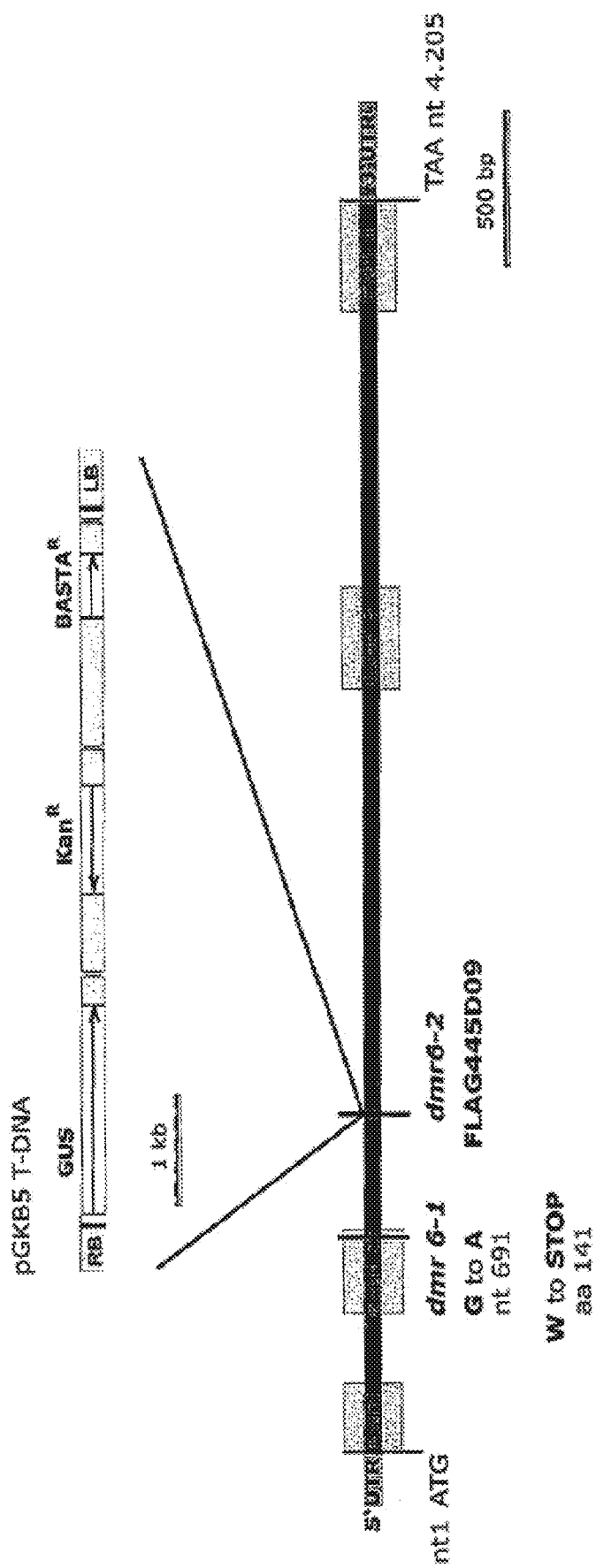
FIG. 7 shows the structure of the *Arabidopsis* DMR6 gene and dmr6-1 and dmr6-2 mutations. The DMR6 gene contains four exons and a coding sequence of 1026 bases. The two alleles are indicated; dmr6-1 with a base change in exon 2, and dmr6-2 with a T-DNA insertion into intron 2.

According to the invention, the gene responsible for resistance to *H. parasitica* in the dmr6 mutants of van Damme et al., 2005, supra, has been cloned by a combination of mapping and sequencing of candidate genes. Previously, the recessive dmr6 mutation was mapped near the nga139 marker on chromosome 5 to a region encompassing 74 genes. Fine mapping linked the dmr6 locus to a mapping interval containing the BACs T13K7 and K18P6 between the markers At5g24420 and At5g24590 located in the corresponding genes. This allowed the dmr6 interval to be confined to a region of 18 candidate genes. Comparative sequence analysis of the 18 genes in dmr6 and the parental line, Ler eds 1-2 revealed a point mutation in the second exon of the At5g24530 gene. This single base change of G to A, typical for an EMS mutation, changes a TGG a (trp codon) to a TGA (premature stop codon) at nucleotide position 691 of the coding sequence (FIG. 7). The early stop codon truncates the predicted oxidoreductase enzyme of 342 aa at position 141 before the conserved catalytic domain suggesting that dmr6 is a null-allele. The At5g24530 coding sequence (FIG. 2) is predicted to encode a protein with a mass of 39.4 kDa. No biological role has so far been described for At5g24530.

At5g24530 is DMR6

A second allele, dmr6-2, was identified in a T-DNA insertion line (FLAG_445D09) from the mutant collection from INRA, Versailles. The presence and location of the T-DNA insert in the second intron of At5g24530 (FIG. 7) was confirmed by PCR and sequence analysis (data not shown). Progeny of the FLAG_445D09 line homozygous for the T-DNA insertion was resistant to *H. parasitica* isolate Waco9, whereas the parental line (Ws-4) was susceptible (FIG. 6A). The At5g24530 transcript could be amplified by RT-PCR using primers in exon 2 and 3 in Ws-4, but not in the homozygous dmr6-2 line (data not shown), indicating that dmr6-2 can be considered a second null-allele.

To corroborate the idea that At5g24530 is required for susceptibility to *H. parasitica* the dmr6-1 mutant was transformed with the cDNA from At5g24530 cloned under control of the 35S promoter. In five independent dmr6-1 T2 seedlings the strong overexpression of At5g24530 was confirmed by RT-PCR (data not shown). All T3 lines, homozygous for the transgene, showed restoration of susceptibility to *H. parasitica* isolate Cala2 (FIG. 6B), confirming that At5g24530 is DMR6. The complementation, together with the identification of two independent dmr6 mutants clearly indicates that a functional DMR6 gene is required for susceptibility to *H. parasitica*.

DMR6 is Transcriptionally Activated During *H. parasitica* Infection

Figure 8:
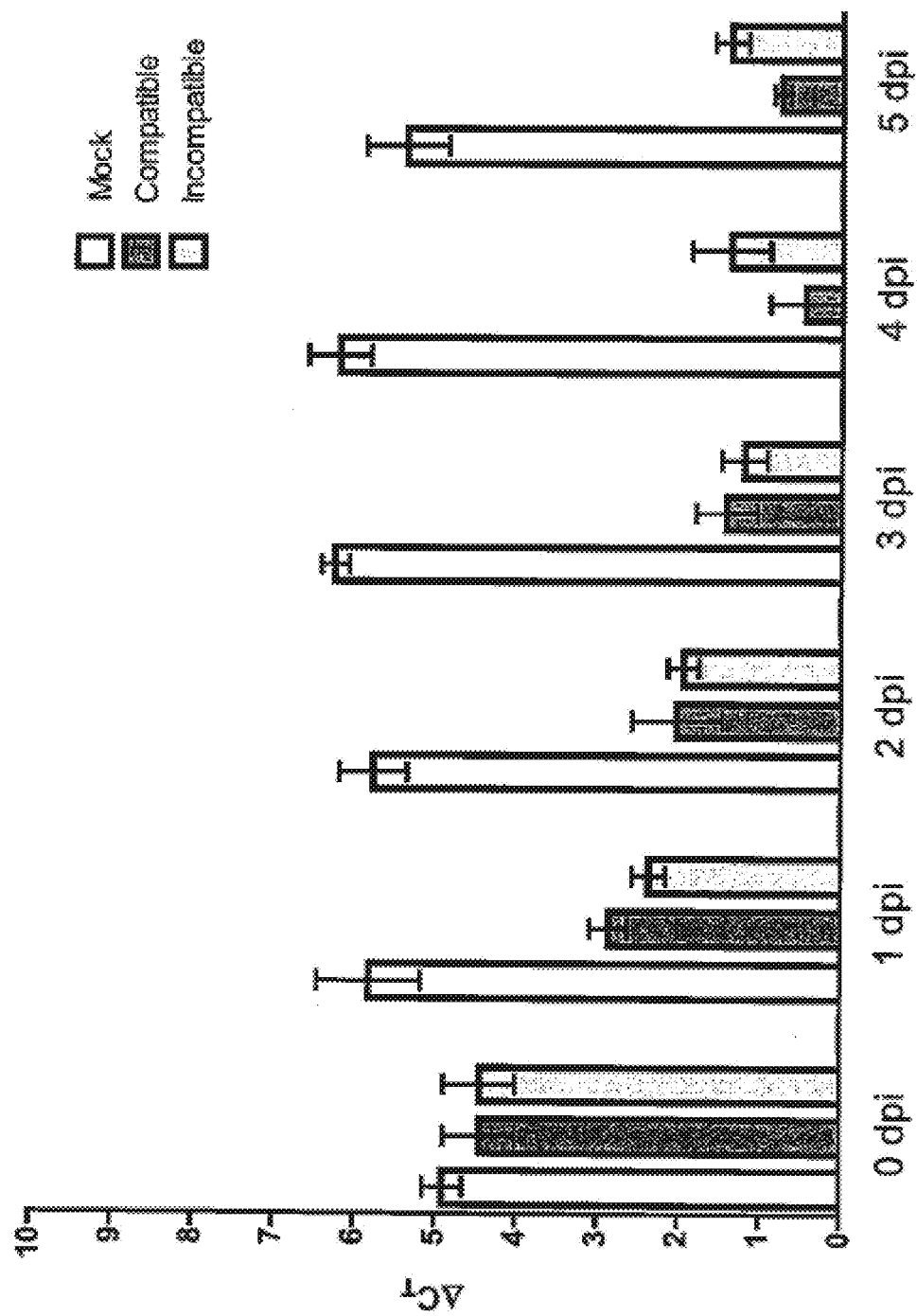
FIG. 8 shows the relative transcript levels of DMR6 in Ler plants either mock treated or inoculated with a compatible or incompatible *H. parasitica* isolate. Transcript levels were determined at different days post inoculation. The difference in cycle threshold (ΔCT) values reflect the number of additional PCR amplification cycles required to reach an arbitrary threshold product concentration as compared to ACTIN2. A lower ΔCT value indicates a higher transcript level.

To study the expression of DMR6 during infection with *H. parasitica* relative transcript levels were measured by quantitative PCR at six different time points from 0 days (2 hours) post inoculation to 5 days post inoculation (dpi) (FIG. 8). RNA was isolated from ten day old Ler seedlings that were spray inoculated with water (mock), compatible, or incompatible *H. parasitica* isolate. At 2 hours post inoculation (0 dpi) the levels of DMR6 transcripts were equal in the different treatments. Starting from 1 dpi, the level of DMR6 transcript was significantly increased in both the compatible and incompatible interaction compared to mock-treated seedlings. The DMR6 transcript level was slightly but significantly higher at 1 dpi in the incompatible interaction ($\Delta CT$ of 3.5, approximately 11 fold induction) than in the compatible ($\Delta CT$ of 3.0, approximately 8 fold induction). The expression level increased further in time to reach a stable high level at 4-5 dpi. At these time points the DMR6 transcript level was higher in the compatible than in the incompatible interaction. The elevated DMR6 transcript levels during compatible and incompatible *H. parasitica* interactions suggest a role of DMR6 in plant defence. The defence-associated expression of DMR6 could be confirmed in our three enhanced-defence mutants, dmr3, dmr4, and dmr5 (Van den Ackerveken et al., unpublished). Furthermore, in silico analysis of DMR6 levels in the Genevestigator Mutant Surveyor (Zimmermann,P., Hennig, L., and Gruissem, W. (2005). Gene-expression analysis and network discovery using Genevestigator. Trends Plant Sci. 10, 407-409) showed that the gene is strongly induced in the pathogen resistant mutants mpk4 and cpr5. In the cpr5/npr1 double mutant the DMR6 transcript level remained high indicating that the induction of DMR6 expression is mostly NPR1 independent. Salicylic acid appears to be an important signal in the induction of DMR6 expression during senescence as nahG transgenic plants (expressing the bacterial salicylate hydroxylase gene) showed only low levels of DMR6 transcript.

To investigate in more detail how the expression of DMR6 is activated during biotic and abiotic stress, DMR6 reporter lines were generated. The localisation of DMR6 expression was studied in transgenic Col-0 and Ler eds 1-2 plants containing the DMR6 promoter linked to the uidA ($\beta$-glucuronidase, GUS) reporter gene (pDMR6::GUS). To visualise both *H. parasitica* hyphal growth, by staining with trypan blue, as well as GUS activity, magenta-Xgluc was used as a 0-glucuronidase substrate yielding a magenta precipitate. In uninfected plants no GUS expression could be detected in the different plant organelles; roots, meristem, flower, pollen and seed. The expression of DMR6 was induced in the compatible interactions, Ler eds 1-2 infected with Cala2 (FIG. 9A), and Col-0 infected with isolate Waco9 (FIG. 9B). GUS expression was also induced in the incompatible interaction Ler eds 1-2 inoculated with isolate Emoy2 (FIG. 9C). As shown in FIGS. 9A and 9B DMR6 expression was confined to the cells in which *H. parasitica* had formed haustoria. Plant cells containing the most recently formed haustoria did not show detectable levels of GUS activity (FIG. 9A, indicated by asterisk). During the incompatible interaction (FIG. 9C) activity of the DMR6 promoter could only be detected in the cells that were in contact with the initial invading hyphae. In death cells, resulting from the hypersensitive response (HR, visualized by trypan blue staining indicated in FIG. 9C by asterisk) no GUS activity could be detected, possibly due to protein degradation in these cells. To test if the DMR6 expression in haustoria-containing cells is caused by a wound-like response, seedlings were wound by incision with scissors and stained for GUS activity 3 days later. No detectable promoter DMR6 GUS expression was seen, indicating that the expression of DMR6 is not induced by wounding (FIG. 9D). Furthermore the local induction of DMR6 expression was tested in response to treatment with benzothiadiazole (BTH), a functional analogue of salicylic acid (SA). At 3 days post BTH treatment GUS activity was mainly localized in the newly formed, but not in the mature leaves (FIG. 9E). Analysis of pDMR6::GUS lines confirm the expression data described above and highlights the strictly localized induction of DMR6 in response to *H. parasitica* infection.

The Dmr6-1 Mutant Constitutively Expresses Defence Associated Transcripts

Figure 10A:
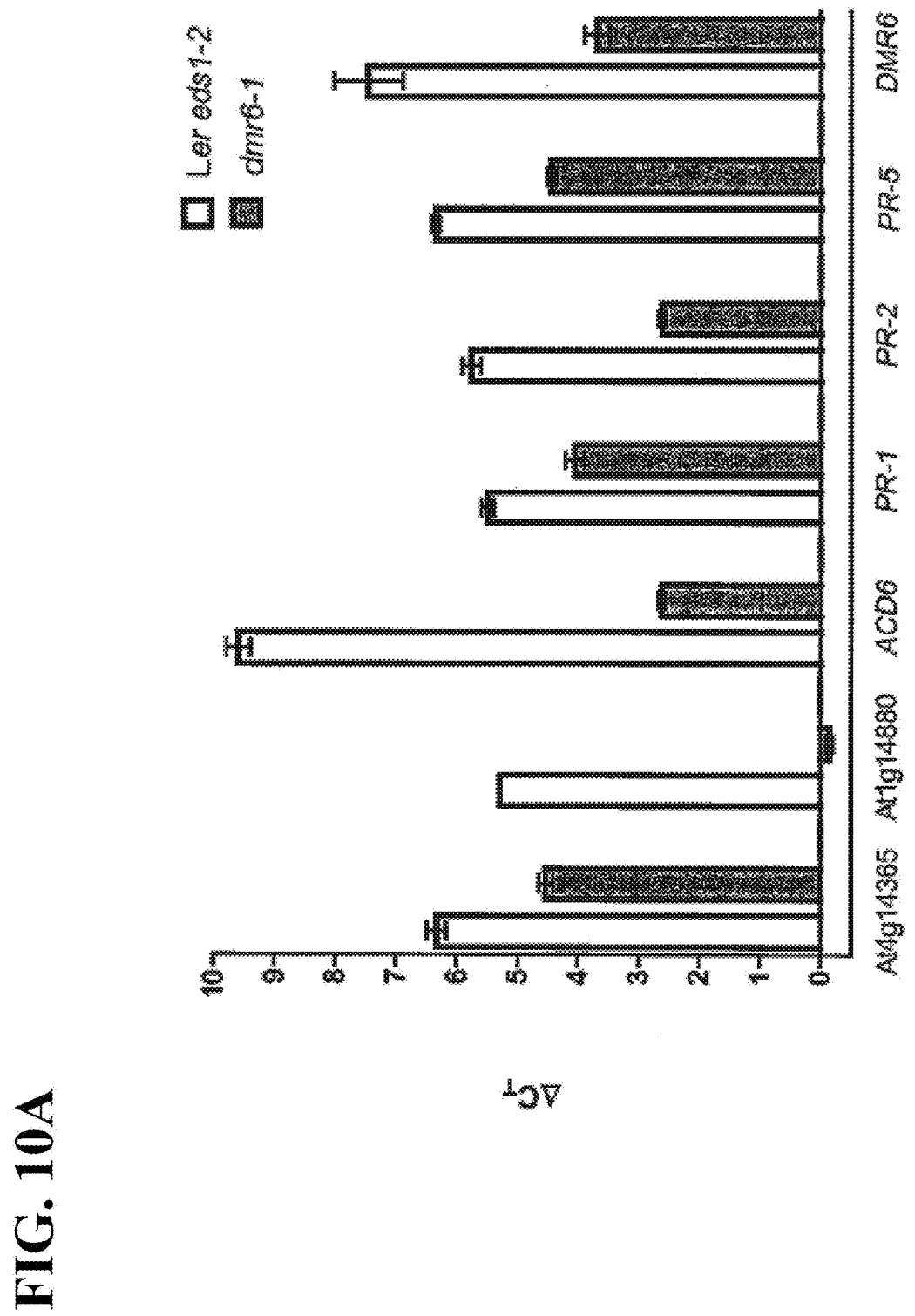
FIGS. 10A and 10B show the Q-PCR analysis of the transcript levels of the genes; At4g14365, At1g14880, ACD6, PR-1, PR-2 and PR-5, selected as up regulated in the dmr6-1 micro array analysis.
Figure 10B:
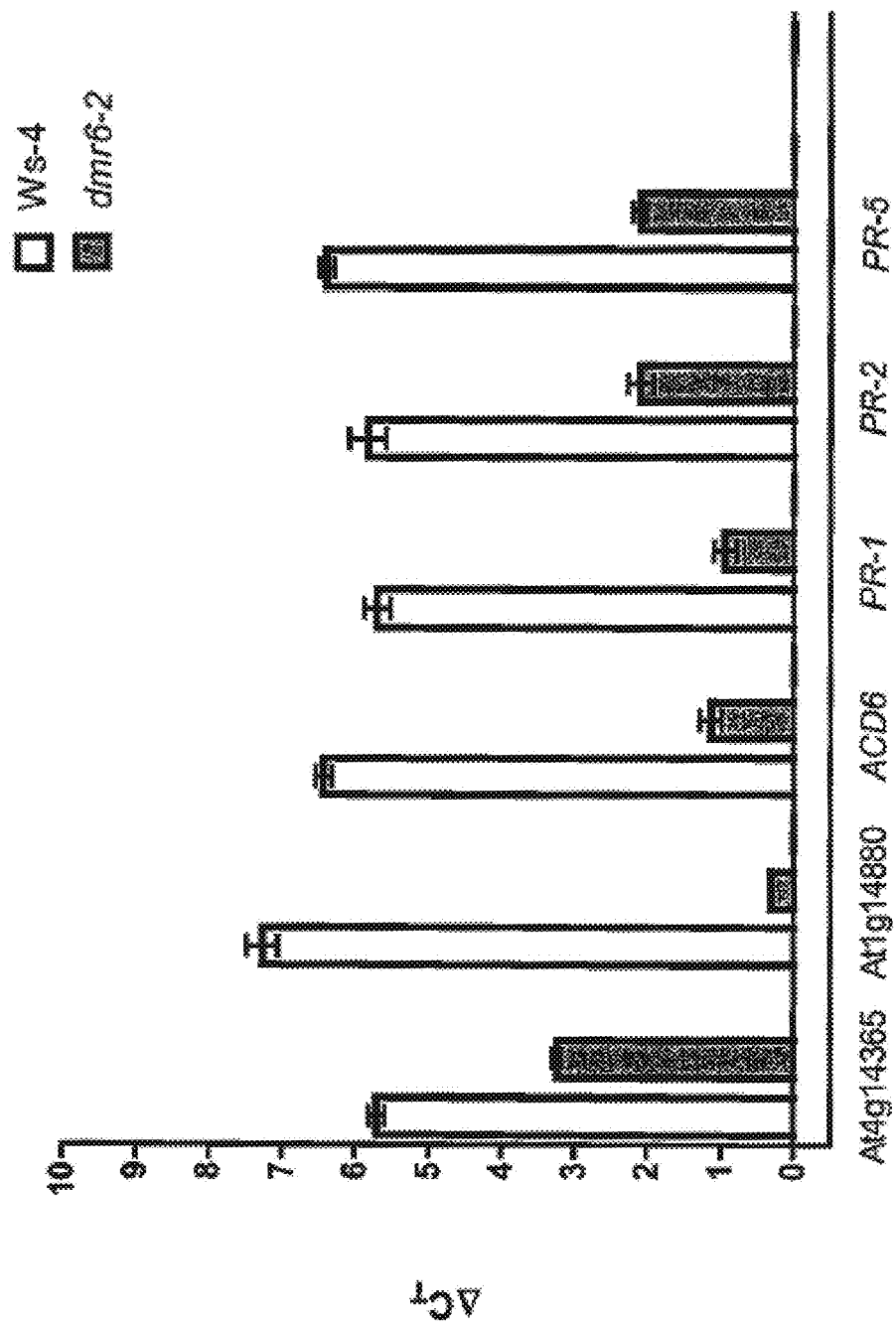

To elucidate how the lack of DMR6 results in *H. parasitica* resistance, the transcriptome of the dmr6-1 mutant compared to the Ler eds 1-2 parental line was analysed. Probes derived from mRNA of the above-ground parts of 14 day old dmr6-1 and Ler eds 1-2 seedlings were hybridised on whole genome CATMA micro arrays. A total of 58 genes were found to be significantly differentially expressed in dmr6-1, of which 51 genes had elevated and 7 genes had reduced transcript levels. A pronounced set of the 51 induced transcripts have been identified as genes associated with activated plant defence responses, e.g., ACD6, PR-5, PR-4/HEL and PAD4. These data indicate that the loss of DMR6 results in the activation of a specific set of defence-associated transcripts. The finding that DMR6 is among the dmr6-1-induced genes corroborates the idea that DMR6 is defence-associated. To test if the induced expression of the defence-associated genes was due to the loss of DMR6 and not due to additional ethane methyl sulfonate (EMS) mutations remaining in the backcrossed dmr6-1 mutant the transcript level of a selection of genes (At4g14365, At1g14880, ACD6, PR-1, PR-2 and PR-5) was verified by quantitative PCR in both the dmr6-1 and dmr6-2 mutant (FIGS. 10A and 10B). We could only test DMR6 transcript levels in the dmr6-1 mutant (FIG. 10A) as the dmr6-2 mutant (FIG. 10B) has a T_DNA insertion disrupting the DMR6 transcript. The induction of DMR6 as observed in the micro array analysis was confirmed by Q-PCR in dmr6-1 compared to Ler eds 1-2 (FIG. 10A). FIGS. 10A and 10B show that all six selected genes were elevated in both dmr6 mutants compared to the parental lines. The observed elevated expression of the selected defence-associated genes in the dmr6 mutants indicates that lack of DMR6 activates a plant defence response. The activation of this set of defence-associated transcripts could be the primary cause of resistance to *H. parasitica* in the dmr6 mutants.

EXAMPLE 2

Identification of DMR6 Orthologs in Crops
1. Screening of Libraries on the Basis of Sequence Homology The nucleotide and amino acid sequences of the DMR6 coding sequence and protein of *Arabidopsis thaliana* are shown in FIG. 2. Public libraries of nucleotide and amino acid sequences were compared with the sequences of FIG. 2. This comparison resulted in identification of the complete DMR6 coding sequences and predicted amino acid sequences in *Aquilegia* species, *Citrus sinensis, Coffea canephora, Cucumis sativus, Gossypium hirsutum, Lactuca sativa, Medicago truncatula, Oryza sativa* (3), *Populus trichocarpa* (2), *Solanum lycopersicum* (2), *Sorghum bicolor, Spinacia oleracea, Vitis vinifera, Zea mays*, and *Zingiber officinale*. The sequence information of the orthologous proteins thus identified is given in Table 1 and visualized in a multiple alignment in FIG. 1. For many other plant species, orthologous DNA fragments could be identified by BlastX as reciprocal best hits to the *Arabidopsis* or other plant DMR6 protein sequences.

Table 1 lists the GI numbers (GenInfo identifier) and Genbank accession number for Expressed Sequence Tags (ESTs) and mRNA or protein sequences of the *Arabidopsis* DMR6 mRNA and orthologous sequences from other plant species. A GI number (GenInfo identifier, sometimes written in lower case, "gi") is a unique integer which identifies a particular sequence. The GI number is a series of digits that are assigned consecutively to each sequence record processed by NCBI. The GI number will thus change every time the sequence changes. The NCBI assigns GI numbers to all sequences processed into Entrez, including nucleotide sequences from DDBJ/EMBL/GenBank, protein sequences from SWISS-PROT, PIR and many others. The GI number thus provides a unique sequence identifier which is independent of the database source that specifies an exact sequence. If a sequence in GenBank is modified, even by a single base pair, a new GI number is assigned to the updated sequence. The accession number stays the same. The GI number is always stable and retrievable. Thus, the reference to GI numbers in the table provides a clear and unambiguous identification of the corresponding sequence.

TABLE 1

Genbank accession numbers and GenInfo identifiers of the *Arabidopsis* *Arabidopsis* DMR6 mRNA and orthologous sequences from other plant species

| Species | Common name | Detail | GI number | Genbank |
|---|---|---|---|---|
| *Arabidopsis thaliana* | Thale cress | mRNA | 42568064 | NM_122361 |
| Aquilegia_sp | *Aquilegia* | ESTs | 75461114 | DT768847.1 |
| | | | 74538666 | DT745001.1 |
| | | | 74562677 | DT760187.1 |
| | | | 75461112 | DT768846.1 |
| | | | 74562675 | DT760186.1 |
| *Citrus sinensis* | Sweet Orange | ESTs | 5793134 | CX672037.1 |
| | | | 57933368 | CX673829.1 |
| | | | 63078039 | CX309185.1 |
| *Coffea canephora* | *Coffea* | ESTs | 82485203 | DV705375.1 |
| | | | 82458236 | DV684837.1 |
| | | | 82461999 | DV688600.1 |
| | | | 82487627 | DV707799.1 |
| *Gossypium hirsutum* | Cotton | ESTs | 109842586 | DW241146.1 |
| | | | 48751103 | CO081622.1 |
| *Sorghum bicolor* | *Sorghum* | ESTs | 45992638 | CN150358.1 |
| | | | 57813436 | CX614669.1 |
| | | | 45985339 | CN145819.1 |
| | | | 57821006 | CX622219.1 |
| | | | 45989371 | CN148311.1 |
| | | | 57821495 | CX622708.1 |
| | | | 45959033 | CN130459.1 |
| | | | 45985193 | CN145752.1 |
| | | | 18058986 | BM322209.1 |
| | | | 45958822 | CN130381.1 |
| | | | 30164583 | CB928312.1 |
| *Medicago truncatula* | Barrel medic | Genome draft | | MtrDRAFT_AC119415g1v1 |
| | | protein | 92878635 | ABE85154 |
| *Oryza sativa* 1 | Rice | Genome | | OSJNBb0060I05.4 |
| | | protein | 18057095 | AAL58118.1 |
| *Oryza sativa* 2 | | mRNA | 115450396 | NM_001055334 |
| | | protein | 115450397 | NP_001048799 |
| Oryza sativa 3 | | mRNA | 115460101 | NM_001060186 |
| | | protein | 115460102 | NP_001053651 |
| *Populus trichocarpa* 1 | Poplar | | Genome: LG_XII: 3095392-3103694 protein: Poptr1_1: 569679, eugene3.00120332 | |
| *Populus trichocarpa* 2 | Poplar | | Genome: LG_XV: 201426-209590 protein: Poptr1_1: 732726, estExt_Genewise1_v1.C_LG_XV0083 | |
| *Solarium lycopersicum* 1 | Tomato | ESTs | 62932307 | BW689896.1 |
| | | | 58229384 | BP885913.1 |
| | | | 117682646 | DB678879.1 |
| | | | 5894550 | AW035794.1 |

TABLE 1-continued Genbank accession numbers and GenInfo identifiers of the *Arabidopsis Arabidopsis* DMR6 mRNA and orthologous sequences from other plant species

| Species | Common name | Detail | GI number | Genbank |
|---|---|---|---|---|
|  |  |  | 117708809 | DB703617.1 |
|  |  |  | 62934028 | BW691617.1 |
|  |  |  | 15197716 | BI422913.1 |
|  |  |  | 4381742 | AI486371.1 |
|  |  |  | 5601946 | AI896044.1 |
|  |  |  | 4387964 | AI484040.1 |
|  |  |  | 4383017 | AI487646. |
|  |  |  | 5278230 | AI780189.1 |
|  |  |  | 12633558 | BG133370.1 |
|  |  |  | 76572794 | DV105461.1 |
|  |  |  | 117692514 | DB718569.1 |
|  |  |  | 4385331 | AI489960.1 |
|  |  |  | 4383253 | AI487882.1 |
|  |  |  | 4384827 | AI489456.1 |
| *Solarium lycopersicum* 2 | Tomato | ESTs | 47104686 | BT013271.1 |
|  |  |  | 14685038 | BI207314.1 |
|  |  |  | 14684816 | BI207092.1 |
| *Zea mays* | Maize | ESTs | 110215403 | EC897301.1 |
|  |  |  | 76291496 | DV031064.1 |
|  |  |  | 91050479 | EB160897.1 |
|  |  |  | 91874282 | EB404239.1 |
|  |  |  | 110540753 | EE044673.1 |
|  |  |  | 78111856 | DV530253.1 |
|  |  |  | 94477588 | EB706546.1 |
|  |  |  | 71441483 | DR822533.1 |
|  |  |  | 78111699 | DV530096.1 |
|  |  |  | 78107139 | DV525557.1 |
|  |  |  | 76017449 | DT944619.1 |
|  |  |  | 91048249 | EB158667.1 |
|  |  |  | 78104908 | DV523326.1 |
|  |  |  | 78088214 | DV516607.1 |
|  |  |  | 76291495 | DV031063.1 |
|  |  |  | 71441482 | DR822532.1 |
|  |  |  | 78088213 | DV516606.1 |
| *Vitis vinifera* | Grape | ESTs | 33396402 | CF202029.1 |
|  |  |  | 33399765 | CF205392.1 |
|  |  |  | 45770972 | CN006824.1 |
|  |  |  | 45770784 | CN006636.1 |
|  |  |  | 45770528 | CN006380.1 |
|  |  |  | 45770631 | CN006483.1 |
|  |  |  | 33400623 | CF206250.1 |
|  |  |  | 33396335 | CF201962.1 |
|  |  |  | 30134763 | CB920101.1 |
|  |  |  | 30305300 | CB982094.1 |
|  |  |  | 71857419 | DT006474.1 |
|  |  |  | 30305235 | CB982029.1 |
| *Zingiber officinale* | Ginger | ESTs | 87108948 | DY375732.1 |
|  |  |  | 87095447 | DY362231.1 |
|  |  |  | 87095448 | DY362232.1 |
|  |  |  | 87094804 | DY361588.1 |
|  |  |  | 87095449 | DY362233.1 |
|  |  |  | 87094803 | DY361587.1 |
| *Lactuca sativa* | Lettuce |  | Sequence described in this patent application |  |
| *Spinacia oleracea* | Spinach |  | Sequence described in this patent application |  |
| *Cucumis sativus* | Cucumber |  | Sequence described in this patent application |  |
| *Nicotiana benthamiana* | Tobacco |  | Sequence described in this patent application |  |

Identification of Orthologs by Means of Heterologous Hybridisation

The DMR6 DNA sequence of *Arabidopsis thaliana* as shown in FIG. 2 is used as a probe to search for homologous sequences by hybridization to DNA of any plant species using standard molecular biological methods. Using this method orthologous genes are detected by southern hybridization on restriction enzyme-digested DNA or by hybridization to genomic or cDNA libraries. These techniques are well known to the person skilled in the art. As an alternative probe the DMR6 DNA sequence of any other more closely related plant species can be used as a probe.

3. Identification of Orthologs by Means of PCR

For many crop species, partial DMR6 mRNA or gene sequences are available that are used to design primers to subsequently PCR amplify the complete cDNA or genomic sequence. When 5' and 3' sequences are available the missing internal sequence is PCR amplified by a DMR6 specific 5' forward primer and 3' reverse primer. In cases where only 5', internal or 3' sequences are available, both forward and reverse primers are designed. In combination with available plasmid polylinker primers, inserts are amplified from genomic and cDNA libraries of the plant species of interest. In a similar way, missing 5' or 3' sequences are amplified by advanced PCR techniques; 5'RACE, 3' RACE, TAIL-PCR, RLM-RACE or vectorette PCR.

As an example the sequencing of the *Lactuca sativa* (lettuce) DMR6 cDNA is provided. From the Genbank EST database at NCBI several *Lactuca* DMR6 ESTs were identified using the tblastn tool starting with the *Arabidopsis* DMR6 amino acid sequence. Clustering and alignment of the ESTs resulted in a consensus sequence for a 5' DMR6 fragment. To obtain the complete lettuce DMR6 cDNA the RLM-RACE kit (Ambion) was used on mRNA from lettuce seedlings. The 3' mRNA sequence was obtained by using two primers that were designed in the 5' DMR6 consensus sequence derived from ESTs (Lsat_dmr6_fw1: CGAT-CAAGGTCAACACATGG (SEQ ID NO: 24), and Lsat_dmr6_fw2: TCAACCATTACCCAGTGTGC) (SEQ ID NO: 25) and the 3'RACE primers from the kit. Based on the assembled sequence new primers were designed to amplify the complete DMR6 coding sequence from cDNA to provide the nucleotide sequence and derived protein sequence as presented in FIG. 3.

The complete DMR6 coding sequences from more than 10 different plants species have been identified from genomic and EST databases. From the alignment of the DNA sequences, conserved regions in the coding sequence were selected for the design of degenerate oligonucleotide primers (for the degenerate nucleotides the abbreviations are according to the IUB nucleotide symbols that are standard codes used by all companies synthesizing oligonucleotides; G=Guanine, A=Adenine, T=Thymine, C=Cytosine, R=A or G, Y=C or T, M=A or C, K=G or T, S=C or G, W=A or T, B=C or G or T, D=G or A or T, H=A or C or T, V=A or C or G, N=A or C or G or T).

The procedure for obtaining internal DMR6 cDNA sequences of a given plant species is as follows:
1. mRNA is isolated using standard methods,
2. cDNA is synthesized using an oligo dT primer and standard methods,
3. using degenerate forward and reverse oligonucleotides a PCR reaction is carried out,
4. PCR fragments are separated by standard agarose gel electrophoresis and fragments of the expected size are isolated from the gel,
5. isolated PCR fragments are cloned in a plasmid vector using standard methods,
6. plasmids with correct insert sizes, as determined by PCR, are analyzed by DNA sequencing,
7. Sequence analysis using blastX reveals which fragments contain the correct internal DMR6 sequences,
8. The internal DNA sequence can then be used to design gene- and species-specific primers for 5' and 3' RACE to obtain the complete DMR6 coding sequence by RLM-RACE (as described above).

As an example the sequencing of the *Cucumis sativus* (cucumber) DMR6 cDNA is provided. For cucumber several primer combinations between the following primers were successful in amplifying a stretch of internal coding sequence from cDNA; forward primers dmr6_deg_fw1B (TTCCAGGTDATTAAYCAYGG) (SEQ ID NO: 26), dmr6_deg_fw2B CATAAYTGGAGRGAYTAYCT) (SEQ ID NO: 27), dmr6_deg_fw3B (GARCAAGGRCAR-CAYATGGC) (SEQ ID NO: 28) and dmr6_deg_fw4 (AATCCTCCTTCHTTCAAGGA) (SEQ ID NO: 29) and reverse primers dmr6_deg_rv3B (AGTGCATTKGGGTCH-GTRTG) (SEQ ID NO: 30), dmr6_deg_rv4 (AATGTTRAT-GACAAARGCAT) (SEQ ID NO: 31) and dmr6_deg_rv5 (GCCATRTGYTGYCCTTGYTC) (SEQ ID NO: 32). After cloning and sequencing of the amplified fragments cucumber DMR6-specific primers were designed for 5' RACE (Cuc_dmr6_rv1: TCCGGACATTGAAACTTGTG (SEQ ID NO: 33) and Cuc_dmr6 rv2: TCAAAGAACTGCTTGC-CAAC) (SEQ ID NO: 34) and 3' RACE (Cuc_dmr6_fw1: CGCACTCACCATTCTCCTTC (SEQ ID NO: 35) and Cuc_dmr6_fw2: GGCCTCCAAGTCCTCAAAG) (SEQ ID NO: 36). Finally the complete cucumber DMR6 cDNA sequence was amplified and sequenced (FIG. 5). A similar approach was a used for spinach, *Spinacia oleracea* (FIG. 4), *Solanum lycopersicum* (FIG. 12) and *Nicotiana benthamiana* (FIG. 13).

Orthologs identified as described in this example can be modified using well-known techniques to induce mutations that reduce the DMR6 expression or activity, to obtain non-genetically modified plants resistant to Fungi or Oomycota. Alternatively, the genetic information of the orthologs can be used to design vehicles for gene silencing, and to transform the corresponding crop plants to obtain plants that are resistant to Oomycota.

EXAMPLE 3

Mutation of Seeds

Seeds of the plant species of interest are treated with a mutagen in order to introduce random point mutations in the genome. Mutated plants are grown to produce seeds and the next generation is screened for the absence of reduction of DMR6 transcript levels or activity. This is achieved by monitoring the level of DMR6 gene expression, or by searching for nucleotide changes (mutations) by the TILLING method, by DNA sequencing, or by any other method to identify nucleotide changes. The selected plants are homozygous or are made homozygous by selfing or intercrossing. The selected homozygous plants with absent or reduced DMR6 transcript activity are tested for increased resistance to the pathogen of interest to confirm the increased disease resistance.

EXAMPLE 4

Transfer of a Mutated Allele into the Background of a Desired Crop

Introgression of the desired mutant allele into a crop is achieved by crossing and genotypic screening of the mutant allele. This is a standard procedure in current-day marker assistant breeding of crops.

EXAMPLE 5

Use of the DMR6 Promoter for Pathogen-Induced Gene Expression and the Generation of Disease Resistant Plants Precise control of transgene expression is pivotal to the engineering of plants with increased disease resistance. In the past, constitutive overexpression of transgenes frequently has resulted in poor quality plants. It has therefor been suggested to use pathogen-inducible promoters, by which the transgenes are expressed only when and where they are needed—at infection sites.

Local and inducible expression of engineered genes, e.g. master switch genes, elicitor or Avr genes, anti-microbial genes, or toxic genes, results in the activation of defence or cell death that will lead to pathogen resistance, such as described by Gurr and Rushton (Trends in Biotechnology 23: 275-282, 2005). A good example is provided by De wit (Annu. Rev. Phytopathol. 30: 391-418, 1992) who proposes the use of the Avr9-Cf9 combination to achieve induced cell death leading to disease resistance. The tissue-specificity and inducibility of expression is of prime importance for such approaches, as described by Gurr and Rushton (Trends in Biotechnology 23: 283-290, 2005).

According to the present invention, the DMR6 promoter has been demonstrated to show a strong, inducible, localized expression based on promoter-GUS analysis. Thus, the DMR6 promoter is very suitable for engineering disease resistance in transgenic plants. The DMR6 promoter consists of a region of 2.5 kb that is upstream of the *Arabidopsis* DMR6 coding sequence (ATG start codon) and includes the 5'UTR (as depicted in FIG. 11). This pathogen-inducible promoter is then used to engineer suitable transgene constructs, using standard techniques known the person skilled in the art.

subsequently, this vector was transformed into a *Arabidopsis thaliana* mutant dmr6-1.

Briefly, mRNA was isolated using standard methods and cDNA was synthesized using an oligo dT primer and standard methods. Subsequently, PCR fragments were generated using primer pairs for each crop as depicted in Table 3 below. The generated PCR products were cloned into a pENTR/D-TOPO vector using the pENTR/D-TOPO cloning kit from Invitrogen and resulting plasmids with correct insert sizes, as determined by PCR, were analyzed by DNA sequencing. Recombination to the pB7WG2,0 vector was done using LR clonase II from Invitrogen and the resulting plasmids were analyzed by PCR and digestion with restriction enzymes. Suitable plasmids were transformed into *Agrobacterium tumefaciens* C58C1 PGV2260 and plasmids from *Agrobacterium* were analyzed by PCR and digestion with restriction enzymes.

TABLE 3

Primer pairs for cloning dmr6 orthologs in a suitable plant expression vector.

| *Arabidopsis thaliana* | AtDMR6_fw | CACCATGGCGGCAAAGCTGAT A (SEQ ID NO: 85) |
| --- | --- | --- |
| | AtDMR6UTR_rv | GACAAACACAAAGGCCAAAGA (SEQ ID NO: 86) |
| *Cucumis sativa* | cuc_fw | CACCATGAGCAGTGTGATGGA GAT (SEQ ID NO: 87) |
| | cucUTR_rv | TGGGCCAAAAAGTTTATCCA (SEQ ID NO: 88) |
| *Spinacia oleracea* | spi_fw | CACCATGGCAAACAAGATATT ATCCAC (SEQ ID NO: 89) |
| | spiUTR_rv | TTGCTGCCTACAAAAGTACAA A (SEQ ID NO: 90) |
| *Lactuca sativa* | Lsat_fw | CACCATGGCCGCAAAAGTCAT CTC (SEQ ID NO: 91) |
| | LsatUTR_rv | CATGGAAACACATATTCCTTCA (SEQ ID NO: 92) |
| *Solanum lycopersicum* | Slyc1dmr6_fw | CACCATGGAAACCAAAGTTAT TTCTAGC (SEQ ID NO: 93) |
| | Slyc1dmr6UTR_rv | GGGACATCCCTATGAACCAA (SEQ ID NO: 94) |

Using orthologous DNA sequences from a given plant species primers are designed for PCR. These are then used to screen genomic libraries of the plant species of interest to identify the genomic clones that contain the DMR6 ortholog with its promoter and regulatory sequences. Alternatively, the genomic clones are isolated by screening a library with a labelled PCR fragment corresponding to the DMR6 orthologous gene. Sequencing reveals the nucleotide sequence of the promoter. The region of 2-5 kb upstream the DMR6 orthologous coding sequence (ATG start codon), so including the 5'UTR, is then amplified by PCR to engineer transgene constructs for plant transformation.

EXAMPLE 6

This example demonstrates the complementation of mutant dmr6-1 in *Arabidopsis thaliana* by DMR6 orthologs from 4 different crop species. For this, DMR6 orthologs of *Cucumis sativa* (Cs), *Spinacia oleracea* (So), *Lactuca sativa* (Ls) and *Solanum lycopersicum* (Sl) were cloned into a plant expression vector under the control of the 35S promoter and,

*Arabidopsis thaliana* dmr6-1 plants were transformed with the above constructs by dipping into *Agrobacterium* solution and overexpression of crops DMR6 in *Arabidopsis* T1 plants is verified by RT-PCR using the crops DMR6 cloning primers (Table 3). Finally, *Arabidopsis* T2 and T3 plants were infected with *Hyaloperonospora parasitica* Cala2 to confirm complementation. The results are shown in FIG. 14.

Figure 14:
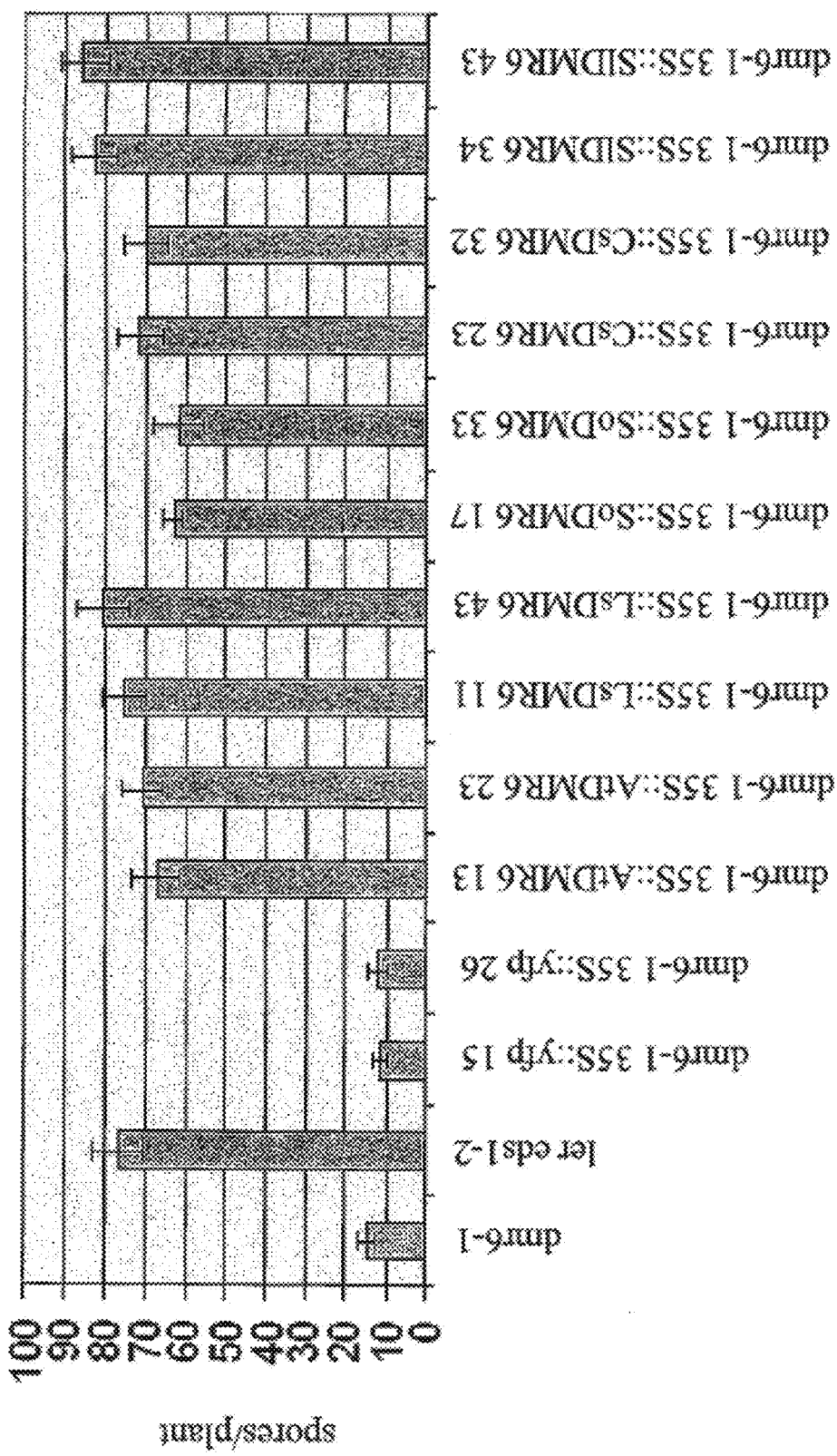
FIG. 14 shows complementation of *Arabidopsis thaliana* dmr6-1 with DMR6 derived from *Cucumis sativa* (Cs), *Spinacia oleracea* (Si), *Lactuca sativa* (Ls) and *Solanum lycopersicum* (So).

As shown in FIG. 14, all DMR6 orthologs tested were capable of complementing *Arabidopsis thaliana* mutant dmr6-1 indicating that the DMR6 orthologs identified encode DMR6 proteins with a similar functionality as *Arabidopsis thaliana* DMR6.

EXAMPLE 7

Mutations in the *Brassica oleracea* DMR6 Genes, DMR6-1 and DMR6-2, Result in Downy Mildew Resistance
Experimental Procedures
Mutation of Seeds A rapid cycling *Brassica oleracea* line that is fully susceptible to downy mildew (i.e., *Hyaloperonospora parasitica/Hyaloperonospora brassicae*) (FastPlantsR, https:// fastplants.org/origin/) was used to generate DMR6 mutant lines. *B. oleracea* contains two DMR6 genes, designated DMR6-1 (BoDMR6_Scf108) and DMR6-2 (BoDMR6_Scf155). The rapid cycling *B. oleracea* is used as a model plant and as a research tool for *B. oleracea*, since it is representative of all *B. oleracea* species. The rapid cycling line is able to interbreed with each other *B. oleracea* species. It is well known in the art that results obtained using the rapid cycling *B. oleracea* line are predictive for all *B. oleracea* species. Knock out mutants with premature stop codons were generated in both genes using EMS mutagenesis, and the mutants in DMR6-1 were designated "bodmr6-1" while the mutants in DMR6-2 were designated "bodmr6-2". Table 4 shows the sequence details for the mutations in the DMR6-1 and DMR6-2 genes of *B. oleracea*, whereby three different mutations were identified in the DMR6-1 gene and only one mutation was identified in DMR6-2.

TABLE 4

Mutations in the DMR6-1 and DMR6-2 genes of the *Brassica oleracea* rapid cycling line

| Allele | CDS Position | Nucleotide Change | Amino Acid Change | SNP Name in Protein |
|---|---|---|---|---|
| bodmr6-1-1 | 181 | C to T | R to STOP | R61* |
| bodmr6-1-2 | 691 | C to T | Q to STOP | Q234* |
| bodmr6-1-3 | 714 | G to A | W to STOP | W201* |
| bodmr6-2 | 368 | G to A | W to STOP | W123* |

Briefly, the bodmr6-1-1 mutation was at position 181 in the DMR6-1 gene, and it turned a Cytosine (C) into a Thymine (C to T mutation). This mutation resulted in a change at the amino acid level, converting an Arginine (R) at position 61 in the protein into a premature stop codon (R61*). The bodmr6-1-2 mutation was a C to T mutation at position 691 in the DMR6-1 gene that resulted in a change at the amino acid level from a Glutamine (Q) at position 234 in the protein to a premature stop codon (Q234*). The bodmr6-1-3 mutation was a Guanine (G) to an Adenine (G to A mutation) at position 714 in the DMR6-1 gene that resulted in a change at the amino acid level from a Tryptophan (W) at position 201 in the protein to a premature stop codon (W201*). Finally, the bodmr6-2 mutation was a G to A mutation at position 368 in the DMR6-2 gene, which resulted in a change at the amino acid level from a W at position 123 in the protein to a premature stop codon (W123*). These identified mutations are located before an essential iron binding residue which is conserved in all 2OG oxygenases; without this residue, 2OG oxygenases such as DMR6 are catalytically inactive (Wilmouth et al. (2002), Structure, 10:93-103). Therefore, these premature stop codons cause a complete loss of enzyme function.

FIGS. 22A-22F show the nucleotide alignment of the DMR6-1 mutant alleles with the corresponding wild type sequence of DMR6-1, whereby the mutant alleles (BoDMR6_C181T_scf=SEQ ID NO: 128; BoDMR6_C691T_scf=SEQ ID NO: 129; BoDMR6_G714A_scf=SEQ ID NO: 130) are shown below the wild type sequence (BoDMR6_WT_scf108=SEQ ID NO: 114). FIGS. 23A-23E show the nucleotide alignment of the DMR6-2 mutant allele with the corresponding wild type sequence of DMR6-2, whereby the mutant allele (BoDMR6_G368A_scf=SEQ ID NO: 131) is shown below the wild type sequence (BoDMR6_WT_scf155=SEQ ID NO: 115). FIGS. 24A-24B show the polypeptide alignment of the DMR6-1 mutant polypeptides with the corresponding wild type polypeptide of DMR6-1, whereby the mutant polypeptides (BoDMR6_C181T_scf=SEQ ID NO: 141; BoDMR6_C691T_scf=SEQ ID NO: 142; BoDMR6_G714A_scf=SEQ ID NO: 143) are shown below the wild type polypeptide (BoDMR6_WT_scf108=SEQ ID NO: 112). FIGS. 25A-25B show the polypeptide alignment of the DMR6-2 mutant polypeptide with the corresponding wild type polypeptide of DMR6-2, whereby the mutant polypeptide (BoDMR6_G368A_scf=SEQ ID NO: 144) is shown below the wild type polypeptide (BoDMR6_WT_scf155=SEQ ID NO: 113).

Creating Homozygous DMR6 Mutant Plants

Plants carrying the bodmr6-1-1 and bodmr6-2 mutant alleles were crossed to produce a first segregating F2 population (F2 pop. 1). This F2 population was genotyped to identify the presence of the mutant DMR6-1 and mutant DMR6-2 alleles. Two different genotypes were distinguished, as follows: wild type (i.e., DMR6-1R6-DMR6-1; DMR6-2/DMR6-2), referred to as "AA BB", and homozygous double mutant (bodmr6-1-1/bodmr6-1-1; bodmr6-2/bodmr6-2). Plants with these two genotypes were then used in test assays.

Plants carrying the bodmr6-1-2 allele were crossed with plants carrying the bodmr6-2 mutant allele to produce a second segregating F2 population (F2 pop. 2). This F2 population was genotyped to identify the presence of the mutant DMR6-1 and mutant DMR6-2 alleles. Two different genotypes were distinguished, as follows: wild type (i.e., DMR6-1R6-1/DMR6-1; DMR6-2/DMR6-2), referred to as "AA BB", and homozygous double mutant (bodmr6-1-2 bodmr6-1-2; bodmr6-2 bodmr6-2). Plants with these two genotypes were then used in test assays.

Plants carrying the bodmr6-1-3 allele were crossed with plants carrying the bodmr6-2 mutant allele to produce a third segregating F2 population (F2 pop. 3). This F2 population was genotyped to identify the presence of the mutant DMR6-1 and mutant DMR6-2 alleles. Two different genotypes were distinguished, as follows: wild type (i.e., DMR6-1/DMR6-1; DMR6-2/DMR6-2), referred to as "AA BB", and homozygous double mutant (bodmr6-1-3 bodmr6-1-3; bodmr6-2 bodmr6-2). Plants with these two genotypes were then used in test assays.

Genotyping

Plants were genotyped by PCR and High-Resolution Melting Curve (HRM) using primers and probes (listed in Table 5A and Table 5B) designed to identify the mutant alleles listed in Table 4.

TABLE 5A

Primers used for genotyping

| Allele | Forward | Reverse |
|---|---|---|
| bodmr6-1-1 | AGTCCAACAAATCCACCAAGC (SEQ ID NO: 116) | CCTTTTCAGGCACATAAGTTCA (SEQ ID NO: 117) |

TABLE 5A-continued

Primers used for genotyping

| Allele | Forward | Reverse |
|---|---|---|
| bodmr6-1-2 | ATTCTTCTCCAAGATGCTACCG (SEQ ID NO: 118) | GGATTAACGGCGAACCACT (SEQ ID NO: 119) |
| bodmr6-1-3 | CCAAGATGCTACCGTTTGTG (SEQ ID NO: 120) | TTGATGACAAAAGCATCAGGA (SEQ ID NO: 121) |
| bodmr6-2 | CCGAGATTATCGACGAGCTT (SEQ ID NO: 122) | TTGTCGATAGGATAACAATGA AGTC (SEQ ID NO: 123) |

TABLE 5B

Probes used for genotyping

| Allele | Probe |
|---|---|
| bodmr6-1-1 | GCTTGCTCCTGATTCGGGC (SEQ ID NO: 124) |
| bodmr6-1-2 | CGTTTGTGGTCTATAGATCTTGATCGT (SEQ ID NO: 125) |
| bodmr6-1-3 | CAGTGATTCGCCGTTAATCCACC (SEQ ID NO: 126) |
| bodmr6-2 | GAAGAGGTTAATAATTAGAGAGACTATCTC (SEQ ID NO: 127) |

The full sequence of the dmr6-1-1 mutant allele is SEQ ID NO: 128, the full sequence of the dmr6-1-2 mutant allele is SEQ ID NO: 129, the full sequence of the dmr6-1-3 mutant allele is SEQ ID NO: 130, and the full sequence of the dmr6-2 mutant allele is SEQ ID NO: 131.

Whole Plant Downy Mildew Test

The F2 pop. 1 *B. oleracea* plants described above were used to perform the whole plant downy mildew test, which enables phenotyping without wounding or damaging plant tissues. Plants with the first leaf pair were used, as this is the optimal developmental stage for a downy mildew test. Thirteen homozygous mutant plants and fifteen wild type plants were tested.

Plants were inoculated with downy mildew isolate *Hyaloperonospora parasitica/Hyaloperonospora brassicae* Y113 (collected on *B. oleracea* in Dannstadt, Germany). At time point 0, plants were inoculated with $2 \times 10^4$ spores (20,000 spores/mL). Once infected, plants were kept in a plastic tent built in a climate cell, which was kept at 15° C. with a day-night cycle of 16 hours light-8 hours dark (16:8 cycle). The plants were scored 8 to 9 days after inoculation using the scoring scale shown in Table 6, below.

TABLE 6

Whole plant downy mildew test and leaf disc test scoring scale

| Score | Phenotype leaves/leaf discs | Assessment |
|---|---|---|
| 1 | 100% sporulation, covered with spores on both side of the leaf tissue | Susceptible |
| 3 | 50% sporulation on both side of the leaf tissue | Susceptible |
| 5 | Less than 25% sporulation on one side of the leaf tissue | Susceptible |
| 7 | No sporulation, some necrosis | Resistant |
| 9 | No sporulation/no necrosis | Resistant |

*Even disease scores of 2, 4, 6, and 8 are used to designate intermediate disease severity, i.e., a severity that is in between the neighbouring odd scores.

Leaf Disc Downy Mildew Test

The F2 pop. 1, F2 pop. 2, and F2 pop. 3 *B. oleracea* plants described above were used in the leaf disc assay, which allows high-throughput disease testing. Plants with four true leaves were used, as this is the optimal developmental stage for leaf disc sampling.

Plants were inoculated with downy mildew isolate *Hyaloperonospora parasitica/Hyaloperonospora brassicae* Y113 (collected on *B. oleracea* in Dannstadt, Germany). At time point 0, plants were inoculated with $2 \times 10^4$ spores (20,000 spores/mL). Once infected, plants were kept in a plastic tent built in a climate cell, which was kept at 15° C. with a day-night cycle of 16 hours light-8 hours dark (16:8 cycle). The plants were scored 8 to 9 days after inoculation using the scoring scale shown in Table 6.

Results

Figure 15:
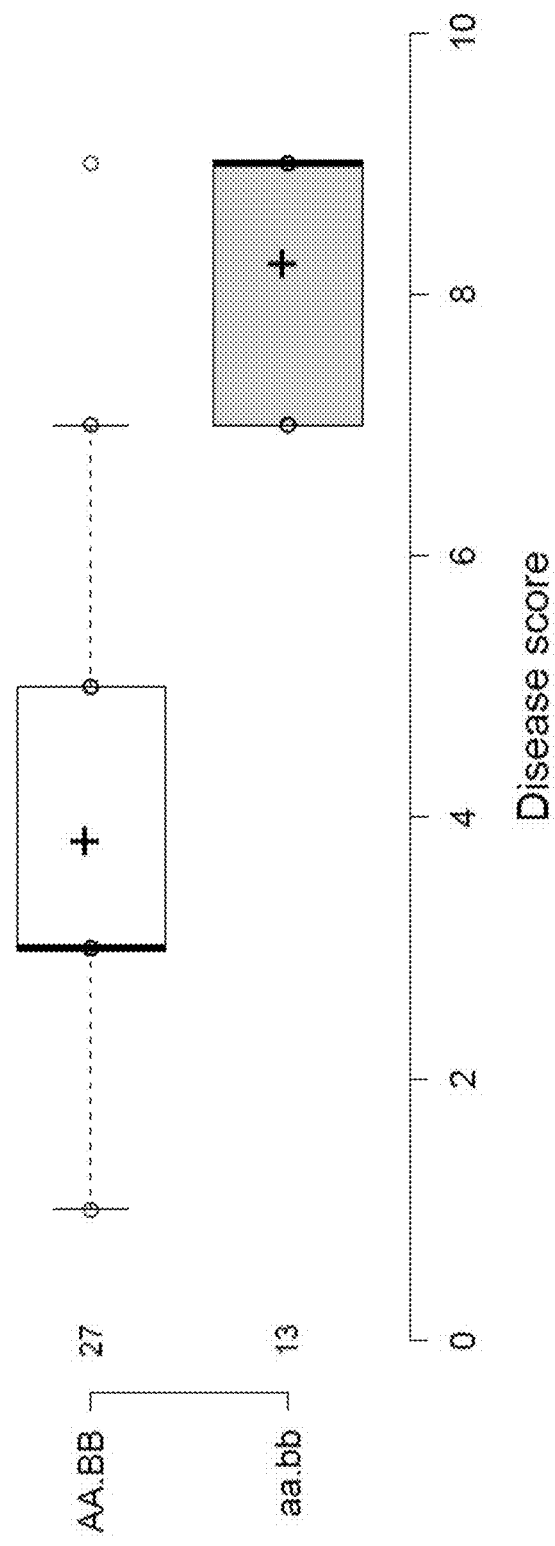
FIG. 15 shows a box plot of the whole plant downy mildew test results obtained 8 days post infection (dpi) from a segregating F2 population of rapid cycling *Brassica oleracea* (FastPlant®, https://fastplants.org/origin/) containing the mutant alleles bodmr6-1-1 and bodmr6-2. The y-axis lists the genotypes, and provides the number of plants tested: wild type ("AA BB"), 27 plants; and homozygous double mutant for mutant alleles bodmr6-1-1 and bodmr6-2 ("aa bb"), 13 plants. For all genotypes, "+" is the sample mean, "o" is a single data point, and the box reflects the variation within each genotype. The disease score shown on the x-axis ranges from 0 (susceptible) to 9 (resistant) (see Table 6).

FIG. 15 shows the results of the whole plant downy mildew test on the segregating F2 population 1. The average score of wild type ("AA BB") plants are clearly distinct from the average scores of homozygous double mutant plants ("aa bb"). Specifically, wild type plants have an average score of 4 (i.e., susceptible), while homozygous double mutant plants have an average score of about 8 (i.e., resistant). These results demonstrate that homozygous double mutants were resistant to downy mildew. The phenotypes of exemplary wild type ("AA BB") and homozygous double mutant ("aa bb") leaves inoculated with downy mildew are shown in FIG. 16.

Figure 17A:
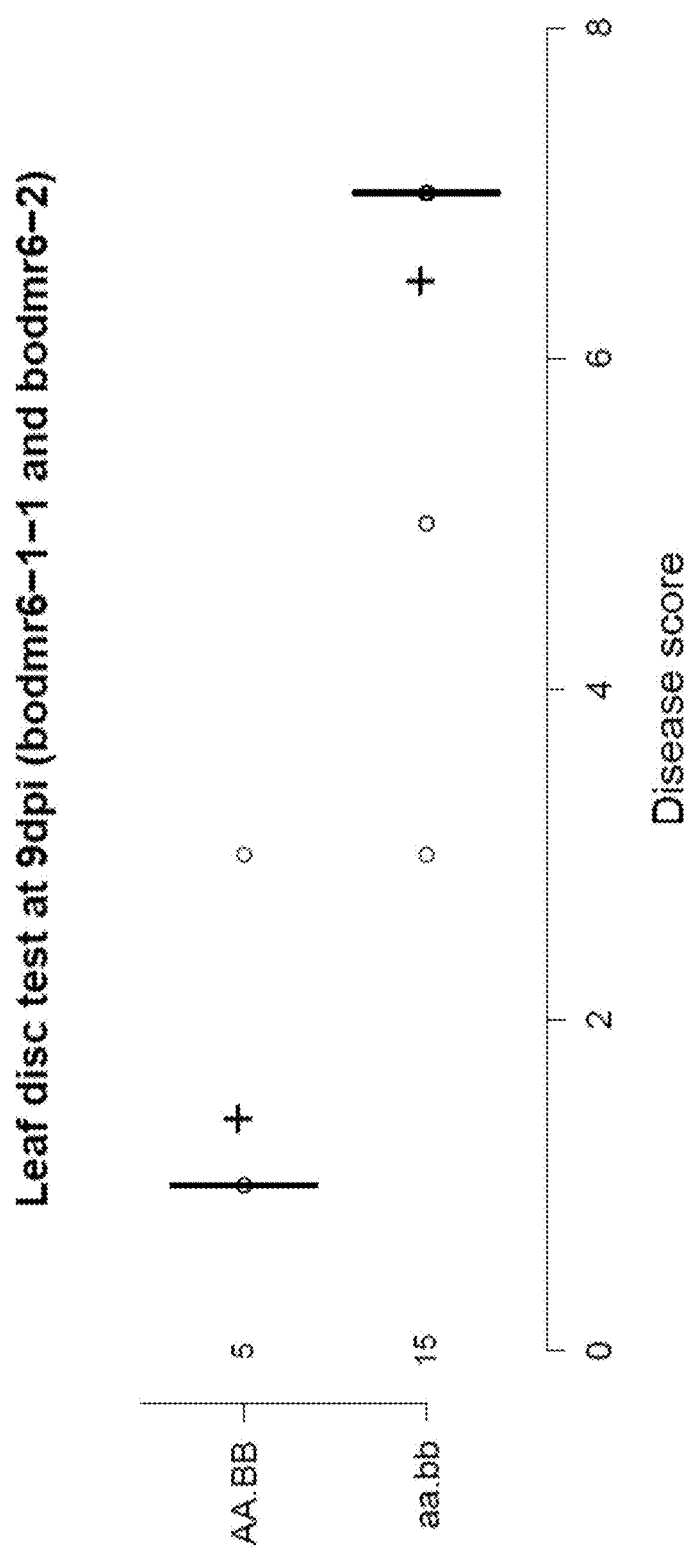
FIGS. 17A-17C show box plots of the leaf disc downy mildew test results obtained 9 dpi from three different segregating F2 populations of rapid cycling *Brassica oleracea* (FastPlant®, https://fastplants.org/origin/).
Figure 17B:
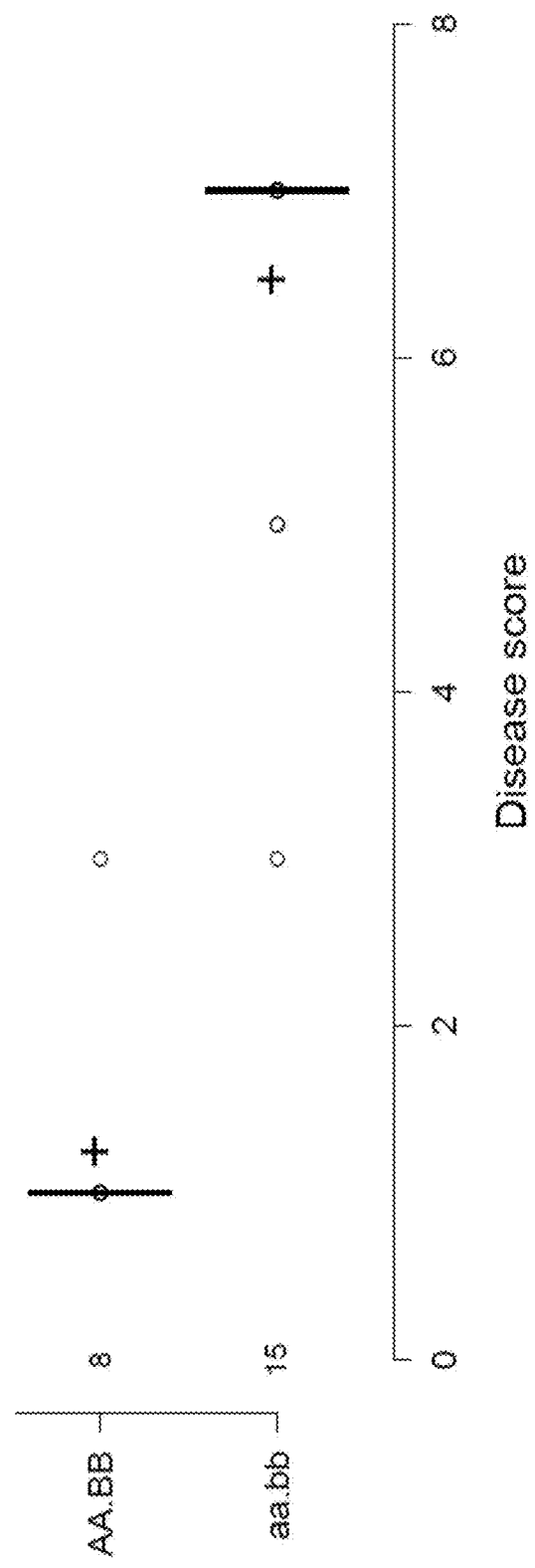
Figure 17C:
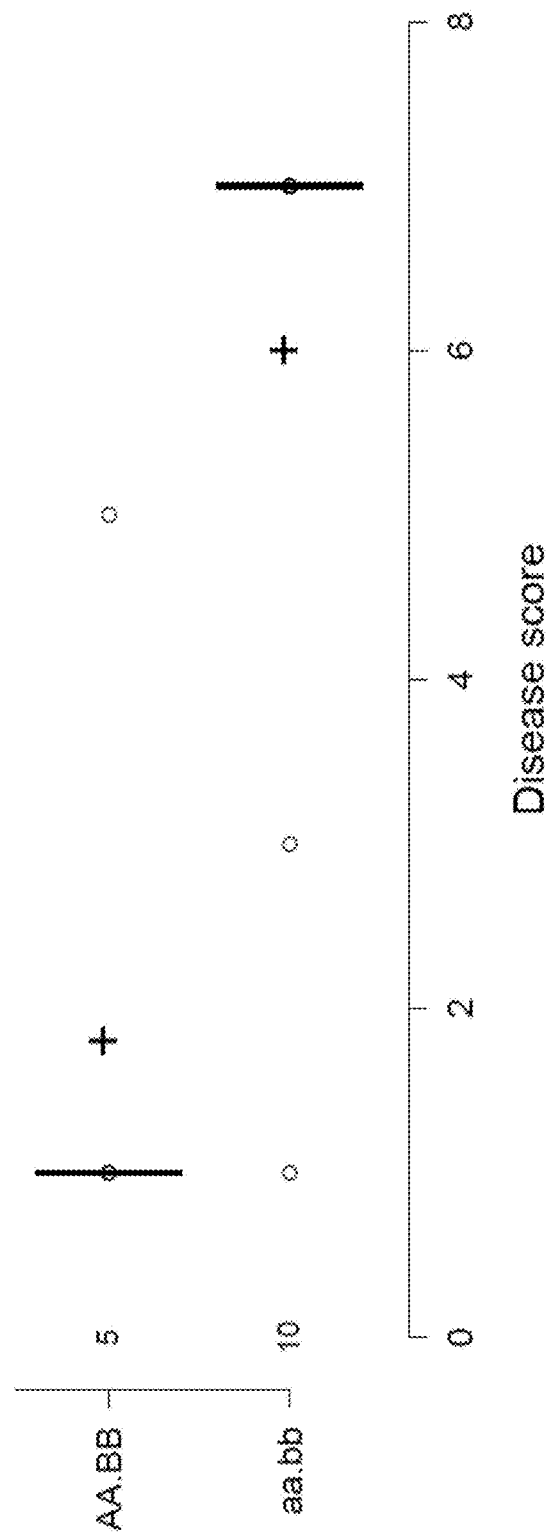
Figure 18A:
FIGS. 18A-18D show exemplary images of infected plants from a *Xanthomonas campestris campestris* (Xcc) test with different disease severity scores.
Figure 18B:
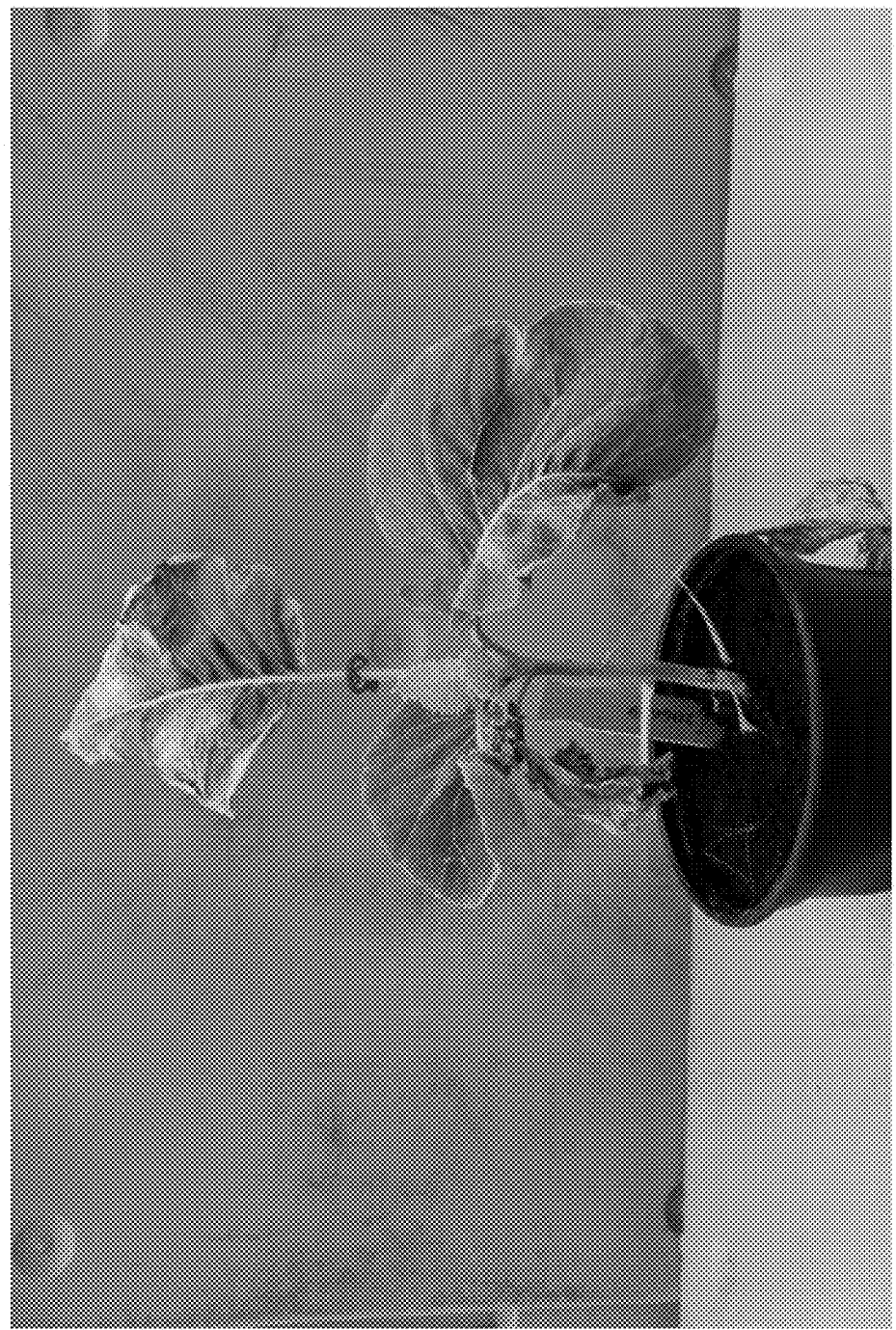
Figure 18C:
Figure 18D:

FIGS. 17A-17C show the results of the leaf disc downy mildew test on the segregating F2 pop. 1, F2 pop. 2, and F2 pop. 3. In all three segregating F2 populations, the wild type plants ("AA BB") were susceptible (score of about 1), and the double mutant plants ("aa bb") were resistant (score of about 6 to 7). All three DMR6-1 mutant alleles (i.e., bodmr6-1-1, bodmr6-1-2, and bodmr6-1-3), conferred resistance when a DMR6-2 mutant allele (i.e., bodmr6-2) was also present.

These results show that homozygous double mutants with all three combinations of mutant alleles (bodmr6-1-1 and bodmr6-2; bodmr6-1-2 and bodmr6-2; or bodmr6-1-3 and bodmr6-2) in *B. oleracea* are resistant to downy mildew when measured using the leaf disc test. In addition, homozygous double mutants with the alleles bodmr6-1-1 and bodmr6-2 in *B. oleracea* are resistant to downy mildew when measured using the whole plant test.

EXAMPLE 8

*Brassica oleracea* Plants with a Double Knockout of DMR6-1 and DMR6-2 have Intermediate Resistance to *Xanthomonas campestris Campestris* and Resistance to Downy Mildew Background The bacterial pathogen *Xanthomonas campestris campestris* (Xcc) is a major problem in areas with warm and wet conditions. Xcc infects plant leaves by wounds or through the hydathodes, and Xcc race 1 (Xcc 1) and race 4 (Xcc 4) are the most prevalent Xcc races in areas where *Brassica* crops are grown. Xcc race determination is based on Vicente et al. (2013), Molecular Plant Pathology, 14(1): 2-18.

Experimental Procedures

Plasmids for Gene Editing

Plasmids obtained and methods used were essentially as described by Belhaj et al. (2013), Plant Methods, 9:39. A plasmid with a customized single guide RNA (sgRNA) was created using an oligo (SEQ ID NO: 132). The newly created plasmid and plasmid pICSL11021 (containing CAS9; https://www.addgene.org/49771/) were harvested from *E. coli* cultures using the Qiagen Maxi prep kit. Plasmids were checked via both Sanger sequencing and restriction analysis and subsequently used for transfection. Mutations obtained in the DMR6-1 and DMR6-2 genes via gene editing (GE) all resulted in frameshift mutations leading to premature stop codons.

Protoplast Transfection and Regeneration

The starting material used for protoplast isolation was 16 to 19 day old leaves of cauliflower (i.e., *Brassica oleracea*) double haploid (DH) line 194190 in vitro seedlings (susceptible to downy mildew and Xcc). The protoplast isolation protocol was as follows:

1. Cut leaves feather-like in TVL, and keep in dark for 1 hour.
2. Replace TVL with 15 ml 0.6% enzyme solution, and incubate overnight in the dark at 25° C.
3. Filter liquids and tissue residue through 100 µm filter (yellow Greiner) and rinse with 30 ml CPW 20S.
4. Transfer to 4 round-bottom tubes.
5. Centrifuge for 10 minutes at 600 rpm without brakes.
6. Collect the floating protoplasts with a pasteur-pipet and transfer them to glass tubes containing W5.
7. Centrifuge for 6 min at 600 rpm with brakes.
8. Discard supernatant, collect the pellets in a glass tube, and fill the tube up with 10 ml of W5. Centrifuge for 6 minutes at 600 rpm with brakes. Repeat once.
9. Count the protoplasts (pps) and adjust to 1,000,000 pps/ml with MaMg.

The isolated protoplasts were then transfected using the CRISPR plasmids. The protoplast transfection protocol was as follows:

1. Add plasmid DNA, 5 µg CAS-9-2+20 g gRNA15 sgRNA to the bottom of a10 ml red-capped round-bottom tube.
2. Add 0.5 ml of the 1,000,000 pps/ml MaMg preparation (see step 9 of protoplast isolation protocol), and mix gently.
3. Add 0.5 ml PEG4000 Fluka solution (using a P1000 with a cut-off tip), mix immediately, and leave at room temperature for 20 min.
4. Add 9 ml of W5 and mix carefully. Centrifuge for 6 min at 600 rpm with brakes and repeat once.
5. Take up 80,000 pps/ml B-medium. Add 3 ml per 3 cm TC petri dish and close with parafilm.
6. Place dishes in the dark at 25° C.

Next, the transfected protoplasts were regenerated. The cell division and regeneration protocol was as follows:

1. 9 days after transfection, add 1.5 ml C-medium.
2. 23 days after transfection, transfer calli and medium contained in 1 small dish to 1 deep 9 cm petri dish with 15 ml K3-soft medium.
3. When the calli are 3 mm in size, transfer them to K3-solid medium for regenerating shoots.
4. When shoots formed transfer them to MS20 for rooting.

The composition of the media and stocks used in the protoplast transfection and regeneration processes are shown in Tables 7A and 7B, below.

TABLE 7A

Composition of media and stocks used for protoplast protocols

| | 1 l |
|---|---|
| 0.6% enzyme solution[1,3] | |
| 10x K3 stock | 100 ml |
| Cellulase onozuka R-10 | 6 g |
| Macerozyme R-10 | 10 g |
| Sucrose | 136.9 g |
| MES | 586 mg |
| 2,4-D | 1 mg |
| BAP | 0.5 mg |
| CPW 20S[1] | |
| 10x CPW stock | 100 ml |
| Sucrose | 200 g |
| pH | 5.8 |
| MaMg[1] | 500 ml |
| Mannitol | 45 g |
| MgCl$_2$•6H$_2$O | 1520 mg |
| MES | 500 mg |
| pH | 5.6-5.8 |

| | 1 l |
|---|---|
| K3-soft[2] | |
| 10x K3 stock | 100 ml |
| Sucrose | 68.4 g |
| Sea-plaque agarose | 2 g |
| BAP | 0.5 mg |
| 2,4-D | 0.1 mg |
| NAA | 0.1 mg |
| pH | 5.8 |
| K3-solid[2] | |
| 10x K3 stock | 100 ml |
| Sucrose | 5 g |
| Sea-plaque agarose | 7 g |
| Zeatin | 1 mg |
| BAP | 0.5 mg |
| IAA | 0.1 mg |
| pH | 5.8 |

[1]Filter sterilize;
[2]Autoclave;
[3]Store in freezer

TABLE 7B

Composition of media and stocks used for protoplast protocols

| TVL[2] | g/l |
|---|---|
| Sorbitol | 54.65 |
| CaCl$_2$•2H$_2$O | 7.35 |
| MES | 0.586 |
| pH | 5.8 |

| | mg/l |
|---|---|
| 10x K3 stock[1,3] | |
| NH$_4$NO$_3$ | 2500 |
| CaCl$_2$•2H$_2$O | 3000 |
| KNO$_3$ | 25000 |
| MgSO$_4$•7H$_2$O | 2500 |

TABLE 7B-continued

Composition of media and stocks used for protoplast protocols

| | |
|---|---|
| (NH$_4$)$_2$SO$_4$ | 1340 |
| NaH$_2$PO$_4$ | 1500 |
| NaFeEDTA | 430 |
| MnSO$_4$•1H$_2$O | 100 |
| H$_3$BO$_3$ | 30 |
| ZnSO$_4$•7H$_2$O | 20 |
| KI | 10 |
| Na$_2$MoO$_4$•2H$_2$O | 2.5 |
| CoCl$_2$•6H$_2$O | 0.25 |
| CuSO$_4$•5H$_2$O | 0.25 |
| Xylose | 2500 |
| Myo inositol | 1000 |
| Thiamine•HCl | 100 |
| Nicotinic acid | 10 |
| Pyridoxin•HCl | 10 |
| 10x CPW stock solution[1,3] | |
| KH$_2$PO$_4$ | 272 |
| KNO$_3$ | 1010 |
| CaCl$_2$•2H$_2$O | 14800 |
| MgSO$_4$•7H$_2$O | 2460 |
| KI | 1.6 |
| CuSO$_4$•5H$_2$O | 0.25 |

| W5[1] | g/l |
|---|---|
| CaCl$_2$•2H$_2$O | 18.4 |
| NaCl | 9 |
| KCl | 0.8 |
| Glucose | 1 |
| pH | 5.8 |

| | mg/l |
|---|---|
| B-medium[1] | |
| CaCl$_2$•2H$_2$O | 750 |
| KNO$_3$ | 2500 |
| MgSO$_4$•7H$_2$O | 250 |
| (NH$_4$)$_2$SO$_4$ | 134 |
| NaH$_2$PO$_4$ | 150 |
| Na$_2$EDTA | 37.3 |
| FeSO$_4$•7H$_2$O | 27.8 |
| MnSO$_4$•1H$_2$O | 10 |
| H$_3$BO$_3$ | 3 |
| ZnSO$_4$•7H$_2$O | 2 |
| KI | 0.75 |
| Na$_2$MoO$_4$•2H$_2$O | 0.25 |
| CoCl$_2$•6H$_2$O | 0.025 |
| CuSO$_4$•5H$_2$O | 0.025 |
| Myo-inositol | 100 |
| Thiamine•HCl | 10 |
| Nicotinic acid | 1 |
| Pyridoxine•HCl | 1 |
| Glucose | 20000 |
| Mannitol | 70000 |
| NAA | 1 |
| BAP | 1 |
| 2,4-D | 0.25 |
| pH | 5.8 |
| C-medium[1] | |
| NH$_4$NO$_3$ | 200 |
| KH$_2$PO$_4$ | 75 |
| CaCl$_2$•2H$_2$O | 525 |
| KNO$_3$ | 1250 |
| MgSO$_4$•7H$_2$O | 250 |
| (NH$_4$)$_2$SO$_4$ | 67 |
| NaH$_2$PO$_4$ | 75 |
| Na$_2$EDTA | 37.3 |
| FeSO$_4$•7H$_2$O | 27.8 |
| MnSO$_4$•1H$_2$O | 10 |
| H$_3$BO$_3$ | 3 |
| ZnSO$_4$•7H$_2$O | 2 |
| KI | 0.75 |
| Na$_2$MoO$_4$•2H$_2$O | 0.25 |
| COCl$_2$•6H$_2$O | 0.025 |
| CuSO$_4$•5H$_2$O | 0.025 |
| Myo-inositol | 100 |
| Thiamine•HCl | 10 |
| Nicotinic acid | 1 |
| Pyridoxine•HCl | 1 |
| Glucose | 40000 |
| Mannitol | 20000 |
| NAA | 0.2 |
| BAP | 1 |
| pH | 5.8 |

[1]Filter sterilize;
[2]Autoclave;
[3]Do not adjust pH and store at 0-5° C.

Genotyping of Regenerated Plants

After multiple prescreening rounds of both calli and microcalli, plantlets were genotyped. DNA was isolated from the leaves of plantlets, and two independent DNA isolations were sequenced using amplicon deep sequencing (at least 100× coverage) and results were analyzed using CRISPRESSO (http://crispresso.rocks/) with default settings. The sequencing primers used are shown in Table 8, below, whereby primers B09 and F02 were used together and primers BoDMR6.12ex3f1 BC and BoDMR6.12ex3f1 BC were used together. In addition to genotyping, ploidv of the selected plants was confirmed to be 2N via flow cytometry.

TABLE 8

Sequencing primers for plantlet genotyping

| Primer name | Primer sequence |
|---|---|
| B09 | ACACTCTTTCCCTACACGACGCTCTTCCGATCTGCTTTTG CAGGGAAGTTGTG (SEQ ID NO: 133) |
| F02 | CTCGGCATTCCTGCTGAACCGCTCTTCCGATCTACCGCAA ACGGTAGCATCT (SEQ ID NO: 134) |
| BoDMR6.12ex3f1 BC | ACACTCTTTCCCTACACGACGCTCTTCCGATCTGTCAACA CATGGCAGTCAAC (SEQ ID NO: 135) |
| BoDMR6.12ex3r1 BC | CTCGGCATTCCTGCTGAACCGCTCTTCCGATCTGTCGGTA TGAGCAGGTAAAC (SEQ ID NO: 136) |

A double knockout (i.e., knockout mutations in both DMR6-1 and DMR6-2) line was generated using the above methods. FIGS. 22A-22F show the nucleotide alignment of the DMR6-1 knockout allele with the corresponding wild type sequence of DMR6-1, whereby the knockout allele (BoDMR6_-5 bp_scf1=SEQ ID NO: 137) is shown below the wild type sequence (BoDMR6_WT_scf108=SEQ ID NO: 114). FIGS. 23A-23E show the nucleotide alignment of the DMR6-2 knockout allele with the corresponding wild type sequence of DMR6-2, whereby the knockout allele (BoDMR6_-1bp_scf1=SEQ ID NO: 138) is shown below the wild type sequence (BoDMR6_WT_scf155=SEQ ID NO: 115). FIGS. 24A-24B show the polypeptide alignment of the DMR6-1 knockout polypeptide with the corresponding wild type polypeptide of DMR6-1, whereby the knockout polypeptide (BoDMR6_-5 bp_scf1=SEQ ID NO: 139) is shown below the wild type polypeptide (BoDMR6_WT_scf108=SEQ ID NO: 112). FIGS. 25A-25B show the polypeptide alignment of the DMR6-2 knockout polypeptide with the corresponding wild type polypeptide of DMR6-2, whereby the knockout polypeptide (BoDMR6_-1bp_scf1=SEQ ID NO: 140) is shown below the wild type polypeptide (BoDMR6_WT_scf155=SEQ ID NO: 113). The double knockout line was referred to as "GE" for "Genome Editing". In addition to the GE line, a wild type line was produced from the same process, i.e., plants were regenerated from protoplasts that did not contain the double mutation. This line was referred to as "GE.WT" or "WT".

Preparation for Xcc Test

The plants used in the Xcc test were control plants, GE plants, and GE.WT plants. The control plants were a panel of three lines: KT38 (susceptible to Xcc), Resistant line 1 (R1; resistant to Xcc 1 and Xcc 4), and Resistant line 2 (R2; resistant to Xcc 1 and Xcc 4). R1 and R2 have been used in *Brassica oleracea* breeding as sources of resistance, and it is thought that their resistances are classical resistance genes that are race-specific. The control plants were first sown, and then transferred to 1 liter pots. These pots were placed in a clean greenhouse for development. Plants were considered sufficiently mature for testing when they had at least 5 to 6 true leaves.

The GE plants and GE.WT plants were produced as described above. GE plants (cuttings) from in vitro tissue culture were transferred to a GMO greenhouse. The plants were potted in 1 liter pots, and grown in the GMO greenhouse. Plants were considered sufficiently mature for testing when they had at least 5 to 6 expanded leaves.

The pathogens used in the Xcc test were Xcc race 1 (Xcc 1) and Xcc race 4 (Xcc 4) isolates from the pathogen collection. If there were doubts about the purity of the isolate, it was plated on semi-selective media to check whether it was clean before beginning the preparation. For preparation, the chosen isolate was plated on KB plates and grown for 2 days. Then, the bacteria were washed off of the plates and diluted with normal tap water to an OD of 0.4. In these tests, Xcc 1 and Xcc 4 were used, as they are the most prevalent in *B. oleracea* growing areas, but Xcc 1 and Xcc 6 would have been another option (Vicente et al. (2013), Molecular Plant Pathology, 14(1): 2-18).

Xcc Test Protocol

For testing, a climate cell or greenhouse was used that was kept at 25° C. with a day-night cycle of 16 hours light-8 hours dark (16:8 cycle). In this climate cell or greenhouse, a tent was built to cover the plants so that they could be maintained at high humidity. Inside the tent, containers were used to create a surface for the plants to stand in that could be filled with water. The day before infection, plants were placed in the containers, and the containers were filled with water so that the plants were standing in a shallow layer of water. At this point, a ring was placed on the youngest formed true leaf of the plants if needed.

The plants were infected by spraying them with a fine mist of the bacterial suspension (preparation described above). Then, the tent was closed to maintain humidity. The day after infection, the tent was slightly opened to avoid secondary infections. In order to keep the humidity high during the test, a layer of water was kept in the containers during the first 2 to 3 weeks. After that, the water layer was not maintained so that secondary infections and/or rotting would not occur.

Scoring of local infection began as soon as the first symptoms appeared. Local infection symptoms were scored for all of the leaves that were fully developed at the time of infection. Scoring of systemic infection was done one, two, and three weeks after infection. Systemic infection symptoms were scored for any new leaves that emerged after the infection.

For both local and systemic infections, a scale of 1 to 9 was used to score the severity of infection. Table 9 provides a detailed description of the Xcc test scoring scale. A score of 9 corresponded to a plant that was completely healthy with an absence of symptoms. A score of 1 corresponded to a plant that was completely wilted/dead. At the end of systemic infection scoring, susceptible plants scored 1. FIGS. 18A-18D show exemplary images of plants scored as 1, 3, 5, and 7.

TABLE 9

| Xcc test scoring scale | | | |
|---|---|---|---|
| Local infection | | Systemic infection | |
| Infection severity | Phenotype | Infection severity | Phenotype |
| 1 | All leaves are more than 50% infected | 1 | Plant is dead |
| 3 | All leaves are less than 50% infected | 3 | All new leaves are infected |
| 4 | More than 2, but not all leaves infected | 4 | More than 2, but not all new leaves infected |
| 5 | 1 or 2 leaves infected with V-shaped lesions | 5 | 1 or 2 new leaves infected with V-shaped lesions |
| 7 | No clear infection, but some leaves show spots | 7 | No clear infection, but older leaves show some symptoms |

TABLE 9-continued

| Xcc test scoring scale | | | |
|---|---|---|---|
| Local infection | | Systemic infection | |
| Infection severity | Phenotype | Infection severity | Phenotype |
| 9 | Nothing to see, completely clean plant | 9 | Nothing to see, completely clean plant |

Downy Mildew Whole Plant Test G

The downy mildew whole plant test was performed as described in Example 7.

Results

Figure 19A:
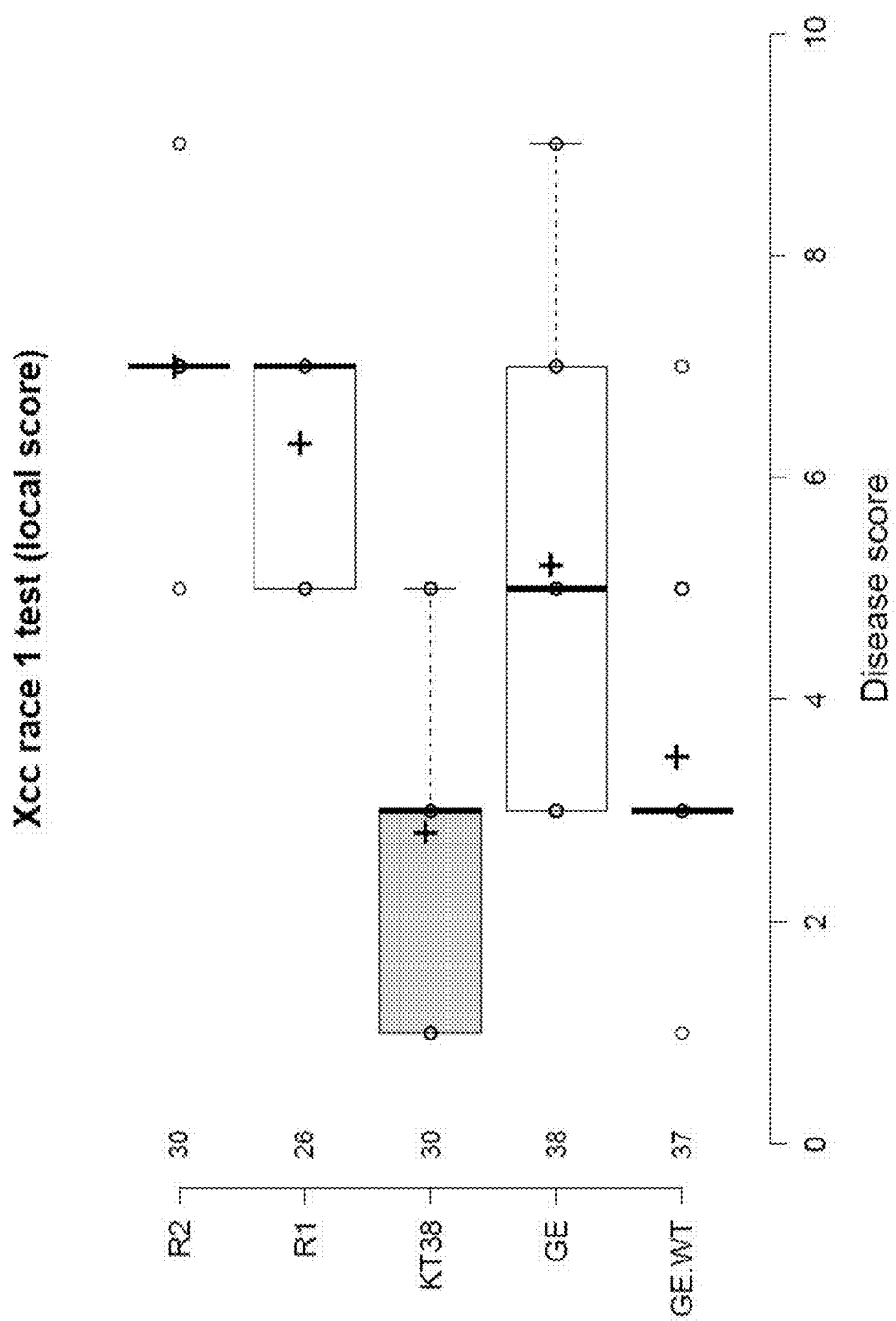
FIGS. 19A-19D show box plots of results from Xcc tests using different Xcc strains (Xcc 1 or Xcc 4) to infect DMR6-1 and DMR6-2 double knockout and wild type plants.
Figure 19B:
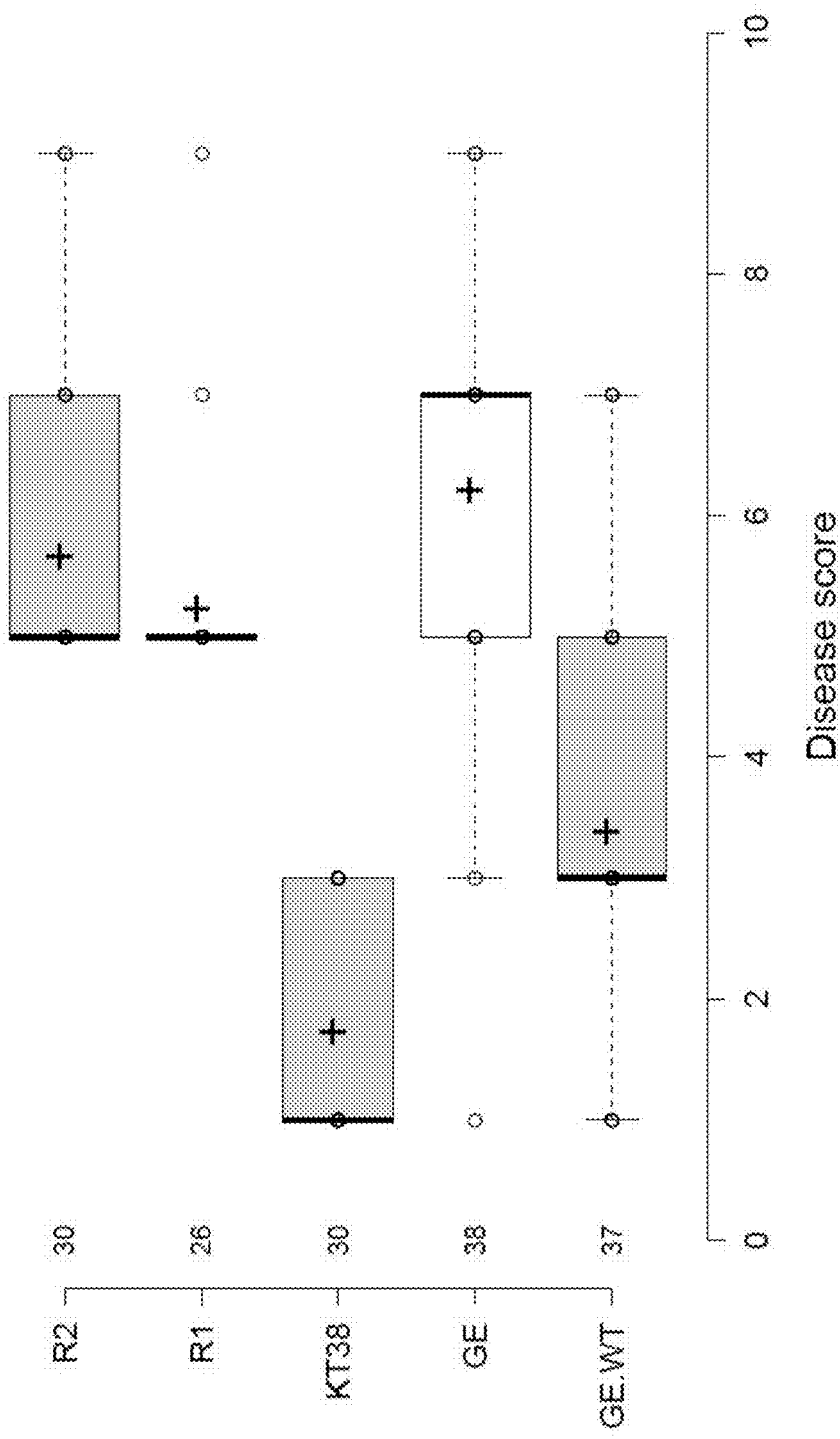

FIGS. 19A and 19B show the results of the Xcc test using Xcc 1. FIG. 19A shows local infection scores. Both of the resistant control plant lines (R1 and R2) had an average local infection score of about 7, while the susceptible control plant line (KT38) had an average local infection score of about 2. The wild type plants processed with the same protocol as the GE plants (GE.WT) had an average local infection score of about 3. The DMR6-1 and DMR6-2 double knockout plants (GE) had an average local infection score of about 5, which was intermediate between the resistant and susceptible control line results. FIG. 19B shows systemic infection scores. Both R1 and R2 had an average systemic infection score of about 5 to 6, while KT38 had an average systemic infection score of about 1 to 2. GE.WT had an average systemic infection score of about 3. GE had an average systemic infection score of about 6, which was comparable to the resistant control line (R1 and R2) results.

Figure 19C:
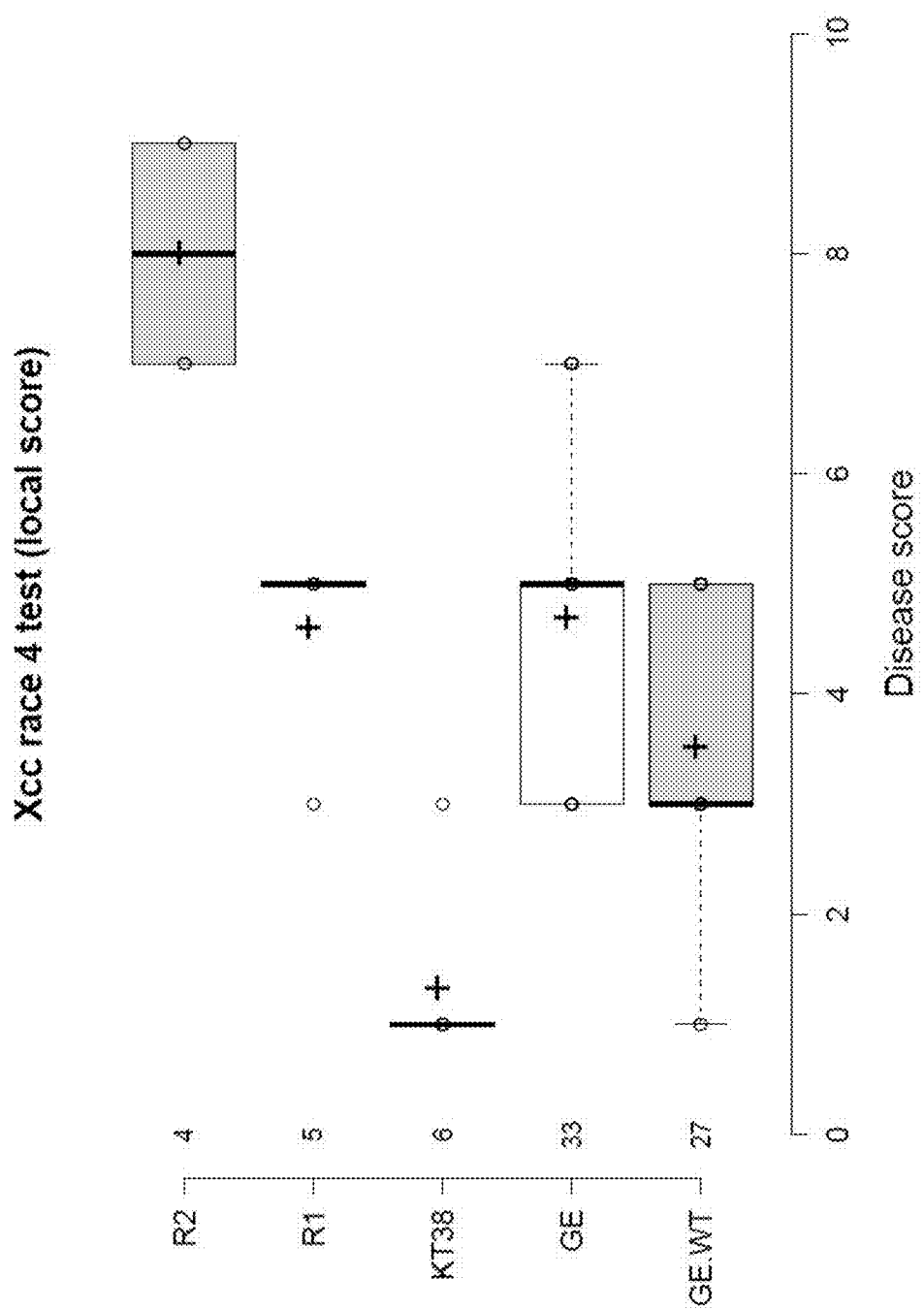
Figure 19D:
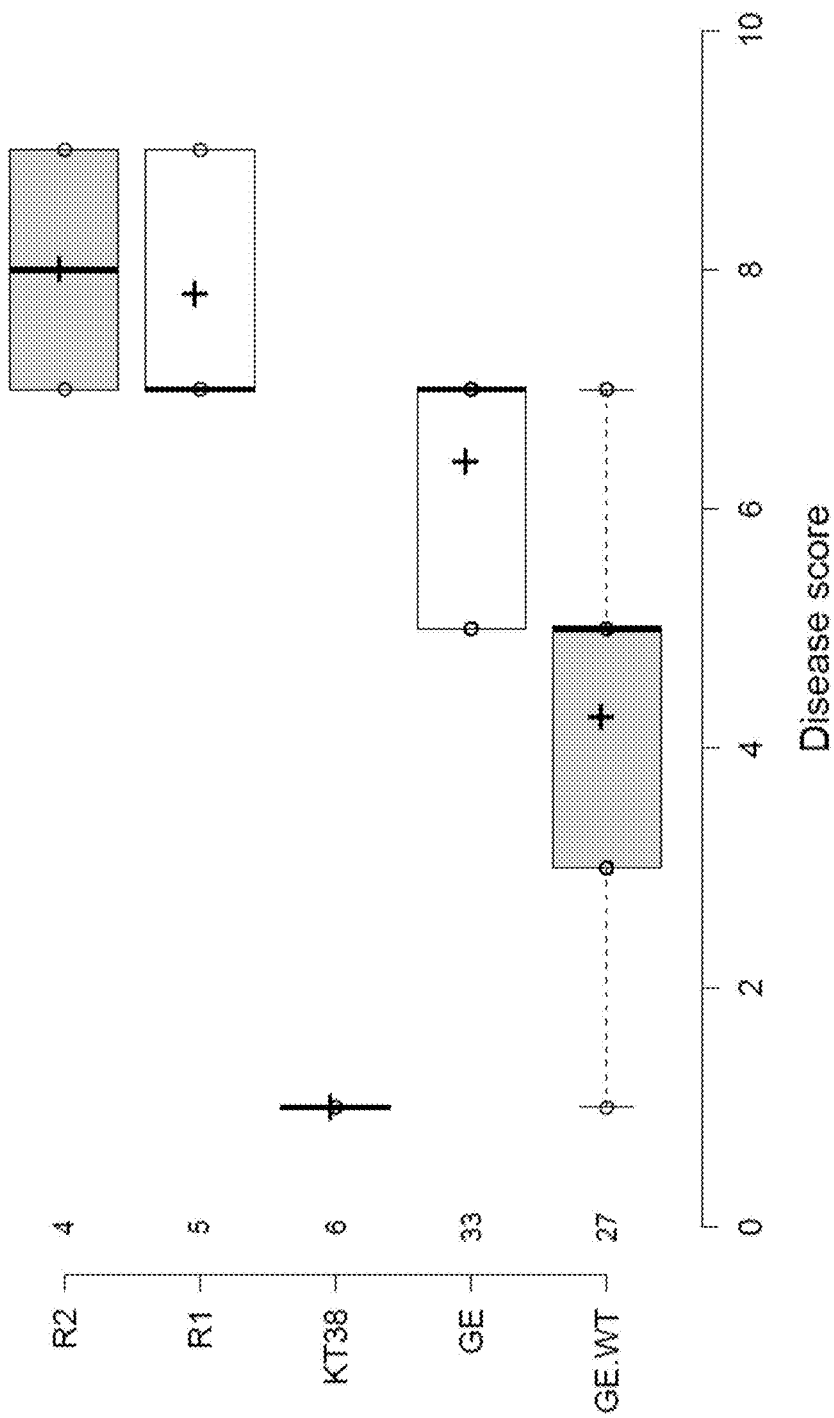
Figure 20:
FIG. 20 shows an exemplary image of the systemic resistance phenotype of a DMR6-1 and DMR6-2 double knockout plant (GE; on right) and a wild type plant processed with the same protocol as the GE plant (i.e., a plant regenerated from a protoplast that did not contain the double mutation; GE.WT, on left). Pictures were taken four weeks after infection with Xcc.

FIGS. 19C and 19D show the results of the Xcc test using Xcc 4. FIG. 19C shows local infection scores. The resistant control line R1 had an average local infection score of about 5, while the resistant control line R2 had an average local infection score of about 8. The susceptible control line (KT38) had an average local infection score of about 1. GE.WT had an average local infection score of about 3. GE had an average local infection score of about 5, which was the same as the R1 score, and intermediate between the R2 and KT38 scores. FIG. 19D shows systemic infection scores. Both R1 and R2 had an average systemic infection score of about 8, while KT38 had an average systemic infection score of about 1. GE.WT had an average systemic infection score of about 4, and GE had an average systemic infection score of about 7. FIG. 20 shows an exemplary image of the systemic resistance phenotype of a GE plant (on right) compared to a GE.WT plant (on left).

For both Xcc 1 and Xcc 4, the local infection score results showed that GE plants were more resistant than GE.WT and KT38 plants. The resistant control plants, R1 and R2, were more resistant than GE plants. The systemic infection score results for both Xcc 1 and Xcc 4 showed that GE plants were more resistant than GE.WT and KT38. The comparison to the resistant controls revealed differences between Xcc 1 and Xcc 4: R1 and R2 plants were more resistant to Xcc 4 than GE plants, but GE, R1, and R2 plants all had a similar resistance to Xcc 1.

Figure 21:
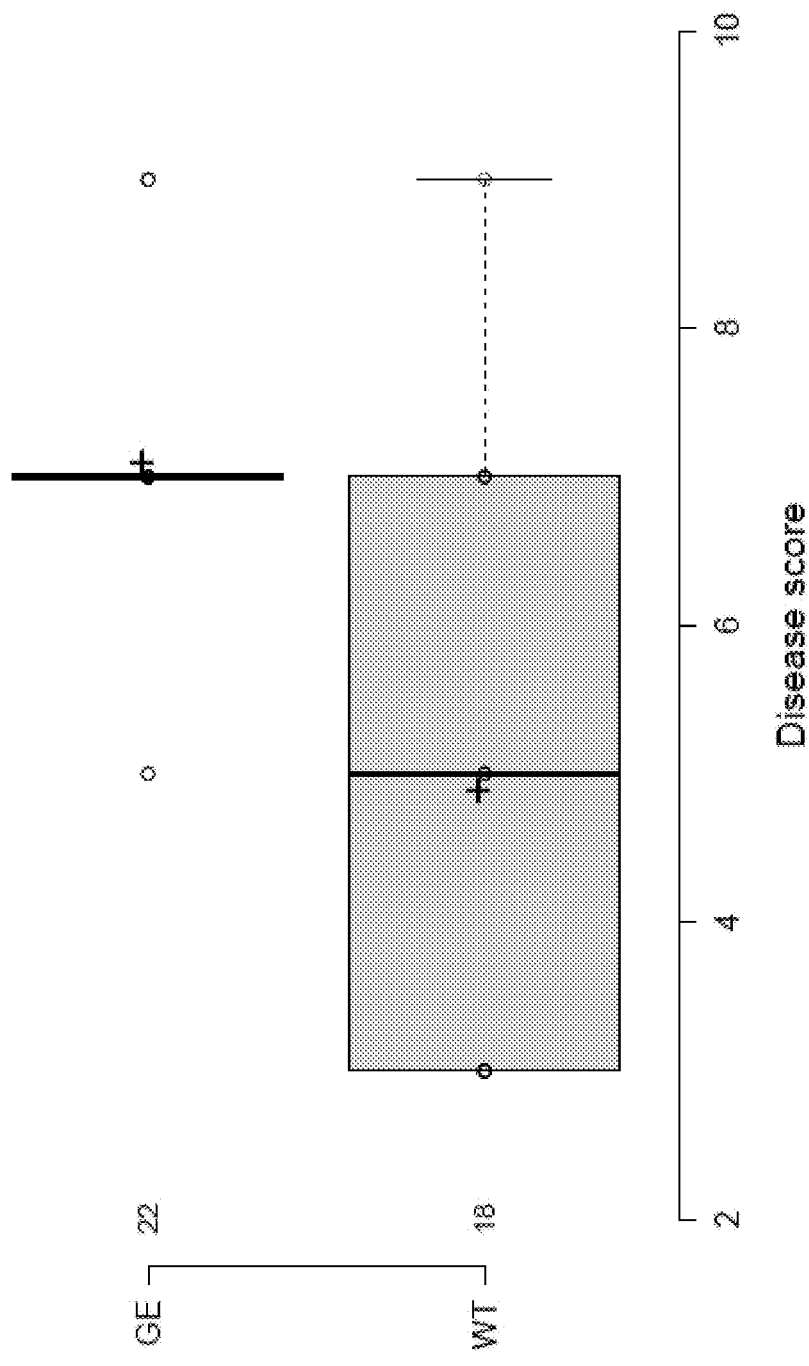
FIG. 21 shows a box plot of whole plant downy mildew test results obtained 8 dpi from DMR6-1 and DMR6-2 double knockout plants (GE, 22 plant), and wild type plants processed with the same protocol as the GE plants (i.e., plants regenerated from protoplasts that did not contain the double mutation; WT, 18 plants). "+" is the sample mean, "∘" is a single data point, the box reflects the variation within each genotype, the results are the combined results from two independent tests, and the disease score shown on the x-axis ranges from 2 (susceptible) to 9 (resistant).

FIG. 21 shows the result of the downy mildew whole plant test. WT plants had an average disease score of about 5 (i.e., susceptible), while GE plants had an average disease score of about 7 (i.e., resistant).

Taken together, these results show that DMR6-1 and DMR6-2 double knockout plants have intermediate resistance to Xcc (i.e., Xcc 1 and Xcc 4) and resistance to downy mildew.

EXAMPLE 9

Testing a Double Knockout of DMR6-1 and DMR6-2 in *Brassica* Species for Resistance to Downy Mildew and Xcc Experimental Procedures Additional cauliflower lines, broccoli lines, and kohlrabi lines containing a double knockout of DMR6-1 and DMR6-2 will be produced using the mutant alleles described in Examples 7 and 8. These double knockout lines will be tested for resistance to downy mildew and Xcc as described in Examples 7 and 8.

Successful lines will be combined with resistant QTL identified from known resistant lines R1 and R2. These lines containing stacked resistant traits will be developed commercially.

Results

The cauliflower lines, broccoli lines, and kohlrabi lines containing a double knockout of DMR6-1 and DMR6-2 are resistant to downy mildew and are intermediate resistant to Xcc. The lines containing stacked resistant traits are resistant to downy mildew and are intermediate resistant to Xcc.

What is claimed is:

1. A mutant *Brassica oleracea* plant, wherein the plant has a reduced activity or a reduced level of a DMR6-1 polypeptide comprising at least 95% sequence identity to SEQ ID NO: 112 as compared to a corresponding wild type *Brassica oleracea* plant, and wherein the mutant *Brassica oleracea* plant has at least one non-natural mutation introduced into a DMR6-1 coding sequence comprising at least 95% sequence identity to SEQ ID NO: 114; wherein the mutant *Brassica oleracea* plant further has a reduced activity or a reduced level of a DMR6-2 polypeptide comprising at least 95% sequence identity to SEQ ID NO: 113 as compared to a corresponding wild type *Brassica oleracea* plant, and wherein the mutant *Brassica oleracea* plant has at least one non-natural mutation introduced into a DMR6-2 coding sequence comprising at least 95% sequence identity to SEQ ID NO: 115; and wherein the plant exhibits resistance to *Hyaloperonospora parasitica/Hyaloperonospora brassicae*.

2. The mutant *Brassica oleracea* plant of claim 1, wherein the DMR6-1 coding sequence comprises SEQ ID NO: 114; and wherein the DMR6-2 coding sequence comprises SEQ ID NO: 115.

3. The mutant *Brassica oleracea* plant of claim 1, wherein the DMR6-1 polypeptide comprises SEQ ID NO: 112; and wherein the DMR6-2 polypeptide comprises SEQ ID NO: 113.

4. The mutant *Brassica oleracea* plant of claim 1, wherein the plant further exhibits intermediate resistance to *Xanthomonas campestris campestris*.

5. The mutant *Brassica oleracea* plant of claim 1, wherein the at least one non-natural mutation introduced into the DMR6-1 coding sequence is a premature stop codon, and wherein the at least one non-natural mutation introduced into the DMR6-2 coding sequence is a premature stop codon.

6. The mutant *Brassica oleracea* plant of claim 1, wherein the at least one non-natural mutation introduced into the DMR6-1 coding sequence reduces an activity or a level of the DMR6-1 polypeptide as compared to a corresponding wild type *Brassica oleracea* plant; and
wherein the at least one non-natural mutation introduced into the DMR6-2 coding sequence reduces an activity or a level of the DMR6-2 polypeptide as compared to a corresponding wild type *Brassica oleracea* plant.

7. The mutant *Brassica oleracea* plant of claim 6, wherein the DMR6-1 polypeptide comprises SEQ ID NO: 112; and wherein the DMR6-2 polypeptide comprises SEQ ID NO: 113.

8. The mutant *Brassica oleracea* plant of claim 6, wherein the DMR6-1 coding sequence comprises SEQ ID NO: 114; and wherein the DMR6-2 coding sequence comprises SEQ ID NO: 115.

9. The mutant *Brassica oleracea* plant of claim 6, wherein the at least one non-natural mutation introduced into the DMR6-1 polypeptide is selected from the group consisting of a premature stop codon introduced into the DMR6-1 coding sequence, a frameshift mutation introduced into the DMR6-1 coding sequence, an insertion introduced into the DMR6-1 coding sequence, a deletion of a part or a whole of the DMR6-1 coding sequence, an altered amino acid in a conserved domain of the DMR6-1 polypeptide, a modified upstream sequence, a mutated promoter element, and an activated repressor element; and wherein the at least one non-natural mutation that reduces the activity or level of the DMR6-2 polypeptide is selected from the group consisting of a premature stop codon introduced into the DMR6-2 coding sequence, a frameshift mutation introduced into the DMR6-2 coding sequence, an insertion introduced into the DMR6-2 coding sequence, a deletion of a part or a whole of the DMR6-2 coding sequence, an altered amino acid in a conserved domain of the DMR6-2 polypeptide, a modified upstream sequence, a mutated promoter element, and an activated repressor element.

10. The mutant *Brassica oleracea* plant of claim 1, wherein the plant is a *Brassica oleracea* cultivar selected from the group consisting of cabbage, kohlrabi, kale, Brussels sprouts, collard greens, broccoli, Romanesco broccoli, and cauliflower.

11. The mutant *Brassica oleracea* plant of claim 1, wherein the at least one non-natural mutation introduced into the DMR6-1 coding sequence is selected from the group consisting of a single nucleotide change from C to T at a position corresponding to nucleotide 181 of reference sequence SEQ ID NO: 114, a single nucleotide change from C to T at a position corresponding to nucleotide 691 of reference sequence SEQ ID NO: 114, a single nucleotide change from G to A at a position corresponding to nucleotide 714 of reference sequence SEQ ID NO: 114, and a deletion of five nucleotides starting at a position corresponding to nucleotide 601 of reference sequence SEQ ID NO: 114; and wherein the at least one non-natural mutation introduced into the DMR6-2 coding sequence is selected from the group consisting of a single nucleotide change from G to A at a position corresponding to nucleotide 368 of reference sequence SEQ ID NO: 115, and a deletion of the nucleotide at a position corresponding to nucleotide 600 of reference sequence SEQ ID NO: 115.

12. A seed, tissue, or plant part of the *Brassica oleracea* plant of claim 1, wherein the seed, tissue, or plant part comprises the reduced activity or the reduced level of the DMR6-1 polypeptide and the reduced activity or the reduced level of the DMR6-2 polypeptide, and wherein the seed, tissue, or plant part comprises at least one non-natural mutation in the DMR6-1 coding sequence and at least one non-natural mutation in the DMR6-2 coding sequence.

13. A method for obtaining a mutant *Brassica oleracea* plant which is resistant to *Hyaloyeronosyora parasitica/ Hyaloyeronosyora brassicae*, comprising reducing an activity or a level of a DMR6-1 polypeptide comprising at least 95% sequence identity to SEQ ID NO: 112 in a *Brassica oleracea* plant as compared to a corresponding wild type *Brassica oleracea* plant by introducing at least one non-natural mutation into a DMR6-1 coding sequence comprising at least 95% sequence identity to SEQ ID NO: 114, and reducing an activity or a level of a DMR6-2 polypeptide comprising at least 95% sequence identity to SEQ ID NO: 113 in a *Brassica oleracea* plant as compared to a corresponding wild type *Brassica oleracea* plant by introducing at least one non-natural mutation into a DMR6-2 coding sequence comprising at least 95% sequence identity to SEQ ID NO: 115.

14. The method of claim 13, wherein the at least one non-natural mutation introduced into the DMR6-1 coding sequence is achieved by a mutagenic treatment, a radiation treatment, or a gene editing technique, and wherein the at least one non-natural mutation introduced into the DMR6-2 coding sequence is achieved by a mutagenic treatment, a radiation treatment, or a gene editing technique.

15. The method of claim 13, wherein the mutant *Brassica oleracea* plant further exhibits intermediate resistance to *Xanthomonas* camyestris camyestris.

16. A mutant *Brassica oleracea* plant produced from the method of claim 13, wherein the plant comprises at least one non-natural mutation in the DMR6-1 coding sequence and at least one non-natural mutation in the DMR6-2 coding sequence, and wherein the plant comprises the reduced activity or the reduced level of the DMR6-1 polypeptide and the reduced activity or the reduced level of the DMR6-2 polypeptide.

17. The mutant *Brassica oleracea* plant of claim 16, wherein the plant is a *Brassica oleracea* cultivar selected from the group consisting of cabbage, kohlrabi, kale, Brussels sprouts, collard greens, broccoli, Romanesco broccoli, and cauliflower.

18. The mutant *Brassica oleracea* plant of claim 16, wherein the DMR6-1 polypeptide comprises SEQ ID NO: 112; and wherein the DMR6-2 polypeptide comprises SEQ ID NO: 113.

19. The mutant *Brassica oleracea* plant of claim 16, wherein the DMR6-1 coding sequence comprises SEQ ID NO: 114; and wherein the DMR6-2 coding sequence comprises SEQ ID NO: 115.

20. A seed, tissue, or plant part of the mutant *Brassica oleracea* plant of claim 16, wherein the seed, tissue, or plant part comprises at least one non-natural mutation in the DMR6-1 coding sequence and at least one non-natural mutation in the DMR6-2 coding sequence, and wherein the seed, tissue, or plant part comprises the reduced activity or the reduced level of the DMR6-1 polypeptide and the reduced activity or the reduced level of the DMR6-2 polypeptide.

* * * * *

SEQUENCE LISTING

<160> NUMBER OF SEQ ID NOS: 144

<210> SEQ ID NO 1
<211> LENGTH: 33
<212> TYPE: DNA
<213> ORGANISM: Artificial Sequence
<220> FEATURE:
<223> OTHER INFORMATION: forward primer

<400> SEQUENCE: 1
ttctgggatc caatggcggc aaagcttgat atc    33

```
<210> SEQ ID NO 2
<211> LENGTH: 39
<212> TYPE: DNA
<213> ORGANISM: Artificial Sequence
<220> FEATURE:
<223> OTHER INFORMATION: reverse primer

<400> SEQUENCE: 2
gatatatgaa ttcttagttg tttagaaaat tctcgaggc                              39

<210> SEQ ID NO 3
<211> LENGTH: 33
<212> TYPE: DNA
<213> ORGANISM: Artificial Sequence
<220> FEATURE:
<223> OTHER INFORMATION: RNAiDMR6F

<400> SEQUENCE: 3
aaaaagcagg ctgaccgtcc acgtctctct gaa                                    33

<210> SEQ ID NO 4
<211> LENGTH: 33
<212> TYPE: DNA
<213> ORGANISM: Artificial Sequence
<220> FEATURE:
<223> OTHER INFORMATION: RANiDMR6R

<400> SEQUENCE: 4
agaaagctgg gtgaaacgat gcgaccgata gtc                                    33

<210> SEQ ID NO 5
<211> LENGTH: 29
<212> TYPE: DNA
<213> ORGANISM: Artificial Sequence
<220> FEATURE:
<223> OTHER INFORMATION: attB1

<400> SEQUENCE: 5
ggggacaagt ttgtacaaaa aagcaggct                                         29

<210> SEQ ID NO 6
<211> LENGTH: 29
<212> TYPE: DNA
<213> ORGANISM: Artificial Sequence
<220> FEATURE:
<223> OTHER INFORMATION: attB2

<400> SEQUENCE: 6
ggggaccact ttgtacaaga aagctgggt                                         29

<210> SEQ ID NO 7
<211> LENGTH: 26
<212> TYPE: DNA
<213> ORGANISM: Artificial Sequence
<220> FEATURE:
<223> OTHER INFORMATION: internal primer for At5G24530

<400> SEQUENCE: 7
gagaagtggg atttaaaata gaggaa                                            26

<210> SEQ ID NO 8
<211> LENGTH: 22
<212> TYPE: DNA
<213> ORGANISM: Artificial Sequence
<220> FEATURE:
<223> OTHER INFORMATION: QDMR6F
```

<400> SEQUENCE: 8
tgtcatcaac ataggtgacc ag                                        22

<210> SEQ ID NO 9
<211> LENGTH: 22
<212> TYPE: DNA
<213> ORGANISM: Artificial Sequence
<220> FEATURE:
<223> OTHER INFORMATION: QDMR6R

<400> SEQUENCE: 9
cgatagtcac ggattttctg tg                                        22

<210> SEQ ID NO 10
<211> LENGTH: 20
<212> TYPE: DNA
<213> ORGANISM: Artificial Sequence
<220> FEATURE:
<223> OTHER INFORMATION: Forward primer for gene At1g114880

<400> SEQUENCE: 10
ctcaaggaga atggtccaca                                           20

<210> SEQ ID NO 11
<211> LENGTH: 20
<212> TYPE: DNA
<213> ORGANISM: Artificial Sequence
<220> FEATURE:
<223> OTHER INFORMATION: Reverse primer for gene At1g14880

<400> SEQUENCE: 11
cgacttggcc aaatgtgata                                           20

<210> SEQ ID NO 12
<211> LENGTH: 21
<212> TYPE: DNA
<213> ORGANISM: Artificial Sequence
<220> FEATURE:
<223> OTHER INFORMATION: Forward primer for gene At4g14365

<400> SEQUENCE: 12
tggttttctg aggcatgtaa a                                         21

<210> SEQ ID NO 13
<211> LENGTH: 20
<212> TYPE: DNA
<213> ORGANISM: Artificial Sequence
<220> FEATURE:
<223> OTHER INFORMATION: Reverse primer for gene Atfg14365

<400> SEQUENCE: 13
agtgcaggaa cattggttgt                                           20

<210> SEQ ID NO 14
<211> LENGTH: 20
<212> TYPE: DNA
<213> ORGANISM: Artificial Sequence
<220> FEATURE:
<223> OTHER INFORMATION: Forward primer for gene ACD6

<400> SEQUENCE: 14
tggacagttc tggagcagat                                           20

<210> SEQ ID NO 15
<211> LENGTH: 18

```
<212> TYPE: DNA
<213> ORGANISM: Artificial Sequence
<220> FEATURE:
<223> OTHER INFORMATION: Reverse primer for gene ACD6

<400> SEQUENCE: 15
caactcctcc gctgtgag                                                   18

<210> SEQ ID NO 16
<211> LENGTH: 23
<212> TYPE: DNA
<213> ORGANISM: Artificial Sequence
<220> FEATURE:
<223> OTHER INFORMATION: Forward primer for gene PR-5

<400> SEQUENCE: 16
ggcaaatatc tccagtattc aca                                             23

<210> SEQ ID NO 17
<211> LENGTH: 22
<212> TYPE: DNA
<213> ORGANISM: Artificial Sequence
<220> FEATURE:
<223> OTHER INFORMATION: Reverse primer for gene PR-5

<400> SEQUENCE: 17
ggtagggcaa ttgttcctta ga                                              22

<210> SEQ ID NO 18
<211> LENGTH: 20
<212> TYPE: DNA
<213> ORGANISM: Artificial Sequence
<220> FEATURE:
<223> OTHER INFORMATION: Forward primer for gene PR-2

<400> SEQUENCE: 18
aaggagctta gcctcaccac                                                 20

<210> SEQ ID NO 19
<211> LENGTH: 20
<212> TYPE: DNA
<213> ORGANISM: Artificial Sequence
<220> FEATURE:
<223> OTHER INFORMATION: Reverse primer for gene PR-2

<400> SEQUENCE: 19
gagggaagca agaatggaac                                                 20

<210> SEQ ID NO 20
<211> LENGTH: 20
<212> TYPE: DNA
<213> ORGANISM: Artificial Sequence
<220> FEATURE:
<223> OTHER INFORMATION: Forward primer for gene PR-1

<400> SEQUENCE: 20
gaacacgtgc aatggagttt                                                 20

<210> SEQ ID NO 21
<211> LENGTH: 21
<212> TYPE: DNA
<213> ORGANISM: Artificial Sequence
<220> FEATURE:
<223> OTHER INFORMATION: Reverse primer for gene PR-1

<400> SEQUENCE: 21
```

```
ggttccacca ttgttacacc t                                              21
```

<210> SEQ ID NO 22
<211> LENGTH: 19
<212> TYPE: DNA
<213> ORGANISM: Artificial Sequence
<220> FEATURE:
<223> OTHER INFORMATION: Forward priemr for gene ACT2

<400> SEQUENCE: 22

```
aatcacagca cttgcacca                                                 19
```

<210> SEQ ID NO 23
<211> LENGTH: 20
<212> TYPE: DNA
<213> ORGANISM: Artificial Sequence
<220> FEATURE:
<223> OTHER INFORMATION: Reverse primer for gene ACT2

<400> SEQUENCE: 23

```
gagggaagca agaatggaac                                                20
```

<210> SEQ ID NO 24
<211> LENGTH: 20
<212> TYPE: DNA
<213> ORGANISM: Artificial Sequence
<220> FEATURE:
<223> OTHER INFORMATION: Lettuce dmr6 primer

<400> SEQUENCE: 24

```
cgatcaaggt caacacatgg                                                20
```

<210> SEQ ID NO 25
<211> LENGTH: 20
<212> TYPE: DNA
<213> ORGANISM: Artificial Sequence
<220> FEATURE:
<223> OTHER INFORMATION: Lettuce dmr6 primer

<400> SEQUENCE: 25

```
tcaaccatta cccagtgtgc                                                20
```

<210> SEQ ID NO 26
<211> LENGTH: 20
<212> TYPE: DNA
<213> ORGANISM: Artificial Sequence
<220> FEATURE:
<223> OTHER INFORMATION: Cucumber dmr6 forward primer

<400> SEQUENCE: 26

```
ttccaggtda ttaaycaygg                                                20
```

<210> SEQ ID NO 27
<211> LENGTH: 20
<212> TYPE: DNA
<213> ORGANISM: Artificial Sequence
<220> FEATURE:
<223> OTHER INFORMATION: Cucumber dmr6 forward primer

<400> SEQUENCE: 27

```
cataaytgga grgaytayct                                                20
```

<210> SEQ ID NO 28
<211> LENGTH: 20
<212> TYPE: DNA
<213> ORGANISM: Artificial Sequence

```
<220> FEATURE:
<223> OTHER INFORMATION: Cucumber dmr6 forward primer

<400> SEQUENCE: 28
garcaaggrc arcayatggc                                               20

<210> SEQ ID NO 29
<211> LENGTH: 20
<212> TYPE: DNA
<213> ORGANISM: Artificial Sequence
<220> FEATURE:
<223> OTHER INFORMATION: Cucumber dmr6 forward primer

<400> SEQUENCE: 29
aatcctcctt chttcaagga                                               20

<210> SEQ ID NO 30
<211> LENGTH: 20
<212> TYPE: DNA
<213> ORGANISM: Artificial Sequence
<220> FEATURE:
<223> OTHER INFORMATION: Cucumber dmr6 reverse primer

<400> SEQUENCE: 30
agtgcattkg ggtchgtrtg                                               20

<210> SEQ ID NO 31
<211> LENGTH: 20
<212> TYPE: DNA
<213> ORGANISM: Artificial Sequence
<220> FEATURE:
<223> OTHER INFORMATION: Cucumber dmr6 reverse primer

<400> SEQUENCE: 31
aatgttratg acaaargcat                                               20

<210> SEQ ID NO 32
<211> LENGTH: 20
<212> TYPE: DNA
<213> ORGANISM: Artificial Sequence
<220> FEATURE:
<223> OTHER INFORMATION: Cucumber dmr6 reverse primer

<400> SEQUENCE: 32
gccatrtgyt gyccttgytc                                               20

<210> SEQ ID NO 33
<211> LENGTH: 20
<212> TYPE: DNA
<213> ORGANISM: Artificial Sequence
<220> FEATURE:
<223> OTHER INFORMATION: Cucumber dmr6 reverse primer

<400> SEQUENCE: 33
tccggacatt gaaacttgtg                                               20

<210> SEQ ID NO 34
<211> LENGTH: 20
<212> TYPE: DNA
<213> ORGANISM: Artificial Sequence
<220> FEATURE:
<223> OTHER INFORMATION: Cucumber dmr6 reverse primer

<400> SEQUENCE: 34
tcaaagaact gcttgccaac                                               20
```

<210> SEQ ID NO 35
<211> LENGTH: 20
<212> TYPE: DNA
<213> ORGANISM: Artificial Sequence
<220> FEATURE:
<223> OTHER INFORMATION: Cucumber dmr6 forward primer

<400> SEQUENCE: 35
cgcactcacc attctccttc                                              20

<210> SEQ ID NO 36
<211> LENGTH: 19
<212> TYPE: DNA
<213> ORGANISM: Artificial Sequence
<220> FEATURE:
<223> OTHER INFORMATION: Cucumber dmr6 forward primer

<400> SEQUENCE: 36
ggcctccaag tcctcaaag                                               19

<210> SEQ ID NO 37
<211> LENGTH: 25
<212> TYPE: DNA
<213> ORGANISM: Artificial Sequence
<220> FEATURE:
<223> OTHER INFORMATION: Forward primer gene At5G24210

<400> SEQUENCE: 37
tttgggaaca gaaaaagttg gaggt                                        25

<210> SEQ ID NO 38
<211> LENGTH: 25
<212> TYPE: DNA
<213> ORGANISM: Artificial Sequence
<220> FEATURE:
<223> OTHER INFORMATION: Reverse primer gene At5G24210

<400> SEQUENCE: 38
catattcaaa agggaaaatc ccaga                                        25

<210> SEQ ID NO 39
<211> LENGTH: 25
<212> TYPE: DNA
<213> ORGANISM: Artificial Sequence
<220> FEATURE:
<223> OTHER INFORMATION: Forward primer gene At5g24420

<400> SEQUENCE: 39
tggggttgtg gtttattctg ttgac                                        25

<210> SEQ ID NO 40
<211> LENGTH: 26
<212> TYPE: DNA
<213> ORGANISM: Artificial Sequence
<220> FEATURE:
<223> OTHER INFORMATION: Reverse primer gene At5g24420

<400> SEQUENCE: 40
tggccaatag tagttgatac gcaaga                                       26

<210> SEQ ID NO 41
<211> LENGTH: 25
<212> TYPE: DNA
<213> ORGANISM: Artificial Sequence
<220> FEATURE:
<223> OTHER INFORMATION: Forward primer gene At5g24820

<400> SEQUENCE: 41
tctcgggtaa gacacaagtc gagat                                           25

<210> SEQ ID NO 42
<211> LENGTH: 25
<212> TYPE: DNA
<213> ORGANISM: Artificial Sequence
<220> FEATURE:
<223> OTHER INFORMATION: Reverse primer gene At5g24820

<400> SEQUENCE: 42
tattccaact tgcgacgtag agcat                                           25

<210> SEQ ID NO 43
<211> LENGTH: 24
<212> TYPE: DNA
<213> ORGANISM: Artificial Sequence
<220> FEATURE:
<223> OTHER INFORMATION: Forward primer gene At5g24950-60

<400> SEQUENCE: 43
ccaattgggt tatttacttc gatt                                            24

<210> SEQ ID NO 44
<211> LENGTH: 24
<212> TYPE: DNA
<213> ORGANISM: Artificial Sequence
<220> FEATURE:
<223> OTHER INFORMATION: Reverse primer gene At5g24950-60

<400> SEQUENCE: 44
cggcttttaa caacatattt tcca                                            24

<210> SEQ ID NO 45
<211> LENGTH: 25
<212> TYPE: DNA
<213> ORGANISM: Artificial Sequence
<220> FEATURE:
<223> OTHER INFORMATION: Forward primer gene At5g25270

<400> SEQUENCE: 45
aacacatcac caagatgaat ccaga                                           25

<210> SEQ ID NO 46
<211> LENGTH: 25
<212> TYPE: DNA
<213> ORGANISM: Artificial Sequence
<220> FEATURE:
<223> OTHER INFORMATION: Reverse primer gene At5g25270

<400> SEQUENCE: 46
cctctgcccc aagaaatatt gagat                                           25

<210> SEQ ID NO 47
<211> LENGTH: 24
<212> TYPE: DNA
<213> ORGANISM: Artificial Sequence
<220> FEATURE:
<223> OTHER INFORMATION: Forward primer gene At5G24450 with 18 INDEL

<400> SEQUENCE: 47
agctttgtat ggtagtgcca atga                                            24

<210> SEQ ID NO 48

<210> SEQ ID NO 48
<211> LENGTH: 24
<212> TYPE: DNA
<213> ORGANISM: Artificial Sequence
<220> FEATURE:
<223> OTHER INFORMATION: Reverse primer gene At5G24450 18 INDEL

<400> SEQUENCE: 48
gcggtatacg ggggttaaaa tcta                                          24

<210> SEQ ID NO 49
<211> LENGTH: 22
<212> TYPE: DNA
<213> ORGANISM: Artificial Sequence
<220> FEATURE:
<223> OTHER INFORMATION: Forward primer At5g24490 TaqI enzyme

<400> SEQUENCE: 49
atggccaacc actctttgtt ac                                            22

<210> SEQ ID NO 50
<211> LENGTH: 22
<212> TYPE: DNA
<213> ORGANISM: Artificial Sequence
<220> FEATURE:
<223> OTHER INFORMATION: Reverse primer gene At5g24490 TaqI enzyme

<400> SEQUENCE: 50
acaagcaaga agaacagcga ag                                            22

<210> SEQ ID NO 51
<211> LENGTH: 24
<212> TYPE: DNA
<213> ORGANISM: Artificial Sequence
<220> FEATURE:
<223> OTHER INFORMATION: Forward primer gene At5g24520-30 TaqI enzyme

<400> SEQUENCE: 51
gaaatttggt tgttggcatt tatc                                          24

<210> SEQ ID NO 52
<211> LENGTH: 25
<212> TYPE: DNA
<213> ORGANISM: Artificial Sequence
<220> FEATURE:
<223> OTHER INFORMATION: Reverse primer gene At5g24520-30 TaqI enzme

<400> SEQUENCE: 52
tcaagatctt catattctca ttcca                                         25

<210> SEQ ID NO 53
<211> LENGTH: 25
<212> TYPE: DNA
<213> ORGANISM: Artificial Sequence
<220> FEATURE:
<223> OTHER INFORMATION: Forward primer gene At5G24540/50 41 INDEL

<400> SEQUENCE: 53
cagctgaagt atgtttcatc ccttt                                         25

<210> SEQ ID NO 54
<211> LENGTH: 24
<212> TYPE: DNA
<213> ORGANISM: Artificial Sequence
<220> FEATURE:
<223> OTHER INFORMATION: Reverse primer gene At5G24540/50 41 INDEL

<400> SEQUENCE: 54

```
cttgcaattg ttgggactag gtaa                                          24

<210> SEQ ID NO 55
<211> LENGTH: 24
<212> TYPE: DNA
<213> ORGANISM: Artificial Sequence
<220> FEATURE:
<223> OTHER INFORMATION: Forward primer gene At5G24550/60 14 INDEL

<400> SEQUENCE: 55
tcactaacca gtgaaaaagg ttgc                                          24

<210> SEQ ID NO 56
<211> LENGTH: 24
<212> TYPE: DNA
<213> ORGANISM: Artificial Sequence
<220> FEATURE:
<223> OTHER INFORMATION: Reverse primer gene At5G24550/60 14 INDEL

<400> SEQUENCE: 56
tatacagcga atagcaaagc caag                                          24

<210> SEQ ID NO 57
<211> LENGTH: 24
<212> TYPE: DNA
<213> ORGANISM: Artificial Sequence
<220> FEATURE:
<223> OTHER INFORMATION: Forward primer gene At5g24470 HphI enzyme

<400> SEQUENCE: 57
ccgcgagtgt aatatatctc tcct                                          24

<210> SEQ ID NO 58
<211> LENGTH: 24
<212> TYPE: DNA
<213> ORGANISM: Artificial Sequence
<220> FEATURE:
<223> OTHER INFORMATION: Reverse primer gene At5g24470 HphI enzyme

<400> SEQUENCE: 58
cagtttaacg catgaagtgc tagt                                          24

<210> SEQ ID NO 59
<211> LENGTH: 24
<212> TYPE: DNA
<213> ORGANISM: Artificial Sequence
<220> FEATURE:
<223> OTHER INFORMATION: Forward primer gene At5g24590 PdmI enzyme

<400> SEQUENCE: 59
gcatcatttg taccgtactg agtc                                          24

<210> SEQ ID NO 60
<211> LENGTH: 24
<212> TYPE: DNA
<213> ORGANISM: Artificial Sequence
<220> FEATURE:
<223> OTHER INFORMATION: Reverse primer gene At5g24590 PdmI enzyme

<400> SEQUENCE: 60
tagtggatac tctgtccctg aggt                                          24

<210> SEQ ID NO 61
<211> LENGTH: 1026
<212> TYPE: DNA
```

<213> ORGANISM: Arabidopsis thaliana

<400> SEQUENCE: 61

```
atggcggcaa agctgatatc caccggtttc cgtcatacta ctttgccgga aaactatgtc      60
cggccaatct ccgaccgtcc acgtctctct gaagtctctc aactcgaaga tttccctctc     120
atcgatctct cttccactga tcgatctttt ctcatccaac aaatccacca agcttgtgcc     180
cgattcggat tttttcaggt cataaatcac ggagttaaca acaaataat agatgagatg      240
gtgagtgttg cgcgtgagtt ctttagcatg tctatggaag aaaaaatgaa gctatattca     300
gacgatccaa cgaagacaac aagattatcg acgagcttca atgtgaagaa agaagaagtc     360
aacaattgga gagactatct aagactccat tgttatccta tccacaagta tgtcaatgag     420
tggccgtcaa accctccttc tttcaaggaa atagtaagta atacagtag agaagtaaga      480
gaagtgggat ttaaaataga ggaattaata tcagagagct taggtttaga aaagattac     540
atgaagaaag tgcttggtga acaaggtcaa cacatggcag tcaactatta tcctccatgt     600
cctgaacctg agctcactta cggtttacct gctcataccg acccaaacgc cctaaccatt    660
cttcttcaag acactactgt ttgcggtctc cagatcttga tcgacggtca gtggttcgcc    720
gttaatccac atcctgatgc tttgtcatc aacataggtg accagttaca ggcattaagt     780
aatggagtat acaaaagtgt ttggcatcgc gctgtaacaa acacagaaaa tccgagacta    840
tcggtcgcat cgtttctgtg cccagctgac tgtgctgtca tgagcccggc caagcccttg    900
tgggaagctg aggacgatga aacgaaacca gtctacaaag atttcactta tgcagagtat    960
tacaagaagt tttggagtag gaatctggac caagaacatt gcctcgagaa ttttctaaac   1020
aactaa                                                             1026
```

<210> SEQ ID NO 62
<211> LENGTH: 341
<212> TYPE: PRT
<213> ORGANISM: Arabidopsis thaliana

<400> SEQUENCE: 62

```
Met Ala Ala Lys Leu Ile Ser Thr Gly Phe Arg His Thr Thr Leu Pro
  1               5                  10                  15

Glu Asn Tyr Val Arg Pro Ile Ser Asp Arg Pro Arg Leu Ser Glu Val
                 20                  25                  30

Ser Gln Leu Glu Asp Phe Pro Leu Ile Asp Leu Ser Ser Thr Asp Arg
             35                  40                  45

Ser Phe Leu Ile Gln Gln Ile His Gln Ala Cys Ala Arg Phe Gly Phe
         50                  55                  60

Phe Gln Val Ile Asn His Gly Val Asn Lys Gln Ile Ile Asp Glu Met
 65                  70                  75                  80

Val Ser Val Ala Arg Glu Phe Phe Ser Met Ser Met Glu Glu Lys Met
                 85                  90                  95

Lys Leu Tyr Ser Asp Asp Pro Thr Lys Thr Thr Arg Leu Ser Thr Ser
                100                 105                 110

Phe Asn Val Lys Lys Glu Glu Val Asn Asn Trp Arg Asp Tyr Leu Arg
            115                 120                 125

Leu His Cys Tyr Pro Ile His Lys Tyr Val Asn Glu Trp Pro Ser Asn
        130                 135                 140

Pro Pro Ser Phe Lys Glu Ile Val Ser Lys Tyr Ser Arg Glu Val Arg
145                 150                 155                 160

Glu Val Gly Phe Lys Ile Glu Glu Leu Ile Ser Glu Ser Leu Gly Leu
```

```
            165                 170                 175
Glu Lys Asp Tyr Met Lys Lys Val Leu Gly Glu Gln Gly Gln His Met
                180                 185                 190
Ala Val Asn Tyr Tyr Pro Pro Cys Pro Glu Pro Glu Leu Thr Tyr Gly
            195                 200                 205
Leu Pro Ala His Thr Asp Pro Asn Ala Leu Thr Ile Leu Leu Gln Asp
        210                 215                 220
Thr Thr Val Cys Gly Leu Gln Ile Leu Ile Asp Gly Gln Trp Phe Ala
225                 230                 235                 240
Val Asn Pro His Pro Asp Ala Phe Val Ile Asn Ile Gly Asp Gln Leu
                245                 250                 255
Gln Ala Leu Ser Asn Gly Val Tyr Lys Ser Val Trp His Arg Ala Val
            260                 265                 270
Thr Asn Thr Glu Asn Pro Arg Leu Ser Val Ala Ser Phe Leu Cys Pro
        275                 280                 285
Ala Asp Cys Ala Val Met Ser Pro Ala Lys Pro Leu Trp Glu Ala Glu
        290                 295                 300
Asp Asp Glu Thr Lys Pro Val Tyr Lys Asp Phe Thr Tyr Ala Glu Tyr
305                 310                 315                 320
Tyr Lys Lys Phe Trp Ser Arg Asn Leu Asp Gln Glu His Cys Leu Glu
                325                 330                 335
Asn Phe Leu Asn Asn
            340

<210> SEQ ID NO 63
<211> LENGTH: 335
<212> TYPE: PRT
<213> ORGANISM: Aquilegia sp.

<400> SEQUENCE: 63

Met Glu Ser Ser Asn Val Leu Leu Thr Gly Thr Arg His Ser Asn Leu
1               5                   10                  15
Pro Glu Asn Tyr Val Arg Ser Val Ser Asp Arg Pro Arg Leu Ser Glu
            20                  25                  30
Val Lys Asp Cys Glu Asn Val Pro Val Ile Asp Leu Ser Val Ala Asp
        35                  40                  45
Glu Ser Leu Leu Ala Gln Gln Ile Gly Asn Ala Cys Lys Ser His Gly
    50                  55                  60
Phe Phe Gln Val Ile Asn His Gly Val Asn Ser Glu Leu Val Glu Lys
65                  70                  75                  80
Met Met Glu Ile Ser His Glu Phe Phe His Leu Pro Leu Asp Val Lys
                85                  90                  95
Met Gln Phe Tyr Ser Asp Asp Pro Thr Lys Thr Met Arg Leu Ser Thr
            100                 105                 110
Ser Phe Asn Leu Lys Lys Glu Ser Val His Asn Trp Arg Asp Tyr Leu
        115                 120                 125
Arg Leu His Cys His Pro Ile Glu Lys Tyr Val Gln Glu Trp Pro Ser
    130                 135                 140
Val Pro Ser Thr Phe Lys Asp Val Val Ala Thr Tyr Cys Lys Glu Val
145                 150                 155                 160
Arg Lys Leu Gly Leu Arg Leu Leu Gly Ser Ile Ser Leu Ser Leu Gly
                165                 170                 175
Leu Glu Glu Asp Tyr Ile Glu Lys Val Leu Gly Asp Gln Gly Gln His
            180                 185                 190
```

```
Met Ala Val Asn Tyr Tyr Pro Pro Cys Pro Glu Pro Glu Leu Thr Tyr
            195                 200                 205

Gly Leu Pro Arg His Thr Asp Pro Asn Thr Ile Thr Ile Leu Leu Gln
210                 215                 220

Gly Gln Glu Val Ala Gly Leu Gln Val Leu His Asn Gly Lys Trp Val
225                 230                 235                 240

Ala Val Asn Pro Tyr Pro Asn Ala Phe Val Val Asn Ile Gly Asp Gln
            245                 250                 255

Ile Gln Ala Leu Ser Asn Gly Asn Tyr Ala Ser Val Trp His Arg Ala
            260                 265                 270

Thr Val Asn Thr Asp Arg Glu Arg Ile Ser Val Ala Ser Phe Leu Cys
            275                 280                 285

Pro Ala Asn Asp Ala Ile Ile Cys Pro Ala Val Lys Asp Gly Ser Pro
            290                 295                 300

Ser Met Tyr Lys Lys Phe Thr Tyr Asp Glu Tyr Tyr Lys Lys Phe Trp
305                 310                 315                 320

Ser Gly Asn Leu Asp Gln Gln His Cys Leu Glu Leu Phe Lys Glu
            325                 330                 335

<210> SEQ ID NO 64
<211> LENGTH: 337
<212> TYPE: PRT
<213> ORGANISM: Citrus sinensis

<400> SEQUENCE: 64

Met Asp Thr Lys Val Leu Ser Ser Gly Ile Arg Tyr Thr Asn Leu Pro
1               5                   10                  15

Glu Gly Tyr Val Arg Pro Glu Ser Glu Arg Pro Asn Leu Ser Glu Val
            20                  25                  30

Ser Glu Cys Lys Asn Val Pro Val Ile Asp Leu Ala Cys Asp Asp Arg
            35                  40                  45

Ser Leu Ile Val Gln Gln Val Ala Asp Ala Cys Lys Asn Tyr Gly Phe
        50                  55                  60

Phe Gln Ala Ile Asn His Glu Val Pro Leu Glu Thr Val Glu Arg Val
65                  70                  75                  80

Leu Glu Val Ala Lys Glu Phe Phe Asn Leu Pro Val Glu Glu Lys Leu
                85                  90                  95

Lys Leu Tyr Ser Asp Asp Pro Ser Lys Thr Met Arg Leu Ser Thr Ser
            100                 105                 110

Phe Asn Val Asn Lys Glu Lys Val His Asn Trp Arg Asp Tyr Leu Arg
            115                 120                 125

Leu His Cys Tyr Pro Leu Asp Lys Tyr Val Pro Glu Trp Pro Ser Asn
        130                 135                 140

Pro Ser Thr Phe Lys Glu Phe Val Ser Thr Tyr Cys Ser Glu Val Arg
145                 150                 155                 160

Gly Leu Gly Tyr Arg Val Leu Glu Leu Ile Ser Glu Ser Leu Gly Leu
                165                 170                 175

Glu Lys Asp Tyr Ile Lys Lys Val Leu Gly Glu Gln Gly Gln His Met
            180                 185                 190

Ala Val Asn Phe Tyr Pro Pro Cys Pro Glu Pro Glu Leu Thr Tyr Gly
            195                 200                 205

Leu Pro Gly His Thr Asp Pro Asn Ala Leu Thr Ile Leu Leu Gln Asp
        210                 215                 220

Leu Glu Val Ala Gly Leu Gln Val Leu Lys Asp Asp Lys Trp Val Ala
225                 230                 235                 240
```

Val Asn Pro Leu Pro Asn Ala Phe Val Ile Asn Ile Gly Asp Gln Leu
            245                 250                 255

Gln Ala Leu Ser Asn Gly Arg Tyr Lys Ser Val Trp His Arg Ala Ile
            260                 265                 270

Val Asn Ala Glu Lys Ala Arg Met Ser Val Ala Ser Phe Leu Cys Pro
            275                 280                 285

Asn Asn Asp Ala Met Ile Ser Pro Pro Lys Ala Leu Thr Glu Asp Gly
            290                 295                 300

Ser Gly Ala Val Tyr Arg Asp Phe Thr Tyr Ala Glu Tyr Tyr Ser Lys
305                 310                 315                 320

Phe Trp Ser Arg Asn Leu Asp Gln Glu His Cys Leu Glu Leu Phe Lys
                325                 330                 335

Asn

<210> SEQ ID NO 65
<211> LENGTH: 337
<212> TYPE: PRT
<213> ORGANISM: Coffea canephora

<400> SEQUENCE: 65

Met Glu Thr Lys Val Ile Ser Ser Gly Ile Lys Tyr Thr Ser Leu Pro
1               5                   10                  15

Glu Ser Tyr Val Arg Pro Glu Ser Glu Arg Pro Arg Leu Ser Glu Val
            20                  25                  30

Ser Asp Cys Gln Asn Val Pro Val Val Asp Leu Gly Phe Gly Asp Arg
            35                  40                  45

Asn Leu Met Val Arg Gln Ile Gly Asp Ala Cys Arg Asp Tyr Gly Phe
50                  55                  60

Phe Gln Val Ile Asn His Gly Val Ser Lys Asp Ala Val Asp Lys Met
65                  70                  75                  80

Leu Glu Thr Ala Thr Glu Phe Phe Ser Leu Pro Val Glu Glu Lys Leu
                85                  90                  95

Lys Leu Tyr Ser Asp Asp Pro Ser Lys Thr Thr Arg Leu Ser Thr Ser
            100                 105                 110

Phe Asn Val Lys Lys Glu Thr Val His Asn Trp Arg Asp Tyr Leu Arg
            115                 120                 125

Leu His Cys Tyr Pro Leu Glu Lys Tyr Val Pro Glu Trp Pro Ser Asn
            130                 135                 140

Pro Pro Ser Phe Lys Glu Met Val Ser Asn Tyr Cys Val Gln Ile Arg
145                 150                 155                 160

Glu Leu Gly Leu Arg Leu Glu Glu Ala Ile Ala Glu Ser Leu Gly Leu
                165                 170                 175

Asp Lys Glu Cys Ile Lys Lys Val Leu Gly Asp Gly Gln His Met
            180                 185                 190

Ala Val Asn Tyr Tyr Pro Pro Cys Pro Gln Pro Asp Leu Thr Tyr Gly
            195                 200                 205

Leu Pro Gly His Thr Asp Pro Asn Ala Leu Thr Ile Leu Leu Gln Asp
210                 215                 220

Leu Asn Val Ala Gly Leu Gln Val Leu Arg Asp Gly Arg Trp Leu Ala
225                 230                 235                 240

Val Lys Pro His Pro Asp Ala Phe Val Val Asn Ile Gly Asp Gln Leu
            245                 250                 255

Gln Ala Leu Ser Asn Gly Ile Tyr Lys Ser Val Trp His Arg Ala Val
            260                 265                 270

```
Val Asn Ala Asp Gln Pro Arg Leu Ser Val Ala Ser Phe Leu Cys Pro
        275                 280                 285

Cys Asp His Ala Val Ile Ser Ala Pro Lys Pro Leu Thr Ala Asp Gly
        290                 295                 300

Ser Pro Val Val Tyr Arg Asp Phe Thr Tyr Ala Gln Tyr Tyr Lys Lys
305                 310                 315                 320

Phe Trp Ser Arg Asn Leu Asp Gln Glu His Cys Leu Glu Leu Phe Lys
                325                 330                 335

Asn

<210> SEQ ID NO 66
<211> LENGTH: 1029
<212> TYPE: DNA
<213> ORGANISM: Cucumis sativus

<400> SEQUENCE: 66
atgagcagtg tgatggagat ccaactttg tgttcagggg acgtcacga gaagttgcca      60
gagaagtatg aacggcctga atcggatagg ccgcggctgt cggaggtgtg ttgttgggac    120
aaggttccaa taatcgactt gggatgcgag gagagagaga tgattgtgaa gcaagtggag    180
gaggcctgca agtcttacgg cttttccag gttataaatc atggtgtgag gaagtggag*     240
gtggagaaag tgatagaagt tggcaagcag ttctttgagc tgccgatgga ggagaagttg    300
aaatttatt cagacgaccc ttccaagacc gtcagactct ccacaagttt caatgtccgg     360
aaagagcaat ttcgcaactg agggattat ctcagactcc attgctatcc tctctccaac     420
tacaccccc attggccctc taacccacca tccttcaggg aaatagtgag tagttattgc     480
aatgaagtac gaaagttgg gtacagaata gaggagctaa tatcggagag cttgggctg      540
gagaaggaat acataaggaa gaagttgggt gaacaaggtc agcacatggc tataaattat    600
tatccgccat gtccccaacc agaactcacc tacgggctcc ctggccatac ggatcccaac    660
gcactcacca ttctccttca ggatctccat gtcgccggcc tccaagtcct caaagatgga    720
aagtggctag cggtcaaccc ccaccccaat gcctttgtaa tcaatatagg cgaccaattg    780
caggcattga gcaatgggt gtacaagagc gtttggcacc gagcggtggt caatgttgat     840
aagcccaggc tgtcggtcgc ttcttttctc tgcccttgtg atgacgccct cattactcct    900
gcaccgctcc tctcccagcc ttcccccatt tacagacctt tcacctacgc ccagtactac    960
aatactttt ggagcagaaa cttggatcaa caacattgct tggaactatt taaaaaccac    1020
cctccttaa                                                           1029

<210> SEQ ID NO 67
<211> LENGTH: 342
<212> TYPE: PRT
<213> ORGANISM: Cucumis sativus

<400> SEQUENCE: 67

Met Ser Ser Val Met Glu Ile Gln Leu Leu Cys Ser Gly Gly Arg His
1               5                   10                  15

Glu Lys Leu Pro Glu Lys Tyr Glu Arg Pro Glu Ser Asp Arg Pro Arg
            20                  25                  30

Leu Ser Glu Val Cys Cys Trp Asp Lys Val Pro Ile Ile Asp Leu Gly
        35                  40                  45

Cys Glu Glu Arg Glu Met Ile Val Lys Gln Val Glu Glu Ala Cys Lys
    50                  55                  60
```

```
Ser Tyr Gly Phe Phe Gln Val Ile Asn His Gly Val Arg Lys Glu Leu
 65                  70                  75                  80

Val Glu Lys Val Ile Glu Val Gly Lys Gln Phe Phe Glu Leu Pro Met
                 85                  90                  95

Glu Glu Lys Leu Lys Phe Tyr Ser Asp Asp Pro Ser Lys Thr Val Arg
            100                 105                 110

Leu Ser Thr Ser Phe Asn Val Arg Lys Glu Gln Phe Arg Asn Trp Arg
        115                 120                 125

Asp Tyr Leu Arg Leu His Cys Tyr Pro Leu Ser Asn Tyr Thr Pro His
    130                 135                 140

Trp Pro Ser Asn Pro Pro Ser Phe Arg Glu Ile Val Ser Ser Tyr Cys
145                 150                 155                 160

Asn Glu Val Arg Lys Val Gly Tyr Arg Ile Glu Glu Leu Ile Ser Glu
                165                 170                 175

Ser Leu Gly Leu Glu Lys Glu Tyr Ile Arg Lys Lys Leu Gly Glu Gln
            180                 185                 190

Gly Gln His Met Ala Ile Asn Tyr Tyr Pro Pro Cys Pro Gln Pro Glu
        195                 200                 205

Leu Thr Tyr Gly Leu Pro Gly His Thr Asp Pro Asn Ala Leu Thr Ile
    210                 215                 220

Leu Leu Gln Asp Leu His Val Ala Gly Leu Gln Val Leu Lys Asp Gly
225                 230                 235                 240

Lys Trp Leu Ala Val Asn Pro His Pro Asn Ala Phe Val Ile Asn Ile
                245                 250                 255

Gly Asp Gln Leu Gln Ala Leu Ser Asn Gly Val Tyr Lys Ser Val Trp
            260                 265                 270

His Arg Ala Val Val Asn Val Asp Lys Pro Arg Leu Ser Val Ala Ser
        275                 280                 285

Phe Leu Cys Pro Cys Asp Asp Ala Leu Ile Thr Pro Ala Pro Leu Leu
    290                 295                 300

Ser Gln Pro Ser Pro Ile Tyr Arg Pro Phe Thr Tyr Ala Gln Tyr Tyr
305                 310                 315                 320

Asn Thr Phe Trp Ser Arg Asn Leu Asp Gln Gln His Cys Leu Glu Leu
                325                 330                 335

Phe Lys Asn His Pro Pro
            340

<210> SEQ ID NO 68
<211> LENGTH: 337
<212> TYPE: PRT
<213> ORGANISM: Gossypium hirsutum

<400> SEQUENCE: 68

Met Asp Thr Lys Val Leu Ser Ser Gly Ile His Tyr Ser Ser Leu Pro
  1               5                  10                  15

Glu Ser Tyr Val Arg Pro Glu Ser Glu Arg Pro Arg Leu Ser Glu Val
                 20                  25                  30

Ser Gln Cys Asp Asn Val Pro Val Ile Asp Leu Gly Cys Glu Asp Arg
             35                  40                  45

Ser His Ile Val Gln Gln Ile Ala Leu Ala Cys Ile Asn Tyr Gly Phe
         50                  55                  60

Phe Gln Val Ile Asn His Gly Val Ser Lys Glu Ala Val Glu Arg Met
 65                  70                  75                  80

Leu Gln Val Ala His Asp Phe Phe Gly Leu Pro Val Glu Glu Lys Met
                 85                  90                  95
```

```
Lys Leu Tyr Ser Asp Asp Pro Ser Lys Thr Met Arg Leu Ser Thr Ser
                100                 105                 110
Phe Asn Val Lys Lys Glu Lys Val His Asn Trp Arg Asp Tyr Leu Arg
                115                 120                 125
Leu His Cys Tyr Pro Leu His Lys Tyr Val Pro Glu Trp Pro Ser Asn
            130                 135                 140
Pro Pro Ser Phe Lys Gln Ile Val Ser Asp Tyr Cys Val Gln Val Arg
145                 150                 155                 160
Glu Leu Gly Tyr Arg Leu Gln Glu Leu Ile Ser Glu Ser Leu Gly Leu
                165                 170                 175
Glu Lys Asp Tyr Ile Lys Lys Val Leu Gly Glu Gln Gly Gln His Met
            180                 185                 190
Ala Val Asn Tyr Pro Pro Cys Pro Glu Pro Glu Leu Thr Tyr Gly
            195                 200                 205
Leu Pro Gly His Thr Asp Pro Asn Ala Leu Thr Ile Leu Leu Gln Asp
    210                 215                 220
Leu Gln Val Ala Gly Leu Gln Val Leu Lys Asp Gly Lys Trp Leu Ala
225                 230                 235                 240
Val Asn Pro Gln Thr Asn Ala Phe Val Ile Asn Ile Gly Asp Gln Leu
                245                 250                 255
Gln Ala Leu Ser Asn Gly Thr Tyr Lys Ser Val Trp His Arg Ala Ile
            260                 265                 270
Val Asn Thr Asp Lys Pro Arg Met Ser Val Ala Ser Phe Leu Cys Pro
        275                 280                 285
Tyr Asp His Ala Leu Ile Ser Pro Ala Lys Pro Leu Thr Gln His Gly
305                 310                 315                 320
Cys Gly Ala Val Tyr Arg Asp Phe Thr Tyr Ala Glu Tyr Tyr Ser Lys
305                 310                 315                 320
Phe Trp Gly Arg Asn Leu Asp Gln Glu His Cys Leu Glu Leu Phe Lys
                325                 330                 335
Asn
```

<210> SEQ ID NO 69
<211> LENGTH: 1014
<212> TYPE: DNA
<213> ORGANISM: Lactuca sativa

<400> SEQUENCE: 69

| | | | | | |
|---|---|---|---|---|---|
| atggccgcaa | aagtcatctc | cagtggattc | cggtatacta | ctctaccgga | gagctacgtc | 60 |
| cgtccggtta | acgacagacc | taacctatct | caagtttccg | attgcaacga | cgttcctgtt | 120 |
| attgacatcg | gttgtggtga | tagacaactc | ataagccaac | aaattggcga | tgcttgtaga | 180 |
| agatacggtt | ttttccaggt | gattaatcat | ggtgtgcctg | atgaaatagt | ggagaaaatg | 240 |
| caacaagtag | gtagggagtt | tttcctgttg | cctgtggaag | agaagatgaa | gctttactca | 300 |
| gaggatccat | cgaagacgat | gaggctatcc | accagcttta | acgtccaaaa | agaacaaatt | 360 |
| cataactggc | gagattatct | ccgccttcac | tgttatcctc | tggatcaata | cagtcctgaa | 420 |
| tggccttcaa | atccttctta | tttcaaggaa | tatgttggta | attattgtac | agcagtgcga | 480 |
| aatttaggaa | tgagaatatt | agaatcaata | tcagaaagtt | tagggttaca | aaaagaagaa | 540 |
| ataaaaacta | tattggcga | tcaaggtcaa | cacatggcca | tcaaccatta | cccagtgtgc | 600 |
| cctgagcccg | agctaaccta | cgggctaccc | gggcacacag | accccaatgc | tctcaccatc | 660 |
| cttctacagg | acacactggt | ctctggtctt | caggttctca | agatggcaa | atggttagcc | 720 |

```
gttaaaccac accctaatgc gtttgtaatt aacattggtg atcagttaga ggcggtgagt    780
aatggtgaat ataaaagtgt atggcatcga gctgtggtta actcagacaa cccgcgaatg    840
tctatagctt cgttttttgtg tccttgtaat gacaccgtta ttagggctcc taaagaaata    900
ataaaggaag gatcgaaacc tgttttcaaa gaatttactt atgcagaata ctacgcgaag    960
ttttggacaa gaaaccttga tcaagaacat tgcttagaat tcttcaagaa ctag         1014
```

<210> SEQ ID NO 70
<211> LENGTH: 337
<212> TYPE: PRT
<213> ORGANISM: Lactuca sativa

<400> SEQUENCE: 70

```
Met Ala Ala Lys Val Ile Ser Ser Gly Phe Arg Tyr Thr Thr Leu Pro
1               5                   10                  15

Glu Ser Tyr Val Arg Pro Val Asn Asp Arg Pro Asn Leu Ser Gln Val
            20                  25                  30

Ser Asp Cys Asn Asp Val Pro Val Ile Asp Ile Gly Cys Gly Asp Arg
        35                  40                  45

Gln Leu Ile Ser Gln Gln Ile Gly Asp Ala Cys Arg Arg Tyr Gly Phe
    50                  55                  60

Phe Gln Val Ile Asn His Gly Val Pro Asp Glu Ile Val Glu Lys Met
65                  70                  75                  80

Gln Gln Val Gly Arg Glu Phe Phe Leu Leu Pro Val Glu Glu Lys Met
                85                  90                  95

Lys Leu Tyr Ser Glu Asp Pro Ser Lys Thr Met Arg Leu Ser Thr Ser
            100                 105                 110

Phe Asn Val Gln Lys Glu Gln Ile His Asn Trp Arg Asp Tyr Leu Arg
        115                 120                 125

Leu His Cys Tyr Pro Leu Asp Gln Tyr Ser Pro Glu Trp Pro Ser Asn
    130                 135                 140

Pro Ser Tyr Phe Lys Glu Tyr Val Gly Asn Tyr Cys Thr Ala Val Arg
145                 150                 155                 160

Asn Leu Gly Met Arg Ile Leu Glu Ser Ile Ser Glu Ser Leu Gly Leu
                165                 170                 175

Gln Lys Glu Glu Ile Lys Thr Ile Leu Gly Asp Gln Gly Gln His Met
            180                 185                 190

Ala Ile Asn His Tyr Pro Val Cys Pro Glu Pro Glu Leu Thr Tyr Gly
        195                 200                 205

Leu Pro Gly His Thr Asp Pro Asn Ala Leu Thr Ile Leu Leu Gln Asp
    210                 215                 220

Thr Leu Val Ser Gly Leu Gln Val Leu Lys Asp Gly Lys Trp Leu Ala
225                 230                 235                 240

Val Lys Pro His Pro Asn Ala Phe Val Ile Asn Ile Gly Asp Gln Leu
                245                 250                 255

Glu Ala Val Ser Asn Gly Glu Tyr Lys Ser Val Trp His Arg Ala Val
            260                 265                 270

Val Asn Ser Asp Asn Pro Arg Met Ser Ile Ala Ser Phe Leu Cys Pro
        275                 280                 285

Cys Asn Asp Thr Val Ile Arg Ala Pro Lys Glu Ile Ile Lys Glu Gly
    290                 295                 300

Ser Lys Pro Val Phe Lys Glu Phe Thr Tyr Ala Glu Tyr Tyr Ala Lys
305                 310                 315                 320
```

```
Phe Trp Thr Arg Asn Leu Asp Gln Glu His Cys Leu Glu Phe Phe Lys
            325                 330                 335
Asn

<210> SEQ ID NO 71
<211> LENGTH: 338
<212> TYPE: PRT
<213> ORGANISM: Medicago truncatula

<400> SEQUENCE: 71

Met Asp Thr Lys Val Leu Ser Ser Gly Ile His Tyr Ser Lys Leu Pro
1               5                   10                  15

Glu Ser Tyr Ile Arg Pro Glu Ser Asp Arg Pro Cys Leu Ser Gln Val
            20                  25                  30

Ser Glu Phe Glu Asn Val Pro Ile Ile Asp Leu Gly Ser His Asn Arg
        35                  40                  45

Thr Gln Ile Val Gln Gln Ile Gly Glu Ala Cys Ser Ser Tyr Gly Phe
    50                  55                  60

Phe Gln Val Val Asn His Gly Val Pro Leu Glu Glu Leu Lys Lys Thr
65                  70                  75                  80

Ala Glu Val Ala Tyr Asp Phe Phe Lys Leu Pro Val Glu Glu Lys Met
                85                  90                  95

Lys Leu Tyr Ser Asp Asp Pro Thr Lys Thr Met Arg Leu Ser Thr Ser
            100                 105                 110

Phe Asn Val Asn Lys Glu Val His Asn Trp Arg Asp Tyr Leu Arg
        115                 120                 125

Leu His Cys Tyr Pro Leu Asp Asn Tyr Val Pro Glu Trp Pro Ser Asn
    130                 135                 140

Pro Pro Ser Phe Lys Glu Thr Val Ala Asn Tyr Cys Lys Glu Val Arg
145                 150                 155                 160

Glu Leu Gly Leu Arg Ile Glu Glu Tyr Ile Ser Glu Ser Leu Gly Leu
                165                 170                 175

Glu Lys Asp Tyr Leu Arg Asn Ala Leu Gly Glu Gln Gly Gln His Met
            180                 185                 190

Ala Val Asn Tyr Tyr Pro Pro Cys Pro Gln Pro Glu Leu Thr Tyr Gly
        195                 200                 205

Leu Pro Gly His Thr Asp Pro Asn Ala Leu Thr Ile Leu Leu Gln Asp
    210                 215                 220

Leu His Val Ala Gly Leu Gln Val Leu Lys Asp Gly Lys Trp Leu Ala
225                 230                 235                 240

Ile Asn Pro Ile Pro Asp Ala Phe Val Ile Asn Ile Gly Asp Gln Leu
                245                 250                 255

Gln Ala Leu Ser Asn Gly Leu Tyr Lys Ser Val Trp His Arg Ala Ile
            260                 265                 270

Val Asn Ala Glu Lys Pro Arg Leu Ser Val Ala Ser Phe Leu Cys Pro
        275                 280                 285

Asp Asn Glu Ala Leu Ile Cys Pro Ala Lys Pro Leu Thr Glu Asp Gly
    290                 295                 300

Ser Gly Ala Val Tyr Arg Gly Phe Thr Tyr Pro Glu Tyr Tyr Ser Lys
305                 310                 315                 320

Phe Trp Ser Arg Asp Leu Glu Lys Glu His Cys Leu Glu Phe Phe Lys
                325                 330                 335

Asn Asn
```

<210> SEQ ID NO 72
<211> LENGTH: 342
<212> TYPE: PRT
<213> ORGANISM: Oryza sativa

<400> SEQUENCE: 72

```
Met Ala Ala Glu Ala Glu Gln Gln His Gln Leu Leu Ser Thr Ala Val
1               5                   10                  15

His Asp Thr Met Pro Gly Lys Tyr Val Arg Pro Glu Ser Gln Arg Pro
            20                  25                  30

Arg Leu Asp Leu Val Val Ser Asp Ala Arg Ile Pro Val Val Asp Leu
        35                  40                  45

Ala Ser Pro Asp Arg Ala Ala Val Val Ser Ala Val Gly Asp Ala Cys
    50                  55                  60

Arg Thr His Gly Phe Phe Gln Val Val Asn His Gly Ile Asp Ala Ala
65                  70                  75                  80

Leu Ile Ala Ser Val Met Glu Val Gly Arg Glu Phe Phe Arg Leu Pro
                85                  90                  95

Ala Glu Glu Lys Ala Lys Leu Tyr Ser Asp Asp Pro Ala Lys Lys Ile
            100                 105                 110

Arg Leu Ser Thr Ser Phe Asn Val Arg Lys Glu Thr Val His Asn Trp
        115                 120                 125

Arg Asp Tyr Leu Arg Leu His Cys Tyr Pro Leu His Gln Phe Val Pro
    130                 135                 140

Asp Trp Pro Ser Asn Pro Pro Ser Phe Lys Glu Ile Ile Gly Thr Tyr
145                 150                 155                 160

Cys Thr Glu Val Arg Glu Leu Gly Phe Arg Leu Tyr Glu Ala Ile Ser
                165                 170                 175

Glu Ser Leu Gly Leu Glu Gly Gly Tyr Met Arg Glu Thr Leu Gly Glu
            180                 185                 190

Gln Glu Gln His Met Ala Val Asn Tyr Tyr Pro Gln Cys Pro Glu Pro
        195                 200                 205

Glu Leu Thr Tyr Gly Leu Pro Ala His Thr Asp Pro Asn Ala Leu Thr
    210                 215                 220

Ile Leu Leu Met Asp Asp Gln Val Ala Gly Leu Gln Val Leu Asn Asp
225                 230                 235                 240

Gly Lys Trp Ile Ala Val Asn Pro Gln Pro Gly Ala Leu Val Ile Asn
                245                 250                 255

Ile Gly Asp Gln Leu Gln Ala Leu Ser Asn Gly Lys Tyr Arg Ser Val
            260                 265                 270

Trp His Arg Ala Val Val Asn Ser Asp Arg Glu Arg Met Ser Val Ala
        275                 280                 285

Ser Phe Leu Cys Pro Cys Asn Ser Val Glu Leu Gly Pro Ala Lys Lys
    290                 295                 300

Leu Ile Thr Asp Asp Ser Pro Ala Val Tyr Arg Asn Tyr Thr Tyr Asp
305                 310                 315                 320

Glu Tyr Tyr Lys Lys Phe Trp Ser Arg Asn Leu Asp Gln Glu His Cys
                325                 330                 335

Leu Glu Leu Phe Arg Thr
            340
```

<210> SEQ ID NO 73
<211> LENGTH: 342
<212> TYPE: PRT
<213> ORGANISM: Oryza sativa

<400> SEQUENCE: 73

Met Ala Asp Gln Leu Ile Ser Thr Ala Asp His Asp Thr Leu Pro Gly
1               5                   10                  15

Asn Tyr Val Arg Pro Glu Ala Gln Arg Pro Arg Leu Ala Asp Val Leu
            20                  25                  30

Ser Asp Ala Ser Ile Pro Val Asp Leu Ala Asn Pro Asp Arg Ala
        35                  40                  45

Lys Leu Val Ser Gln Val Gly Ala Ala Cys Arg Ser His Gly Phe Phe
    50                  55                  60

Gln Val Leu Asn His Gly Val Pro Val Glu Leu Thr Leu Ser Val Leu
65                  70                  75                  80

Ala Val Ala His Asp Phe Phe Arg Leu Pro Ala Glu Glu Lys Ala Lys
                85                  90                  95

Leu Tyr Ser Asp Asp Pro Ala Lys Lys Ile Arg Leu Ser Thr Ser Phe
            100                 105                 110

Asn Val Arg Lys Glu Thr Val His Asn Trp Arg Asp Tyr Leu Arg Leu
        115                 120                 125

His Cys Tyr Pro Leu His Arg Tyr Leu Pro Asp Trp Pro Ser Asn Pro
    130                 135                 140

Pro Ser Phe Arg Glu Ile Ile Ser Thr Tyr Cys Lys Glu Val Arg Glu
145                 150                 155                 160

Leu Gly Phe Arg Leu Tyr Gly Ala Ile Ser Glu Ser Leu Gly Leu Glu
                165                 170                 175

Gln Asp Tyr Ile Lys Lys Val Leu Gly Glu Gln Glu Gln His Met Ala
            180                 185                 190

Val Asn Phe Tyr Pro Lys Cys Pro Glu Pro Glu Leu Thr Phe Gly Leu
        195                 200                 205

Pro Ala His Thr Asp Pro Asn Ala Leu Thr Ile Leu Leu Met Asp Gln
    210                 215                 220

Gln Val Ala Gly Leu Gln Val Leu Lys Glu Gly Arg Trp Ile Ala Val
225                 230                 235                 240

Asn Pro Gln Pro Asn Ala Leu Val Ile Asn Ile Gly Asp Gln Leu Gln
                245                 250                 255

Ala Leu Ser Asn Gly Arg Tyr Lys Ser Val Trp His Arg Ala Val Val
            260                 265                 270

Asn Ser Asp Lys Ala Arg Met Ser Val Ala Ser Phe Leu Cys Pro Cys
        275                 280                 285

Asn Asp Val Leu Ile Gly Pro Ala Gln Lys Leu Ile Thr Asp Gly Ser
    290                 295                 300

Pro Ala Val Tyr Arg Asn Tyr Thr Tyr Asp Glu Tyr Tyr Lys Lys Phe
305                 310                 315                 320

Trp Ser Arg Asn Leu Asp Gln Glu His Cys Leu Glu Leu Phe Arg Thr
                325                 330                 335

Thr Pro Thr Asp Thr Ser
            340

<210> SEQ ID NO 74
<211> LENGTH: 340
<212> TYPE: PRT
<213> ORGANISM: Oryza sativa

<400> SEQUENCE: 74

Met Ala Thr Thr Gln Leu Leu Ser Thr Val Glu His Arg Glu Thr Leu
1               5                   10                  15

Pro Glu Gly Tyr Ala Arg Pro Glu Ser Asp Arg Pro Arg Leu Ala Glu
            20                  25                  30

Val Ala Thr Asp Ser Asn Ile Pro Leu Ile Asp Leu Ala Ser Pro Asp
        35                  40                  45

Lys Pro Arg Val Ile Ala Glu Ile Ala Gln Ala Cys Arg Thr Tyr Gly
    50                  55                  60

Phe Phe Gln Val Thr Asn His Gly Ile Ala Glu Glu Leu Leu Glu Lys
65                  70                  75                  80

Val Met Ala Val Ala Leu Glu Phe Phe Arg Leu Pro Pro Glu Glu Lys
                85                  90                  95

Glu Lys Leu Tyr Ser Asp Glu Pro Ser Lys Lys Ile Arg Leu Ser Thr
            100                 105                 110

Ser Phe Asn Val Arg Lys Glu Thr Val His Asn Trp Arg Asp Tyr Leu
        115                 120                 125

Arg Leu His Cys His Pro Leu Glu Glu Phe Val Pro Glu Trp Pro Ser
    130                 135                 140

Asn Pro Ala Gln Phe Lys Glu Ile Met Ser Thr Tyr Cys Arg Glu Val
145                 150                 155                 160

Arg Gln Leu Gly Leu Arg Leu Leu Gly Ala Ile Ser Val Ser Leu Gly
                165                 170                 175

Leu Glu Glu Asp Tyr Ile Glu Lys Val Leu Gly Glu Gln Glu Gln His
            180                 185                 190

Met Ala Val Asn Tyr Tyr Pro Arg Cys Pro Glu Pro Asp Leu Thr Tyr
        195                 200                 205

Gly Leu Pro Lys His Thr Asp Pro Asn Ala Leu Thr Ile Leu Leu Pro
    210                 215                 220

Asp Pro His Val Ala Gly Leu Gln Val Leu Arg Asp Gly Asp Gln Trp
225                 230                 235                 240

Ile Val Val Asn Pro Arg Pro Asn Ala Leu Val Val Asn Leu Gly Asp
                245                 250                 255

Gln Ile Gln Ala Leu Ser Asn Asp Ala Tyr Lys Ser Val Trp His Arg
            260                 265                 270

Ala Val Val Asn Pro Val Gln Glu Arg Met Ser Val Ala Ser Phe Met
        275                 280                 285

Cys Pro Cys Asn Ser Ala Val Ile Ser Pro Ala Arg Lys Leu Val Ala
    290                 295                 300

Asp Gly Asp Ala Pro Val Tyr Arg Ser Phe Thr Tyr Asp Glu Tyr Tyr
305                 310                 315                 320

Lys Lys Phe Trp Ser Arg Asn Leu Asp Gln Glu His Cys Leu Glu Leu
                325                 330                 335

Phe Lys Gly Gln
            340

<210> SEQ ID NO 75
<211> LENGTH: 338
<212> TYPE: PRT
<213> ORGANISM: Populus trichocarpa

<400> SEQUENCE: 75

Met Asp Thr Lys Val Leu Ser Ser Gly Ile Gln Tyr Thr Asn Leu Pro
1               5                   10                  15

Ala Ser Tyr Val Arg Pro Glu Ser Glu Arg Pro Arg Leu Trp Glu Val
            20                  25                  30

Ser Thr Cys Glu Asn Val Pro Val Ile Asp Leu Gly Cys Gln Glu Arg
        35                  40                  45

Asp Gln Ile Val Gln Gln Val Gly Asp Ala Cys Lys Asn Tyr Gly Phe
            50                  55                  60

Phe Gln Val Ile Asn His Gly Val Ser Leu Glu Ala Val Glu Lys Met
65                  70                  75                  80

Leu Gly Val Ala His Asp Phe Phe Ser Leu Pro Val Glu Glu Lys Leu
                85                  90                  95

Lys Leu Tyr Ser Asp Asp Pro Ser Lys Thr Met Arg Leu Ser Thr Ser
            100                 105                 110

Phe Asn Val Asn Lys Glu Lys Val His Asn Trp Arg Asp Tyr Leu Arg
        115                 120                 125

Leu His Cys Tyr Pro Leu Asp Lys Tyr Ala Pro Glu Trp Pro Ser Lys
    130                 135                 140

Pro Pro Pro Phe Lys Asp Ile Val Ser Ser Tyr Cys Ile Gln Val Arg
145                 150                 155                 160

Glu Leu Gly Phe Arg Ile Gln Glu Leu Ile Ser Glu Ser Leu Gly Leu
                165                 170                 175

Glu Lys Asp His Val Lys Asn Val Leu Gly Glu Gln Gly Gln His Met
            180                 185                 190

Ala Val Asn Phe Tyr Pro Pro Cys Pro Glu Pro Glu Leu Thr Phe Gly
        195                 200                 205

Leu Pro Gly His Thr Asp Pro Asn Ala Leu Thr Ile Leu Leu Gln Asp
    210                 215                 220

Gln Ser Val Ala Gly Leu Gln Val Leu Lys Asp Gly Lys Trp Val Ala
225                 230                 235                 240

Val Asp Pro His Pro Asp Ala Phe Val Ile Asn Ile Gly Asp Gln Leu
                245                 250                 255

Gln Ala Leu Ser Asn Gly Arg Tyr Lys Ser Val Trp His Arg Ala Ile
            260                 265                 270

Thr Asn Thr Asp Lys Ala Arg Met Ser Val Ala Ser Phe Leu Cys Pro
        275                 280                 285

Tyr Asp Asn Ala Leu Ile Thr Pro Pro Lys Ala Leu Thr Asp Asp Gly
    290                 295                 300

Thr Gly Ala Val Tyr Arg Asp Phe Thr Tyr Ala Glu Tyr Tyr Lys Lys
305                 310                 315                 320

Phe Trp Ser Arg Asp Leu Asp Gln Glu His Cys Leu Glu Leu Phe Lys
                325                 330                 335

Asn Lys

<210> SEQ ID NO 76
<211> LENGTH: 338
<212> TYPE: PRT
<213> ORGANISM: Populus trichocarpa

<400> SEQUENCE: 76

Met Asp Thr Lys Val Ile Ser Ser Gly Val His Tyr Thr Asn Leu Pro
1               5                   10                  15

Ala Ser Tyr Val Arg Pro Glu Ser Glu Arg Pro Arg Leu Ser Glu Val
            20                  25                  30

Ser Thr Cys Glu Asp Val Pro Val Ile Asp Leu Gly Cys Gln Asp Arg
        35                  40                  45

Asn Gln Ile Val Gln Gln Val Gly Asp Ala Cys Glu His Tyr Gly Phe
    50                  55                  60

Phe Gln Val Ile Asn His Gly Val Ser Leu Glu Ala Val Glu Lys Met
65                  70                  75                  80

Leu Gly Val Ala His Asp Phe Phe Ser Leu Pro Val Glu Glu Lys Leu
                85                  90                  95

Lys Leu Tyr Ser Asp Asp Pro Ser Lys Thr Met Arg Leu Ser Thr Ser
            100                 105                 110

Phe Asn Val Asn Lys Glu Lys Val His Asn Trp Arg Asp Tyr Leu Arg
        115                 120                 125

Leu His Cys Tyr Pro Leu Asp Lys Tyr Val Pro Glu Trp Pro Ser Asn
    130                 135                 140

Pro Pro Pro Phe Lys Glu Ile Val Arg Ser Tyr Ser Ile Gln Val Arg
145                 150                 155                 160

Glu Leu Gly Phe Arg Ile Gln Glu Leu Ile Ser Glu Ser Leu Gly Leu
                165                 170                 175

Glu Lys Asp His Ile Lys Asn Val Leu Gly Glu Gln Gly Gln His Met
            180                 185                 190

Ala Val Asn Phe Tyr Pro Pro Cys Pro Glu Pro Glu Leu Thr Tyr Gly
        195                 200                 205

Leu Pro Ala His Thr Asp Pro Asn Ala Leu Thr Ile Leu Leu Gln Asp
    210                 215                 220

Leu Ser Val Ala Gly Leu Gln Val Leu Leu Lys Asp Gly Lys Trp Val
225                 230                 235                 240

Ala Val Asn Pro His Pro Asp Ala Phe Val Ile Asn Ile Gly Asp Gln
                245                 250                 255

Leu Gln Ala Leu Ser Asn Gly Arg Tyr Lys Ser Val Trp His Arg Ala
            260                 265                 270

Ile Thr Asn Thr Asp Lys Ala Arg Met Ser Val Ala Ser Phe Leu Cys
        275                 280                 285

Pro Phe Asp Asn Ala Leu Ile Thr Pro Pro Lys Ala Leu Thr Asp Asp
    290                 295                 300

Gly Thr Gly Ala Ile Tyr Arg Asp Phe Thr Tyr Ala Glu Tyr Tyr Lys
305                 310                 315                 320

Lys Phe Trp Ser Arg Asn Leu Asp Gln Glu His Cys Leu Glu Leu Phe
                325                 330                 335

Lys Asn

<210> SEQ ID NO 77
<211> LENGTH: 337
<212> TYPE: PRT
<213> ORGANISM: Solanum lycopersicum

<400> SEQUENCE: 77

Met Glu Thr Lys Val Ile Ser Ser Gly Ile Asn His Ser Thr Leu Pro
1               5                   10                  15

Gln Ser Tyr Ile Arg Pro Glu Ser Asp Arg Pro Arg Leu Ser Glu Val
            20                  25                  30

Val Asp Cys Glu Asn Val Pro Ile Ile Asp Leu Ser Cys Gly Asp Gln
        35                  40                  45

Ala Gln Ile Ile Arg Gln Ile Gly Glu Ala Cys Gln Thr Tyr Gly Phe
    50                  55                  60

Phe Gln Val Ile Asn His Gly Val Pro Lys Glu Val Val Glu Lys Met
65                  70                  75                  80

Leu Gly Val Ala Gly Glu Phe Phe Asn Leu Pro Val Glu Glu Lys Leu
                85                  90                  95

Lys Leu Tyr Ser Asp Asp Pro Ser Lys Thr Met Arg Leu Ser Thr Ser
            100                 105                 110

```
Phe Asn Val Lys Lys Glu Thr Val His Asn Trp Arg Asp Tyr Leu Arg
            115                 120                 125

Leu His Cys Tyr Pro Leu Glu Lys Tyr Ala Pro Glu Trp Pro Ser Asn
130                 135                 140

Pro Ser Ser Phe Arg Glu Ile Val Ser Arg Tyr Cys Arg Glu Ile Arg
145                 150                 155                 160

Gln Leu Gly Phe Arg Leu Glu Glu Ala Ile Ala Glu Ser Leu Gly Leu
                165                 170                 175

Asp Lys Glu Cys Ile Lys Asp Val Leu Gly Glu Gln Gly Gln His Met
            180                 185                 190

Ala Ile Asn Tyr Tyr Pro Pro Cys Pro Gln Pro Glu Leu Thr Tyr Gly
        195                 200                 205

Leu Pro Ala His Thr Asp Pro Asn Ser Leu Thr Ile Leu Leu Gln Asp
210                 215                 220

Leu Gln Val Ala Gly Leu Gln Val Leu Lys Asp Gly Lys Trp Leu Ala
225                 230                 235                 240

Val Lys Pro Gln Pro Asp Ala Phe Val Ile Asn Leu Gly Asp Gln Leu
                245                 250                 255

Gln Ala Val Ser Asn Gly Lys Tyr Arg Ser Val Trp His Arg Ala Ile
            260                 265                 270

Val Asn Ser Asp Gln Ala Arg Met Ser Val Ala Ser Phe Leu Cys Pro
        275                 280                 285

Cys Asp Ser Ala Lys Ile Ser Ala Pro Lys Leu Leu Thr Glu Asp Gly
290                 295                 300

Ser Pro Val Ile Tyr Gln Asp Phe Thr Tyr Ala Glu Tyr Tyr Asn Lys
305                 310                 315                 320

Phe Trp Ser Arg Asn Leu Asp Gln Gln His Cys Leu Glu Leu Phe Lys
                325                 330                 335

Asn

<210> SEQ ID NO 78
<211> LENGTH: 342
<212> TYPE: PRT
<213> ORGANISM: Solanum lycopersicum

<400> SEQUENCE: 78

Met Thr Thr Thr Ser Val Leu Ser Gly Phe Asn His Ser Thr Leu
1               5                   10                  15

Pro Gln Ser Tyr Val Arg Pro Glu Ser Gln Arg Pro Cys Met Ser Glu
            20                  25                  30

Val Val Asp Ser Asp Asp Leu Val Pro Val Ile Asp Met Ser Cys Thr
        35                  40                  45

Asn Arg Asn Val Ile Val His Gln Ile Gly Glu Ala Cys Arg Leu Tyr
    50                  55                  60

Gly Phe Phe Gln Val Ile Asn His Gly Val Ser Lys Lys Val Ile Asp
65                  70                  75                  80

Glu Met Leu Gly Val Ser His Glu Phe Phe Lys Leu Pro Val Glu Glu
                85                  90                  95

Lys Met Lys Leu Tyr Ser Asp Asp Pro Ser Lys Thr Met Arg Leu Ser
            100                 105                 110

Thr Ser Phe Asn Val Lys Lys Glu Thr Val His Asn Trp Arg Asp Tyr
        115                 120                 125

Leu Arg Leu His Cys Tyr Pro Leu Asp Lys Tyr Ala Pro Glu Trp Pro
    130                 135                 140
```

-continued

```
Ser Asn Pro Pro Ser Phe Arg Glu Ile Val Ser Lys Tyr Cys Met Glu
145                 150                 155                 160

Val Arg Glu Leu Gly Tyr Arg Leu Glu Glu Ala Ile Ser Glu Ser Leu
            165                 170                 175

Gly Leu Glu Lys Asp Cys Ile Lys Asn Val Leu Gly Glu Gln Gly Gln
        180                 185                 190

His Met Ala Ile Asn Phe Tyr Pro Gln Cys Pro Gln Pro Glu Leu Thr
    195                 200                 205

Tyr Gly Leu Pro Ala His Thr Asp Pro Asn Ala Ile Thr Ile Leu Leu
210                 215                 220

Gln Asp Leu Gln Val Ala Gly Leu Gln Val Leu Lys Asp Gly Lys Trp
225                 230                 235                 240

Leu Ser Ile Lys Pro Gln Pro Asn Ala Phe Val Ile Asn Leu Gly Asp
                245                 250                 255

Gln Leu Glu Ala Leu Ser Asn Gly Lys Tyr Lys Ser Ile Trp His Arg
            260                 265                 270

Ala Ile Val Asn Ser Asp Lys Ala Arg Met Ser Val Ala Ser Phe Leu
        275                 280                 285

Cys Pro Asn Asp Cys Ser Ile Ile Ser Ala Pro Lys Thr Leu Thr Glu
290                 295                 300

Asp Gly Ser Ser Ala Ile Tyr Arg His Phe Thr Tyr Ala Glu Tyr Tyr
305                 310                 315                 320

Glu Lys Phe Trp Ser Arg Asn Leu Asp Gln Glu Tyr Cys Leu Glu Leu
                325                 330                 335

Phe Lys Asn Asp Gly Thr
            340

<210> SEQ ID NO 79
<211> LENGTH: 336
<212> TYPE: PRT
<213> ORGANISM: Sorghum bicolor

<400> SEQUENCE: 79

Met Ala Glu Gln Leu Leu Ser Thr Ala Val His Asp Thr Leu Pro Gly
1               5                   10                  15

Ser Tyr Val Arg Pro Glu Ser Gln Arg Pro Arg Leu Ala Glu Val Val
            20                  25                  30

Thr Gly Ala Arg Ile Pro Val Val Asp Leu Gly Ser Pro Asp Arg Ala
        35                  40                  45

Ala Val Val Ala Ala Ile Gly Asp Ala Cys Arg Ser His Gly Phe Phe
    50                  55                  60

Gln Val Leu Asn His Gly Val His Ala Asp Leu Val Ala Ala Val Met
65                  70                  75                  80

Ala Val Gly Arg Ala Phe Phe Arg Leu Ser Pro Glu Glu Lys Ala Lys
                85                  90                  95

Leu Tyr Ser Asp Asp Pro Ala Arg Lys Ile Arg Leu Ser Thr Ser Phe
            100                 105                 110

Asn Val Arg Lys Glu Thr Val His Asn Trp Arg Asp Tyr Leu Arg Leu
        115                 120                 125

His Cys His Pro Leu Asp Glu Phe Val Pro Asp Trp Pro Ser Asn Pro
    130                 135                 140

Pro Asp Phe Lys Asp Thr Met Ser Thr Tyr Cys Lys Glu Val Arg Glu
145                 150                 155                 160

Leu Gly Phe Arg Leu Tyr Ala Ala Ile Ser Glu Ser Leu Gly Leu Glu
```

```
                165                 170                 175
Ala Ser Tyr Met Lys Glu Thr Leu Gly Glu Gln Glu Gln His Met Ala
            180                 185                 190

Val Asn Phe Tyr Pro Pro Cys Pro Glu Pro Glu Leu Thr Tyr Gly Leu
        195                 200                 205

Pro Ala His Thr Asp Pro Asn Ala Leu Thr Ile Leu Leu Met Asp Gln
    210                 215                 220

Asp Val Ala Gly Leu Gln Val Leu His Gly Gly Lys Trp Val Ala Val
225                 230                 235                 240

Asn Pro Gln Pro Gly Ala Leu Ile Ile Asn Ile Gly Asp Gln Leu Gln
                245                 250                 255

Ala Leu Ser Asn Gly Gln Tyr Arg Ser Val Trp His Arg Ala Val Val
            260                 265                 270

Asn Ser Asp Arg Glu Arg Met Ser Val Ala Ser Phe Leu Cys Pro Cys
        275                 280                 285

Asn His Val Val Leu Gly Pro Ala Lys Lys Leu Val Thr Glu Asp Thr
    290                 295                 300

Pro Ala Val Tyr Arg Ser Tyr Thr Tyr Asp Glu Tyr Tyr Lys Lys Phe
305                 310                 315                 320

Trp Ser Arg Asn Leu Asp Gln Glu His Cys Leu Glu Leu Phe Arg Thr
                325                 330                 335

<210> SEQ ID NO 80
<211> LENGTH: 1020
<212> TYPE: DNA
<213> ORGANISM: Spinacia oleracea

<400> SEQUENCE: 80
atggcaaaca agatattatc caccggaatt ccttacaaaa ccctccccga aagctacatc      60
cgacccgaaa tgagaggcc  aacttatct  caagtctccg attgcgagaa tgtccctgtt     120
attgacttgg gtgccaaaga ccgtactcaa acaatccacc aagtcttcaa tgcttgtaaa     180
aattacgggt ttttccaggt gattaatcat ggggtgtcaa aggaattagc ggagaagatg     240
caaaaggtag ctcgagagtt cttcgatatg tcggttgagg aaaaaatgaa attatatagt     300
gacgatccaa ctaaaacact aagattgtct acaagtttta cgttaacaa  agaggaagtt     360
cataattgga gagattatct taggctccat tgttggcctc ttgagcaata tgtccccgaa     420
tggccttcta accccccttc cttcaaggaa atagtgagca agtacataaa agaagttagg     480
gaacttggtt tcagagtcca agaactaata tcagagagtt tagggttgga gaaagattac     540
ataaagaatg tcctaggaga tcaaggacaa cacatggctc ttaattatta ccctgagtgc     600
ccggagccag atgacata   cgggttgccg gtcatactg  accctaatgc ccttaccatc     660
cttctccaag acttgcaagt atctggcctt caaattttta aggatggtaa atggcttgct     720
gtcaaacctc aacctgatgc ttttgtcatt aacattggtg atcaattgca ggcattaagt     780
aacggtatat acaagagtgt atggcacaga gcagttgtga acacagataa gccaagatta     840
tcagtagctt cattcctctg ccccgccaat gatgcgttga agcgcgcc   aacacctctg     900
accgccaacg gatcaccggc tgtatataga gactatacgt atcctgagta ctacaagact     960
ttctggagta ggaacttgga ccaagagcac tgcttggagc ttttttaaaaa ccaaacctag   1020

<210> SEQ ID NO 81
<211> LENGTH: 339
<212> TYPE: PRT
<213> ORGANISM: Spinacia oleracea
```

<400> SEQUENCE: 81

Met Ala Asn Lys Ile Leu Ser Thr Gly Ile Pro Tyr Lys Thr Leu Pro
1               5                   10                  15

Glu Ser Tyr Ile Arg Pro Glu Asn Glu Arg Pro Asn Leu Ser Gln Val
            20                  25                  30

Ser Asp Cys Glu Asn Val Pro Val Ile Asp Leu Gly Ala Lys Asp Arg
        35                  40                  45

Thr Gln Thr Ile His Gln Val Phe Asn Ala Cys Lys Asn Tyr Gly Phe
    50                  55                  60

Phe Gln Val Ile Asn His Gly Val Ser Lys Glu Leu Ala Glu Lys Met
65                  70                  75                  80

Gln Lys Val Ala Arg Glu Phe Phe Asp Met Ser Val Glu Glu Lys Met
                85                  90                  95

Lys Leu Tyr Ser Asp Asp Pro Thr Lys Thr Leu Arg Leu Ser Thr Ser
            100                 105                 110

Phe Asn Val Asn Lys Glu Glu Val His Asn Trp Arg Asp Tyr Leu Arg
        115                 120                 125

Leu His Cys Trp Pro Leu Glu Gln Tyr Val Pro Glu Trp Pro Ser Asn
    130                 135                 140

Pro Pro Ser Phe Lys Glu Ile Val Ser Lys Tyr Ile Lys Glu Val Arg
145                 150                 155                 160

Glu Leu Gly Phe Arg Val Gln Glu Leu Ile Ser Glu Ser Leu Gly Leu
                165                 170                 175

Glu Lys Asp Tyr Ile Lys Asn Val Leu Gly Asp Gln Gly Gln His Met
            180                 185                 190

Ala Leu Asn Tyr Tyr Pro Glu Cys Pro Glu Pro Glu Met Thr Tyr Gly
        195                 200                 205

Leu Pro Gly His Thr Asp Pro Asn Ala Leu Thr Ile Leu Leu Gln Asp
    210                 215                 220

Leu Gln Val Ser Gly Leu Gln Ile Phe Lys Asp Gly Lys Trp Leu Ala
225                 230                 235                 240

Val Lys Pro Gln Pro Asp Ala Phe Val Ile Asn Ile Gly Asp Gln Leu
                245                 250                 255

Gln Ala Leu Ser Asn Gly Ile Tyr Lys Ser Val Trp His Arg Ala Val
            260                 265                 270

Val Asn Thr Asp Lys Pro Arg Leu Ser Val Ala Ser Phe Leu Cys Pro
        275                 280                 285

Ala Asn Asp Ala Leu Ile Ser Ala Pro Thr Pro Leu Thr Ala Asn Gly
    290                 295                 300

Ser Pro Ala Val Tyr Arg Asp Tyr Thr Tyr Pro Glu Tyr Tyr Lys Thr
305                 310                 315                 320

Phe Trp Ser Arg Asn Leu Asp Gln Glu His Cys Leu Glu Leu Phe Lys
                325                 330                 335

Asn Gln Thr

<210> SEQ ID NO 82
<211> LENGTH: 338
<212> TYPE: PRT
<213> ORGANISM: Vitis sp.

<400> SEQUENCE: 82

Met Glu Ser Lys Val Leu Ser Thr Gly Ile Arg Tyr Leu Thr Leu Pro
1               5                   10                  15

Gln Ser Tyr Ile Arg Pro Glu Pro Arg Pro Arg Leu Ser Gln Val
            20                  25                  30

Ser Glu Cys Lys His Val Pro Ile Ile Asp Leu Gly Lys Asp Val Asn
        35                  40                  45

Arg Ala Gln Leu Ile Gln His Ile Ala Asp Ala Cys Arg Leu Tyr Gly
    50                  55                  60

Phe Phe Gln Val Ile Asn His Gly Val Ala Ala Glu Met Met Glu Lys
65                  70                  75                  80

Met Leu Glu Val Ala Asp Glu Phe Tyr Arg Leu Pro Val Glu Glu Lys
                85                  90                  95

Met Lys Leu Tyr Ser Asp Asp Pro Thr Lys Thr Met Arg Leu Ser Thr
            100                 105                 110

Ser Phe Asn Val Asn Lys Glu Lys Val His Asn Trp Arg Asp Tyr Leu
        115                 120                 125

Arg Leu His Cys Tyr Pro Leu Asp Gln Tyr Thr Pro Glu Trp Pro Ser
    130                 135                 140

Asn Pro Pro Ser Phe Lys Glu Ile Val Ser Ser Tyr Cys Lys Glu Val
145                 150                 155                 160

Arg Glu Leu Gly Phe Arg Leu Gln Glu Met Ile Ser Glu Ser Leu Gly
                165                 170                 175

Leu Glu Lys Asp His Ile Lys Asn Val Phe Gly Glu Gln Gly Gln His
            180                 185                 190

Met Ala Val Asn Tyr Tyr Pro Pro Cys Pro Gln Pro Glu Leu Thr Tyr
        195                 200                 205

Gly Leu Pro Gly His Thr Asp Pro Asn Ala Leu Thr Ile Leu Leu Gln
    210                 215                 220

Asp Leu Arg Val Ala Gly Leu Gln Val Leu Lys Asp Gly Thr Trp Leu
225                 230                 235                 240

Ala Ile Lys Pro His Pro Gly Ala Phe Val Val Asn Ile Gly Asp Gln
                245                 250                 255

Leu Gln Ala Val Ser Asn Gly Lys Tyr Lys Ser Val Trp His Arg Ala
            260                 265                 270

Val Val Asn Ala Glu Ser Glu Arg Leu Ser Val Ala Ser Phe Leu Cys
        275                 280                 285

Pro Cys Asn Asp Ala Val Ile Gly Pro Ala Lys Pro Leu Thr Glu Asp
    290                 295                 300

Gly Ser Ala Pro Ile Tyr Lys Asn Phe Thr Tyr Ala Glu Tyr Tyr Lys
305                 310                 315                 320

Lys Phe Trp Gly Arg Asp Leu Asp Gln Glu His Cys Leu Glu Leu Phe
                325                 330                 335

Lys Asn

<210> SEQ ID NO 83
<211> LENGTH: 336
<212> TYPE: PRT
<213> ORGANISM: Zea mays

<400> SEQUENCE: 83

Met Ala Glu His Leu Leu Ser Thr Ala Val His Asp Thr Leu Pro Gly
1               5                   10                  15

Ser Tyr Val Arg Pro Glu Pro Glu Arg Pro Arg Leu Ala Glu Val Val
            20                  25                  30

Thr Gly Ala Arg Ile Pro Val Val Asp Leu Gly Ser Pro Asp Arg Gly
        35                  40                  45

```
Ala Val Val Ala Ala Val Gly Asp Ala Cys Arg Ser His Gly Phe Phe
    50                  55                  60

Gln Val Val Asn His Gly Ile His Ala Ala Leu Val Ala Val Met
65                  70                  75                  80

Ala Ala Gly Arg Gly Phe Phe Arg Leu Pro Pro Glu Glu Lys Ala Lys
                85                  90                  95

Leu Tyr Ser Asp Asp Pro Ala Arg Lys Ile Arg Leu Ser Thr Ser Phe
            100                 105                 110

Asn Val Arg Lys Glu Thr Val His Asn Trp Arg Asp Tyr Leu Arg Leu
            115                 120                 125

His Cys His Pro Leu Asp Glu Phe Leu Pro Asp Trp Pro Ser Asn Pro
130                 135                 140

Pro Asp Phe Lys Glu Thr Met Gly Thr Tyr Cys Lys Glu Val Arg Glu
145                 150                 155                 160

Leu Gly Phe Arg Leu Tyr Ala Ala Ile Ser Glu Ser Leu Gly Leu Glu
                165                 170                 175

Ala Ser Tyr Met Lys Glu Ala Leu Gly Glu Gln Glu Gln His Met Ala
            180                 185                 190

Val Asn Phe Tyr Pro Pro Cys Pro Glu Pro Glu Leu Thr Tyr Gly Leu
            195                 200                 205

Pro Ala His Thr Asp Pro Asn Ala Leu Thr Ile Leu Leu Met Asp Pro
210                 215                 220

Asp Val Ala Gly Leu Gln Val Leu His Ala Gly Gln Trp Val Ala Val
225                 230                 235                 240

Asn Pro Gln Pro Gly Ala Leu Ile Ile Asn Ile Gly Asp Gln Leu Gln
                245                 250                 255

Ala Leu Ser Asn Gly Gln Tyr Arg Ser Val Trp His Arg Ala Val Val
            260                 265                 270

Asn Ser Asp Arg Glu Arg Met Ser Val Ala Ser Phe Leu Cys Pro Cys
            275                 280                 285

Asn His Val Val Leu Gly Pro Ala Arg Lys Leu Val Thr Glu Asp Thr
290                 295                 300

Pro Ala Val Tyr Arg Asn Tyr Thr Tyr Asp Lys Tyr Tyr Ala Lys Phe
305                 310                 315                 320

Trp Ser Arg Asn Leu Asp Gln Glu His Cys Leu Glu Leu Phe Arg Thr
                325                 330                 335

<210> SEQ ID NO 84
<211> LENGTH: 346
<212> TYPE: PRT
<213> ORGANISM: Zingiber officinale

<400> SEQUENCE: 84

Met Ala Asp Met Leu Leu Ser Ile Gly Glu His Asp Thr Met Pro Arg
1               5                   10                  15

Asn Tyr Val Arg Pro Glu Asn Glu Arg Pro His Leu Asp Asn Val Ile
                20                  25                  30

Ala Asp Ala Asn Ile Pro Val Val Asp Phe Gly Ala Pro Asp Lys Ser
            35                  40                  45

Gln Ile Ile Ser Gln Ile Glu Lys Ala Cys Arg Leu Tyr Gly Phe Phe
    50                  55                  60

Gln Val Val Asn His Gly Ile Ala Ala Glu Leu Ile Lys Lys Val Leu
65                  70                  75                  80

Ala Ile Ala Leu Glu Phe Phe Arg Leu Pro Gln Glu Glu Lys Ala Lys
                85                  90                  95
```

Leu Tyr Ser Asp Asp Pro Ala Lys Lys Ile Arg Leu Ser Thr Ser Phe
                100                 105                 110

Asn Val Arg Lys Glu Thr Val His Asn Trp Arg Asp Tyr Leu Arg Leu
            115                 120                 125

His Cys Tyr Pro Leu Glu Glu Phe Ile Pro Asp Trp Pro Ser Asn Pro
130                 135                 140

Ser Ser Phe Lys Asp Val Phe Gly Ser Tyr Cys Gln Gln Val Arg Lys
145                 150                 155                 160

Leu Gly Phe Arg Ile Leu Gly Ile Ile Ser Leu Ser Leu Gly Leu Glu
                165                 170                 175

Glu Glu Tyr Leu Val Arg Val Leu Gly Glu Gln Glu Gln His Met Ala
            180                 185                 190

Val Asn Tyr Tyr Pro Lys Cys Pro Glu Pro Glu Leu Thr Tyr Gly Leu
        195                 200                 205

Pro Ala His Thr Asp Pro Asn Ala Leu Thr Ile Leu Leu Gln Asp Pro
    210                 215                 220

His Val Ser Gly Leu Gln Val His Lys Asp Gly Lys Trp Ile Ala Val
225                 230                 235                 240

Asp Pro Lys Pro Asn Ala Phe Val Ile Asn Ile Gly Asp Gln Leu Gln
                245                 250                 255

Ala Leu Ser Asn Gly Arg Tyr Lys Ser Val Trp His Arg Ala Val Val
            260                 265                 270

Asn Ser Asn Lys Glu Arg Met Ser Val Ala Ser Phe Leu Cys Pro Cys
        275                 280                 285

Asn Ser Val Leu Ile Ser Pro Pro Glu Lys Leu Ile Ala Asp Gly Cys
    290                 295                 300

Pro Ala Val Tyr Arg Ser Tyr Thr Tyr Asp Glu Tyr Tyr Lys Lys Phe
305                 310                 315                 320

Trp Ser Arg Asn Leu Asp Gln Glu His Cys Leu Glu Leu Phe Lys Lys
                325                 330                 335

Glu Arg Glu Thr Cys Pro Asp Ala Pro Thr
            340                 345

<210> SEQ ID NO 85
<211> LENGTH: 22
<212> TYPE: DNA
<213> ORGANISM: Artificial Sequence
<220> FEATURE:
<223> OTHER INFORMATION: forward primer AtDMR6_fw

<400> SEQUENCE: 85
caccatggcg gcaaagctga ta                                           22

<210> SEQ ID NO 86
<211> LENGTH: 21
<212> TYPE: DNA
<213> ORGANISM: Artificial Sequence
<220> FEATURE:
<223> OTHER INFORMATION: reverse primer AtDMR6UTR_rv

<400> SEQUENCE: 86
gacaaacaca aaggccaaag a                                            21

<210> SEQ ID NO 87
<211> LENGTH: 24
<212> TYPE: DNA
<213> ORGANISM: Artificial Sequence
<220> FEATURE:

<223> OTHER INFORMATION: forward primer cuc_fw

<400> SEQUENCE: 87
caccatgagc agtgtgatgg agat         24

<210> SEQ ID NO 88
<211> LENGTH: 20
<212> TYPE: DNA
<213> ORGANISM: Artificial Sequence
<220> FEATURE:
<223> OTHER INFORMATION: reverse primer cucUTR_rv

<400> SEQUENCE: 88
tgggccaaaa agtttatcca         20

<210> SEQ ID NO 89
<211> LENGTH: 27
<212> TYPE: DNA
<213> ORGANISM: Artificial Sequence
<220> FEATURE:
<223> OTHER INFORMATION: forward primer spi_fw

<400> SEQUENCE: 89
caccatggca aacaagatat tatccac         27

<210> SEQ ID NO 90
<211> LENGTH: 22
<212> TYPE: DNA
<213> ORGANISM: Artificial Sequence
<220> FEATURE:
<223> OTHER INFORMATION: reverse primer spiUTR_rv

<400> SEQUENCE: 90
ttgctgccta caaaagtaca aa         22

<210> SEQ ID NO 91
<211> LENGTH: 24
<212> TYPE: DNA
<213> ORGANISM: Artificial Sequence
<220> FEATURE:
<223> OTHER INFORMATION: forward primer Lsat_fw

<400> SEQUENCE: 91
caccatggcc gcaaaagtca tctc         24

<210> SEQ ID NO 92
<211> LENGTH: 22
<212> TYPE: DNA
<213> ORGANISM: Artificial Sequence
<220> FEATURE:
<223> OTHER INFORMATION: reverse primer LsatUTR_rv

<400> SEQUENCE: 92
catggaaaca catattcctt ca         22

<210> SEQ ID NO 93
<211> LENGTH: 28
<212> TYPE: DNA
<213> ORGANISM: Artificial Sequence
<220> FEATURE:
<223> OTHER INFORMATION: forward primer Slyc1dmr6_fw

<400> SEQUENCE: 93
caccatggaa accaaagtta tttctagc         28

-continued

<210> SEQ ID NO 94
<211> LENGTH: 20
<212> TYPE: DNA
<213> ORGANISM: Artificial Sequence
<220> FEATURE:
<223> OTHER INFORMATION: reverse primer Slyc1dmr6UTR_rv

<400> SEQUENCE: 94
gggacatccc tatgaaccaa           20

<210> SEQ ID NO 95
<211> LENGTH: 1013
<212> TYPE: DNA
<213> ORGANISM: Solanum lycopersicum

<400> SEQUENCE: 95
atggaaacca aagttatttc tagcggaatc aaccactcta ctcttcctca aagttacatc        60
cgacccgaat ccgatagacc acgtctatcg gaagtggtcg attgtgaaaa tgttccaata       120
attgacttaa gttgcggaga tcaagctcaa ataattcgtc aaattggaga agcttgtcaa       180
acttatggtt tctttcaggt aattaatcat ggtgtaccaa aggaagttgt agagaaaatg       240
ctaggggtag ctggggaatt tttcaattta ccagtagaag agaaactaaa attatattca       300
gatgatcctt caaagaccat gagattatca acaagtttta atgttaaaaa ggagacagtt       360
cataattgga gagattatct cagacttcat tgttatcctc tagagaagta tgctcctgaa       420
tggccttcta atccatcatc tttcagggaa atcgtgagca gatattgcag ggaaattcgt       480
caactcggat ttagattaga agaagccata gcagaaagcc tggggttaga taaagagtgt       540
ataaaagatg tattgggtga acaaggacaa catatggcta tcaattatta tcctccttgt       600
ccacaaccag aacttactta tgggcttccg gcccatactg atccaaattc acttacaatt       660
cttcttcaag acttgcaagt tgcgggtctt caagttctta agatggcaa atggttagct       720
gtaaaacctc aacctgacgc ctttgtcatt aatcttgggg atcaattgca ggcagtaagt       780
aacggtaagt acagaagtgt atggcatcga gctattgtga attcagatca agctaggatg       840
tcagtggctt cgtttctatg tccgtgtgat agcgcgaaaa tcagtgcacc aaagctgctg       900
acagaagatg gatctccagt gatttatcaa gactttacgt atgctgagta ttacaacaag       960
ttctggagca ggaatttgga ccagcaacat tgtttggaac ttttcaagaa taa             1013

<210> SEQ ID NO 96
<211> LENGTH: 337
<212> TYPE: PRT
<213> ORGANISM: Solanum lycopersicum

<400> SEQUENCE: 96

Met Glu Thr Lys Val Ile Ser Ser Gly Ile Asn His Ser Thr Leu Pro
1               5                   10                  15

Gln Ser Tyr Ile Arg Pro Glu Ser Asp Arg Pro Arg Leu Ser Glu Val
            20                  25                  30

Val Asp Cys Glu Asn Val Pro Ile Ile Asp Leu Ser Cys Gly Asp Gln
        35                  40                  45

Ala Gln Ile Ile Arg Gln Ile Gly Glu Ala Cys Gln Thr Tyr Gly Phe
    50                  55                  60

Phe Gln Val Ile Asn His Gly Val Pro Lys Glu Val Val Glu Lys Met
65                  70                  75                  80

Leu Gly Val Ala Gly Glu Phe Phe Asn Leu Pro Val Glu Glu Lys Leu
                85                  90                  95

| | | | | | | | | | | | | |
|---|---|---|---|---|---|---|---|---|---|---|---|---|
|Lys|Leu|Tyr|Ser|Asp|Asp|Pro|Ser|Lys|Thr|Met|Arg|Leu|Ser|Thr|Ser|
| | | |100| | | |105| | | |110| |

| Phe | Asn | Val | Lys | Lys | Glu | Thr | Val | His | Asn | Trp | Arg | Asp | Tyr | Leu | Arg |
| 115 | | | | | 120 | | | | | 125 | | | | | |

Phe Asn Val Lys Lys Glu Thr Val His Asn Trp Arg Asp Tyr Leu Arg
            115                 120                 125

Leu His Cys Tyr Pro Leu Glu Lys Tyr Ala Pro Glu Trp Pro Ser Asn
        130                 135                 140

Pro Ser Ser Phe Arg Glu Ile Val Ser Arg Tyr Cys Arg Glu Ile Arg
145                 150                 155                 160

Gln Leu Gly Phe Arg Leu Glu Glu Ala Ile Ala Glu Ser Leu Gly Leu
                165                 170                 175

Asp Lys Glu Cys Ile Lys Asp Val Leu Gly Glu Gln Gly His Met
                180                 185                 190

Ala Ile Asn Tyr Tyr Pro Pro Cys Pro Gln Pro Glu Leu Thr Tyr Gly
            195                 200                 205

Leu Pro Ala His Thr Asp Pro Asn Ser Leu Thr Ile Leu Leu Gln Asp
210                 215                 220

Leu Gln Val Ala Gly Leu Gln Val Leu Lys Asp Gly Lys Trp Leu Ala
225                 230                 235                 240

Val Lys Pro Gln Pro Asp Ala Phe Val Ile Asn Leu Gly Asp Gln Leu
                245                 250                 255

Gln Ala Val Ser Asn Gly Lys Tyr Arg Ser Val Trp His Arg Ala Ile
            260                 265                 270

Val Asn Ser Asp Gln Ala Arg Met Ser Val Ala Ser Phe Leu Cys Pro
            275                 280                 285

Cys Asp Ser Ala Lys Ile Ser Ala Pro Lys Leu Leu Thr Glu Asp Gly
290                 295                 300

Ser Pro Val Ile Tyr Gln Asp Phe Thr Tyr Ala Glu Tyr Tyr Asn Lys
305                 310                 315                 320

Phe Trp Ser Arg Asn Leu Asp Gln Gln His Cys Leu Glu Leu Phe Lys
                325                 330                 335

Asn

<210> SEQ ID NO 97
<211> LENGTH: 1014
<212> TYPE: DNA
<213> ORGANISM: Nicotiana benthamiana

<400> SEQUENCE: 97

```
atggaagcaa aagttctttc agcggaatc cgccactcta ctatccctca agttacatc     60 cgccctcaat ccgataggcc gcgcctttct gaagttgctg attgtgaaaa cgttccagta    120
gttgatatag gttgcggtga tagaaacctt attgttcatc aaattggtga agcctgtcgt    180
ctttatggtt ttttccaggt aattaatcat ggtgtaccaa gaatttaat agacgaaatg     240 ctagagatag ctggggaatt ttttaggctt ccagttgaag agaagttgaa attgtactca    300
gatgacccat cgaagacgat gagattgtcg actagtttta atgtgaaaaa ggagaaggtt    360
cacaattgga gagattatct cagacttcat tgttatcctc ttgaaaatta cgctcctgaa    420
tggccttcca atccttcctc tttcagggaa atcgtgagca gatattgcat ggaagttcga    480
caactcgggt tcagattgca ggaagccata gcagagagcc taggcttaga gaaagagtgt    540
ataaaggatg tatttgggcga acaaggtcaa cacatggcta tcaatttcta tcctccttgt    600
ccacaaccag aactcactta tgggctgcca gcacatactg atccaaatgc ccttacaatt    660
cttcttcaag acttagaagt agctggtctt caagttctta agatggcga atggttggcc    720
```

```
gtcaagcctc aaccagatgc ctttgtcatt aatcttggtg atcaactgca ggcagtgagt    780
aatgggagat acaaaagcgt atggcatcga gctattgtaa attcagacaa agccaggttg    840
tcagtggctt cgttcctttg tccgtgcgat agcgcgaaaa tcagtgctcc aaagctcctc    900
actgaagatg gatctcctgt catttatcag gactttacct atgctgagta ttacaaaaag    960
ttctggagca ggaatttgga ccaggaacat tgtttggaac ttttcaagaa ctaa         1014
```

<210> SEQ ID NO 98
<211> LENGTH: 337
<212> TYPE: PRT
<213> ORGANISM: Nicotiana benthamiana

<400> SEQUENCE: 98

```
Met Glu Ala Lys Val Leu Ser Ser Gly Ile Arg His Ser Thr Ile Pro
 1               5                  10                  15

Gln Ser Tyr Ile Arg Pro Gln Ser Asp Arg Pro Arg Leu Ser Glu Val
            20                  25                  30

Ala Asp Cys Glu Asn Val Pro Val Val Asp Ile Gly Cys Gly Asp Arg
        35                  40                  45

Asn Leu Ile Val His Gln Ile Gly Glu Ala Cys Arg Leu Tyr Gly Phe
    50                  55                  60

Phe Gln Val Ile Asn His Gly Val Pro Lys Asn Leu Ile Asp Glu Met
65                  70                  75                  80

Leu Glu Ile Ala Gly Glu Phe Phe Arg Leu Pro Val Glu Glu Lys Leu
                85                  90                  95

Lys Leu Tyr Ser Asp Asp Pro Ser Lys Thr Met Arg Leu Ser Thr Ser
           100                 105                 110

Phe Asn Val Lys Lys Glu Lys Val His Asn Trp Arg Asp Tyr Leu Arg
       115                 120                 125

Leu His Cys Tyr Pro Leu Glu Asn Tyr Ala Pro Glu Trp Pro Ser Asn
   130                 135                 140

Pro Ser Ser Phe Arg Glu Ile Val Ser Arg Tyr Cys Met Glu Val Arg
145                 150                 155                 160

Gln Leu Gly Phe Arg Leu Gln Glu Ala Ile Ala Glu Ser Leu Gly Leu
                165                 170                 175

Glu Lys Glu Cys Ile Lys Asp Val Leu Gly Glu Gln Gly Gln His Met
           180                 185                 190

Ala Ile Asn Phe Tyr Pro Pro Cys Pro Gln Pro Glu Leu Thr Tyr Gly
       195                 200                 205

Leu Pro Ala His Thr Asp Pro Asn Ala Leu Thr Ile Leu Leu Gln Asp
   210                 215                 220

Leu Glu Val Ala Gly Leu Gln Val Leu Lys Asp Gly Glu Trp Leu Ala
225                 230                 235                 240

Val Lys Pro Gln Pro Asp Ala Phe Val Ile Asn Leu Gly Asp Gln Leu
                245                 250                 255

Gln Ala Val Ser Asn Gly Arg Tyr Lys Ser Val Trp His Arg Ala Ile
           260                 265                 270

Val Asn Ser Asp Lys Ala Arg Leu Ser Val Ala Ser Phe Leu Cys Pro
       275                 280                 285

Cys Asp Ser Ala Lys Ile Ser Ala Pro Lys Leu Leu Thr Glu Asp Gly
   290                 295                 300

Ser Pro Val Ile Tyr Gln Asp Phe Thr Tyr Ala Glu Tyr Tyr Lys Lys
305                 310                 315                 320

Phe Trp Ser Arg Asn Leu Asp Gln Glu His Cys Leu Glu Leu Phe Lys
```

Asn

<210> SEQ ID NO 99
<211> LENGTH: 1026
<212> TYPE: DNA
<213> ORGANISM: Arabidopsis thaliana

<400> SEQUENCE: 99

```
atggcggcaa agctgatatc caccggtttc cgtcatacta ctttgccgga aaactatgtc      60
cggccaatct ccgaccgtcc acgtctctct gaagtctctc aactcgaaga tttccctctc     120
atcgatctct cttccactga tcgatctttt ctcatccaac aaatccacca agcttgtgcc     180
cgattcggat tttttcaggt cataaatcac ggagttaaca acaaataat agatgagatg      240
gtgagtgttg cgcgtgagtt ctttagcatg tctatggaag aaaaaatgaa gctatattca     300
gacgatccaa cgaagacaac aagattatcg acgagcttca atgtgaagaa agaagaagtc     360
aacaattgga gagactatct aagactccat tgttatccta tccacaagta tgtcaatgag     420
tggccgtcaa accctccttc tttcaaggaa atagtaagta aatacagtag agaagtaaga     480
gaagtgggat ttaaaataga ggaattaata tcagagagct taggtttaga aaagattac      540
atgaagaaag tgcttggtga acaaggtcaa cacatggcag tcaactatta tcctccatgt     600
cctgaacctg agctcactta cggtttacct gctcataccg acccaaacgc cctaaccatt     660
cttcttcaag acactactgt ttgcggtctc cagatcttga tcgacggtca gtggttcgcc     720
gttaatccac atcctgatgc tttttgtcatc aacataggtg accagttaca ggcattaagt     780
aatggagtat acaaaagtgt ttggcatcgc gctgtaacaa acacagaaaa tccgagacta     840
tcggtcgcat cgtttctgtg cccagctgac tgtgctgtca tgagcccggc caagcccttg     900
tgggaagctg aggacgatga aacgaaacca gtctacaaag atttcactta tgcagagtat     960
tacaagaagt tttggagtag gaatctggac caagaacatt gcctcgagaa ttttctaaac    1020
aactaa                                                               1026
```

<210> SEQ ID NO 100
<211> LENGTH: 341
<212> TYPE: PRT
<213> ORGANISM: Arabidopsis thaliana

<400> SEQUENCE: 100

```
Met Ala Ala Lys Leu Ile Ser Thr Gly Phe Arg His Thr Thr Leu Pro
1               5                   10                  15

Glu Asn Tyr Val Arg Pro Ile Ser Asp Arg Pro Arg Leu Ser Glu Val
            20                  25                  30

Ser Gln Leu Glu Asp Phe Pro Leu Ile Asp Leu Ser Ser Thr Asp Arg
        35                  40                  45

Ser Phe Leu Ile Gln Gln Ile His Gln Ala Cys Ala Arg Phe Gly Phe
    50                  55                  60

Phe Gln Val Ile Asn His Gly Val Asn Lys Gln Ile Ile Asp Glu Met
65                  70                  75                  80

Val Ser Val Ala Arg Glu Phe Phe Ser Met Ser Met Glu Glu Lys Met
                85                  90                  95

Lys Leu Tyr Ser Asp Asp Pro Thr Lys Thr Thr Arg Leu Ser Thr Ser
            100                 105                 110

Phe Asn Val Lys Lys Glu Glu Val Asn Asn Trp Arg Asp Tyr Leu Arg
        115                 120                 125
```

Leu His Cys Tyr Pro Ile His Lys Tyr Val Asn Glu Trp Pro Ser Asn
            130                 135                 140

Pro Pro Ser Phe Lys Glu Ile Val Ser Lys Tyr Ser Arg Glu Val Arg
145                 150                 155                 160

Glu Val Gly Phe Lys Ile Glu Glu Leu Ile Ser Glu Ser Leu Gly Leu
                165                 170                 175

Glu Lys Asp Tyr Met Lys Lys Val Leu Gly Glu Gln Gly Gln His Met
            180                 185                 190

Ala Val Asn Tyr Tyr Pro Pro Cys Pro Glu Pro Glu Leu Thr Tyr Gly
            195                 200                 205

Leu Pro Ala His Thr Asp Pro Asn Ala Leu Thr Ile Leu Leu Gln Asp
210                 215                 220

Thr Thr Val Cys Gly Leu Gln Ile Leu Ile Asp Gly Gln Trp Phe Ala
225                 230                 235                 240

Val Asn Pro His Pro Asp Ala Phe Val Ile Asn Ile Gly Asp Gln Leu
                245                 250                 255

Gln Ala Leu Ser Asn Gly Val Tyr Lys Ser Val Trp His Arg Ala Val
            260                 265                 270

Thr Asn Thr Glu Asn Pro Arg Leu Ser Val Ala Ser Phe Leu Cys Pro
            275                 280                 285

Ala Asp Cys Ala Val Met Ser Pro Ala Lys Pro Leu Trp Glu Ala Glu
290                 295                 300

Asp Asp Glu Thr Lys Pro Val Tyr Lys Asp Phe Thr Tyr Ala Glu Tyr
305                 310                 315                 320

Tyr Lys Lys Phe Trp Ser Arg Asn Leu Asp Gln Glu His Cys Leu Glu
                325                 330                 335

Asn Phe Leu Asn Asn
            340

<210> SEQ ID NO 101
<211> LENGTH: 1014
<212> TYPE: DNA
<213> ORGANISM: Lactuca sativa

<400> SEQUENCE: 101

```
atggccgcaa aagtcatctc cagtggattc cggtatacta ctctaccgga gagctacgtc    60
cgtccggtta acgacagacc taacctatct caagtttccg attgcaacga cgttcctgtt   120
attgacatcg ttgtggtga tagacaactc ataagccaac aaattggcga tgcttgtaga   180
agatacggtt ttttccaggt gattaatcat ggtgtgcctg atgaaatagt ggagaaaatg   240
caacaagtag gtagggagtt tttcctgttg cctgtggaag agaagatgaa gctttactca   300
gaggatccat cgaagacgat gaggctatcc accagcttta acgtccaaaa agaacaaatt   360
cataactggc gagattatct ccgccttcac tgttatcctc tggatcaata cagtcctgaa   420
tggccttcaa atccttctta tttcaaggaa tatgttggta ttattgtac agcagtgcga   480
aatttaggaa tgagaatatt agaatcaata tcagaaagtt tagggttaca aaagaagaa   540
ataaaaacta tattaggcga tcaaggtcaa cacatggcca tcaaccatta cccagtgtgc   600
cctgagcccg agctaaccta cgggctaccc gggcacacag accccaatgc tctcaccatc   660
cttctacagg acacactggt ctctggtctt caggttctca agatggcaa atggttagcc   720
gttaaaccac accctaatgc gtttgtaatt aacattggtg atcagttaga ggcggtgagt   780
aatggtgaat ataaaagtgt atggcatcga gctgtggtta actcagacaa cccgcgaatg   840
```

```
tctatagctt cgtttttgtg tccttgtaat gacaccgtta ttagggctcc taaagaaata      900
ataaaggaag gatcgaaacc tgttttcaaa gaatttactt atgcagaata ctacgcgaag      960
ttttggacaa gaaaccttga tcaagaacat tgcttagaat tcttcaagaa ctag            1014
```

<210> SEQ ID NO 102
<211> LENGTH: 337
<212> TYPE: PRT
<213> ORGANISM: Lactuca sativa

<400> SEQUENCE: 102

```
Met Ala Ala Lys Val Ile Ser Ser Gly Phe Arg Tyr Thr Thr Leu Pro
1               5                   10                  15

Glu Ser Tyr Val Arg Pro Val Asn Asp Arg Pro Asn Leu Ser Gln Val
            20                  25                  30

Ser Asp Cys Asn Asp Val Pro Val Ile Asp Ile Gly Cys Gly Asp Arg
        35                  40                  45

Gln Leu Ile Ser Gln Gln Ile Gly Asp Ala Cys Arg Arg Tyr Gly Phe
    50                  55                  60

Phe Gln Val Ile Asn His Gly Val Pro Asp Glu Ile Val Glu Lys Met
65                  70                  75                  80

Gln Gln Val Gly Arg Glu Phe Phe Leu Leu Pro Val Glu Glu Lys Met
                85                  90                  95

Lys Leu Tyr Ser Glu Asp Pro Ser Lys Thr Met Arg Leu Ser Thr Ser
            100                 105                 110

Phe Asn Val Gln Lys Glu Gln Ile His Asn Trp Arg Asp Tyr Leu Arg
        115                 120                 125

Leu His Cys Tyr Pro Leu Asp Gln Tyr Ser Pro Glu Trp Pro Ser Asn
    130                 135                 140

Pro Ser Tyr Phe Lys Glu Tyr Val Gly Asn Tyr Cys Thr Ala Val Arg
145                 150                 155                 160

Asn Leu Gly Met Arg Ile Leu Glu Ser Ile Ser Glu Ser Leu Gly Leu
                165                 170                 175

Gln Lys Glu Glu Ile Lys Thr Ile Leu Gly Asp Gln Gly Gln His Met
            180                 185                 190

Ala Ile Asn His Tyr Pro Val Cys Pro Glu Pro Glu Leu Thr Tyr Gly
        195                 200                 205

Leu Pro Gly His Thr Asp Pro Asn Ala Leu Thr Ile Leu Leu Gln Asp
    210                 215                 220

Thr Leu Val Ser Gly Leu Gln Val Leu Lys Asp Gly Lys Trp Leu Ala
225                 230                 235                 240

Val Lys Pro His Pro Asn Ala Phe Val Ile Asn Ile Gly Asp Gln Leu
                245                 250                 255

Glu Ala Val Ser Asn Gly Glu Tyr Lys Ser Val Trp His Arg Ala Val
            260                 265                 270

Val Asn Ser Asp Asn Pro Arg Met Ser Ile Ala Ser Phe Leu Cys Pro
        275                 280                 285

Cys Asn Asp Thr Val Ile Arg Ala Pro Lys Glu Ile Ile Lys Glu Gly
    290                 295                 300

Ser Lys Pro Val Phe Lys Glu Phe Thr Tyr Ala Glu Tyr Tyr Ala Lys
305                 310                 315                 320

Phe Trp Thr Arg Asn Leu Asp Gln Glu His Cys Leu Glu Phe Phe Lys
                325                 330                 335

Asn
```

<210> SEQ ID NO 103
<211> LENGTH: 1020
<212> TYPE: DNA
<213> ORGANISM: Spinacia oleracea

<400> SEQUENCE: 103

| | | |
|---|---|---|
| atggcaaaca agatattatc caccggaatt ccttacaaaa ccctcccga aagctacatc | 60 |
| cgacccgaaa tgagagggcc caacttatct caagtctccg attgcgagaa tgtccctgtt | 120 |
| attgacttgg gtgccaaaga ccgtactcaa acaatccacc aagtcttcaa tgcttgtaaa | 180 |
| aattacgggt ttttccaggt gattaatcat ggggtgtcaa aggaattagc ggagaagatg | 240 |
| caaaaggtag ctcgagagtt cttcgatatg tcggttgagg aaaaaatgaa attatatagt | 300 |
| gacgatccaa ctaaaacact aagattgtct acaagtttta cgttaacaa agaggaagtt | 360 |
| cataattgga gagattatct taggctccat tgttggcctc ttgagcaata tgtccccgaa | 420 |
| tggccttcta acccccttc cttcaaggaa atagtgagca agtacataaa agaagttagg | 480 |
| gaacttggtt tcagagtcca agaactaata tcagagagtt tagggttgga gaaagattac | 540 |
| ataaagaatg tcctaggaga tcaaggacaa cacatggctc ttaattatta ccctgagtgc | 600 |
| ccggagccag agatgacata cggggttgccg ggtcatactg accctaatgc ccttaccatc | 660 |
| cttctccaag acttgcaagt atctggcctt caaattttta aggatggtaa atggcttgct | 720 |
| gtcaaacctc aacctgatgc tttttgtcatt aacattggtg atcaattgca ggcattaagt | 780 |
| aacggtatat acaagagtgt atggcacaga gcagttgtga acacagataa gccaagatta | 840 |
| tcagtagctt cattcctctg ccccgccaat gatgcgttga taagcgcgcc aacacctctg | 900 |
| accgccaacg gatcaccggc tgtatataga gactatacgt atcctgagta ctacaagact | 960 |
| ttctggagta ggaacttgga ccaagagcac tgcttggagc ttttttaaaaa ccaaacctag | 1020 |

<210> SEQ ID NO 104
<211> LENGTH: 339
<212> TYPE: PRT
<213> ORGANISM: Spinacia oleracea

<400> SEQUENCE: 104

```
Met Ala Asn Lys Ile Leu Ser Thr Gly Ile Pro Tyr Lys Thr Leu Pro
1               5                   10                  15

Glu Ser Tyr Ile Arg Pro Glu Asn Glu Arg Pro Asn Leu Ser Gln Val
            20                  25                  30

Ser Asp Cys Glu Asn Val Pro Val Ile Asp Leu Gly Ala Lys Asp Arg
        35                  40                  45

Thr Gln Thr Ile His Gln Val Phe Asn Ala Cys Lys Asn Tyr Gly Phe
    50                  55                  60

Phe Gln Val Ile Asn His Gly Val Ser Lys Glu Leu Ala Glu Lys Met
65                  70                  75                  80

Gln Lys Val Ala Arg Glu Phe Phe Asp Met Ser Val Glu Glu Lys Met
                85                  90                  95

Lys Leu Tyr Ser Asp Asp Pro Thr Lys Thr Leu Arg Leu Ser Thr Ser
            100                 105                 110

Phe Asn Val Asn Lys Glu Glu Val His Asn Trp Arg Asp Tyr Leu Arg
        115                 120                 125

Leu His Cys Trp Pro Leu Glu Gln Tyr Val Pro Glu Trp Pro Ser Asn
    130                 135                 140

Pro Pro Ser Phe Lys Glu Ile Val Ser Lys Tyr Ile Lys Glu Val Arg
145                 150                 155                 160
```

Glu Leu Gly Phe Arg Val Gln Glu Leu Ile Ser Ser Leu Gly Leu
            165                 170                 175

Glu Lys Asp Tyr Ile Lys Asn Val Leu Gly Asp Gly Gln His Met
        180                 185                 190

Ala Leu Asn Tyr Tyr Pro Glu Cys Pro Glu Pro Glu Met Thr Tyr Gly
            195                 200                 205

Leu Pro Gly His Thr Asp Pro Asn Ala Leu Thr Ile Leu Leu Gln Asp
        210                 215                 220

Leu Gln Val Ser Gly Leu Gln Ile Phe Lys Asp Gly Lys Trp Leu Ala
225                 230                 235                 240

Val Lys Pro Gln Pro Asp Ala Phe Val Ile Asn Ile Gly Asp Gln Leu
            245                 250                 255

Gln Ala Leu Ser Asn Gly Ile Tyr Lys Ser Val Trp His Arg Ala Val
        260                 265                 270

Val Asn Thr Asp Lys Pro Arg Leu Ser Val Ala Ser Phe Leu Cys Pro
        275                 280                 285

Ala Asn Asp Ala Leu Ile Ser Ala Pro Thr Pro Leu Thr Ala Asn Gly
        290                 295                 300

Ser Pro Ala Val Tyr Arg Asp Tyr Thr Tyr Pro Glu Tyr Tyr Lys Thr
305                 310                 315                 320

Phe Trp Ser Arg Asn Leu Asp Gln Glu His Cys Leu Glu Leu Phe Lys
                325                 330                 335

Asn Gln Thr

<210> SEQ ID NO 105
<211> LENGTH: 1029
<212> TYPE: DNA
<213> ORGANISM: Cucumis sativus

<400> SEQUENCE: 105

```
atgagcagtg tgatggagat ccaacttttg tgttcagggg acgtcacga gaagttgcca      60
gagaagtatg aacggcctga atcggatagg ccgcggctgt cggaggtgtg ttgttgggac    120
aaggttccaa taatcgactt gggatgcgag gagagagaga tgattgtgaa gcaagtggag    180
gaggcctgca agtcttacgg cttttttccag gttataaatc atggtgtgag gaaggaattg    240
gtggagaaag tgatagaagt tggcaagcag ttctttgagc tgccgatgga ggagaagttg    300
aaattttatt cagacgaccc ttccaagacc gtcagactct ccacaagttt caatgtccgg    360
aaagagcaat ttcgcaactg gagggattat ctcagactcc attgctatcc tctctccaac    420
tacacccccc attggccctc taacccacca tccttcaggg aaatagtgag tagttattgc    480
aatgaagtac gaaagttgg gtacagaata gaggagctaa tatcggagag cttgggctg    540
gagaaggaat acataaggaa gaagttgggt gaacaaggtc agcacatggc tataaattat    600
tatccgccat gtccccaacc agaactcacc tacgggctcc ctggccatac ggatcccaac    660
gcactcacca ttctccttca ggatctccat gtcgccggcc tccaagtcct caagatgga    720
aagtggctag cggtcaaccc ccaccccaat gcctttgtaa tcaatatagg cgaccaattg    780
caggcattga gcaatggggt gtacaagagc gtttggcacc gagcggtggt caatgttgat    840
aagcccaggc tgtcggtcgc ttcttttctc tgcccttgtg atgacgccct cattactcct    900
gcaccgctcc tctcccagcc ttcccccatt tacagacctt tcacctacgc ccagtactac    960
aatactttt ggagcagaaa cttggatcaa caacattgct ggaactatt taaaaaccac   1020
cctccttaa                                                         1029
```

<210> SEQ ID NO 106
<211> LENGTH: 342
<212> TYPE: PRT
<213> ORGANISM: Cucumis sativus

<400> SEQUENCE: 106

```
Met Ser Ser Val Met Glu Ile Gln Leu Leu Cys Ser Gly Gly Arg His
1               5                   10                  15
Glu Lys Leu Pro Glu Lys Tyr Glu Arg Pro Glu Ser Asp Arg Pro Arg
                20                  25                  30
Leu Ser Glu Val Cys Cys Trp Asp Lys Val Pro Ile Ile Asp Leu Gly
            35                  40                  45
Cys Glu Glu Arg Glu Met Ile Val Lys Gln Val Glu Glu Ala Cys Lys
        50                  55                  60
Ser Tyr Gly Phe Phe Gln Val Ile Asn His Gly Val Arg Lys Glu Leu
65                  70                  75                  80
Val Glu Lys Val Ile Glu Val Gly Lys Gln Phe Phe Glu Leu Pro Met
                85                  90                  95
Glu Glu Lys Leu Lys Phe Tyr Ser Asp Asp Pro Ser Lys Thr Val Arg
                100                 105                 110
Leu Ser Thr Ser Phe Asn Val Arg Lys Glu Gln Phe Arg Asn Trp Arg
            115                 120                 125
Asp Tyr Leu Arg Leu His Cys Tyr Pro Leu Ser Asn Tyr Thr Pro His
        130                 135                 140
Trp Pro Ser Asn Pro Pro Ser Phe Arg Glu Ile Val Ser Ser Tyr Cys
145                 150                 155                 160
Asn Glu Val Arg Lys Val Gly Tyr Arg Ile Glu Glu Leu Ile Ser Glu
                165                 170                 175
Ser Leu Gly Leu Glu Lys Glu Tyr Ile Arg Lys Lys Leu Gly Glu Gln
                180                 185                 190
Gly Gln His Met Ala Ile Asn Tyr Tyr Pro Pro Cys Pro Gln Pro Glu
            195                 200                 205
Leu Thr Tyr Gly Leu Pro Gly His Thr Asp Pro Asn Ala Leu Thr Ile
        210                 215                 220
Leu Leu Gln Asp Leu His Val Ala Gly Leu Gln Val Leu Lys Asp Gly
225                 230                 235                 240
Lys Trp Leu Ala Val Asn Pro His Pro Asn Ala Phe Val Ile Asn Ile
                245                 250                 255
Gly Asp Gln Leu Gln Ala Leu Ser Asn Gly Val Tyr Lys Ser Val Trp
                260                 265                 270
His Arg Ala Val Val Asn Val Asp Lys Pro Arg Leu Ser Val Ala Ser
            275                 280                 285
Phe Leu Cys Pro Cys Asp Asp Ala Leu Ile Thr Pro Ala Pro Leu Leu
        290                 295                 300
Ser Gln Pro Ser Pro Ile Tyr Arg Pro Phe Thr Tyr Ala Gln Tyr Tyr
305                 310                 315                 320
Asn Thr Phe Trp Ser Arg Asn Leu Asp Gln Gln His Cys Leu Glu Leu
                325                 330                 335
Phe Lys Asn His Pro Pro
            340
```

<210> SEQ ID NO 107
<211> LENGTH: 3003
<212> TYPE: DNA

<213> ORGANISM: Arabidopsis thaliana

<400> SEQUENCE: 107

```
cattttcta taaatccaaa ctaacatcta ctttctttaa atctataacc ctaaacactt      60
ttttaaactc aaaccgatat ataattttgt ttaattttaa atctaaactc tagtgactta     120
tttataaacc caaacctaaa aataatttcg ttttattgta aatttaaact ctaatttata     180
tttataaatc taaactgact tataattttg tttaattgta aaatctaaat tttaaatata     240
attaatcttg tttaattaaa agtatacaga tttgttatt tagtttatta tataatatga     300
tataataact agtttaaatt aaaagtaaga gtttattctt agaggtaaat gcaagtattg     360
tccgaaaaaa caaatctaat tcaagtagtg tccgaaaaaa aattctaact agtttgatag     420
ttaaaatttt gatttaaaaa aggaaaaaaa tcaaacaaga tattaattag aagtgtgaga     480
cacggcacaa gagtcacatg agtgtacgta cttatcaaga ttgactctgt ctgagtctga     540
agtcccaaac catgatggca ccacttccac atacgatcgt gccccgtatt ttggatagaa     600
tacggacagt ggttttcgtt tggacacgtg tcctgcttta tctcttcgtc gccccaaaaa     660
ataccacaat gtcttatctc aaccacacgt gttctgctta tcccaacctc acaatttgta     720
ccaaaataca cactttgcat ggaagatttt ctaattatac aactcacatt attcgaattt     780
aaatttcgat tttttagttt caagaaaatc attctttgat gggtacttgt cttatttaac     840
aggttgtata cttgtattca ttgttctgcc aaatgaaaat aaaaatgaaa atgatgttca     900
ttgtttaata aaagtactaa gataacaatc acgacaaatt tctgtctagt tcattaaata     960
tttaatcaaa ctctaaacga ttttcaaaca attttttaaa ttcaaaaaat aagttacata    1020
tctttgttta acataatata ataaaaataa catgaataaa ttattttaac ataaaaaatt    1080
cagttttca aaaataagtt tagaagttta cgttctaaaa taaggtaaaa tatgaatgct    1140
gttttaagac gcaatctaga taatttttt taataaaaac cgagatacat ttaaatctat    1200
ctaataact tataactacc taattgttac ataatctacc aatttaactc tatgtaaaat    1260
aaaactgatt ttagtaacat ttaagcagta cgagaatgct agcgcctaat taaacgatct    1320
tctaatccac tttcttgaat atttgtttta actaaatcta aacaaaaata tagttatata    1380
accacaaata ttaatgaaat ttaaacttat agtaactgaa atacccaaaa ctaaaaaaaa    1440
aaaccaaaat tataataatt ataaataaga agatattagt ttatgtttac aatcgaaata    1500
atcaaataaa tgattgtctt tatttaggac tacgatcaag aaccgaatgg gcttttccaa    1560
accaaaccga gatttgaatt ttatggtgcg gattcggtta actggagaat agctatcaac    1620
aacaatttaa aatagattta gctagatcgg tttggttcgg ttcgttttgt attctctgtc    1680
actcctcaca atcgcttata ttttatattg tatgtttaaa agtcaacatc gaaatattgt    1740
acgttagtat gtcacttatg ataatgttta ttcgtaaaca caatttgaaa aggtcaaaga    1800
aagaggaaag atagttaatc aagcccttgt tgtcaaaaat aattattta tttactgtca    1860
tcgtaatgtt tatcaatgca gttattaatc tcatttttt ctcttccgaa gtcgacgaac    1920
aataaaaaaa accaatctca ttcgaagtac ttattactga tatgatgctg agctgacaca    1980
gtcgtaagcc ttggacaaca atcattcatg acgtcactgc tgtgacgcta gaatgatgac    2040
attatatcaa tgttttttg tctgaatttt gttatggtaa aaataatgaa atgtagagc     2100
ttgagtattt tgattttcgt tttattgtaa actagctgaa tctgaatctt gagcagttaa    2160
ttaattcgt aatttattaa ttctattctg acttttaaa atataatata tattaactt      2220
ggtagatgct taaggtaatt ctttttaat aaataagatg gttagagtat cttaaagtta    2280
```

```
gcttataaga aaatcggaaa aattactttt ggtgggttaa ttgtttctgt ttgaagtaat    2340
gtgtgtagat ttttcttatg aatttagatt aaaaactatt tgttttcag atgttttaag     2400 aaaaaaattg tcattcatag cttgtccatt cttacatacc ttaataagaa aaattataaa    2460
gttttgtgga ttcacggaag ctaatctagg ttatgtattt gcccaaaaaa taatctaggt    2520
tttgttatgg aattaagaag gaaaaaaaaa ttgagataaa tagtatataa aaacaattta    2580
aactaagtat tattagctta attgataaag attttaggtg aaacttaaaa atagttggtt    2640
aaagagatta caaacattaa ccaaattaac caagaacctc ctagtattta aaaaaaacac    2700
ttaaaaatat ccaaacattt aatttttaa tcataaatct tataaaaccc acagctgtcc     2760
tttcgaaaat ccactatatt cggtggatta agaattaaaa atcattcgaa taatatgcat    2820
acttatataa caaaaacaat tcacttgaaa acataatcaa ttgagagtag gaccgagtaa    2880
cactgcattg ttttatatat atcatcgatg cacatcgcat acataatata ctcaaagtcg    2940
agccttcctt cctttatctc ttatacccct tttgattctt cttcaatttt ctgacatcaa    3000
atg                                                                  3003

<210> SEQ ID NO 108
<211> LENGTH: 24
<212> TYPE: DNA
<213> ORGANISM: Artificial Sequence
<220> FEATURE:
<223> OTHER INFORMATION: LP primer

<400> SEQUENCE: 108
caggtttatg gcatatctca cgtc                                           24

<210> SEQ ID NO 109
<211> LENGTH: 24
<212> TYPE: DNA
<213> ORGANISM: Artificial Sequence
<220> FEATURE:
<223> OTHER INFORMATION: T-DNA right border primer

<400> SEQUENCE: 109
tgataccaga cgttgcccgc ataa                                           24

<210> SEQ ID NO 110
<211> LENGTH: 25
<212> TYPE: DNA
<213> ORGANISM: Artificial Sequence
<220> FEATURE:
<223> OTHER INFORMATION: RB4 primer

<400> SEQUENCE: 110
tcacgggttg gggtttctac aggac                                          25

<210> SEQ ID NO 111
<211> LENGTH: 24
<212> TYPE: DNA
<213> ORGANISM: Artificial Sequence
<220> FEATURE:
<223> OTHER INFORMATION: LP or RP primer

<400> SEQUENCE: 111
atgtccaagt ccaatagcca caag                                           24

<210> SEQ ID NO 112
<211> LENGTH: 341
<212> TYPE: PRT
```

<213> ORGANISM: Brassica oleracea

<400> SEQUENCE: 112

Met Ala Ala Lys Leu Ile Ser Thr Gly Ile Arg His Thr Thr Leu Pro
1               5                   10                  15

Glu Asn Tyr Val Arg Pro Leu Ser Asn Arg Pro Cys Leu Ser Asp Val
            20                  25                  30

Ser Pro Leu Lys Asp Phe Pro Ile Ile Asp Leu Ser Ser Thr Asp Arg
        35                  40                  45

Ser Arg Leu Val Gln Gln Ile His Gln Ala Cys Ser Arg Phe Gly Phe
    50                  55                  60

Phe Gln Val Ile Asn His Arg Val Ser Lys Asp Thr Ile Asp Gly Met
65                  70                  75                  80

Val Ser Val Ala Asn Glu Phe Phe Ser Met Ser Met Glu Glu Lys Met
                85                  90                  95

Lys Leu Tyr Ser Asp Asp Pro Thr Lys Thr Thr Arg Leu Ser Thr Ser
            100                 105                 110

Phe Asn Val Lys Lys Glu Glu Val Asn Asn Trp Arg Asp Tyr Leu Arg
        115                 120                 125

Leu His Cys Tyr Pro Ile Ser Lys Tyr Val His Glu Trp Pro Ser Asn
    130                 135                 140

Pro Pro Ser Phe Lys Glu Val Val Ser Arg Tyr Ser Thr Asp Val Arg
145                 150                 155                 160

Glu Leu Gly Phe Thr Ile Glu Glu Leu Ile Ser Glu Ser Leu Gly Leu
                165                 170                 175

Glu Lys Asp His Met Arg Lys Val Leu Gly Glu Gln Gln His Met
            180                 185                 190

Ala Val Asn Tyr Tyr Pro Pro Cys Pro Glu Pro Glu Leu Thr Tyr Gly
        195                 200                 205

Leu Pro Ala His Thr Asp Pro Asn Ala Leu Thr Ile Leu Leu Gln Asp
    210                 215                 220

Ala Thr Val Cys Gly Leu Gln Ile Leu Ile Asp Gly Gln Trp Phe Ala
225                 230                 235                 240

Val Asn Pro His Pro Asp Ala Phe Val Ile Asn Ile Gly Asp Gln Phe
                245                 250                 255

Glu Ala Leu Ser Asn Gly Ile Tyr Lys Ser Val Trp His Arg Ala Val
            260                 265                 270

Thr Asn Thr Glu Lys Pro Arg Leu Ser Val Ala Ser Phe Leu Cys Pro
        275                 280                 285

Ala Asp Cys Ala Val Ile Ser Pro Ala Lys Pro Leu Trp Glu Ala Glu
    290                 295                 300

Glu Asp Glu Ala Lys Pro Ile Tyr Arg Asp Tyr Thr Tyr Ala Glu Tyr
305                 310                 315                 320

Tyr Lys Lys Phe Trp Ser Arg Asn Leu Asp Gln Glu His Cys Leu Glu
                325                 330                 335

Asn Phe Leu Asn Asp
            340

<210> SEQ ID NO 113
<211> LENGTH: 341
<212> TYPE: PRT
<213> ORGANISM: Brassica oleracea

<400> SEQUENCE: 113

Met Ala Ala Lys Leu Leu Ser Thr Gly Phe Arg His Ser Thr Leu Pro

```
1               5                   10                  15
Glu Asn Tyr Val Arg Pro Leu Ser Asp Arg Pro Arg Leu Ser Gln Val
                20                  25                  30

Ser Gln Leu Glu Asp Phe Pro Leu Ile Asp Ile Ser Ser Thr Asp Arg
                35                  40                  45

Ser Arg Leu Val Gln Lys Ile His Gln Ala Cys Ala Arg Phe Gly Phe
    50                  55                  60

Phe Gln Val Ile Asn His Gly Val Ser Lys Ala Thr Ile Asp Glu Met
65                  70                  75                  80

Val Ser Val Ala His Glu Phe Phe Gly Met Pro Met Asp Glu Lys Met
                85                  90                  95

Lys Leu Tyr Ser Asp Asp Pro Thr Lys Thr Pro Arg Leu Ser Thr Ser
                100                 105                 110

Phe Asn Val Lys Glu Glu Val Asn Asn Trp Arg Asp Tyr Leu Arg
                115                 120                 125

Leu His Cys Tyr Pro Ile Asp Lys Tyr Val His Glu Trp Pro Ser Asn
    130                 135                 140

Pro Pro Ser Phe Lys Glu Val Val Ser Lys Tyr Ser Arg Glu Ile Arg
145                 150                 155                 160

Glu Leu Gly Leu Lys Ile Glu Glu Leu Ile Ser Glu Ser Leu Gly Leu
                165                 170                 175

Glu Lys Asp Tyr Met Lys Lys Val Leu Gly Glu Gln Gly Gln His Met
                180                 185                 190

Ala Val Asn Tyr Tyr Pro Pro Cys Pro Glu Pro Glu Leu Thr Tyr Gly
                195                 200                 205

Leu Pro Ala His Thr Asp Pro Asn Ala Leu Thr Ile Leu Leu Gln Asp
    210                 215                 220

Ala Thr Val Cys Gly Leu Gln Ile Leu Ile Asp Gly His Trp Phe Ala
225                 230                 235                 240

Val Asn Pro Arg Pro Asp Ala Phe Val Ile Asn Ile Gly Asp Gln Leu
                245                 250                 255

Gln Ala Leu Ser Asn Gly Val Tyr Lys Ser Val Trp His Arg Ala Val
                260                 265                 270

Thr Asn Thr Glu Asn Pro Arg Leu Ser Ile Ala Ser Phe Met Cys Pro
    275                 280                 285

Asp Asn Gly Ala Val Ile Ser Pro Ala Lys Pro Leu Trp Glu Ala Lys
    290                 295                 300

Glu Glu Glu Ala Lys Pro Ile Tyr Arg Asp Tyr Thr Tyr Ala Glu Tyr
305                 310                 315                 320

Tyr Lys Lys Phe Trp Ser Arg Asn Leu Asp Gln Glu His Cys Leu Glu
                325                 330                 335

Asn Phe Leu Asn Asp
            340
```

<210> SEQ ID NO 114
<211> LENGTH: 1026
<212> TYPE: DNA
<213> ORGANISM: Brassica oleracea

<400> SEQUENCE: 114

```
atggcagcaa agctaatatc caccggtatt cgtcacacaa ctttgccgga aaactatgtt      60
cggccactct ccaaccgtcc atgtctctct gacgtctctc cacttaaaga tttccctatc     120
atcgacctat cttccacaga tcgatctcgg ctagtccaac aaatccacca agcttgctcc     180
```

```
cgattcgggt tttttcaggt cataaatcac agagttagca aagatacaat agatggaatg     240
gtgagtgttg cgaacgagtt ctttagcatg tctatggagg aaaaaatgaa gctgtactcg     300
gacgatccaa cgaagacgac gagattatca acgagcttca atgtgaaaaa agaagaggtc     360
aacaattgga gagactatct tagactacat tgttatccta tcagcaagta tgtccatgag     420
tggccttcaa accctccttc tttcaaggaa gttgtgagta gatacagtac agatgtaaga     480
gaactgggat ttactataga ggaactgata tcagagagcc tgggtttaga aaagatcac      540 atgaggaaag tgcttggtga acaaggtcaa cacatggcag tcaactatta ccctccatgt     600
cctgagcctg agctcactta tggtttacct gctcacaccg acccaaacgc actcaccatt     660
cttctccaag atgctaccgt tgtggtctac cagatcttga tcgacggcca gtggttcgcc     720
gttaatccac atcctgatgc ttttgtcatc aacattggtg accagttcga ggcattgagt     780
aacggaatat acaaaagtgt tggcatcga gcagtaacaa acaccgaaaa accgagatta      840
tcggtcgcat catttctgtg cccagctgac tgcgctgtca taagcccggc aaagcccttg     900
tgggaagccg aggaggacga ggctaagcca atatacagag actacactta cgcagagtac     960
tacaaaaagt tttggagtag gaatctggac caagagcatt gccttgagaa ctttctaaac    1020
gactag                                                               1026

<210> SEQ ID NO 115
<211> LENGTH: 1026
<212> TYPE: DNA
<213> ORGANISM: Brassica oleracea

<400> SEQUENCE: 115
atggcggcaa agcttttatc caccggtttc cgtcactcta ctttgccgga aaactatgtc     60
cggccactct ctgaccgtcc acgtctctcc caagtttctc agcttgaaga tttccctctc     120
atcgatatat cttcaacaga tcgatctcgg ctcgtccaaa aaatccacca agcttgcgcc     180
cgatttggtt tctttcaggt tataaatcat ggtgttagca agcaactat agatgagatg      240 gtgagtgttg cgcatgagtt ttttggcatg cctatggacg aaaaaatgaa gctatactcg     300
gacgatccaa caaagacacc gagattatcg acgagcttta atgtgaagga agaagaggtt     360
aataattgga gagactatct aagacttcat tgttatccta tcgacaagta tgtccatgag     420
tggccttcca acccaccttc tttcaaggaa gttgtgagta aatacagtag agaaataaga     480
gaattgggac ttaaaataga ggaattgata tcagagagct taggtttaga aaagattac      540 atgaagaaag tgcttggtga acaaggtcaa cacatggcag tcaactatta tcctccatgt     600
cctgagcctg agctcaccta tggtttacct gctcataccg acccaaatgc cctcaccatt     660
cttctccaag atgctaccgt tgcggtctc cagatcttga tcgacggtca ctggtttgct     720
gttaatcctc gtcctgatgc ttttgtcatc aacattggtg accagttgca ggcattgagt     780
aacggagtat acaaaagtgt tggcatcga gcagtgacaa acactgaaaa cccgagacta     840
tcgatcgcat catttatgtg tcctgataac ggtgctgtca taagcccggc aaagcccctg     900
tgggaagcca aggaggaaga ggccaagcca atctacagag actacactta tgcagagtac     960
tacaagaagt tttggagtag gaatctggac caagaacatt gcctcgaaaa ctttctaaac    1020
gactag                                                               1026

<210> SEQ ID NO 116
<211> LENGTH: 21
<212> TYPE: DNA
<213> ORGANISM: Artificial Sequence
```

<220> FEATURE:
<223> OTHER INFORMATION: Synthetic Construct

<400> SEQUENCE: 116
agtccaacaa atccaccaag c                                              21

<210> SEQ ID NO 117
<211> LENGTH: 22
<212> TYPE: DNA
<213> ORGANISM: Artificial Sequence
<220> FEATURE:
<223> OTHER INFORMATION: Synthetic Construct

<400> SEQUENCE: 117 cctttttcagg cacataagtt ca                                            22

<210> SEQ ID NO 118
<211> LENGTH: 22
<212> TYPE: DNA
<213> ORGANISM: Artificial Sequence
<220> FEATURE:
<223> OTHER INFORMATION: Synthetic Construct

<400> SEQUENCE: 118
attcttctcc aagatgctac cg                                             22

<210> SEQ ID NO 119
<211> LENGTH: 19
<212> TYPE: DNA
<213> ORGANISM: Artificial Sequence
<220> FEATURE:
<223> OTHER INFORMATION: Synthetic Construct

<400> SEQUENCE: 119
ggattaacgg cgaaccact                                                 19

<210> SEQ ID NO 120
<211> LENGTH: 20
<212> TYPE: DNA
<213> ORGANISM: Artificial Sequence
<220> FEATURE:
<223> OTHER INFORMATION: Synthetic Construct

<400> SEQUENCE: 120
ccaagatgct accgtttgtg                                                20

<210> SEQ ID NO 121
<211> LENGTH: 21
<212> TYPE: DNA
<213> ORGANISM: Artificial Sequence
<220> FEATURE:
<223> OTHER INFORMATION: Synthetic Construct

<400> SEQUENCE: 121
ttgatgacaa aagcatcagg a                                              21

<210> SEQ ID NO 122
<211> LENGTH: 20
<212> TYPE: DNA
<213> ORGANISM: Artificial Sequence
<220> FEATURE:
<223> OTHER INFORMATION: Synthetic Construct

<400> SEQUENCE: 122
ccgagattat cgacgagctt                                                20

<210> SEQ ID NO 123
<211> LENGTH: 25
<212> TYPE: DNA
<213> ORGANISM: Artificial Sequence
<220> FEATURE:
<223> OTHER INFORMATION: Synthetic Construct

<400> SEQUENCE: 123
ttgtcgatag gataacaatg aagtc                                    25

<210> SEQ ID NO 124
<211> LENGTH: 19
<212> TYPE: DNA
<213> ORGANISM: Artificial Sequence
<220> FEATURE:
<223> OTHER INFORMATION: Synthetic Construct

<400> SEQUENCE: 124
gcttgctcct gattcgggc                                           19

<210> SEQ ID NO 125
<211> LENGTH: 27
<212> TYPE: DNA
<213> ORGANISM: Artificial Sequence
<220> FEATURE:
<223> OTHER INFORMATION: Synthetic Construct

<400> SEQUENCE: 125
cgtttgtggt ctatagatct tgatcgt                                  27

<210> SEQ ID NO 126
<211> LENGTH: 23
<212> TYPE: DNA
<213> ORGANISM: Artificial Sequence
<220> FEATURE:
<223> OTHER INFORMATION: Synthetic Construct

<400> SEQUENCE: 126
cagtgattcg ccgttaatcc acc                                      23

<210> SEQ ID NO 127
<211> LENGTH: 30
<212> TYPE: DNA
<213> ORGANISM: Artificial Sequence
<220> FEATURE:
<223> OTHER INFORMATION: Synthetic Construct

<400> SEQUENCE: 127
gaagaggtta ataattagag agactatctc                               30

<210> SEQ ID NO 128
<211> LENGTH: 1026
<212> TYPE: DNA
<213> ORGANISM: Artificial Sequence
<220> FEATURE:
<223> OTHER INFORMATION: Synthetic Construct

<400> SEQUENCE: 128
atggcagcaa agctaatatc caccggtatt cgtcacacaa ctttgccgga aaactatgtt    60
cggccactct ccaaccgtcc atgtctctct gacgtctctc cacttaaaga tttccctatc   120
atcgacctat cttccacaga tcgatctcgg ctagtccaac aaatccacca agcttgctcc   180
tgattcgggt tttttcaggt cataaatcac agagttagca agatacaat agatggaatg    240 gtgagtgttg cgaacgagtt ctttagcatg tctatggagg aaaaaatgaa gctgtactcg   300

```
gacgatccaa cgaagacgac gagattatca acgagcttca atgtgaaaaa agaagaggtc    360
aacaattgga gagactatct tagactacat tgttatccta tcagcaagta tgtccatgag    420
tggccttcaa accctccttc tttcaaggaa gttgtgagta gatacagtac agatgtaaga    480
gaactgggat ttactataga ggaactgata tcagagagcc tgggtttaga aaaagatcac    540
atgaggaaag tgcttggtga acaaggtcaa cacatggcag tcaactatta ccctccatgt    600
cctgagcctg agctcactta tggtttacct gctcacaccg acccaaacgc actcaccatt    660
cttctccaag atgctaccgt ttgtggtcta cagatcttga tcgacggcca gtggttcgcc    720
gttaatccac atcctgatgc tttttgtcatc aacattggtg accagttcga ggcattgagt    780
aacggaatat acaaaagtgt ttggcatcga gcagtaacaa acaccgaaaa accgagatta    840
tcggtcgcat catttctgtg cccagctgac tgcgctgtca taagcccggc aaagcccttg    900
tgggaagccg aggaggacga ggctaagcca atatacagag actacactta cgcagagtac    960
tacaaaaagt tttggagtag gaatctggac caagagcatt gccttgagaa ctttctaaac    1020
gactag                                                              1026

<210> SEQ ID NO 129
<211> LENGTH: 1026
<212> TYPE: DNA
<213> ORGANISM: Artificial Sequence
<220> FEATURE:
<223> OTHER INFORMATION: Synthetic Construct

<400> SEQUENCE: 129
atggcagcaa agctaatatc caccggtatt cgtcacacaa ctttgccgga aaactatgtt     60
cggccactct ccaaccgtcc atgtctctct gacgtctctc cacttaaaga tttccctatc    120
atcgacctat cttccacaga tcgatctcgg ctagtccaac aaatccacca agcttgctcc    180
cgattcgggt tttttcaggt cataaatcac agagttagca aagatacaat agatggaatg    240
gtgagtgttg cgaacgagtt cctttagcatg tctatggagg aaaaaatgaa gctgtactcg    300
gacgatccaa cgaagacgac gagattatca acgagcttca atgtgaaaaa agaagaggtc    360
aacaattgga gagactatct tagactacat tgttatccta tcagcaagta tgtccatgag    420
tggccttcaa accctccttc tttcaaggaa gttgtgagta gatacagtac agatgtaaga    480
gaactgggat ttactataga ggaactgata tcagagagcc tgggtttaga aaaagatcac    540
atgaggaaag tgcttggtga acaaggtcaa cacatggcag tcaactatta ccctccatgt    600
cctgagcctg agctcactta tggtttacct gctcacaccg acccaaacgc actcaccatt    660
cttctccaag atgctaccgt ttgtggtcta tagatcttga tcgacggcca gtggttcgcc    720
gttaatccac atcctgatgc tttttgtcatc aacattggtg accagttcga ggcattgagt    780
aacggaatat acaaaagtgt ttggcatcga gcagtaacaa acaccgaaaa accgagatta    840
tcggtcgcat catttctgtg cccagctgac tgcgctgtca taagcccggc aaagcccttg    900
tgggaagccg aggaggacga ggctaagcca atatacagag actacactta cgcagagtac    960
tacaaaaagt tttggagtag gaatctggac caagagcatt gccttgagaa ctttctaaac    1020
gactag                                                              1026

<210> SEQ ID NO 130
<211> LENGTH: 1026
<212> TYPE: DNA
<213> ORGANISM: Artificial Sequence
<220> FEATURE:
```

<223> OTHER INFORMATION: Synthetic Construct

<400> SEQUENCE: 130

| | |
|---|---|
| atggcagcaa agctaatatc accggtatt cgtcacacaa ctttgccgga aaactatgtt | 60 |
| cggccactct ccaaccgtcc atgtctctct gacgtctctc cacttaaaga tttccctatc | 120 |
| atcgacctat cttccacaga tcgatctcgg ctagtccaac aaatccacca agcttgctcc | 180 |
| cgattcgggt tttttcaggt cataaatcac agagttagca agatacaat agatggaatg | 240 |
| gtgagtgttg cgaacgagtt ctttagcatg tctatggagg aaaaaatgaa gctgtactcg | 300 |
| gacgatccaa cgaagacgac gagattatca acgagcttca atgtgaaaaa agaagaggtc | 360 |
| aacaattgga gagactatct tagactacat tgttatccta tcagcaagta tgtccatgag | 420 |
| tggccttcaa accctccttc tttcaaggaa gttgtgagta gatacagtac agatgtaaga | 480 |
| gaactgggat ttactataga ggaactgata tcagagagcc tgggtttaga aaagatcac | 540 |
| atgaggaaag tgcttggtga acaaggtcaa cacatggcag tcaactatta ccctccatgt | 600 |
| cctgagcctg agctcactta tggtttacct gctcacaccg acccaaacgc actcaccatt | 660 |
| cttctccaag atgctaccgt tgtggtcta cagatcttga tcgacggcca gtgattcgcc | 720 |
| gttaatccac atcctgatgc ttttgtcatc aacattggtg accagttcga ggcattgagt | 780 |
| aacggaatat acaaaagtgt tggcatcga gcagtaacaa acaccgaaaa accgagatta | 840 |
| tcggtcgcat catttctgtg cccagctgac tgcgctgtca taagcccggc aaagcccttg | 900 |
| tgggaagccg aggaggacga ggctaagcca atatacagag actacactta cgcagagtac | 960 |
| tacaaaaagt tttggagtag gaatctggac caagagcatt gccttgagaa ctttctaaac | 1020 |
| gactag | 1026 |

<210> SEQ ID NO 131
<211> LENGTH: 1026
<212> TYPE: DNA
<213> ORGANISM: Artificial Sequence
<220> FEATURE:
<223> OTHER INFORMATION: Synthetic Construct

<400> SEQUENCE: 131

| | |
|---|---|
| atggcggcaa agcttttatc accggtttc cgtcactcta ctttgccgga aaactatgtc | 60 |
| cggccactct ctgaccgtcc acgtctctcc caagtttctc agcttgaaga tttccctctc | 120 |
| atcgatatat cttcaacaga tcgatctcgg ctcgtccaaa aaatccacca agcttgcgcc | 180 |
| cgatttggtt tctttcaggt tataaatcat ggtgttagca agcaactat agatgagatg | 240 |
| gtgagtgttg cgcatgagtt ttttggcatg cctatggacg aaaaaatgaa gctatactcg | 300 |
| gacgatccaa caaagacacc gagattatcg acgagcttta atgtgaagga agaagaggtt | 360 |
| aataattaga gagactatct aagacttcat tgttatccta tcgacaagta tgtccatgag | 420 |
| tggccttcca accccaccttc tttcaaggaa gttgtgagta aatacagtag agaaataaga | 480 |
| gaattgggac ttaaaataga ggaattgata tcagagagct taggtttaga aaagattac | 540 |
| atgaagaaag tgcttggtga acaaggtcaa cacatggcag tcaactatta tcctccatgt | 600 |
| cctgagcctg agctcaccta tggtttacct gctcataccg acccaaatgc cctcaccatt | 660 |
| cttctccaag atgctaccgt tgcggtctc cagatcttga tcgacggtca ctggtttgct | 720 |
| gttaatcctc gtcctgatgc ttttgtcatc aacattggtg accagttgca ggcattgagt | 780 |
| aacggagtat acaaaagtgt tggcatcga gcagtgacaa cactgaaaa cccgagacta | 840 |
| tcgatcgcat catttatgtg tcctgataac ggtgctgtca taagcccggc aaagcccctg | 900 |

```
tgggaagcca aggaggaaga ggccaagcca atctacagag actacactta tgcagagtac      960
tacaagaagt tttggagtag gaatctggac caagaacatt gcctcgaaaa ctttctaaac     1020
gactag                                                                1026
```

<210> SEQ ID NO 132
<211> LENGTH: 20
<212> TYPE: DNA
<213> ORGANISM: Artificial Sequence
<220> FEATURE:
<223> OTHER INFORMATION: Synthetic Construct

<400> SEQUENCE: 132

```
gtgagctcag gctcaggaca                                                   20
```

<210> SEQ ID NO 133
<211> LENGTH: 53
<212> TYPE: DNA
<213> ORGANISM: Artificial Sequence
<220> FEATURE:
<223> OTHER INFORMATION: Synthetic Construct

<400> SEQUENCE: 133

```
acactctttc cctacacgac gctcttccga tctgcttttg cagggaagtt gtg              53
```

<210> SEQ ID NO 134
<211> LENGTH: 52
<212> TYPE: DNA
<213> ORGANISM: Artificial Sequence
<220> FEATURE:
<223> OTHER INFORMATION: Synthetic Construct

<400> SEQUENCE: 134

```
ctcggcattc ctgctgaacc gctcttccga tctaccgcaa acggtagcat ct               52
```

<210> SEQ ID NO 135
<211> LENGTH: 53
<212> TYPE: DNA
<213> ORGANISM: Artificial Sequence
<220> FEATURE:
<223> OTHER INFORMATION: Synthetic Construct

<400> SEQUENCE: 135

```
acactctttc cctacacgac gctcttccga tctgtcaaca catggcagtc aac              53
```

<210> SEQ ID NO 136
<211> LENGTH: 53
<212> TYPE: DNA
<213> ORGANISM: Artificial Sequence
<220> FEATURE:
<223> OTHER INFORMATION: Synthetic Construct

<400> SEQUENCE: 136

```
ctcggcattc ctgctgaacc gctcttccga tctgtcggta tgagcaggta aac              53
```

<210> SEQ ID NO 137
<211> LENGTH: 606
<212> TYPE: DNA
<213> ORGANISM: Artificial Sequence
<220> FEATURE:
<223> OTHER INFORMATION: Synthetic Construct

<400> SEQUENCE: 137

```
atggcagcaa agctaatatc caccggtatt cgtcacacaa ctttgccgga aaactatgtt       60
```

```
cggccactct ccaaccgtcc atgtctctct gacgtctctc cacttaaaga tttccctatc    120
atcgacctat cttccacaga tcgatctcgg ctagtccaac aaatccacca agcttgctcc    180
cgattcgggt tttttcaggt cataaatcac agagttagca aagatacaat agatggaatg    240
gtgagtgttg cgaacgagtt ctttagcatg tctatggagg aaaaaatgaa gctgtactcg    300
gacgatccaa cgaagacgac gagattatca acgagcttca atgtgaaaaa gaagaggtc    360
aacaattgga gagactatct tagactacat tgttatccta tcagcaagta tgtccatgag    420
tggccttcaa accctccttc tttcaaggaa gttgtgagta gatacagtac agatgtaaga    480
gaactgggat ttactataga ggaactgata tcagagagcc tgggtttaga aaagatcac     540
atgaggaaag tgcttggtga acaaggtcaa cacatggcag tcaactatta ccctccatgt    600
gcctga                                                               606
```

<210> SEQ ID NO 138
<211> LENGTH: 699
<212> TYPE: DNA
<213> ORGANISM: Artificial Sequence
<220> FEATURE:
<223> OTHER INFORMATION: Synthetic Construct

<400> SEQUENCE: 138

```
atggcggcaa agcttttatc caccggtttc cgtcactcta ctttgccgga aaactatgtc     60
cggccactct ctgaccgtcc acgtctctcc caagtttctc agcttgaaga tttccctctc    120
atcgatatat cttcaacaga tcgatctcgg ctcgtccaaa aaatccacca agcttgcgcc    180
cgatttggtt tctttcaggt tataaatcat ggtgttagca aagcaactat agatgagatg    240
gtgagtgttg cgcatgagtt ttttggcatg cctatggacg aaaaaatgaa gctatactcg    300
gacgatccaa caaagacacc gagattatcg acgagcttta atgtgaagga agaagaggtt    360
aataattgga gagactatct aagacttcat tgttatccta tcgacaagta tgtccatgag    420
tggccttcca accccccttc tttcaaggaa gttgtgagta aatacagtag agaaataaga    480
gaattgggac ttaaaataga ggaattgata tcagagagct taggtttaga aaagattac     540
atgaagaaag tgcttggtga acaaggtcaa cacatggcag tcaactatta tcctccatgc    600
ctgagcctga gctcacctat ggtttacctg ctcataccga cccaaatgcc ctcaccattc    660
ttctccaaga tgctaccgtt tgcggtctcc agatcttga                           699
```

<210> SEQ ID NO 139
<211> LENGTH: 201
<212> TYPE: PRT
<213> ORGANISM: Artificial Sequence
<220> FEATURE:
<223> OTHER INFORMATION: Synthetic Construct

<400> SEQUENCE: 139

```
Met Ala Ala Lys Leu Ile Ser Thr Gly Ile Arg His Thr Thr Leu Pro
1               5                   10                  15

Glu Asn Tyr Val Arg Pro Leu Ser Asn Arg Pro Cys Leu Ser Asp Val
            20                  25                  30

Ser Pro Leu Lys Asp Phe Pro Ile Ile Asp Leu Ser Ser Thr Asp Arg
        35                  40                  45

Ser Arg Leu Val Gln Gln Ile His Gln Ala Cys Ser Arg Phe Gly Phe
    50                  55                  60

Phe Gln Val Ile Asn His Arg Val Ser Lys Asp Thr Ile Asp Gly Met
65                  70                  75                  80
```

```
Val Ser Val Ala Asn Glu Phe Phe Ser Met Ser Met Glu Glu Lys Met
            85                  90                  95

Lys Leu Tyr Ser Asp Asp Pro Thr Lys Thr Thr Arg Leu Ser Thr Ser
            100                 105                 110

Phe Asn Val Lys Lys Glu Glu Val Asn Asn Trp Arg Asp Tyr Leu Arg
            115                 120                 125

Leu His Cys Tyr Pro Ile Ser Lys Tyr Val His Glu Trp Pro Ser Asn
            130                 135                 140

Pro Pro Ser Phe Lys Glu Val Val Ser Arg Tyr Ser Thr Asp Val Arg
145                 150                 155                 160

Glu Leu Gly Phe Thr Ile Glu Glu Leu Ile Ser Glu Ser Leu Gly Leu
            165                 170                 175

Glu Lys Asp His Met Arg Lys Val Leu Gly Glu Gln Gly Gln His Met
            180                 185                 190

Ala Val Asn Tyr Tyr Pro Pro Cys Ala
            195                 200
```

<210> SEQ ID NO 140
<211> LENGTH: 232
<212> TYPE: PRT
<213> ORGANISM: Artificial Sequence
<220> FEATURE:
<223> OTHER INFORMATION: Synthetic Construct

<400> SEQUENCE: 140

```
Met Ala Ala Lys Leu Leu Ser Thr Gly Phe Arg His Ser Thr Leu Pro
1               5                   10                  15

Glu Asn Tyr Val Arg Pro Leu Ser Asp Arg Pro Arg Leu Ser Gln Val
            20                  25                  30

Ser Gln Leu Glu Asp Phe Pro Leu Ile Asp Ile Ser Ser Thr Asp Arg
            35                  40                  45

Ser Arg Leu Val Gln Lys Ile His Gln Ala Cys Ala Arg Phe Gly Phe
        50                  55                  60

Phe Gln Val Ile Asn His Gly Val Ser Lys Ala Thr Ile Asp Glu Met
65                  70                  75                  80

Val Ser Val Ala His Glu Phe Phe Gly Met Pro Met Asp Glu Lys Met
            85                  90                  95

Lys Leu Tyr Ser Asp Asp Pro Thr Lys Thr Pro Arg Leu Ser Thr Ser
            100                 105                 110

Phe Asn Val Lys Glu Glu Val Asn Asn Trp Arg Asp Tyr Leu Arg
            115                 120                 125

Leu His Cys Tyr Pro Ile Asp Lys Tyr Val His Glu Trp Pro Ser Asn
            130                 135                 140

Pro Pro Ser Phe Lys Glu Val Val Ser Lys Tyr Ser Arg Glu Ile Arg
145                 150                 155                 160

Glu Leu Gly Leu Lys Ile Glu Glu Leu Ile Ser Glu Ser Leu Gly Leu
            165                 170                 175

Glu Lys Asp Tyr Met Lys Lys Val Leu Gly Glu Gln Gly Gln His Met
            180                 185                 190

Ala Val Asn Tyr Tyr Pro Pro Cys Leu Ser Leu Ser Ser Pro Met Val
            195                 200                 205

Tyr Leu Leu Ile Pro Thr Gln Met Pro Ser Pro Phe Phe Ser Lys Met
            210                 215                 220

Leu Pro Phe Ala Val Ser Arg Ser
225                 230
```

```
<210> SEQ ID NO 141
<211> LENGTH: 60
<212> TYPE: PRT
<213> ORGANISM: Artificial Sequence
<220> FEATURE:
<223> OTHER INFORMATION: Synthetic Construct

<400> SEQUENCE: 141

Met Ala Ala Lys Leu Ile Ser Thr Gly Ile Arg His Thr Thr Leu Pro
1               5                   10                  15

Glu Asn Tyr Val Arg Pro Leu Ser Asn Arg Pro Cys Leu Ser Asp Val
            20                  25                  30

Ser Pro Leu Lys Asp Phe Pro Ile Ile Asp Leu Ser Ser Thr Asp Arg
        35                  40                  45

Ser Arg Leu Val Gln Gln Ile His Gln Ala Cys Ser
    50                  55                  60

<210> SEQ ID NO 142
<211> LENGTH: 230
<212> TYPE: PRT
<213> ORGANISM: Artificial Sequence
<220> FEATURE:
<223> OTHER INFORMATION: Synthetic Construct

<400> SEQUENCE: 142

Met Ala Ala Lys Leu Ile Ser Thr Gly Ile Arg His Thr Thr Leu Pro
1               5                   10                  15

Glu Asn Tyr Val Arg Pro Leu Ser Asn Arg Pro Cys Leu Ser Asp Val
            20                  25                  30

Ser Pro Leu Lys Asp Phe Pro Ile Ile Asp Leu Ser Ser Thr Asp Arg
        35                  40                  45

Ser Arg Leu Val Gln Gln Ile His Gln Ala Cys Ser Arg Phe Gly Phe
    50                  55                  60

Phe Gln Val Ile Asn His Arg Val Ser Lys Asp Thr Ile Asp Gly Met
65                  70                  75                  80

Val Ser Val Ala Asn Glu Phe Phe Ser Met Ser Met Glu Glu Lys Met
                85                  90                  95

Lys Leu Tyr Ser Asp Asp Pro Thr Lys Thr Thr Arg Leu Ser Thr Ser
            100                 105                 110

Phe Asn Val Lys Lys Glu Glu Val Asn Asn Trp Arg Asp Tyr Leu Arg
        115                 120                 125

Leu His Cys Tyr Pro Ile Ser Lys Tyr Val His Glu Trp Pro Ser Asn
    130                 135                 140

Pro Pro Ser Phe Lys Glu Val Val Ser Arg Tyr Ser Thr Asp Val Arg
145                 150                 155                 160

Glu Leu Gly Phe Thr Ile Glu Glu Leu Ile Ser Glu Ser Leu Gly Leu
                165                 170                 175

Glu Lys Asp His Met Arg Lys Val Leu Gly Glu Gln Gly Gln His Met
            180                 185                 190

Ala Val Asn Tyr Tyr Pro Pro Cys Pro Glu Pro Glu Leu Thr Tyr Gly
        195                 200                 205

Leu Pro Ala His Thr Asp Pro Asn Ala Leu Thr Ile Leu Leu Gln Asp
    210                 215                 220

Ala Thr Val Cys Gly Leu
225                 230

<210> SEQ ID NO 143
```

<211> LENGTH: 237
<212> TYPE: PRT
<213> ORGANISM: Artificial Sequence
<220> FEATURE:
<223> OTHER INFORMATION: Synthetic Construct

<400> SEQUENCE: 143

Met Ala Ala Lys Leu Ile Ser Thr Gly Ile Arg His Thr Thr Leu Pro
1               5                   10                  15

Glu Asn Tyr Val Arg Pro Leu Ser Asn Arg Pro Cys Leu Ser Asp Val
            20                  25                  30

Ser Pro Leu Lys Asp Phe Pro Ile Ile Asp Leu Ser Ser Thr Asp Arg
        35                  40                  45

Ser Arg Leu Val Gln Gln Ile His Gln Ala Cys Ser Arg Phe Gly Phe
    50                  55                  60

Phe Gln Val Ile Asn His Arg Val Ser Lys Asp Thr Ile Asp Gly Met
65                  70                  75                  80

Val Ser Val Ala Asn Glu Phe Phe Ser Met Ser Met Glu Glu Lys Met
                85                  90                  95

Lys Leu Tyr Ser Asp Asp Pro Thr Lys Thr Thr Arg Leu Ser Thr Ser
            100                 105                 110

Phe Asn Val Lys Lys Glu Glu Val Asn Asn Trp Arg Asp Tyr Leu Arg
        115                 120                 125

Leu His Cys Tyr Pro Ile Ser Lys Tyr Val His Glu Trp Pro Ser Asn
    130                 135                 140

Pro Pro Ser Phe Lys Glu Val Val Ser Arg Tyr Ser Thr Asp Val Arg
145                 150                 155                 160

Glu Leu Gly Phe Thr Ile Glu Glu Leu Ile Ser Glu Ser Leu Gly Leu
                165                 170                 175

Glu Lys Asp His Met Arg Lys Val Leu Gly Glu Gln Gly Gln His Met
            180                 185                 190

Ala Val Asn Tyr Tyr Pro Pro Cys Pro Glu Pro Glu Leu Thr Tyr Gly
        195                 200                 205

Leu Pro Ala His Thr Asp Pro Asn Ala Leu Thr Ile Leu Leu Gln Asp
    210                 215                 220

Ala Thr Val Cys Gly Leu Gln Ile Leu Ile Asp Gly Gln
225                 230                 235

<210> SEQ ID NO 144
<211> LENGTH: 122
<212> TYPE: PRT
<213> ORGANISM: Artificial Sequence
<220> FEATURE:
<223> OTHER INFORMATION: Synthetic Construct

<400> SEQUENCE: 144

Met Ala Ala Lys Leu Leu Ser Thr Gly Phe Arg His Ser Thr Leu Pro
1               5                   10                  15

Glu Asn Tyr Val Arg Pro Leu Ser Asp Arg Pro Arg Leu Ser Gln Val
            20                  25                  30

Ser Gln Leu Glu Asp Phe Pro Leu Ile Asp Ile Ser Ser Thr Asp Arg
        35                  40                  45

Ser Arg Leu Val Gln Lys Ile His Gln Ala Cys Ala Arg Phe Gly Phe
    50                  55                  60

Phe Gln Val Ile Asn His Gly Val Ser Lys Ala Thr Ile Asp Glu Met
65                  70                  75                  80

Val Ser Val Ala His Glu Phe Phe Gly Met Pro Met Asp Glu Lys Met

-continued

```
                85                  90                  95
Lys Leu Tyr Ser Asp Asp Pro Thr Lys Thr Pro Arg Leu Ser Thr Ser
            100                 105                 110

Phe Asn Val Lys Glu Glu Val Asn Asn
        115                 120
```